US009289509B2

(12) United States Patent
Osterroth et al.

(10) Patent No.: US 9,289,509 B2
(45) Date of Patent: Mar. 22, 2016

(54) USES OF IMMUNOCONJUGATES TARGETING CD138

(75) Inventors: Frank Osterroth, Dietzenbach (DE); Christoph Uherek, Seligenstadt (DE); Christoph Bruecher, Eschborn (DE); Benjamin Daelken, Frankfurt am Main (DE); Andre Engling, Frankfurt (DE); Thomas Haeder, Dreieichenhain (DE); Andrea Wartenberg-Demand, Linden (DE); Gabriele Niemann, Karlsruhe (DE); Chantal Zuber, Frankfurt (DE); Niklas Czeloth, Dreieich (DE); Silke Aigner, Frankenthal (DE); Steffen Zeng, Muenster (DE); Gregor Schulz, Umkirch (DE)

(73) Assignees: Biotest AG, Dreieich (DE); Immunogen Inc., Waltham, MA (US)

( * ) Notice: Subject to any disclaimer, the term of this patent is extended or adjusted under 35 U.S.C. 154(b) by 0 days.

(21) Appl. No.: 12/774,705

(22) Filed: May 5, 2010

(65) Prior Publication Data

US 2011/0123554 A1    May 26, 2011

Related U.S. Application Data

(60) Provisional application No. 61/176,069, filed on May 6, 2009, provisional application No. 61/259,430, filed on Nov. 9, 2009.

(51) Int. Cl.
*A61K 39/395* (2006.01)
*A61K 47/48* (2006.01)
*B82Y 5/00* (2011.01)

(52) U.S. Cl.
CPC ..... *A61K 47/48276* (2013.01); *A61K 47/48346* (2013.01); *A61K 47/48569* (2013.01); *B82Y 5/00* (2013.01)

(58) Field of Classification Search
CPC .................................................. A61K 39/395
USPC ............ 424/1.49, 133.1, 134.1, 158.1, 172.1, 424/179.1, 178.1
See application file for complete search history.

(56) References Cited

U.S. PATENT DOCUMENTS

| | | | |
|---|---|---|---|
| 5,034,223 A | 7/1991 | Abrams et al. | |
| 5,612,016 A | 3/1997 | Griffiths et al. | |
| 6,080,777 A | 6/2000 | Schiff | |
| 6,087,362 A | 7/2000 | El-Rashidy | |
| 7,601,354 B2 | 10/2009 | Chari | |
| 8,840,898 B2 * | 9/2014 | Goldmakher | 424/178.1 |
| 2003/0105000 A1 * | 6/2003 | Pero et al. | 514/12 |
| 2004/0241817 A1 | 12/2004 | Umana et al. | |
| 2005/0123549 A1 | 6/2005 | Payne et al. | |
| 2005/0271653 A1 | 12/2005 | Strahilevitz | |
| 2005/0272128 A1 | 12/2005 | Umana et al. | |
| 2006/0045877 A1 | 3/2006 | Goldmakher | |
| 2007/0183971 A1 | 8/2007 | Goldmakher | |
| 2009/0169570 A1 | 7/2009 | Daelken et al. | |
| 2009/0175863 A1 | 7/2009 | Kraus et al. | |
| 2009/0181038 A1 | 7/2009 | Schulz et al. | |
| 2009/0232810 A1 | 9/2009 | Kraus et al. | |
| 2010/0028346 A1 | 2/2010 | Lutz et al. | |

FOREIGN PATENT DOCUMENTS

| | | | | |
|---|---|---|---|---|
| JP | 2008533161 A | | 8/2008 | |
| JP | 2008542192 A | | 11/2008 | |
| WO | WO 03/070234 | * | 8/2003 | ............. A61K 31/13 |
| WO | 2004099379 A2 | | 11/2004 | |
| WO | 2006099479 A2 | | 9/2006 | |
| WO | 2006099875 A1 | | 9/2006 | |
| WO | 2006107451 A2 | | 10/2006 | |
| WO | 2007066109 A1 | | 6/2007 | |
| WO | 2007144046 A2 | | 12/2007 | |
| WO | 2009/080829 A1 | | 7/2009 | |
| WO | 2009/080830 A1 | | 7/2009 | |
| WO | 2009/080831 A1 | | 7/2009 | |
| WO | 2009/080832 A1 | | 7/2009 | |
| WO | 2010/008726 A1 | | 1/2010 | |

OTHER PUBLICATIONS

Busken, C et al. (Digestive Disease Week Abstracts and Itinerary Planner, 2003, abstract No. 850).*
Wiesenthal (http://weisenthal.org/feedback. html, Feb. 4, 2002).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Berenbaum (Clin. Exp Immunol. 28:1-18, 1977).*
Rudikoff et al, (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Burgess et al (J of Cell Bio. 111:2129-2138, 1990).*
Cohen (Int J Radiat Oncol Biol Phys, 1987, 13:251-8).*
Gussow et al. (1991, Methods in Enzymology 203:99-121).*
Gura (Science, 1997, 278:1041-1042).*
Lynch et al. (Pain, 2004, 110: 56-63).*
Tassone et al., "In vitro and in vivo antitumor activity of the maytansinoid immunoconjugate BB4 (BB4-DM1) against DC138+ multiple myeloma cells," in Proc Amer Assoc Cancer Res, vol. 45, abstract #1425 Mar. 2004, abstract.
Supiot et al., "Comparison of the Biologic Effects of MA5 and B-B4 Monoclonal Antibody Labeled with Iodine-131 and Bismuth-213 on Multiple Myeloma," Cancer, vol. 94, No. S4, pp. 1202-1209, 2002.
Post, "Efficacy of an anti-CD138 immunotoxin and doxorubicin on drug-resistant and drug-sensitive myeloma cells," in Inter J. Cancer, vol. 83, pp. 571-576, 1999.
Tassone et al, "In vitro and in vivo activity of the maytansinoid immunocojugate huN901-N2'-Deacetyl-N2'-(3-Mercapto-1-Oxoproply)-maytansine against CD56+ multiple myeloma cells," in Cancer Res, vol. 64, pp. 4629-4636, Jul. 1, 2004.

(Continued)

*Primary Examiner* — Yan Xiao
(74) *Attorney, Agent, or Firm* — Joyce von Natzmer; Agris & von Natzmer LLP

(57) ABSTRACT

Disclosed are methods and treatment regimes that include the administration of immunconjugates targeting CD138 to combat diseases. The immunoconjugate is either used as the sole active ingredient, as part of a treatment regime or as part of an anticancer combination.

49 Claims, 30 Drawing Sheets

(56) References Cited

OTHER PUBLICATIONS

Tassone et al, "Antitumor activity of the maytansinoid immunoconjugate B-B4 (B-B4-DM1) against CD138+ multiple myeloma cells," in Blood Nov. 16, 2003, vol. 102, 45th ASH meeting abstract 449s-450a (abstract), Nov. 16, 2003.
Sharkey et al., "Targeted therapy of Cancer: new prospects for antibodies and immunoconjugates." in CA: A Cancer Journal for Clinicians Jul.-Aug. 2006, vol. 56, No. 4, pp. 226-243, Jul. 2006.
Turner et al.: "131I-Anti CD20 radioimmunotherapy of relapsed or refractory non-Hodgkins lymphoma: a phase II clim'cal trial of a nonmyeloablative dose regimen of chimeric rituximab radiolabeled in a hospital," in Cancer Biotherapy & Radiopharmaceuticals Aug. 2003, vol. 18, No. 4, pp. 513-524, Aug. 8, 2003.
Israel et al.: "Plasmapheresis and inmunological control of cancer," in Lancet Sep. 18, 1976, vol. 2, No. 7986, pp. 642-643, Sep. 18, 1976.
Cortesini: "Pancreas cancer and the role of soluble immunoglobulin-like transcript 3 (ILT3)," in JOP: Journal of the Pancreas 2007, vol. 8, No. 6, pp. 697-703, Nov. 1, 2007.
Fundamental Immunology, William E. Paul M.D., ed., 3rd Ed., pp. 292-295, 1993.
Rudikoff et al., "Single amino acid substitution altering antigen-binding specificity," in Proc. Natl. Acad. Sei. USA, vol. 79, pp. 1979-1983, Mar. 1982.
Colman, "Effects of amino acid sequence changes on antibody-antigen interactions," in Research in Immunology, vol. 145, pp. 33-36, 1994.
MacCallum et al., "Antibody-antigen interactions: contact analysis and binding site topography," in J. Mol. Biol., vol. 262, pp. 732-745, 1996.
Casset et al., "A peptide mimetic of an anti-CD4 monoclonal antibody by rational design," in Biochemical and Biophysical Research Communications, vol. 307, pp. 198-205, 2003.
Bendig, "Humanization of rodent monoclonal antibodies by CDR grafting," in Methods: A Companion to Methods in Enzymology, vol. 8, pp. 83-93, 1995.
Fundamental Immunology, (William E. Paul, M.D. ed., 3d ed. 1993), p. 242.
Buchsbaum, "Experimental approaches to increase radiolabeled antibody localization in tumors," in Cancer Res. Suppl., vol. 55, pp. 5729s-5732s, Dec. 1, 1995.
Chanan-Khan et al., "3689 Phase I Study of IMGN901 in Patients with Relapsed and Relapsed/Refractory CD56-Postiive Multiple Myeloma," in 50th Ash Annual Meeting and Exposition: Online Program and Abstracts, American Society of Hematology, Dec. 6-9, 2008.
Eagan et al.; "Early clinical study of an intermittent schedule for maytansine (NSC-153858): brief communication;" J Natl Cancer Insti (Bethesda); 60; 1978; pp. 93-96.
Edinger et al.; "Noninvasive assessment of tumor cell proliferation in animal models;" Neoplasia; 1; 1999; pp. 303-310.
Facon et al.; "Superiority of melphalan-prednisone (MP) + thalidomide (THAL) over MP and autologous stem cell transplantation in the treatment of newly diagnosed elderly patients with multiple myeloma;" J. Clin. Oncol.; 24(Suppl. 18); Abstract 1; 2006.
Fossella et al.; "Phase II Trial of BB-10901 (huN901-DM1) given weekly for four consecutive weeks every 6 weeks in patients with relapsed SCLC and CD56-positive small cell carcinoma;" J Clin Onco, ASCO Annual Meeting Proceedings; 23(16S), Part I of II; Jun. 1, 2005; 7159; Supplement.
Galsky et al.; "Phase I Trial of the Prostate-Specific Membrane Antigen-Directed Immunoconjugate MLN2704 in Patients With Progressive Metastatic Castration-Resistant Prostate Cancer;" Journal of Clinical Oncology; May 1, 2008; pp. 2147-2154.
Gattei et al.; "Characterization of Anti-CD138 monoclonal antibodies as tools for investigating the molecular polymorphism of syndecan-1 in human lymphoma cells;" Br J Haematol.; 104; 1999; pp. 152-162.
Ghobrial et al.; "Emerging drugs in multiple myeloma;" Expert Opin Emerg Drugs; 12(1); Mar. 2007; pp. 155-163.

Giles et al.; "Phase I study of AVE9633, an AntiCD33-Maytansinoid Immunoconjugate, Administered as an Intravenous Infusion in Patients with Refractory/Relapsed CD33-Positive Acute Myeloid Leukemia (AML);" Blood; 108(11); Nov. 16, 2006.
Greipp et al.; "International staging system for multiple myeloma," J Clin Oncol; 23(15); May 20, 2005; pp. 3412-3420.
Gunaratnum et al.; "G-quadruplex compounds and cis-platin act synergistically to inhibit cancer cell growth in vitro and in vivo;" Biochemical Pharmacology; 78; 2009; pp. 115-122.
Hamann et al.; "An anti-CD33 antibody-calicheamicin conjugate for treatment of acute myeloid leukemia;" Choice of linker; Bioconjug Chem; 13; 2002; pp. 40-46.
Han et al.; "New insights into syndecan-2 expression and tumourigenic activity in colon carcinoma cells;" J Mol Histol; 35(3); 2004; pp. 319-326.
Hashimoto et al.; "Colorectal Association of loss of epithelial syndecan-1 with stage and local metastasis of colorectal adenocarcinomas: an immunohistochemical study of clinically annotated tumors;"BMC Cancer 8; 2008; p. 185.
Helft et al.; "A phase I study of cantuzumab mertansine administered as a single intravenous infusion once weekly in patients with advanced solid tumors;" Clin Cancer Res; 10(13); Jul. 1, 2004; pp. 4363-4368.
Hideshima et al.; "Perifosine, an oral bioactive novel alkylphospholipid, inhibits Akt and induces in vitro and in vivo cytotoxicity in human multiple myeloma cells;" Blood; 107(10); 2006; pp. 4053-4062.
Hideshima et al.; "Understanding multiple myeloma pathogenesis in the bone marrow to identify new therapeutic targets;" Nat Rev Cancer; 7(8); 2007; pp. 585-598.
Hiroshi et al.; "The Monoclonal Antibody nBT062 Conjugated to Cytotoxic Maytansinoids Has Potent and Selective Cytotoxicity against CD138 Positive Multiple Myeloma Cells in Vitro and in Vivo;" Blood; (ASH Annual Meeting Abstracts); 112; Nov. 2008; p. 1716.
Holden et al.; "A phase I study of weekly dosing of trastuzumab-DM1 (T-DM1) in patients (pts) with advanced HER2+ breast cancer (BC);" ASCO Meeting Abstracts; May 20, 2008; p. 1029.
Horvathova et al.; In: al. SFSe, ed. Leucocyte Typing V.; Oxford: Oxford University Press; 1995; pp. 713-714.
Huang et al.; "Validation and reduction of FACT/GOG-Ntx subscale for platinum/paclitaxel-induced neurologic symptoms: a gynecologic oncology group study;" Int J Gynecol Cancer; 17; 2007; pp. 387-393.
Hwang et al.; "New Frontiers in the Treatment of Multiple Myeloma;" Scientific World Journal; 6; Dec. 6, 2006; pp. 1475-1503.
Ikeda et al.; "The monoclonal antibody nBT062 conjugated to maytansinoids has potent and selective cytotoxicity against CD138 positive multiple myeloma cells in vitro and in vivo;" Clin. Cancer Research; 15(12); 2009; available at http://precedings.nature.com/documents/2374/version/1, pp. 4028-4037.
Ishitsuka et al.; "Targeting CD56 by the maytansinoid immunoconjugate IMGN901 (huN901-DM1): a potential therapeutic modality implication against natural killer/T cell malignancy;" Br. J. Haematol; 141(1); Apr. 2008; pp. 129-131.
Issell et al.; "Maytansine;"Cancer Treat Rev; 5; 1978; pp. 199-207.
Jemal et al.; "Cancer statistics;" CA Cancer J Clin; 58; 2008; pp. 71-96.
Kovtun et al.; "Antibody-drug conjugates designed to eradicate tumors with homogeneous and heterogeneous expression of the target antigen;" Cancer Res; 66(6); 2006; pp. 3214-3221.
Kuesters et al.; Correlation of ErbB2 Gene Status, mRNA and Protein Expression in a Panel of >100 Human Tumor Xenografts of Different Origin; Onkologie; 29; 2006; pp. 249-256.
Krebs et al.; "High-throughput generation and engineering of recombinant human antibodies;" J. Immunol. Methods; 254; 2001; pp. 67-84.
Krop et al.; "A Phase I Study of Trastuzumab-DM1, a First-in-Class HER2 Antibody-Drug Conjugate (ADC), in patients with HER2+ Metastatic Breast Cancer;" 14th European Cancer Conference (ECCO 14); Poster #2118; 2007.

(56) References Cited

OTHER PUBLICATIONS

Kupchan et al.; "Structural requirements for antileukemic activity among the naturally occurring and semisynthetic maytansinoids;" J Med Chem; 21; 1978; pp. 31-37.

Kyle et al.; "Multiple myeloma;" N Engl J Med; 351(18); Oct. 28, 2004; pp. 1860-1873.

Kyle et al.; "Criteria for diagnosis, staging, risk stratification dn response assessment of multiple myeloma;" Leukemia; 23; 2009; pp. 3-9.

Kyoizumi et al.; "Implantation and maintenance of functional human bone marrow in SCID-hu mice;" Blood; 79; 1992; pp. 1704-1711.

Kyoizumi et al.; "Preclinical analysis of cytokine therapy in the SCID-hu mouse;" Blood; 81; 1993; pp. 1479-1488.

Lambert JM; "Drug-conjugated monoclonal antibodies for the treatment of cancer;" Current Opinion in Pharmacology; 5; 2005; pp. 543-549.

Langford et al.; "Multiple heparan sulfate chains are required for optimal syndecan-1 function;" J Biol Chem; 273(45); Nov. 6, 1998; pp. 29965-29971.

Legrand et al.; "An open label, dose escalation study of AVE9633 administered as a single agent by intravenous (IV) infusion weekly for 2 weeks in a 4-week cycle to patients with relapsed or refractory CD33-positive Acute Myeloid Leukemia (AML);" Blood; 118(11); Nov. 16, 2007.

Li et al.; "Clinicopathological significance of expression of paxillin, syndecan-1 and EMMPRIN in hepatocellular carcinoma;" World J Gastroenterol. 11(10); 2005; pp. 1445-1451.

Liu et al.; "Eradication of large colon tumor xenografts by targeted delivery of maytansinoids;" Proc Natl Acad Sci U S A; 93; 1996; pp. 8618-8623.

Loussouarn et al.; "Prognostic impact of syndecan-1 expression in invasive ductal breast carcinomas;" Br J Cancer; 28; 2008; pp. 1993-1998.

Lorigan et al.; "Phase I trial of BB-10901 (huN901-DM1) given daily by IV infusion for three consecutive days every three weeks in patients with SCLC and other CD56-positive solid tumors;" European Journal of Cancer Supplements; 4 (12); 2006; pp. 195.

Ludwig et al.; "Supportive care in multiple myelom;" Best Practice & Research Clinical Haematology; 20; Issue 4; 2007; pp. 817-835.

McCann et al.; "Phase II trial of huN901-DM1 in patients with relapsed small cell lung cancer (SCLC) and CD56-positive small cell carcinoma;" J Clin Onco; ASCO Annual Meeting Proceedings Part 1; 25(18S); Jun. 20, 2007; Supplement; p. 18084.

Mateos et al.; "Bortezomib plus melphalan and prednisone in elderly untreated patients with multiple myeloma: results of a multicenter phase 1/2 study;" Blood; 108; 2006; pp. 2165-2172.

McCune et al.; "The SCID-hu mouse: murine model for the analysis of human hematolymphoid differentiation and function;" Science; 241; 1988; pp. 1632-1639.

Mennerich et al.; "Shift of syndecan-1 expression from epithelial to stromal cells during progression of solid tumours;" Eur J Cancer; 40(9); Jun. 2004; pp. 1373-1382.

Milowsky et al.; "Phase I/II trial of the prostate-specific membrane antigen (PSMA)-targeted immunoconjugate MLN2704 in patients (pts) with progressive metastatic castration resistant prostate cancer (CRPC);" J Clin Onco; ASCO Annual Meeting Proceedings Part I; 24(18S); 2006 p. 4500.

Mita et al.; "A phase I study of a CanAg-targeted immunoconjugate, huC242-DM4, in subjects with CanAg-expressing solid tumors;" J Clin Onco; ASCO Annual Meeting Proceedings Part 1; 25(18S); Jun. 20, 2007; Supplement; p. 3062.

Mitsogiannis et al; "Plasmacytoid transitional cell carcinoma of the urinary bladder;" Urology66(1); 2005; p. 194.

Mosmann T.; "Rapid colorimetric assay for cellular growth and survival: application to proliferation and cytotoxicity assays;" J Immunol Methods; 65; 1983 pp. 55-63.

Namikawa et al.; "Growth of human myeloid leukemias in the human marrow environment of SCID-hu mice;" Blood; 82; 1993; pp. 2526-2536.

NCCN Guidelines; "NCCN Clinical Practice Guidelines in Oncology;" Multiple Myeloma V.2.2009; National Comprehensive Cancer Network; Nov. 9, 2008; available at www.nccn.org.

Ning et al.; "Liposomal doxorubicin in combination with bortezomib for relapsed or refractory multiple myeloma;" Oncology (Williston Park); 21(12); November 277; pp. 1503-1508, 2007.

Numa et al.; Syndecan-1 expression in cancer of the uterine cervix: association with lymph node metastasis; Int J Oncol. 20(1); Abstract, 2002.

Ocio et al., "New drugs in multiple myeloma: mechanisms of action and phase I/II clinical findings;" Lancet Oncol: 9 (12); Dec. 2008; pp. 1157-1165.

O'Connell et al.; "CD138 (Syndecan-1), a Plasma Cell Marker Immunohistochemical Profile in Hematopoietic and Nonhematopoietic Neoplasms;" Am J Clin Pathol; 121; 2004; pp. 254-263.

Ojima et al.; "Tumor-specific novel taxoid-monoclonal antibody conjugates;" J. Med. Chem.; 45; 2002; pp. 5620-5623.

Olafsen et al.; "Covalent disulfide-linked anti-CEA diabody allows site-specific conjugation and radiolabeling for tumor targeting applications;" Prot. Eng. Design & Selection 17; 1; 2004; pp. 21-27.

Orosz et al.; "Syndecan-1 expression in different soft tissue tumours;" Anticancer Res; 21(1B); 2001; pp. 733-737.

Padlan, EA; "A possible procedure for reducing the immunogenicity of antibody variable domains while preserving their ligand-binding properties;" Mol. Immunol.; 28; 1991; pp. 489-498.

Palacios et al.; "B-B4 monoclonal antibody and identification of human bone marrow plasma cells;" Br J Haematol; 96 (3); Mar. 1997; pp. 655-657.

Palumbo et al.; "Oral revlimid plus melphalan and prednisone (R-MP) for newly diagnosed multiple myeloma: results of a multicenter Phase I/II study;" Blood; 108; (ASH Annual Meeting Abstracts); Abstract 800; 2006.

Palumbo et al.; "Treatment of newly diagnosed myeloma;" Leukemia; 23; Nov. 13, 2009; pp. 449-456.

Patriarca et al.; "Considerations in the treatment of multiple myeloma: a consensus statement from Italian experts;" Eur J Haematol; 82(2); Feb. 2009; pp. 93-105.

Payne G.; "Progress in immunoconjugate cancer therapeutics;" Cancer Cell; 3; 2003; pp. 207-212.

Pegram et al.; "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment;" J. Clin. Oncol.; 16; 1998; pp. 2659-2671.

Podar et al.; "Bone marrow microenvironment and the identification of new targets for myeloma therapy;" Leukemia; 23 (1); Jan. 2009; pp. 10-24.

Qin et al.; "The pharmacokinetics and pharmacodynamics of IMGN242 (huC242-DM4) in patients with CanAg-expressing solid tumors;" Journal of Clinical Oncology, 2008 ASCO Annual Meeting Proceedings (Post-Meeting Edition); 26(15S); May 20, 2008; Supplement; p. 3066.

Quach et al.: "Mechanism of action of immunomodulatory drugs (ImiDS) in multiple myeloma," Leukemia; 24; 2010; pp. 22-32.

Raje et al.; "Therapeutic use of immunomodulatory drugs in the treatment of multiple myeloma;" Expert Rev Anticancer Ther; 6(9); Sep. 2006; pp. 1239-1247.

Rajkumar et al.; "Combination therapy with lenalidomide plus dexamethasone (Rev/Dex) for newly diagnosed myeloma;" Blood; Dec. 15, 2005; 106(13); pp. 4050-4053.

Rajkumar et al.; "Phase III clinical trial of thalidomide plus dexamethasone compared with dexamethasone alone in newly diagnosed multiple myeloma: A clinical trial coordinated by the Eastern cooperative Oncology Group;" J Clin Oncol 2006; 24; pp. 431-436.

Rajkumar et al.; "A Randomized Trial of Lenalidomide Plus High-Dose Dexamethasone (RD) Versus Lenalidomide Plus Low-Dose Dexamethasone (Rd) in Newly Diagnosed Multiple Myeloma (E4A03): A Trial Coordinated by the Eastern Cooperative Oncology Group;" Blood; 110; 2007; p. 74.

Rawstron et al.; "Circulating plasma cells in multiple myeloma: characterization and correlation with disease stage;" Br J Haematol; 97; 1997; pp. 46-55.

(56) References Cited

OTHER PUBLICATIONS

Remillard et al.; "Antimitotic activity of the potent tumor inhibitor maytansine;" Science; 198; 1975; pp. 1002-1005.
Richardson et al.; "New treatments for multiple myeloma;" Oncology (Williston Park); 19(14); Dec. 2005; pp. 1781-1792.
Richardson et al.; "Lenalidomide in multiple myeloma;" Expert Rev Anticancer Ther, 6(8); Aug. 2006; pp. 1165-1173.
Richardson et al.; "New Drugs for Myeloma;" Oncologist Jun; 12(6); 2007; pp. 664-689.
Richardson et al.; "Lenalodomide, bortezomib, and dexamethasone as front-line-therapy for patients with multiple myeloma (MM): preliminary results of a phase I/II study;" Blood; 110; 2007; p. 63a.
Riechelmann et al.; "Phase I trial with the CD44v6-targeting immunoconjugate bivatuzumab mertansine in head and neck squamous cell carcinoma;" Oral Oncol; 44(9); Sep. 2008; pp. 823-829.
Roh et al.; "Syndecan-1 expression in gallbladder cancer and its prognostic significance;" Eur Surg Res. 41(2); 2008; pp. 245-250.
Roguska et al.; "Humanization of murine monoclonal antibodies through variable domain resurfacing;" Proc Natl Acad Sci U S A; 91; 1994; pp. 969-973.
Ross et al.; "Prostate stem cell antigen as therapy target: tissue expression and in vivo efficacy of an immunoconjugate;" Cancer Res.; May 1, 2002; 62(9) pp. 2546-2553.
Ross et al.; "Anticancer Antibodies;" Am J Clin Path; 119; Apr. 17, 2003; pp. 472-485.
Rowinsky et al.; "SB-408075, a tumor-activated immunoconjugate targeting the C242 CanAg antigen with a potent maytansinoid payload: phase I, pharmacokinetic (PK), and biological studies;" Proc Am Soc Clin Oncol 21: Abstract #118; 2002.
Rupp et al.; "Safety and pharmacokinetics of bivatuzumab mertansine in patients with CD44v6-positive metastatic breast cancer: final results of a phase I study;" Anticancer Drugs; 18(4); Apr. 2007; pp. 477-485.
Salfeld, "Isotype selection in antibody engineering", Nat. Biotechnol. 25 (12), 2007, pp. 1369-1372.
Sanderson et al.; "B lymphocytes express and lose syndecan at specific stages of differentiation;" Cell Regul.; 1989; 1; pp. 27-35.
Sandhu et al.; "Human hematopoiesis in SCID mice implanted with human adult cancellous bone;" Blood; 88; 1996; pp. 1973-1982.
Sankhala et al.; "A phase I and pharmacokinetic study of a CanAg-targeted immunoconjugate, HuC242-DM4, in patients with CanAg-expressing solid tumors;" AACR-NCI-EORTC "Molecular Targets and Cancer Therapeutics" International Conference; Abstract #B70; 2007.
Sasaki et al.; "Bisphosphonate risedronate reduces metastatic human breast cancer burden in bone in nude mice;" Cancer Res.; 55; 1995; pp. 3551-3557.
Sauter et al.; Pharmacokinetics, immunogenicity and safety of bivatuzumab mertansine, a novel CD44v6-targeting immunoconjugate, in patients with squamous cell carcinoma of the head and neck; Int J Oncol.; 30(4); Apr. 2007; pp. 927-935.
Schneider et al.; "Two subsets of peripheral blood plasma cells defined by differential expression of CD45 antigen;" Br J Haematol; 97; 1997; pp. 56-64.
Schuurman, et al.; "Normal human immunoglobulin G4 is bispecific: it has two different antigen-combining sites;" Immunology; 97; 1999; pp. 693-698.
Sebestyen et al.; "Syndecan-1 (CD138) expression in human non-Hodgkin lymphomas. Br J Haematol;" 104(2); 1999; pp. 412-419.
Seftalioglu et al.; "Syndecan-1/CD138 expression in normal myeloid, acute lymphoblastic and myeloblastic leukemia cells;" Acta Histochem; 105; 2003; pp. 213-221.
Seftalioglu et al.; "Syndecan-1 (CD138) expression in acute myeloblastic leukemia cells—an immuno electron microscopic study;" Acta Oncol; 42; 2003; pp. 71-74.
Senter et al.; "Cures and regressions of established tumors with monoclonal antibody auristatin conjugates;" Abstract #2062, American Association for Cancer Res. (San Francisco, CA: American Association for Cancer Res.); vo. 43, Mar. 2002; p. 414.

Shah et al.; "Expression of syndecan-1 and expression of epidermal growth factor receptor are associated with survival in patients with nonsmall cell lung carcinoma;" Cancer 101(7); 2004 ; pp. 1632-1638.
Abdelkefi et al.; "Single autologous stem-cell transplantation followed by maintenance therapy with thalidomide is superior to double autologous transplantaion in multiple myeloma: results of a multicenter randomized clinical trial;" Blood; 111; 2008; pp. 1805-1810.
Akkina et al.; "Modeling human lymphoid precursor cell gene therapy in the SCID-hu mouse;" Blood; 84; 1994; pp. 1393-1398.
Armour et al.; "Recombinant human IgG molecules lacking Fcgamma receptor I binding and monocyte triggering activities;" Eur J Immunol; 29(8); 1999; pp. 2613-2624.
Anderson et al.; Multiple Myeloma: New Insights and Therapeutic Approaches; Hematology; 2000; pp. 147-165.
Anderson et al.; Multiple Myeloma; Hematology Am Soc Hematol Educ Program; 2002; pp. 214-240.
Anttonen et al.: "Syndecan-1 expression has prognostic significance in head and neck carcinoma;" Br J of Cancer 79 (3/4), 1999, pp. 558-564.
Anttonen et al.; "High syndecan-1 expression is associated with favourable outcome in squamous cell lung carcinoma treated with radical surgery;" Lung Cancer; 32(3); Jun. 2001; pp. 297-305.
Aref et al.: "Syndecan-1 in multiple myeloma: relationship to conventional prognostic factors;" Hematology; 8; 2003; pp. 221-228.
Barbareschi et al.; "High syndecan-1 expression in breast carcinoma is related to an aggressive phenotype and to poorer prognosis;" Cancer; 98(3); Aug. 1, 2003; pp. 474-483.
Bataille et al.; "The phenotype of normal, reactive and malignant plasma cells. Identification of "many and multiple myelomas" and of new targets for myeloma therapy;" Haematologica; 91(9); Sep. 2006; pp. 1234-1240.
Bayer-Garner et al.; "Syndecan-1 (CD138) immunoreactivity in bone marrow biopsies of multiple myeloma: shed syndecan-1 accumulates in fibrotic regions;" Mod Pathol.; 14(10); Oct. 2001; pp. 1052-1058.
Beeram et al.; "A phase I study of trastuzumab-DM1 (T-DM1), a first-in-class HER2 antibody-drug conjugate (ADC), in patients (pts) with advanced HER2+ breast cancer (BC);" ASCO Meeting; Abstracts; May 20, 2008; pp. 1028.
Berenson et al.; "New drugs in multiple myeloma;" Curr Opin Support Palliat Care; 2(3); Sep. 2008; pp. 204-210.
Bernfield et al.; "Biology of the syndecans: a family of transmembrane heparan sulfate proteoglycans;" Annu Rev Cell Biol; 8; 1992; pp. 365-393.
Beste et al.; "Small antibody-like proteins with prescribed ligand specificities derived from the lipocalin fold;" Proc. Natl. Acad. Sci. USA; 96; 1999; pp. 1898-1903.
Bhattacharyya et al.; "Maytansine binding to the vinblastine sites of tubulin;" FEBS Lett.; 75; 1977; pp. 159-162.
Bisping et al., "Targeting receptor kinases by a novel indolinone derivative in multiple myeloma: abrogation of stroma-derived interleukin-6 secretion and induction of apoptosis in cytogenetically defined subgroups;" Blood; 107(5); Mar. 1, 2006; pp. 2079-2089.
Bissery et al., "Experimental Antitumor Activity of Taxotere (RP 56976, NSC 628503), a Taxol Analogue", Cancer Research 51, 1991, pp. 4845-4852.
Bladé et al.; "Advances in therapy of multiple myeloma;" Curr Opin Oncol; 20(6); Nov. 2008; pp. 697-704.
Blum et al.; "Maytansine: A Phase I study of an ansa macrolide with antitumor activity;" Cancer Treat Rep; 62; 1978; pp. 435-438.
Brand et al.; "Management of high risk metastatic prostate cancer: the case for novel therapies;" J Urol Dec; 176 (6Pt 2); 2006; pp. S76-S80.
Blättler et al.; "Drugs to Enhance the Therapeutic Potency of Anticancer Antibodies: Antibody-Drug Conjugates as Tumor-Activated Prodrugs;" Ojima, I., Vite, G.D. and Altmann, K.-H., Editors; Anticancer Agents-Frontiers in Cancer Chemotherapy, American Chemical Society, Washington, DC, 2001; 2001; pp. 317-338.
Bross et al.; "Approval summary: gemtuzumab ozogamicin in relapsed acute myeloid leukemia;" Clin Cancer Res; 7; 2001; pp. 1490-1496.

(56) References Cited

OTHER PUBLICATIONS

Cabanillas et al., "Phase I study of maytansine using a 3 day schedule;" Cancer Treat Rep; 62; 1978; pp. 425-428.
Carbone et al.; "AIDS-related plasma-blastic lymphomas of the oral cavity and jaws: a diagnostic dilemma.Ann;" Otol. Rhinol. Laryngol; 108; 1999; pp. 95-99.
Carlsson et al., "Protein thiolation and reversible protein-protein conjugation. N-succinimidyl-3-(2-pyridyldithio) propionate, a new heterobifunctional reagent;" Biochem J; 173; 1978; pp. 723-737.
Carter P; "Improving the efficacy of antibody-based cancer therapies;" Nat Rev Cancer; 1; 2001; pp. 118-129.
Carter and Senter, "Antibody-Drug Conjugates", The Cancer Journal, vol. 14(3), 2008, pp. 154-169.
Chabner et al.; "Initial clinical trials of maytansine, an antitumor plant alkaloid;" Cancer Treat Rep; 62; 1978; pp. 429-433.
Chanan-Khan et al.; "Phase I Study of huN901-DM1 (BB-10901) in Patients with Relapsed and Relapsed/Refractory CD56-Positive Multiple Myeloma;" Blood; 108(11); Abstract #1174 (ASH Meeting); Nov. 16, 2007.
Chanan-Khan et al.; "Phase I Study of IMGN901 in Patients with Relapsed and Relapsed/Refractory CD56-Positive Multiple Myeloma;" Blood (ASH Annual Meeting Abstracts); 112; Nov. 2008; pp. 3689.
Chari et al.; "Immunoconjugates containing novel maytansinoids: promising anticancer drugs;" Cancer Res; 52; 1992; pp. 127-131.
Chari et al.; "Enhancement of the selectivity and antitumor efficacy of a CC-1065 analogue through immunoconjugate formation;" Cancer Res.; 55; 1995; pp. 4079-4084.
Charnaux et al.; "RANTES (CCL5) induces a CCR5-dependent accelerated shedding of syndecan-1 (CD138) and syndecan-4 from HeLa cells and forms complexes with the shed ectodomains of these proteoglycans as well as with those of CD44;" Glycobiology; 15(2); 2005; pp. 119-130.
Chen et al.; "Engraftment of human hematopoietic precursor cells with secondary transfer potential in SCID-hu mice;" Blood; 84; 1994; pp. 2497-2505.
Chilosi et al.; "CD138/syndecan-1: a useful immunohistochemical marker of normal and neoplastic plasma cells on routine trephine bone marrow biopsies;" Mod Pathol.; 12; 1999; pp. 1101-1106.
Choi et al.; "Syndecan-1, a key regulator of cell viability in endometrial cancer;" Int J Cancer 121(4); 2007; pp. 741-750.
Chou and Talalay; "Quantitative analysis of dose-effect relationships: the combined effects of multiple drugs on enzyme inhibitors;" Adv. Enzyme Regul. 22; 1984, pp. 27-55.
Clément et al.; "B-B2 and B-B4, two new mAb against secreting plasma cells;" Leucocyte Typing V; Oxford Press.; 1; 1995; pp. 714-715.
Conejo et al.; "Syndecan-1 expression is up-regulated in pancreatic but not in other gastrointestinal cancers;" Int J Cancer; 88(1); Oct. 1, 2000; pp. 12-20.
Couturier et al.; "Validation of 213Bi-alpha radioimmunotherapy for multiple myeloma;" Clinical Cancer Research 5(10 Suppl.); Oct. 1999; pp. 3165s-3170s.
Davies EJ et al.; "Distribution and Clinical Significance of Heparan Sulfate Proteoglycans;" Ovarian Cancer Clin Cancer Res; 10(15); 2004; pp. 5178-5186.
DeGeorge et al.; "Regulatory considerations for preclinical development of anticancer drugs;" Cancer Chemother Pharmacol; 41(3); 1998; p. 173-85.
Dmoszyńska A.; "Diagnosis and the current trends in multiple myeloma therapy;" Pol Arch Med Wewn; 118(10); Oct. 2008; pp. 563-566.
Dhodapkar et al.; "Syndecan-1 is a multifunctional regulator of myeloma pathobiology: control of tumor cell survival, growth, and bone cell differentiation;" Blood; 91; 1998; pp. 2679-2688.
Dimopoulos et al.; "The role of novel drugs in multiple myeloma;" Annals of Oncology19 (Supplement 7); 2008; pp. vii121-vii127.
Dore et al.; "Identification and location on syndecan-1 core protein of the epitopes of B-B2 and B-B4 monoclonal antibodies;" FEBS Lett; 26; 1998; pp. 67-70.

Dowell et al.; "Pharmacokinetics of gemtuzumab ozogamicin, an antibody-targeted chemotherapy agent for the treatment of patients with acute myeloid leukemia in first relapse;" J Clin Pharmacol; 41; 2001; pp. 1206-1214.
Durie et al.; "Myeloma management guidelines: a consensus report from the Scientific Advisors of the International Myeloma Foundation;" Hematol J, 4(6); 2003; pp. 379-398.
Durie et al.; "International uniform response criteria for multiple myeloma;" Leukemia; 20(12); Dec. 2006; pp. 2220.
Shields et al.; "High resolution mapping of the binding site on human IgG1 for Fc gamma RI, Fc gamma RII, Fc gamma RIII, and FcRn and design of IgG1 variants with improved binding to the Fc gamma R.;" J Biol Chem; 276(9); 2001; pp. 6591-6604.
Sievers et al.; "Efficacy and safety of gemtuzumab ozogamicin in patients with CD33-positive acute myeloid leukemia in first relapse;" J. Clin. Oncol.; 19; 2001; pp. 3244-3254.
Sievers et al.; "Mylotarg: antibody-targeted chemotherapy comes of age;" Curr. Opin. Oncol.; 13; 2001; pp. 522-527.
Smith R.; "Single chain antibody variable region fragments;" available at www.stanford.edu/~smithr/science/scfv.html (last updated on May 2001).
Strobeck M; "Multiple Myeloma therapies;" Nature Reviews Drug Discovery; 6(3); Mar. 2007; pp. 181-182.
Studnicka et al.; "Human-engineered monoclonal antibodies retain full specific binding activity by preserving non-CDR complementarity-modulating residues;" Protein Eng.; 7(6); 1994 pp. 805-814.
Tai et al; "Immunomodulatory drug lenalidomide (CC-5013, IMiD3) augments anti-CD40 SGN-40-induced cytotoxicity in human multiple myeloma: clinical implications;" Cancer Res. Dec. 15, 2005; 65(24):11712-20.
Takimoto et al.; "Principles of oncologic pharmacotherapy;" Cancer Management: A multidisciplinary Approach; 11th Edition; Chapter 3; 2008; Apr. 15, 2009; available at http://www.cancernetwork.com/display/article/10165/1402628.
Tassone et al.; "Cytotoxic activity of the maytansinoid immunoconjugate B-B4-DM1 against CD138+ multiple myeloma cells;" Blood; 104(12); 2004; pp. 3688-3696.
Terpos et al.; "The use of bisphosphonates in multiple myeloma: recommendations of an expert panel on behalf of the European Myeloma Network;" Ann Oncol. 20(8); 2009; pp. 1303-1317.
Tijink et al.; "A phase I dose escalation study with anti-CD44v6 bivatuzumab mertansine in patients with incurable squamous cell carcinoma of the head and neck or esophagus;" Clin Cancer Res; 12(20 Pt 1); Oct. 15, 2006; pp. 6064-6072.
Tolcher et al.; "A Phase I study of huC242-DM4 to assess the safety and pharmacokinetics of huC242-DM4 administered as a single intravenous infusion once every three weeks to subjects with solid tumors;" European Journal of Cancer Supplements;4(12); 2006 p. 66.
Tolcher et al.; "Cantuzumab mertansine, a maytansinoid immunoconjugate directed to the CanAg antigen: a phase I, pharmacokinetic, and biologic correlative study;" J Clin Oncol; 21; 2003; pp. 211-222.
Tomayko et al., "Determination of subcutaneous tumor size in athymic (nude) mice;" Cancer Chemother. Pharmacol, 24; 1989; pp. 148.
Toyoshima et al.; "Expression of syndecan-1 is common in human lung cancers independent of expression of epidermal growth factor receptor;" Lung Cancer 31(2-3); 2001; pp. 193-202.
Urashima et al; "The development of a model for the homing of multiple myeloma cells to human bone marrow;" Blood; 90; 1997; pp. 754-765.
Vogel, CW; "Preparation of immunoconjugates using antibody oligosaccharide moieties;" Methods in Molecular Biology: Bioconjugation protocols strategies and methods; 283; 2007 pp. 87-108.
Vooijs et al; "Efficacy and toxicity of plasma-cell-reactive monoclonal antibodies B-B2 and B-B4 and their immunotoxins;" Cancer Immunol Immunother; 42; 1996; pp. 319-328.
Wang et al.; "Targeted proteasome inhibition by Velcade induces apoptosis in human mesothelioma and breast cancer cell lines;" Cancer Chemother Pharmacol; 66(3) Aug. 2010; pp. 455-466.

(56) References Cited

OTHER PUBLICATIONS

Ward et al.; "Binding activities of a repertoire of single immunoglobin variable domains secreted from *Escherichia coli*;" Nature; 341; 1989; pp. 544-546.

Wargalla et al.; "Rate of internalization of an immunotoxin correlates with cytotoxic activity against human tumor cells;" Proc. Natl. Acad. Sci. USA; 86; 1989; pp. 5146-5150.

Weber et al.; "Lenalidomide plus high-dose dexamethasone provides improved overall survival compared to high-dose dexamethasone alone for relapsed or refractory multiple myeloma (MM): results of 2 Phase III studies (MM-009, MM-010) and subgroup analysis of patients with impaired renal function;" Blood; 108; (ASH Annual Meeting Abstracts); Abstract 3547; 2006.

Wijdenes et al.; "A plasmocyte selective mAb (B-B4) recognizes syndecan-1;" Br J Haematol; 94(2) Aug. 1996; pp. 318-323.

Wijdenes et al.; "CD138;" J Biol Regul Homeost Agents; 16(2) Apr.-Jun. 2002; pp. 152-155.

Witzig et al; "Detection of myeloma cells in the peripheral blood by flow cytometry;" Cytometry; 26; 1996; pp. 113-120.

Xie et al.; "Pharmacokinetics and biodistribution of the antitumor immunoconjugate, cantuzumab mertansine (huC242-DM1), and its two components in mice;" J Pharmacol Exp Ther.; 308(3); Mar. 2004; pp. 1073-1082.

Yang et al.; "Genetically fluorescent melanoma bone and organ metastasis models;" Clin Cancer Res; 5; 1999; pp. 3549-3559.

Yang et al.; "Whole-body optical imaging of green fluorescent protein-expressing tumors and metastases;" Proc Natl Acad Sci U S A; 97; 2000; pp. 1206-1211.

Yang et al.; "The syndecan-1 heparan sulfate proteoglycan is a viable target for myeloma therapy;" Blood; 110(6); Sep. 15, 2007 pp. 2041-2048.

Yasui et al.; "Recent advances in the treatment of Multiple Myeloma;" Curr Pharm Biotechnol; 7(5); Oct. 2006; pp. 381-393.

Yoshitake et al.; "Conjugation of glucose oxidase from Aspergillus niger and rabbit antibodies using N-hydroxysuccinimide ester of N-(4-carboxycyclohexylmethyl)-maleimide;" Eur J Biochem; 101; 1979; pp. 395-399.

Yu et al.; "Antitumor synergy of CV787, a prostate cancer-specific adenovirus, and paclitaxel and docetaxel;" Cancer Research; 61; Jan. 15, 2001; pp. 517-525.

Zellweger et al.; "Tissue microarray analysis reveals prognostic significance of syndecan-1 expression in prostate cancer;" Prostate 55(1); 2003; pp. 20-29.

Alyanakian et al.; "Pharmacokinetics of total immunoglobulin G and immunoglobulin G subclasses in patients undergoing replacement therapy for primary immunodeficiency syndromes;" Vox Sang; 84(3); Apr. 2003; pp. 188-192.

Rajkumar et al.; "Lenalidomide plus high-dose dexamethasone versus lenalidomide plus low-dose dexamethasone as initial therapy for newly diagnosed multiple myeloma: and open-label randomized controlled trail;" Lancet Oncol.; 11(1); Jan. 2010; pp. 29-37.

Inki et al.; "1994 Association between syndecan-1 expression and clinical outcome in squamous cell carcinoma of the head and neck;" Br J Cancer; 7092); Aug. 1994; pp. 319-323.

Chen et al.; "2004 Syndecan-1 expression in locally invasive and metastatic prostate cancer;" Urology; 63(2); Feb. 2004; pp. 402-407.

Takimoto et al., "Chapter 3: Principles of Oncologic Pharmacotherapy in Cancer Management: A Multidisciplinary Approach;" 11th Edition (2008), edited by: Pazdur et al.; available at http://www.cancernetwork.com/cancer-management-11.

Chou TC; "Theoretical basis, experimental design, and computerized simulation of synergism and antagonism in drug combination studies;" Pharmacol Rev; 58(3); Sep. 2006; pp. 621-681. Review.

* cited by examiner

FIG. 1
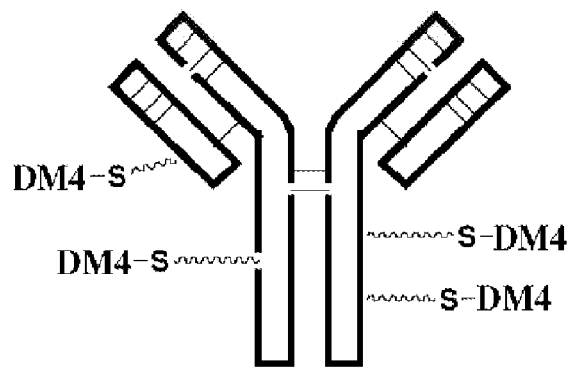
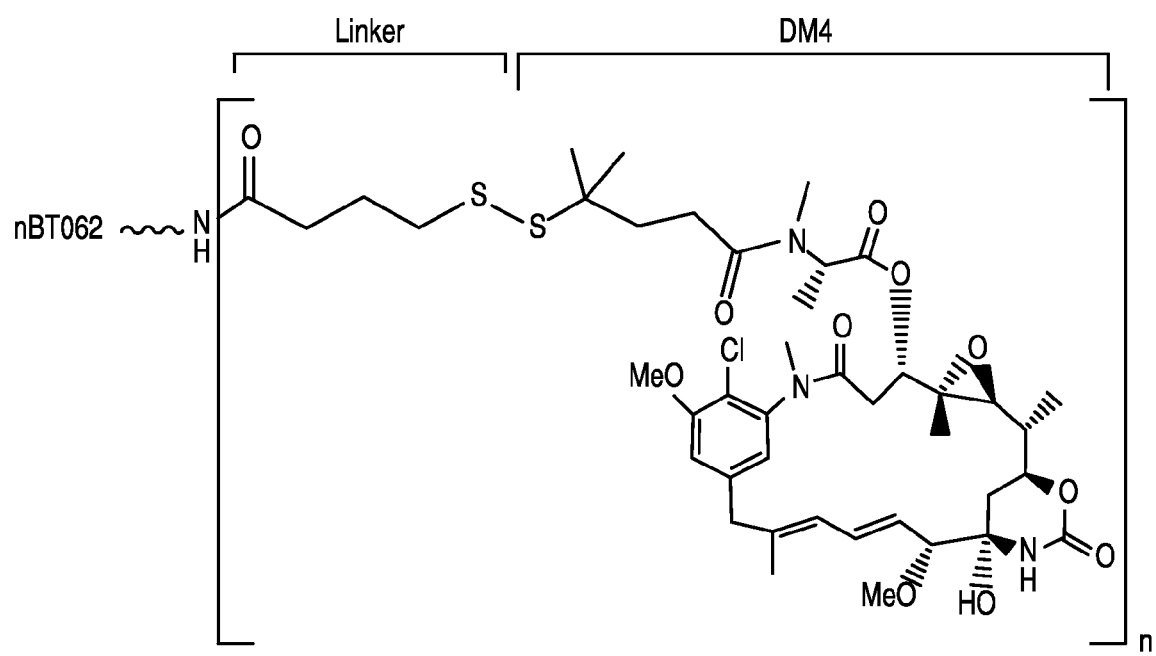
*n is approximately 3.5 drug linked per antibody molecule
FIG. 2

DCC: 1,3-dicyclohexylcarbodiimide
DTT: Dithiothreitol
DME: 1,2-Dimethoxyethane

USES OF IMMUNOCONJUGATES TARGETING CD138

This is the non-provisional U.S. application Ser. No.claiming the benefit under 35 U.S.C. 119(e) to U.S. provisional application 61/176,069, filed May 6, 2009 and U.S. provisional application 61/259,430, filed Nov. 9, 2009.

SEQUENCE LISTING

The instant application contains a Sequence Listing, which has been submitted via EFS-Web and is hereby incorporated by reference in its entirety. Said ASCII copy, created on Mar. 6, 2010 is named 3028-119-Sequence-Listing_ST25-new.txt and is 8,943 bytes in size.

FIELD OF THE INVENTION

The present invention relates to methods and treatment regimes, in particular for human subjects, which include the administration of immunconjugates that are designed to target cells that express CD138. The present invention is also directed at anticancer combinations, pharmaceutical compositions comprising the same, and uses thereof in the treatment of cancers that have target cells that express CD138. The present invention is in particular directed at anticancer combinations that show synergy or other unexpected additive effects in the treatment over treatment involving less than all of the components of the combination.

BACKGROUND

CD138, which acts as a receptor for the extracellular matrix, is overexpressed on multiple myeloma (MM) cells and has been shown to influence MM cell development and/or proliferation. CD138 is also expressed on cells of ovarian carcinoma, cervical cancer (Numa et al., 2002), endometrial cancer (Choi et al., 2007), kidney carcinoma, gall bladder, transitional cell bladder carcinoma, gastric cancer (Wiksten et al. 2008), prostate adenocarcinoma (Zellweger et al., 2003), mammary carcinoma (Loussouarn et al., 2008) non small cell lung carcinoma (Shah et al., 2004), squamous cell lung carcinoma (Toyoshima et al., 2001), colon carcinoma cells and cells of Hodgkin's and non-Hodgkin's lymphomas, colorectal carcinoma (Hashimoto et al, 2008), hepato-carcinoma (Li et al., 2005), chronic lymphocytic leukemia (CLL), pancreatic (Conejo et al., 2000), and head and neck carcinoma (Anttonen et al., 1999) to name just a few.

The publications and other materials, including patents, used herein to illustrate the invention and, in particular, to provide additional details respecting the practice are incorporated by reference. For convenience, the publications are referenced in the following text by author and date and/or are listed alphabetically by author in the appended bibliography.

Tassone et al. (2004) reported excellent binding of the murine IgG1 antibody B-B4 to the CD138 antigen expressed on the surface of MM cells. Tassone also reported high cytotoxic activity of the immunoconjugate B-B4-DM1, which comprises the maytansinoid DM1 as an effector molecule, against multiple myeloma cells (see also US Patent Publ. 20070183971).

Ikeda et al. (2008 and 2009) reported promising in vitro results and results on xenograft models with the immunoconjugate BT062, which is based on B-B4.

While Tassone et al. and Ikeda et al. represent contributions to providing an effective treatment of MM and a composition of matter that may be employed in such a treatment, there remain a number of needs in the art.

There remains in particular a need to provide suitable treatment regimes for diseases associated with CD138 expression, including plasmaproliferative disorders associated with CD138 expression, such as MM. There more in particular remains a need for treatment regimes that ensure that toxicities towards non tumor cells, which also express CD138 are kept to a clinically acceptable level, either by employing only certain tolerable amounts of immunoconjugate and/or by combining the immunoconjugate with cytotoxic agents know to be effective against the disorder in question. There is also a need for treatment regimes that reduce the need for medications that are used to alleviate other symptoms of the disease.

This invention fulfills, in certain embodiments, one or more of these needs as well as other needs in the art which will become more apparent to the skilled artisan once given the following disclosure.

SUMMARY OF THE INVENTION

The invention fulfills one or more of the above described needs by the herein described methods for treating a disease associated with target cells expressing CD138.

The invention is, in one embodiment, directed to a method for treating a disease associated with target cells expressing CD138, comprising:
  administering to a subject, in particular a human subject, in need thereof a effective, which is preferably a tolerable amount, of an immunoconjugate comprising
    at least one targeting agent, e.g., an engineered targeting antibody targeting CD138 expressing cells, and
    at least one effector molecule, wherein said targeting agent is functionally attached to said effector molecule to form said immunoconjugate.
    Preferably at least a part of the engineered targeting antibody confers preferably IgG4 isotype properties or, alternatively any other immunoconjugate described herein.

An immunoconjugate for treating a disease associated with target cells expressing CD138,
wherein the immunoconjugate comprises:
(i) at least one targeting agent targeting CD138 expressing cells, and
(ii) at least one effector molecule,
wherein the targeting agent is functionally attached to the effector molecule to form the immunoconjugate, wherein the immunoconjugate is to be administered in an effective amount, and wherein the effective amount is a tolerable amount.

Use of an immunoconjugate for the manufacture of a medicament for treating a disease associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate, wherein the immunoconjugate is to be administered in an effective amount, and wherein the effective amount is a tolerable amount.

The immunoconjugate is preferably administered to the subject in an amount from 5 mg/m$^2$ to 200 mg/m$^2$ or a pharmacokinetic equivalent thereof.

A combined preparation of an immunoconjugate and an agent for treating adverse side effects, for simultaneous, separate or sequential use in the treatment of a disease associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate, and wherein the immunoconjugate is to be administered in an amount which is a pharmacokinetic equivalent of 5 mg/m² to 200 mg/m² of the immunoconjugate when administered alone.

Use of an immunoconjugate and an agent for treating adverse side effects for the manufacture of a combined preparation for simultaneous, separate or sequential use in the treatment of a disease associated with target cells expressing CD138,
wherein the immunoconjugate comprises:
(i) at least one targeting agent targeting CD138 expressing cells, and
(ii) at least one effector molecule,
wherein the targeting agent is functionally attached to the effector molecule to form the immunoconjugate, and wherein the immunoconjugate is to be administered in an amount which is a pharmacokinetic equivalent of 5 mg/m² to 200 mg/m² of the immunoconjugate when administered alone.

In particular, the immunoconjugate may be administered to the subject in an amount from 5 mg/m² or 10 mg/m² to less than 160 mg/m², preferably to 150 mg/m², 140 mg/m², 130 mg/m² or 120 mg/m².

The maximum concentration of the immunoconjugate in the subject's plasma between 0 to 2 hours after an end of a first administration may be less than 50%, preferably less than 40%, more preferably less than 30%, even more preferably less than 20%, or even less than 10% of a theoretical maximum concentration for said immunoconjugate.

The immunoconjugate may be administered at least four times and a maximum concentration of the immunoconjugate in the subject's plasma between 0 to 2 hours after an end of each of said administrations may be less than 55%, preferably less than 50%, more preferably less than 40%, even more preferably less than 30%, less than 20% or even less than 10% of the theoretical maximum concentration for said immunoconjugate.

Said maximum concentration may be less than 3 µg/ml for 10 mg/m²; less than 8 µg/ml for 20 mg/m², less than 15 µg/ml for 40 mg/m², less than 25 µg/ml for 80 mg/m², less than 30 µg/ml for 120 mg/m².

The maximum concentration of the immunoconjugate after a fourth application in the subject's plasma between 0 to 2 hours after an end of a first administration is may be less than 55%, preferably less than 50%, more preferably less than 40%, even more preferably less than 30%, less than 20% or even less than 10% of the theoretical maximum concentration for said immunoconjugate.

Said maximum concentration may be less than 14 µg/ml for 20 mg/m², less than 15 µg/ml for 40 mg/m² or less than 25 µg/ml for 80 mg/m². The immunoconjugate may be administered intravenously. The immunoconjugate may be administered intravenously in a repeated single dose and the maximum concentration of the immunoconjugate in the subject's plasma between 0 to 2 hours after an end of any administration may be less than 55%, less than 50% or less than 40% of the theoretical maximum concentration for said immunoconjugate. Stable disease may be maintained for at least 4, 5, 6, 7, 8, 9, 10 treatment cycles (for at least 12, 15, 18, 21, 24, 27, 30 weeks). A status of at least stable disease may be maintained for 5, 6, 7, 8, 9 or 10 treatment cycles at 20 mg/m² and optionally, the maximum concentration of the immunoconjugate in the subject's plasma 0 to 2 hours after an end of any administration may be less than 55%, less than 50% or less than 40% of the theoretical maximum concentration for said immunoconjugate. In certain instances, a minor response may be observed after up to 8 treatment cycles.

The invention is also directed at a method for treating a disease associated with target cells expressing CD138 comprising administering to a subject, preferably a human subject, in need of such a treatment an effective amount of an immunoconjugate comprising:
at least one targeting agent targeting cell surface expressed CD138,
at least one effector molecule, wherein said targeting agent is functionally attached to said effector molecule to form said immunoconjugate, wherein said immunoconjugate is administered
in a dose, preferably a repeated single dose, of not more than about 10, 20, 30, 40, 80, 90, 100 or 120 mg/m²,
an average daily dose of about 400 µg/m² to about 6 mg/m², including about 500 µg/m², about 1 mg/m², about 2 mg/m², about 3 mg/m², about 4 mg/m², and/or
an average weekly dose of about 3 mg/m² to about 40 mg/m², including about 5 mg/m², about 10 mg/m², about 15 mg/m², about 20 mg/m², about 25 mg/m², about 30 mg/m² or about 35 mg/m².

The methods referred to herein may allow maintenance of stable disease for about 20, 30, 40, 50, 60, 70, 80, 90 100, 120, 140, 160, 180, 190, 200, 210 or more days and/or for about 1, 2, 3, 4, 5, 6, 7, 8, 9, 10, 11, 12 or more treatment cycles each of about three weeks.

The invention is also directed at a method for treating a disease associated with target cells expressing CD138 comprising administering to a subject, preferably a human subject, in need of such a treatment an effective amount of a immunoconjugate comprising:
at least one targeting agent targeting cell surface expressed CD138,
at least one effector molecule, wherein said targeting agent is functionally attached to said effector molecule to form said immunoconjugate,
wherein said CD138 is, in said subject, expressed on said target cells and on non-target cells, wherein said administration results in moderate or slow plasma clearance, and wherein said non-target cells, in particular epithelial cells, are substantially unaffected.

The effective amount administered may be less than 200 mg/m² or less than a pharmacokinetic equivalent of 200 mg/m² when administered in combination with an agent for treating adverse side effects and wherein said administering may result in a response in said subject, preferably after less than 30, 20, 15, 10, 9, 8, 7, 6, 5 hours.

Said effective amount may be more than 120 mg/m².

Said expression levels of said CD138 on target and non-target cells (e.g. cells of the epithelium) may be comparable.

Said effective amount may be administered as, e.g., a single dose or a single repeated dose or in multiple doses.

Said effective amount may be administered in multiple doses, wherein the cmax value after each administration is more than 55% of the theoretical cmax value.

The disease may be associated with bone pains and/or bone complications and said administration of said immunoconjugate or an anticancer combination according to the present invention may reduce said bone pains and/or bone complications, preferably to an acceptable level. The administration of medication to alleviate the bone pains and/or bone complications can be ceased or reduced from a base level commonly administered by 10%, 20%, 30%, 40%, 50%, 60%, 70%, 80% or 90%. The base level is the level generally recommended for the symptoms to be treated and can be ascertained instructions of use accompanying the medication or is known by the person skilled in art of administering pain medications.

For example, bisphosphonate, e.g., pamidronate, which is typically administered at 90 mg every four weeks or zoledroinic acid, which is typically administered at a dose of 4 mg once a month (Terpos et al., 2009) can be reduced by 10%, 20%, 30%, 40%, 50%, 60%, 70%, 80% or 90% (or at larger time intervals that correspond to this reduction) or could be eliminated.

Said administration may also result in FLC or M-protein levels of at least, stable disease, a minor response or a partial response in said subject, preferably after a first administration.

Said immunoconjugate may comprise an antigen binding region (ABR) against CD138, and a further antibody region, wherein at least part of said further antibody region may be of a human antibody and may confer said IgG4 isotype properties.

Said immunoconjugate may comprise nBT062 or a targeting antibody having at least 80%, 85%, 90%, 95%, 98%, 99% sequence indentity with nBT062 or may correspond to BT062.

The subject may be a human subject.

The method may consist essentially of administering a pharmaceutical composition comprising said immunoconjugate and a pharmaceutically acceptable carrier, wherein an active ingredient of said composition may consist essentially of said immunoconjugate.

Any of the methods described herein may result in stable disease, a response, in particular a minor response, a partial response, a very good partial response, a stringent complete response or a complete response durable for 1, 2, 3, 4, 5, 6, 7, 8, 9, 10, 11, 12 treatment cycles or more wherein said treatment cycles each comprise about 3 weeks with an administration of said immunoconjugate on day 1 of each said treatment cycle.

The invention is also directed to a method for treating a disease associated with target cells expressing CD138, comprising
(i) identifying said disease as being associated with target cells expressing CD138, such as multiple myeloma and as not responding, or responding poorly, to treatment with one or more cytotoxic agents, immunomodulators such as lenalidomide and/or proteasome inhibitors such as bortezomib, and
(ii) administering, preferably intravenously, to said subject an effective amount of an immunconjugate as specificed herein at a dose of less than 200 mg/m$^2$ when said immunoconjugate is administered alone or wherein said effective amount is the pharmacokinetic equivalent of 200 mg/m$^2$ when administered with an agent for treating side effects, including potential side effects,
wherein the subject does not respond, or responds poorly, to treatment with one or more cytotoxic agents, immunomodulators such as lenalidomide and/or proteasome inhibitors such as bortezomib, and wherein said disease is treated.

The invention is also directed at a method treating a disease associated with target cells expressing CD138, comprising administering to a subject in need of such a treatment and displaying high levels of sCD138, such as more than 50 ng/ml, more than 60 ng/ml, more than 70 ng/ml, more than 80 ng/ml, more than 100 ng/ml, more than 150 mg/ml, more than 200 mg/ml, more than 300, 400, 500, 600, 700, 800, 900, 1000, 1100, 1200, 1300, 1400, 1500 ng/ml, an effective amount of an immunoconjugate as specified herein, wherein an amount as low as 20 mg/m$^2$ or as low as 40 mg/m$^2$ is effective to result in a response such as a minor response. Said response may result from the selective binding of the immunoconjugate. Said subject may not respond, or responded poorly, to treatment with cytotoxic agents, immunomodulators such as lenalidomide and/or proteasome inhibitors such as bortezomib.

The engineered targeting antibody may comprise an antigen binding region (ABR) against CD138, and a further antibody region, wherein at least part of said further antibody region is of a human antibody and confers said IgG4 isotype properties.

The disease may be multiple myeloma, in particlar relapsed or refractory multiple myeloma.

Said disease expressing CD138 on target cells may be also selected from the group consisting of renal cell carcinoma, endometrial cancer, cervical cancer, prostate adenocarcinoma, pancreatic carcinoma, gastric cancer, bladder cancer, mammary carcinoma, hepato-carcinoma, colorectal carcinoma, colon carcinoma, squamous cell carcinoma, lung cancer in particular squamous cell lung carcinoma, non Hodgkin lymphoma, thymus, uterus, urinary or ovarian carcinoma.

In preferred embodiments, the immunoconjugate homogenously targets CD138 expressing target cells.

In certain embodiments, the engineered targeting antibody of the present invention may
(i) consist essentially of antigen binding region (ABR) against CD138 of a non-human antibody, or
(ii) comprise an antigen binding region (ABR) against CD138, wherein said antigen binding region is of a non-human antibody, and
a further antibody region, wherein at least part of said further antibody region is of a human antibody.

The ABR may comprise:
(a) heavy chain variable region CDR3 comprising amino acid residues 99 to 111 of SEQ ID NO: 1, and
(b) light chain variable region CDR3 comprising amino acid residues 89 to 97 of SEQ ID NO: 2, respectively.

The ABR may further comprise:
(a) heavy chain variable region CDR1 and CDR2 comprising amino acid residues 31 to 35 and 51 to 68 of SEQ ID NO: 1, and/or
(b) light chain variable region CDR1 and CDR 2 comprising amino acid residues 24 to 34 and 50 to 56 of SEQ ID NO: 2, respectively.

The further antibody region may comprise:
(a) amino acid residues 123 to 448 of SEQ ID NO: 1, and/or
(b) amino acid residues 108 to 214 of SEQ ID NO: 2, respectively and mutations thereof that
  (i) maintain or lower the antibody-dependent cytotoxicity and/or complement-dependent cytotoxicity of the engineered targeting antibody and/or
  (ii) stabilize the engineered targeting antibody.

The antibody may comprise a light chain having at least about 70%, more preferably 80%, 85% or 90%, sequence identity with SEQ ID No: 2 and a heavy chain having at least about 70%, more preferably 80%, 85% or 90%, sequence identity with SEQ ID No: 1, and comprising the antigen binding regions specified above.

The effector molecule may be attached to said engineered targeting antibody via a linker. The linker may comprise a disulfide bond. The effector molecule (e.g., DM4) may provide sterical hindrance between the targeting antibody and the effector molecule. The effector molecule may be at least one maytansinoid (e.g., DM1, DM3, or DM4) taxane or a CC1065, or an analog thereof.

The immunoconjugate may bind CD138 with a targeting variation of less than 150%, 140%, 130%, 120%, 110%, 100%, 90%, 80%, 70%, 60% or 50%.

The immunoconjugate may, in certain embodiments of the methods disclosed herein, comprise:
a targeting agent targeting CD138 comprising
an isolated polypeptide comprising an amino acid sequence of an immunoglobulin heavy chain or part thereof, wherein said immunoglobulin heavy chain or part thereof has at least 70% sequence identity with SEQ ID NO:1. A constant region of said immunoglobulin heavy chain or said part thereof may be an IgG4 isotype constant region.

The targeting agent of the immunoconjugate may comprise a light chain sequence having at least about 70% sequence identity with SEQ ID NO:2. The targeting agent of the immunoconjugate may also comprise a heavy chain sequence having at least about 70% sequence identity with SEQ ID NO:1.

The present invention is also directed at a pharmaceutical composition comprising any of the immunoconjugates specified herein for the inhibition, delay and/or prevention of the growth of tumors and/or spread of tumor cells, and one or more pharmaceutically acceptable excipients.

The pharmaceutical composton may include cytotoxic agents as specified herein.

The present invention is also directed at a kit comprising, in separate containers, said pharmaceutical composition in one or more dosage forms and, in a separate container, instructions how to administer the one or more dosage forms to a subject, in particular a human subject in need thereof, e.g., as repeated single dose or other treatment regime discussed herein.

In particular, in one aspect of the invention the administration of any of the immunoconjugates disclosed herein is to a subject or cells of such a subject, in particular a human subject, benefiting from such administration. The immunoconjugate can also be used for the manufacture of a medicament for the treatment of such a disorder.

An immunoconjugate for treating a disease in a subject associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate, wherein the subject does not respond, or responds poorly, to treatment with one or more cytotoxic agents including immunomodulators and/or proteasome inhibitors,
and wherein the immunoconjugate is to be administered to the subject, preferably intravenously, in an amount from 5 mg/m$^2$ to 200 mg/m$^2$.

Use of an immunoconjugate for the manufacture of a medicament for the treatment of a disease in a subject associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate, wherein the subject does not respond, or responds poorly, to treatment with one or more cytotoxic agents including immunomodulators and/or proteasome inhibitors, and wherein the immunoconjugate is to be administered to the subject, preferably intravenously, in an amount from 5 mg/m$^2$ to 200 mg/m$^2$.

A combined preparation of an immunoconjugate and an agent for treating adverse side effects, for simultaneous, separate or sequential use in treating a disease in a subject associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate, wherein the subject does not respond, or responds poorly, to treatment with one or more cytotoxic agents including immunomodulators and/or proteasome inhibitors,
and wherein the immunoconjugate is to be administered to the subject, preferably intravenously, in a pharmacokinetic equivalent of 5 mg/m$^2$ to 200 mg/m$^2$ of the immunoconjugate when administered alone.

Use of an immunoconjugate and an agent for treating adverse side effects for the manufacture of a combined preparation for simultaneous, separate or sequential use in treating a disease in a subject associated with target cells expressing CD138, wherein the immunoconjugate comprises:
(i) at least one targeting agent targeting CD138 expressing cells, and
(ii) at least one effector molecule, wherein the targeting agent is functionally attached to the effector molecule to form the immunoconjugate,
wherein the subject does not respond, or responds poorly, to treatment with one or more cytotoxic agents including immunomodulators and/or proteasome inhibitors, and wherein the immunoconjugate is to be administered to the subject, preferably intravenously, in a pharmacokinetic equivalent of 5 mg/m$^2$ to 200 mg/m$^2$ of the immunoconjugate when administered alone.

An immunoconjugate for treating a disease in a patient associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate,
wherein the patient displays levels of sCD138 in their plasma of more than 50 ng/ml,
and wherein the immunoconjugate is preferably to be administered in an amount effective to provide at least a minor response.

Use of an immunoconjugate for the manufacture of a medicament for the treatment of a disease associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate,
wherein the patient displays levels of sCD138 in their plasma of more than 50 ng/ml, and wherein the immunoconjugate is preferably to be administered in an amount effective to provide at least a minor response.

In a preferred embodiment the immunoconjugate is to be administered in an amount of at least 20 mg/m$^2$ and more preferably at least 40 mg/m$^2$.

In a preferred embodiment the levels of sCD138 which the patient displays in the plasma is more than 60 ng/ml, more than 70 ng/ml, more than 80 ng/ml, more than 100 ng/ml, more than 150 ng/ml, more than 200 ng/ml, or more than 300, 400, 500, 600, 700, 800, 900, 1000, 1100, 1200, 1300, 1400 or 1500 ng/ml.

The invention is also directed at an anticancer combination comprising
- at least one cytotoxic agent and at least one immunoconjugate comprising a targeting agent targeting CD138 expressing cells, and
- at least one effector molecule, wherein said targeting agent is functionally attached to said effector molecule to form said immunoconjugate, wherein
  (a) the combination has a synergy ratio of more than 1, more than 1.1, more than 1.2, more than 1.3, more than 1.4, or
  (b) the combination has a synergy ratio of about 1 and the effector molecule and the cytotoxic agent have interfering modes of action,
  and wherein said anticancer combination is a pharmaceutical composition or a kit comprising the at least one cytotoxic agent and the at least one immunoconjugate separate containers.

The cytotoxic agent may be a proteasome inhibitor, an immunomodulatory or an anti-angiogenic agent, a DNA alkylating agent or a mixture of two or more thereof.

The cytotoxic agent may be bortezomib, thalidomide, lenalidomide, melphalan or a mixture of two or more thereof.

The effector molecule and the cytotoxic agent of the anticancer combination may have interfering modes of action and wherein these modes of action involve preferably inhibition of microtubule or induction of cell cycle arrest (melphalan, bortezomib and lenalidomide or thalidomide are cytotoxic agents that induce cell cyle arrest). Alternatively, they may have non-interfering modes of action.

If the anticancer combination is part of a pharmaceutical composition, the pharmaceutical composition may comprise at least one pharmaceutically acceptable excipient.

The anticancer combination may also be part of a kit in which the at least one cytotoxic agent and the at least one immunoconjugate are stored separate containers.

The invention is also directed at a method for treating a disease associated with target cells expressing CD138, comprising:
- administering to a patient in need thereof an effective amount of the anticancer combination mentioned herein or an anticancer combination comprising at least one cytotoxic agent and at least one immunoconjugate comprising a targeting agent targeting CD138 expressing cells and at least one effector molecule, wherein said targeting agent is functionally attached to said effector molecule to form said immunoconjugate, and wherein the immunoconjugate overcomes a refractory phenotype of a patient against said cytotoxic agent.

The invention is also directed at a method for treating a disease associated with target cells expressing CD138, comprising:
- administering to a patient in need thereof an effective amount of an anticancer combination discussed herein and wherein the immunoconjugate overcomes a refractory phenotype.

The invention is also directed at a method for treating a non-plasmaproliferative disease associated with target cells expressing CD138, comprising:
- administering to a subject in need thereof or to cells of said non-plasmaproliferative disease an effective amount of an immunoconjugate comprising
  at least one targeting agent targeting CD138 expressing cells, and
  at least one effector molecule, wherein said targeting agent is functionally
  attached to said effector molecule to form said immunoconjugate,
  wherein said CD138 is, in said subject, expressed on said target cells and on non-target cells at comparable levels or wherein said CD138 is, in said subject, expressed on said target cells at levels below that of said non-target cells expressing CD138.

Said non-target cells expressing CD138 may be epithelium cells.

The invention is also directed at a method for treating a non-plasmaproliferative disease associated with target cells expressing CD138, comprising:
administering to a subject in need thereof or to cells of said non-plasmaproliferative disease an effective amount of an immunoconjugate comprising
  at least one targeting agent targeting CD138 expressing cells, and
  at least one effector molecule, wherein said targeting agent is functionally
  attached to said effector molecule to form said immunoconjugate,
wherein the target cells of said disease shed CD138 over a period of 24 hours, 2, 3, 4, 5, 6 days.

Said disease may be mammary carcinoma.

A combined preparation of at least one cytotoxic agent and at least one immunoconjugate, for
simultaneous, separate or sequential use in treating a disease in a subject associated with target cells expressing CD138, wherein the immunoconjugate comprises:
(i) a targeting agent targeting CD138 expressing cells, and
(ii) at least one effector molecule,
wherein the targeting agent is functionally attached to the at least one effector molecule to form the immunoconjugate,
and wherein the subject has a refractory phenotype.

Use of at least one cytotoxic agent and at least one immunoconjugate for the manufacture of a combined preparation for simultaneous, separate or sequential use in treating a disease in a subject associated with target cells expressing CD138, wherein the immunoconjugate comprises:
(i)i) a targeting agent targeting CD138 expressing cells and
(ii) at least one effector molecule
wherein the targeting agent is functionally attached to the at least one effector molecule to form the immunoconjugate,
and wherein the subject has a refractory phenotype.

In a preferred embodiment the combination of the at least one cytotoxic agent and the at least one immunoconjugate has a synergy ratio of more than 1, more than 1.1, more than 1.2, more than 1.3 or more than 1.4. Alternatively, the combination of the at least one cytotoxic agent and the at least one immunoconjugate has a synergy ratio of about 1 and the effector molecule and the cytotoxic agent have overlapping modes of action.

An immunoconjugate for treating a non-plasmaproliferative disease in a subject associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate,
and wherein in the subject CD138 is expressed on the target cells at levels comparable (equivalent) to or below the levels at which CD138 is expressed on non-target cells.

Use of an immunoconjugate for the manufacture of a medicament for treating a non-plasmaproliferative disease in a subject associated with target cells expressing CD138, wherein the immunoconjugate comprises:
(i) at least one targeting agent targeting CD138 expressing cells, and
(ii) at least one effector molecule,
wherein the targeting agent is functionally attached to the effector molecule to form the immunoconjugate, and wherein in the subject CD138 is expressed on the target cells at levels comparable (equivalent) to or below the levels at which CD138 is expressed on non-target cells.

The invention is also directed at a method for treating a non-plasmaproliferative disease associated with target cells expressing CD138, comprising:
administering to a subject in need thereof or to cells of said non-plasmaproliferative disease an effective amount of an immunoconjugate comprising
at least one targeting agent targeting CD138 expressing cells, and
at least one effector molecule, wherein said targeting agent is functionally
attached to said effector molecule to form said immunoconjugate, wherein immunoconjugate induces remission of a solid tumor.

This remission may be a remission followed by time interval which is free of re-growth of said tumor (complete remission). This time interval may be more than 1, 2, 3, 4, 5, 6, 7, 8, 9, 10 weeks, half a year or 1 year or more.

The solid tumor may be a pancreatic carcinoma or a mammary carcinoma.

The disease may renal cell carcinoma, endometrial cancer, cervical cancer, prostate adenocarcinoma, pancreatic carcinoma, gastric cancer, bladder cancer, mammary carcinoma, hepato-carcinoma, colorectal carcinoma, colon carcinoma, squamous cell carcinoma, lung cancer in particular squamous cell lung carcinoma, non Hodgkin lymphoma, thymus, uterus, urinary or ovarian carcinoma.

The solid tumor may be a mammary carcinoma, which is estrogen receptor negative and/or progesterone receptor negative.

BRIEF DESCRIPTION OF THE FIGURES

FIG. 1 provides a schematic representation of nBT062 having effector molecules attached.

FIG. 2 is a chemical representation of BT062.

DETAILED DESCRIPTION OF VARIOUS AND PREFERRED EMBODIMENTS OF THE INVENTION

The present invention relates to the administration to subjects, in particular human subjects (patients), in need thereof, of immunoconjugates comprising CD138 targeting agents described herein and the delivery of the effector molecule(s) of the immunoconjugates to target sites and the release of effector(s) molecule in or at the target site, in particular target cells, tissues and/or organs. More particularly, the present invention relates to immunoconjugates comprising such CD138 targeting agents and potent effector molecules that are attached to the targeting agents. The effector molecules may be activated by cleavage and/or dissociation from the targeting agent portion of the immunoconjugate in or at a target site. The immunoconjugates may be administered alone or as part of an anticancer combination that includes a cytotoxic agent such as, but not limited to, a proteasome inhibitor (e.g., bortezomib), immunomodulatory agent/anti-angiogenic agent (e.g., thalidomide or lenalidomide), DNA alkylating agent (e.g., melphalan) or corticosteroid (e.g., dexamethasone), wherein the anticancer combination has synergy effects or unexpected additive effects in the treatment of cancer over the immunoconjugate used alone in monotheraphy, the cytotoxic agent used alone in monotherapy or both.

The immunoconjugates according to the present invention may be administered to a subject in need of treatment or to cells isolated from such a subject in need of treatment. The effector molecule or molecules may be released from the immunoconjugate by cleavage/dissociation in or at a target cell, tissue and/or organ.

Figure 20:
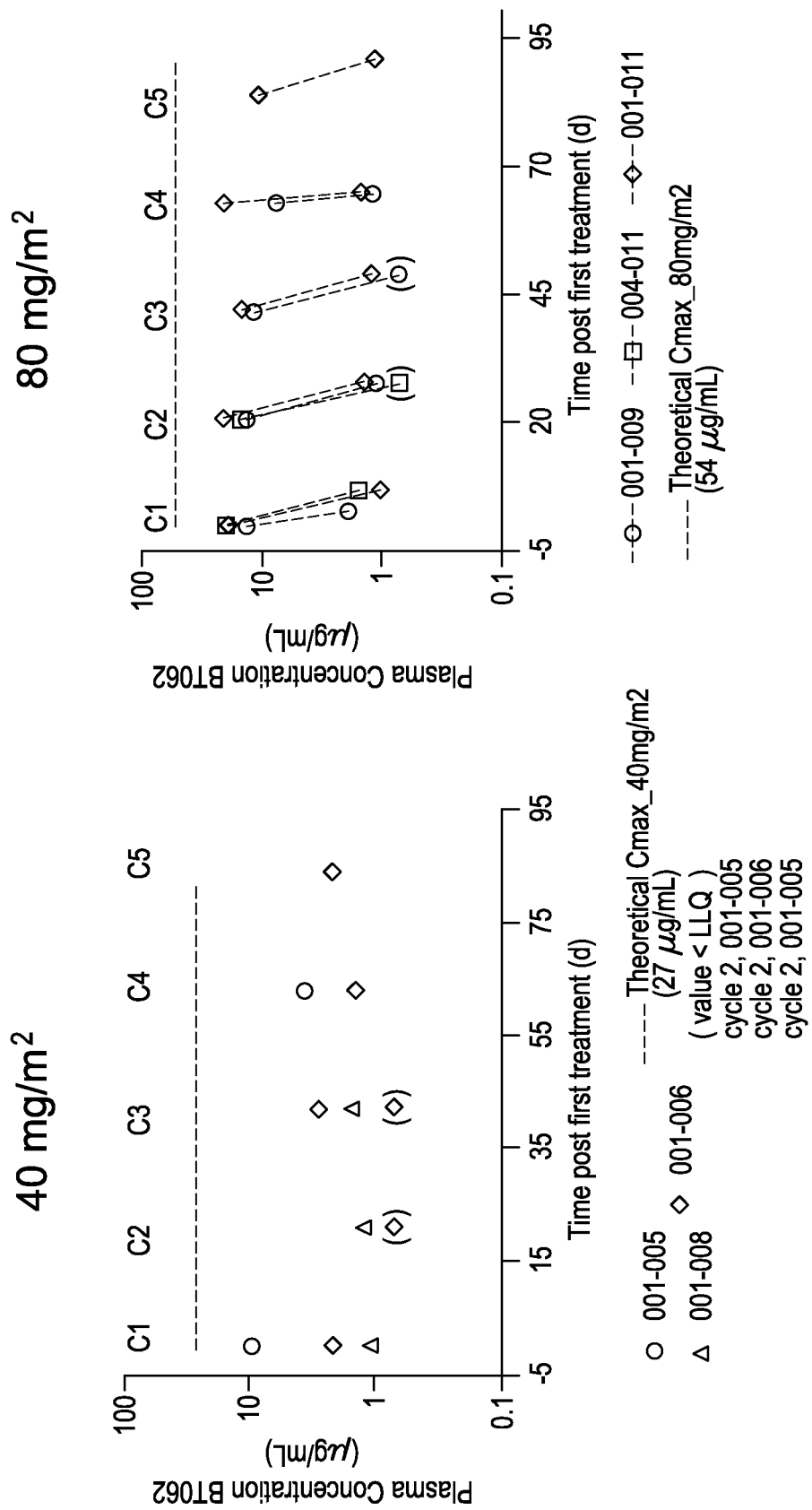
FIGS. 20 and 21 show that the Cmax values are generally similar over several treatment cycles.
Figure 21:
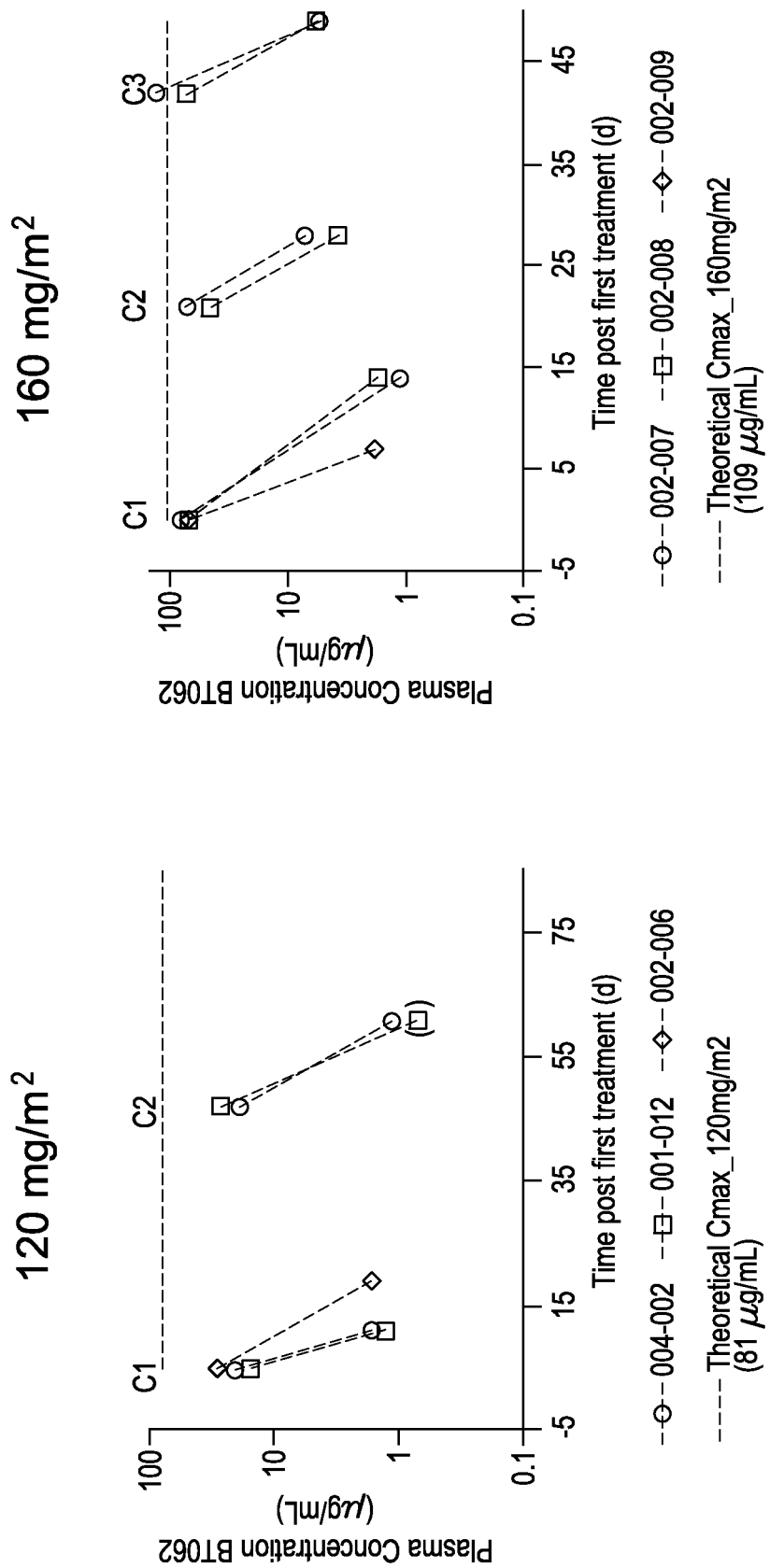

In one example, the immunoconjugate BT062, which targets CD138 expressing cells via the nBT062 antibody and comprises DM4 as an effector molecule, was administered to a patient with relapsed/refractory multiple myeloma four times in an amount of 80 mg/m$^2$ as repeated single doses, wherein the length of each treatment cycle was 21 days with the only dose/per cycle being administered on day one of the cycle. In this example, the immunoconjugate was administered intravenously to the patient so that it could better concentrate in and/or at tumor cells. Measurements of the plasma concentration of BT062 showed that in an initial measurement phase (up to 2 hours after the end of administration) cmax values for BT062 were significantly below the theoretically calculated value while no adverse side effects were observed, suggesting that BT062 concentrates at the tumor target rather than randomly attaching to target and non-target CD138. A "buffer effect" resulting from sCD138 could be excluded (see FIG. 20).

In another example, the immunoconjugate BT062 was administered to a patient with relapsed/refractory multiple myeloma ten times in an amount of 20 mg/m$^2$ each as repeated single doses, wherein the length of each treatment cycle was 21 days with the only dose/per cycle being administered on day one of the cycle. In this example, the immunoconjugate was administered intravenously to the patient so that it could better concentrate in and/or at tumor cells. No additional means were provided to release the effector molecule from the immunoconjugate. Ten treatment cycles were well tolerated and at least stable disease could be achieved for these treatment cycles.

In another example, the immunoconjugate BT062 was administered to a patient with relapsed multiple myeloma four times in an amount of 160 mg/m$^2$ as repeated single doses, wherein the length of each treatment cycle was 21 days with the only dose/per cycle being administered on day one of the cylce. In this example, the immunoconjugate was administered intravenously to the patient so that it could better concentrate in and/or at tumor cells. At this concentration plasma clearance was still below the theoretical cmax, but not to the degree observed with lower doses. However, a strong decrease of the serum FLC level could be observed after just a single treatment. A partial response could be observed after a $2^{nd}$, $3^{rd}$ and $4^{th}$ treatment.

In certain treatment regimes, the administration of medication that alleviate pain and/or bone complications could be discontinued since the patient's pain was diminished upon the administration of the immunoconjugate. As a result, side effects associated with these medications (including bisphosphonates and other osteoporosis medication), such as osteronecrosis of the jar, were avoided.

In yet another example, the immunoconjugate BT062 is co-administered to a patient with relapsed multiple myeloma four times in an amount of 120 mg/m$^2$ with a 10 mg daily oral dose of the Immunomudulatory agent lenalidomide as repeated single doses, wherein the length of each treatment cycle is 21 days with the only dose/per cycle being administered on day one of the cycle. In this example, the immunoconjugate is administered intravenously to the patient so that it can better concentrate in and/or at tumor cells.

In another example, the immunoconjugate BT062 is administered to a patient suffering from a pancreatic tumor as repeated single doses, wherein the length of each treatment cycle is 21 days with the only dose/per cycle being administered on day one of the cycle. In this example, the immunoconjugate is administered intravenously to the patient so that it could better concentrate in and/or at tumor cells.

CD138 or syndecan-1 (also described as SYND1; SYNDECAN; SDC; SCD1; CD138 ANTIGEN, SwissProt accession number: P18827 human) is a membrane glycoprotein that was originally described to be present on cells of epithelial origin, and subsequently found on hematopoietic cells (Sanderson, 1989). CD138 has a long extracellular domain that binds to soluble molecules (e.g., the growth factors EGF, FGF, HGF) and to insoluble molecules (e.g., to the extracellular matrix components collagen and fibronectin) through heparan sulfate chains (Langford, 1998; Yang, 2007) and acts as a receptor for the extracellular matrix. CD138 also mediates cell to cell adhesion through heparin-binding molecules expressed by adherent cells. It has been shown that CD138 has a role as a co-receptor for growth factors of myeloma cells (Bisping, 2006). Studies of plasma cell differentiation showed that CD138 must also be considered as a differentiation antigen (Bataille, 2006).

In malignant hematopoiesis, CD138 is highly expressed on the majority of MM cells, ovarian carcinoma, kidney carcinoma, gall bladder carcinoma, breast carcinoma, prostate cancer, lung cancer, colon carcinoma cells and cells of Hodgkin's and non-Hodgkin's lymphomas, chronic lymphocytic leukemia (CLL) (Horvathova, 1995), acute lymphoblastic leukemia (ALL), acute myeloblastic leukemia (AML) (Seftalioglu, 2003 (a); Seftalioglu, 2003 (b)), solid tissue sarcomas, colon carcinomas as well as other hematologic malignancies and solid tumors that express CD138 (Carbone et al., 1999; Sebestyen et al., 1999; Han et al., 2004; Charnaux et al., 2004; O'Connell et al., 2004; Orosz and Kopper, 2001). Expression of CD138 is also associated with different types of gastrointestinal malignancies (Conejo et al., 2000). As shown in Table 1, a number of tumorigenic cell lines exist associated with CD138 expression/overexpression.

TABLE 1

CD138 expression on different cell lines.

| cell line | Origin | Sensitivity $IC_{50}$ (nM) | CD138 Expression RFI* | receptors/cell |
|---|---|---|---|---|
| NCI-H929 | MM | 0.38 | 502 | 788,752 |
| PC-3 | prostate cancer | 0.79 | 541 | 195,671 |
| U266 | MM | 1.59 | 617 | 782,987 |
| MOLP-2 | MM | 1.78 | 425 | 161,064 |
| SK-BR-3 | breast carcinoma | 2.72 | 485 | 444,350 |
| LNCaP | postate cancer | 7.39 | 179 | 23,388 |
| CAPAN-2 | pancreas carcinoma | 15.51 | 328 | n.d. |
| PANC-1 | pancreas carcinoma | 36.38 | 34 | 18,085 |
| T47D | breast carcinoma | 89.28 | 217 | 42,264 |
| Jurkat | T cell lymphoma | 39.00 | n.d. | 0 |

In the context of MM it was shown that the sensitivity towards BT062 correlates with a higher expression of CD138 (RFI = relative fluorescence index).

The observed sensitivity of, e.g., the breast carcinoma cell lines and pancreas carcinoma cell lines was substantially lower than that of that of the MM cell lines. Nonetheless, as described in the experimental section in xenograft mouse models using cells from patients with breast cancer and pancreatic cancer, not only comparable, but significantly better results than in comparable xenogaft models for MM were obtained. In both instances complete remission could eventually be obtained, while comparable MM models showed marked delay in tumor growth, but not complete remission.

While in pancreatic cancer there appears to be no difference in syndecan-1 mRNA expression between early and advanced tumors, in mammary carcinoma, it was reported that CD138 can be lost over time as reflected by weak or lacking IHC staining. CD138 loss of expression had been reported and was often correlated with a shift of expression, i.e., de novo expression on surrounding stroma (Loussouarn, 2008). As a result, fewer targets for CD138 targeting agents can be expected over time.

Other cancers that have been shown to be positive for CD138 expression are many ovarian adenocarcinomas, transitional cell bladder carcinomas, kidney clear cell carcinomas, squamous cell lung carcinomas; and uterine cancers (see, for example, Davies et al., 2004; Barbareschi et al., 2003; Mennerich et al., 2004; Anttonen et al., 2001; Wijdenes, 2002).

The treatment of active (symptomatic) multiple myeloma and related plasmaproliferative disorders shall serve as an example of diseases that can be treated via immunoconjugates of the present invention.

Plasmaproliferative disorders as used herein means plasma cell and/or hematologic disorders such as MGUS, SMM, Active (symptomatic) MM, Waldenstrom's Macroglobulinemia, solitary plasmacytoma, systemic AL amyloidosis and POEMS syndrome.

Multiple myeloma (MM) refers to a malignant proliferation of plasma cells that typically originates in bone marrow, involves chiefly the skeleton of a patient, and presents clinical features attributable to the particular sites of involvement and abnormalities in formation of plasma proteins. The condition is usually characterized by numerous diffuse foci or nodular accumulations of abnormal or malignant plasma cells in the marrow of various bones (especially the skull), causing palpable swellings of the bones, and occasionally in extraskeletal sites. Upon radiological exam, the bone lesions may have a characteristic "punched out" appearance. The cells involved in the myeloma typically produce abnormal proteins and/or abnormal protein levels in the serum and urine. The disease typically develops from monoclonal gammopathy of undetermined significance (MGUS) to smoldering multiple myeloma (SMM) to active multiple myeloma (MM). Symptoms of these conditions vary, but may include hypercalcemia, renal insufficiency, fatigue, anemia, bone pain, spontaneous fractures, increased frequency or duration of infection, or abnormal urine color or odor. When the present invention refers to Multiple Myeloma it refers to (MGUS), smoldering multiple myeloma (SMM) and active multiple myeloma (MM) as well as other malignant proliferation of plasma cells that may eventually develop into active MM.

MGUS, a clinically benign precursor condition of MM is more common than MM, occurring in 1% of the population over age 50 and 3% of those over age 70 (Greipp and Lust, 1995). It is important to distinguish patients with MGUS from those with MM, as MGUS patients may be safely observed without resort to therapy. However, during long-term follow-up, of 241 patients with MGUS, 59 patients (24.5%) went on to develop MM or a related disorder (See Kyle et al., 1993).

The term gammopathy refers to a primary disturbance in immunoglobulin synthesis of a patient.

Monoclonal gammopathy refers to any of a group of disorders that are typically associated with the proliferation of a single clone of lymphoid or plasma cells (normally visible on serum protein electrophoresis (SPEP) as a single peak) and characterized by the presence of monoclonal immunoglobulin in the serum or urine of a patient.

Smoldering MM (SMM) has been reported to precede the onset of symptomatic multiple myeloma in the elderly. Smoldering multiple myeloma is often considered as an advanced phase of MGUS; even at the time of progression, smoldering multiple myeloma-evolved multiple myeloma usually lacks osteolytic lesions or other cardinal features of symptomatic multiple myeloma.

Clinical symptoms of MM include anemia, hypercalcemia, renal insufficiency, and lytic bone lesions. Distinctions in the course and the severity of the disease as it develops from monoclonal gammopathy of undetermined significance (MGUS) to smoldering multiple myeloma (SMM) to multiple myeloma (MM) are provided in Table 2 below. The table also summarizes methods of detection, diagnosis, and monitoring of these conditions. Such symptoms and techniques are familiar to those of skill in the art.

TABLE 2

Comparison of Clinical Features of MM, SMM, or MGUS

| Characteristic | MM | SMM | MGUS |
|---|---|---|---|
| Marrow plasma Cells | >=10% | >=10% | <10% |
| Serum M-protein | >=3 g/dL | >=3 g/dL | <3 g/dL |
| Bence-Jones protein in urine | >=1 g/24 h Yes | <1 g/24 h Yes | <1 g/24 h Yes |
| Anemia | usually present | Maybe | Absent |
| Hypercalcemia, renal insufficiency | may be present | absent | Absent |
| Lytic bone lesions | usually present | absent | Absent |

MM = multiple myeloma
SMM = smoldering multiple myeloma
MGUS = monoclonal gammopathy of undetermined significance
Classifying stages by severity and clinical features of multiple myeloma
Stages of disease progression
Stage I (active MM)
Relatively few cancer cells have spread throughout the body. The number of red blood cells and the amount of calcium in the blood are normal. No tumors (plasmacytomas) are found in the bone. The amount of M-protein in the blood or urine is very low. There may be no symptoms of disease.

TABLE 2-continued

Comparison of Clinical Features of MM, SMM, or MGUS

| Characteristic | MM | SMM | MGUS |
|---|---|---|---|

Stage II (active MM)
A moderate number of cancer cells have spread throughout the body
Stage III (active MM)
A relatively large number of cancer cells have spread throughout the body. There may be one or more of the following:
A decrease in the number of red blood cells, causing anemia.
The amount of calcium in the blood is very high, because the bones are being damaged.
More than three bone tumors (plasmacytomas) are found.
High levels of M-protein are found in the blood or urine.
Clinical features of MM
Hypercalcemia
Renal insufficiency
Anemia
Monoclonal protein:
SPEP (serum protein electrophoresis)
SPIEP (serum protein immunoelectrophoresis)
Urine protein immunoelectrophoresis (Bence - Jones protein)
Diagnosis of MM
>10% plasma cells in marrow or aggregates on biopsy or a plasmacytoma
Monoclonal protein:
Serum M-protein >3 g/dl or
M-protein in urine Active multiple myeloma (MM) is typically recognized clinically by the proliferation of malignant plasma cells in the bone marrow of a patient. These neoplastic plasma cells produce immunoglobulins and evolve from B-lymphocytes. The immunoglobulins that are produced by the plasma cells may be detected in the blood serum and/or urine of a patient by electrophoresis testing.

As indicated in Table 2, the measurement of serum M-protein is an important tool for assessing MM at different stages.

"M-protein" refers to a monoclonal protein that is typically visualized as a narrow band on electrophoretic gel, or an abnormal arc in immunoelectrophoresis. It represents a proliferation of homogenous immunoglobulin produced by clone cells originating from a single common cell, e.g., a monoclonal immunoglobulin characterized by a heavy chain of a single class and subclass, and light chain of a single type (also referred to as a M-spike and more broadly as a paraprotein).

"Serum protein electrophoresis" (SPE or SPEP) and "immunofixation electrophoresis" (IFE) can detect monoclonal immunoglobulin, which is produced in several plasma cell proliferative disorders including multiple myeloma (MM). Population-wide, up to 61% of these findings are not associated with clinical symptoms, allowing for a diagnosis of monogammopathy of undetermined significance (MGUS). SPE and IFE do not, however, detect all monoclonal immunoglobulins, particularly when only light chains are secreted.

Those "free light chain molecules" (FLCs) include λ and κ light chains. Plasma cells produce one of the five heavy chain types together with either κ or λ molecules. There is normally approximately 40% excess free light chain production over heavy chain synthesis. Plasma cells secrete free light chains (FLC, kappa or lambda) in addition to intact immunoglobulin molecules, and serum light chain levels are determined by the relative rates of synthesis (K>λ) and renal excretion (K>λ). In the presence of a monoclonal immunoglobulin, K:λ ratios may be either higher or lower than the normal range, depending on the class of the involved FLC. The serum half-life of FLCs is 2-6 hours, compared with 5 days for IgA, 6 days for IgM and 21 days for IgG. Thus, measurement of serum FLC levels allows a far more rapid evaluation of tumor response to therapy than measurement of intact immunoglobulin. Likewise, serum FLC measurements allow earlier detection of relapse.

Non-plasmaproliferative diseases also are associated with CD138 expression.

Pancreatic Carcinoma

The majority of cases comprise exocrine type. The majority of these exocrine cancers represent ductal adenocarcinoma (further more rare subtypes comprise cystic tumors, tumors of acinar cells and sarcoma). Endocrine cancer of the pancreas represents a hormone producing tumor.

Carcinoma in situ refers to the early stage of cancer, when it is confined to the layer of cells where it began. In breast cancer, in situ means that the cancer cells remain confined to ducts (ductal carcinoma in situ) or lobules (lobular carcinoma in situ). They have not grown into deeper tissues in the breast or spread to other organs in the body, and are sometimes referred to as non-invasive or pre-invasive breast cancers. Invasive (infiltrating) carcinoma.

The exocrine cells and endocrine cells of the pancreas form completely different types of tumors.

Exocrine Tumors

These are by far the most common type of pancreas cancer and most pancreatic exocrine tumors are malignant. About 95% of cancers of the exocrine pancreas are adenocarcinomas (an adenocarcinoma is a cancer that starts in gland cells). These cancers usually begin in the ducts of the pancreas, but they sometimes develop from the cells that make the pancreatic enzymes (acinar cell carcinomas).

Less common types of ductal cancers of the exocrine pancreas include adenosquamous carcinomas, squamous cell carcinomas, and giant cell carcinomas.

Endocrine Tumors

Tumors of the endocrine pancreas are uncommon. As a group, they are known as pancreatic neuroendocrine tumors (NETs), or sometimes as islet cell tumors. There are several subtypes of islet cell tumors. Each is named according to the type of hormone-making cell it starts in:

The main system used to describe the stages of cancers of the exocrine pancreas is the American Joint Committee on Cancer (AJCC) TNM system as provided by the American Cancer Society (ACS). The TNM system for staging contains 3 key pieces of information:

T describes the size of the primary tumor(s), measured in centimeters (cm), and whether the cancer has spread within the pancreas or to nearby organs. Distinctions are made between TX, T0, T1, T2, T3 and T4, wherein a higher number indicates advancement of the disease.

N describes the spread to nearby (regional) lymph nodes. N categories include, NX, N0 and N1.

M indicates whether the cancer has metastasized (spread) to other organs of the body. (The most common sites of pancreatic cancer spread are the liver, lungs, and the peritoneum—the space around the digestive organs.) M categories include: MX, M0 and M1.

After the T, N, and M categories have been determined, this information is combined to assign a stage, a process called stage grouping.

Stage 0 (Tis, N0, M0): The tumor is confined to the top layers of pancreatic duct cells and has not invaded deeper tissues. It has not spread outside of the pancreas. These tumors are sometimes referred to as pancreatic carcinoma in situ or pancreatic intraepithelial neoplasia III (PanIn III).

Stage IA (T1, N0, M0): The tumor is confined to the pancreas and is less than 2 cm in size. It has not spread to nearby lymph nodes or distant sites.

Stage IB (T2, N0, M0): The tumor is confined to the pancreas and is larger than 2 cm in size. It has not spread to nearby lymph nodes or distant sites.

Stage IIA (T3, N0, M0): The tumor is growing outside the pancreas but not into large blood vessels. It has not spread to nearby lymph nodes or distant sites.

Stage IIB (T1-3, N1, M0): The tumor is either confined to the pancreas or growing outside the pancreas but not into nearby large blood vessels or major nerves. It has spread to nearby lymph nodes but not distant sites.

Stage III (T4, Any N, M0): The tumor is growing outside the pancreas into nearby large blood vessels or major nerves. It may or may not have spread to nearby lymph nodes. It has not spread to distant sites.

Stage IV (Any T, Any N, M1): The cancer has spread to distant sites.

Although not formally part of the TNM system, other factors are also important in determining prognosis (outlook). The grade of the cancer (how abnormal the cells look under the microscope) is sometimes listed on a scale from G1 to G4, with G1 cancers looking the most like normal cells and having the best outlook.

For patients who have surgery, another important factor is the extent of the resection—whether or not all of the tumor is removed. This is sometimes listed on a scale from R0 (where all visible and microscopic tumor was removed) to R2 (where some visible tumor could not be removed).

From a practical standpoint, how far the cancer has spread often can't be determined accurately without surgery. That's why doctors often use a simpler staging system, which divides cancers into groups based on whether or not it is likely they can be removed surgically. These groups are called resectable, locally advanced (unresectable), and metastatic. These terms can be used to describe both exocrine and endocrine pancreatic cancers.

Resectable: If the cancer is only in the pancreas (or has spread just beyond it) and the surgeon can remove the entire tumor, it is called resectable.

Locally advanced (unresectable): If the cancer has not yet spread to distant organs but it still can't be completely removed with surgery, it is called locally advanced. Often the reason the cancer can't be removed is because too much of it is present in nearby blood vessels.

Metastatic: when the cancer has spread to distant organs, it is called metastatic. Surgery may still be done, but the goal would be to relieve symptoms, not to cure the cancer.

Pancreatic neuroendocrine cancers are not staged like cancers of the exocrine pancreas. Instead the statistics are broken down into different stages: localized (only in the pancreas), regional (spread to nearby lymph nodes or tissues), and distant (spread to distant sites, such as the liver).

Bladder tumors are grouped by the way the cancer cells look under a microscope.

Transitional cell carcinoma (also called urothelial carcinoma) is by far the most common type of bladder cancer. Within this group are also subtypes. They are named depending on the shape of the cells and whether they tend to spread and invade other organs. (If they are likely to grow deeper into the bladder wall they are called invasive, if not likely they are non-invasive.) These tumors are divided into grades based on how the cells look under the microscope. If the cells look more like normal cells, the cancer is called a low-grade cancer. When the cells look very abnormal, the cancer is high-grade. Lower-grade cancers tend to grow more slowly and have a better outcome than higher-grade cancers.

Also included in the definition, are squamous cell carcinoma (uncommon; usually invasive); adenocarcinoma (uncommon; almost all are invasive); small cell (rare). Other rare bladder cancers are also included in this definition.

Bladder cancer is also staged:

Stage 0a (Ta, N0, M0):
The cancer is a noninvasive papillary carcinoma. It has grown toward the hollow center of the bladder but has not grown into the muscle or connective tissue of the bladder wall. It has not spread to lymph nodes or distant sites.

Stage 0is (Tis, N0, M0):
The cancer is a flat, noninvasive carcinoma, also known as flat carcinoma in situ (CIS). The cancer is growing in the lining layer of the bladder only. It has neither grown inward toward the hollow part of the bladder nor has it invaded the muscle or connective tissue of the bladder wall. It has not spread to lymph nodes or distant sites.

Stage I (T1, N0, M0):
The cancer has grown into the layer of connective tissue under the lining layer of the bladder without growing into the thick layer of muscle in the bladder wall. The cancer has not spread to lymph nodes or to distant sites.

Stage II (T2, N0, M0):
The cancer has grown into the thick muscle layer of the bladder wall but, it has not passed completely through the muscle to reach the layer of fatty tissue that surrounds the bladder. The cancer has not spread to lymph nodes or to distant sites.

Stage III (T3 or T4a, N0, M0):
The cancer has grown completely through the bladder into the layer of fatty tissue that surrounds the bladder (T3). It may have spread into the prostate, uterus, or vagina (T4a). It is not growing into the pelvic or abdominal wall. The cancer has not spread to lymph nodes or to distant sites.

Stage IV (T4b, N0, M0) or (any T, N1 to 3, M0) or (any T, any N, M1):
The cancer has spread through the bladder wall to the pelvic or abdominal wall (T4b) and/or has spread to lymph nodes (N1-3) and/or to distant sites such as bones, liver, or lungs (M1).

Types of Gall Bladder Carcinoma

More than 9 out of 10 gallbladder cancers are adenocarcinomas. An adenocarcinoma is a cancer that starts in the cells with gland-like properties that line many internal and external surfaces of the body (including the inside the digestive system).

A type of gallbladder adenocarcinoma that deserves special mention is called papillary adenocarcinoma or just papillary cancer. These are gallbladder cancers whose cells are arranged in finger-like projections when viewed under a microscope. In general, papillary cancers are not as likely to grow into the liver or nearby lymph nodes. They tend to have a better prognosis (outlook) than most other kinds of gallbladder adenocarcinomas. About 6% of all gallbladder cancers are papillary adenocarcinomas. There are other types of cancer that can develop in the gallbladder, such as adenosquamous carcinomas, squamous cell carcinomas, and small cell carcinomas, but these are uncommon.

Following stages of gall bladder carcinomas are distinguished based on the TNM system of the AJCC:

Stage 0: Tis, N0, M0: There is a small cancer only in the epithelial layer of the gallbladder. It has not spread outside of the gallbladder.

Stage IA: T1(a or b), N0, M0: The tumor grows into the lamina propria (T1a) or the muscle layer (T1b). It has not spread outside of the gallbladder.

Stage IB: T2, N0, M0: The tumor grows into the perimuscular fibrous tissue. It has not spread outside of the gallbladder.

Stage IIA: T3, N0, M0: The tumor extends through the serosa layer and/or directly grows into the liver and/or one other nearby structure. It has not spread to lymph nodes or to tissues or organs far away from the gallbladder.
Stage IIB: T1 to T3, N1, M0: In addition to any growth in the gallbladder, the tumor has spread to nearby lymph nodes (N1). It has not spread to tissues or organs far away from the gallbladder.
Stage III: T4, any N, M0: Tumor invades the main blood vessels leading into the liver or has reached more than one nearby organ other than the liver. It may or may not have spread to lymph nodes. It has not spread to tissues or organs far away from the gallbladder.
Stage IV: Any T, any N, M1: The tumor has spread to tissues or organs far away from the gallbladder.

Mammary Carcinoma

An adenocarcinoma refers generally to a type of carcinoma that starts in glandular tissue (tissue that makes and secretes a substance). In the context of breast cancer, he ducts and lobules of the breast are glandular tissue, so cancers starting in these areas are often called adenocarcinomas. There are several types of breast cancer, although some of them are quite rare. In some cases a single breast tumor can have a combination of these types or have a mixture of invasive and in situ cancer.

Ductal carcinoma in situ (DCIS; also known as intraductal carcinoma) is the most common type of non-invasive breast cancer.

Invasive (or infiltrating) ductal carcinoma (IDC) is the most common type of breast cancer. Invasive (or infiltrating) ductal carcinoma (IDC) starts in a milk passage (duct) of the breast, breaks through the wall of the duct, and grows into the fatty tissue of the breast. At this point, it may be able to spread (metastasize) to other parts of the body through the lymphatic system and bloodstream. About 8 of 10 invasive breast cancers are infiltrating ductal carcinomas. IDC patients revealed expression of CD138 (Loussouarn et al., 2008).

Triple-negative breast cancer describe breast cancers (usually invasive ductal carcinomas) whose cells lack estrogen receptors and progesterone receptors, and do not have an excess of the HER2 protein on their surfaces. Triple-negative breast cancers tend to grow and spread more quickly than most other types of breast cancer. Because the tumor cells lack these certain receptors, neither hormone therapy nor drugs that target HER2 are effective against these cancers (although chemotherapy can still be useful if needed).

Some other breast cancers that fall under the term "mammary carcinoma" are Inflammatory breast cancer, medullary carcinoma, metaplastic carcinoma, mucinous carcinoma, tubular carcinoma, papillary carcinoma, adenoid cystic carcinoma (adenocystic carcinoma), phyllodes tumor.

Surgery, radiation or chemotherapy constitute standard cancer therapies. Hormone therapy is sometimes employed. Hormone therapy is a form of systemic therapy. It is most often used as an adjuvant therapy to help reduce the risk of cancer recurrence after surgery, although it can be used as neoadjuvant treatment, as well. It is also used to treat cancer that has come back after treatment or has spread. Estrogen promotes the growth of about 2 out of 3 of breast cancers—those containing estrogen receptors (ER-positive cancers) and/or progesterone receptors (PR-positive cancers). Because of this, several approaches to blocking the effect of estrogen or lowering estrogen levels are used to treat ER-positive and PR-positive breast cancers. However, homone therapy is ineffective for patients lacking ERs or PRs.

Mammary Carcinoma Also Follows Such a Staging System:
Stage 0: Atypical cells have not spread outside of the ducts or lobules, the milk producing organs, into the surrounding breast tissue. Referred to as carcinoma in situ, it is classified in two types: "Ductal Carcinoma In Situ" (DCIS), which is very early cancer that is highly treatable and survivable and "Lobular Carcinoma In Situ" (LCIS), which is not a cancer but an indicator that identifies a woman as having an increased risk of developing breast cancer.
Stage I: The cancer is no larger than two centimeters (approximately an inch) and has not spread to surrounding lymph nodes or outside the breast.
Stage II: This stage is divided into two categories according to the size of the tumor and whether or not it has spread to the lymph nodes:
Stage IIA Breast Cancer—the tumor is less than two centimeters and has spread up to three auxiliary underarm lymph nodes. Or, the tumor has grown bigger than two centimeters, but no larger than five centimeters and has not spread to surrounding lymph nodes.
Stage IIB Breast Cancer—the tumor has grown to between two and five centimeters and has spread to up to three auxiliary underarm lymph nodes. Or, the tumor is larger than five centimeters, but has not spread to the surrounding lymph nodes.
Stage III: This stage is also divided into two categories:
Stage III: A Breast Cancer—the tumor is larger than two centimeters but smaller than five centimeters and has spread to up to nine auxiliary underarm lymph nodes.
Stage III B Breast Cancer—the cancer has spread to tissues near the breast including the skin, chest wall, ribs, muscles, or lymph nodes in the chest wall or above the collarbone.
Stage IV: Here, the cancer has spread to other organs or tissues, such as the liver, lungs, brain, skeletal system, or lymph nodes near the collarbone.

Lung Cancer

There are 4 types of neuroendocrine lung tumors, namely, large cell neuroendocrine carcinoma, atypical carcinoid tumor, typical carcinoid tumor and small cell lung cancer. Carcinoid tumors are tumors that start from cells of the diffuse neuroendocrine system. Typical and atypical carcinoid tumors look different under the microscope. Typical carcinoids grow slowly and only rarely spread beyond the lungs and about 9 out of 10 lung carcinoids are typical carcinoids.

For treatment purposes two main types of lung cancer, which are very differently treated, are distinguished, namely, small cell lung cancer (SCLC) and non-small cell lung cancer (NSCLC). If the cancer has features of both types, it is called mixed small cell/large cell cancer.

About 10% to 15% of all lung cancers are the small cell type. Other names for SCLC are oat cell carcinoma and small cell undifferentiated carcinoma.

This cancer often starts in the bronchi near the center of the chest. Although the cancer cells are small, they can divide quickly, form large tumors, and spread to lymph nodes and other organs throughout the body. Surgery is rarely an option and never the only treatment given. Treatment includes cytotoxic agents, such as drugs to kill the widespread disease.

There are 3 sub-types of NSCLC, namely squamous cell carcinoma; adenocarcinoma; large-cell (undifferentiated) carcinoma.

Staging of Non-Small Cell Lung Cancer

The system used to stage non-small cell lung cancer is the AJCC (American Joint Committee on Cancer) system. Stages are described using Roman numerals from 0 to IV (0 to 4). Some stages are further divided into A and B. As a rule, the lower the number, the less the cancer has spread. A higher number, such as stage IV (4), means a more advanced cancer.

A respective staging system, including Stages I to IV, was also developed for squamous cell carcinoma (head and neck cancer). Stage I cancers are small, localized and usually curable, stage II and III cancers typically are locally advanced and/or have spread to local lymph nodes and Stage IV cancers usually are metastatic (have spread to distant parts of the body) and generally are considered inoperable.

Treatment in the context of the present invention includes preventing or slowing the progression, stabilizing the disease state, remitting the disease or ameliorating one or more symptoms of a disorder associated with cells expressing CD-138. Treatment thus includes preventing or slowing down the increase of severity or the remission of the disorder. In the case of MM generally only patients with stage II or III active MM receive primary therapy (stage I patients or patients with SMM are initially only observed in 3 to 6 month intervals), a treatment according to the present invention does not only include the treatment of, e.g., any active stage of MM, but also includes the treatment of forms of disease states that precede the traditionally treated disease state. Treatment in particular also includes preventing the progression from one disease state to the next: in the case of MM, this would, e.g., be the progression from MGUS to SMM or from SMM to active MM stage I or another stage of MM. In case of cancers of the exocrine pancreas, e.g, a progression from Stage I to Stage III, including any worsening as refelected by the categories established by the AJCC within the stages, e.g. from IA to IB. However, the term also includes maintaining the status quo, such as to maintain stable disease and, as discussed below, elicting certain responses in the patient treated. A patient is also successfully "treated" if the patient shows observable and/or measurable reduction in or absence of, inter alia, one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. In general, an effect of a certain treatment on the disease status of a patient can be monitored, in the case of MM, by measuring the M-protein levels in the patient's serum and/or urine and/or the FLC levels in the patient's serum and/or urine. In the case of other disorders associated with cells expressing CD-138, other parameters are measured to assess the effect of a treatment according to the present invention. CRP is an unspecific inflammation parameter for clinical cancer monitoring. To name just a few, for pancreatic cancer, relevant parameters that may be measured are CA 19-9 (carbohydrate antigen 19.9, a tumor marker often elevated in pancreatic cancer), bilirubin, or C-reactive protein. In addition imaging such as sonography, CT, MRT are used. In head and neck cancer, biomarkers which depend on the tumor type are used (e.g., SCC for squamous cell carcinoma, NSE for Merkel cell, CEA); in breast carcinoma, CA 15-3Her$_2$ expression and Cadherin expression may be used as markers, while the treatment monitired by serum markers such as neuron specific enolase (NSE).

The bladder tumor antigen (BTA) and the NMP22 tests can be used along with cystoscopy (using a thin, lighted tube to look in the bladder) in diagnosing the condition in symptomatic subjects. These tests are also being used to follow some patients after treatment, though cystoscopy and urine cytology (using a microscope to look for cancer cells in the urine) are still recommended as the standard tests for diagnosis and follow-up. BTA and NMP22 tests are often used between cystoscopies. Normal values may allow cystoscopy to be done less often. However, these test tests cannot replace urine cytology and cystoscopy.

For advanced bladder cancer, some of the markers used for other cancers such as CEA, CA 125, CA 19-9, and TPA may be elevated and can be used to follow patients during and after treatment. For lung cancer, no established marker exisits, CEA pr NSE might be elevated.

Tumor cells such as myeloma cells or mammary carcinoma cells are known to shed CD138. The loss of surface CD138 is correlated by poor prognosis in myeloma. High levels of soluble CD138 have been also detected in other oncologic oindications such as head and neck or lung cancer (Anttonen et al. 1999). The loss of surface Syndecan-1 is correlates with EMT (epithelial mesenchymal transition) this process describes the transformation of a malignant cell into a less or poorly differentiated cell associated with invasiveness and metastatic stage. This is e.g. reported for metastatic breast cancer (Loussouarn et al., 2008).

An effective amount of an agent, in particular, an immunoconjugate or a pharmaceutical composition comprising an immunoconjugate according to the present invention refers to an amount required to "treat" a disease or disorder in a subject, in particular a human subject (patient). In the case of cancer such as MM, the effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treatment".

"A pharmacokinetic equivalent" of, e.g., 200 mg/m$^2$ refers to the amount of immunoconjugate that results in equal pharmacokinetics observed at dosages of 200 mg/m$^2$ when the immunoconjugate is administered in combination, including co-adminstered with an agent for treating actual including potential adverse side effects primarily on non-target cells that also express CD138. Those equivalents might be somewhat less than 200 or somewhat more than 200, depending on the other agent. Included are, e.g., effective amounts of less than 160, less than 170, less than 180, less than 190 and less than 210, less than 220, less than 230 and less than 240 mg/m$^2$. For example, the person skilled in the art, would expect that co-administration with corticosteroids or with antibiotics would allow slightly higher doses of the immunoconjugate even in cases of side effects on skin, which, can, however, be readily ascertained by the person skilled in the art.

To evaluate the success of the administration of a drug, here an immunoconjugate (its ability to produce a functional response, i.e., its efficacy), different "responses" to an administration are distinguished.

In the context of MM and other plasmaproliferative diseases, responses are distinguished as follows:

the term complete response (CR) refers to the negative immunofixation of serum and urine and disappearance of any soft tissue plasmacytomas and <5% plasma cells in bone marrow;

the term stringent complete response (sCR) refers to CR as defined above, plus normal FLC ratio and absence of clonal cells in bone marrow by immunohistochemistry or immunofluorescence;

the term very good partial response (VGPR) refers to serum and urine M-component detectable by immunofixation, but not on electrophoresis or ≥90% or greater reduction in serum M-component plus urine M-component <100 mg per 24 h;

the term partial response (PR) refers to ≥50% reduction of serum M protein and reduction in 24-h urinary M protein by ≥90% or to <200 mg per 24 h, if the serum and urine M protein are unmeasurable, a ≥50% decrease in the difference between involved and uninvolved FLC levels is required in place of the M protein criteria, if serum and urine M protein are unmeasurable, and serum free light assay is also unmeasurable, ≥50% reduction in bone marrow plasma cells is required in place of M protein, provided baseline percentage was ≥30%, in addition to the above criteria, if present at baseline, ≥50% reduction in the size of soft tissue plasmacytomas is also required (Durie et al., 2006).

The term minor response (MR) in relation to patients with relapsed/refractory myeloma refers in the context of the present invention to ≥25% but <49% reduction of serum M protein and reduction in 24 h urine M protein by 50-89%, which still exceeds 200 mg per 24 h, in addition to the above criteria, if present at baseline, 25-49% reduction in the size of soft tissue plasmacytomas is also required, no increase in size or number of lytic bone lesions (development of compression fracture does not exclude response).

However, a response, though not formally classified, also includes an at least 30%, preferably at least 40% or 50% reduction in serum FLC levels. This is in particular of significance in cases where M-protein cannot be measured.

The term stable disease (SD) refers, in the context of the plasmaproliferative diseases of the present invention, to the not meeting of criteria for CR, VGPR, PR or progressive disease, while the term progressive disease (PD) refers to the increase of 25% from lowest response value in any one or more of the following:

Serum M-component (absolute increase must be ≥0.5 g/100 ml) and/or

Urine M-component (absolute increase must be ≥200 mg per 24 h) and/or

Only in patients without measurable serum and urine M-protein levels: the difference between involved and uninvolved FLC levels (absolute increase must be >100 mg/l)

Bone marrow plasma cell percentage (absolute % must be ≥10%)

Definite development of new bone lesions or soft tissue plasmacytomas or definite increase in the size of existing bone lesions or soft tissue plasmacytomas Development of hypercalcemia (corrected serum calcium >11.5 mg/100 ml) that can be attributed solely to the plasma cell proliferative disorder.

The term relapsed myeloma refers herein to a form of active MM in a subject, wherein said subject underwent at least one prior treatment regime, and which does not meet the criteria for relapsed/refractory myeloma.

The term refractory myeloma generally refers to a state of the disease when the number of plasma cells continues to increase even though treatment is give, that is the disease has, at the time of assessment, been proven irreceptive to the treatment regime administered.

The term relapsed/refractory myeloma refers herein to the relapse of disease while on salvage therapy, or progression within 60 days of most recent therapy.

The term refractory phenotype includes any type of refractory myeloma, that is, refractory and relapsed/refractory myeloma.

The term relapsed or refractory myeloma covers relapsed, refractory and relapsed/refractory myeloma.

In the clinical study discussed in more detail below, the subjects had been treated with at least one immunomodulator and a proteosome inhibitor therapy, which have failed, prior to entering the study. Disease was considered treatment refractory if the subject experienced progressive disease (PD) on his or her previous regimen.

The term "progression to", e.g., "active MM" in relation to patients with SMM refers in the context of the present invention to evidence of progression based on the IMWG (International Myeloma Working Group) criteria for progressive disease in MM and any one or more of the following felt related to the underlying clonal plasma cell proliferative disorder, development of new soft tissue plasmacytomas or bone lesions, hypercalcemia (>11 mg/100 ml), decrease in hemoglobin of ≥2 g/100 ml, and serum creatinine level ≥2 mg/100 ml. (Kyle & Rajkumar, 2009).

The pathogenesis of multiple myeloma involves binding of myeloma cells, via cell-surface adhesion molecules, to bone marrow stroma cells (BMSCs) as well as the extracellular matrix (ECM). This binding triggers, and thus can be made ultimately responsible, for multiple myeloma cell growth, drug resistance, and migration of MM cells in the bone marrow milieu (Munshi et al. 2008). In particular, the adhesion of multiple myeloma cells to ECM via syndecan-1 (CD138) to type I collagen, induces the expression of matrix metalloproteinase 1, thus promoting bone resorption and tumour invasion (Hideshima et al. 2007). Interactions between multiple myeloma cells and the bone marrow microenvironment results in activatation of a pleiotropic proliferative and anti-apoptotic cascade.

For multiple myeloma patients, but also for patients suffering from other diseases that are associated with bone pains, a number of supportive treatments exist to treat this and other symptoms. Appropriate medications include bisphosphonates (e.g. pamidronate, zoledronic acid) which can slow the bone damage. It has been demonstrated that these agents are able to reduce osteolytic bone lesions and prevent fractures (Ludwig et al., 2007). They are mostly given through a vein to decrease the risk of bone complications like fractures and to lower abnormally high blood calcium levels (Hypercalcemia). Data suggest that bisphosphonates reduces bone pain associated with MM. Patients may also have surgery if their bones are weak or break.

In one embodiment, the immunoconjugates reduce, in particular reduce to an acceptable level, bone pains and/or bone complications, such as osteonecrosis. A reduction to an acceptable level involves in particular the ability to discontinue the administration of a medication that alleviates these pains or is aimed at reducing said bone complications. Bisphosphonates, such as pamidronate, zoledronic acid and clodronate, are commonly administered to allegivate bone complications, such as ostenecrosis in MM patients and thereby to alleviate bone pains associated with said complications. Common bisphosphonates include, for oral administration, FOSOMAX, BONIVA, ACTONEL, DIDRONEL and SKELID, for intravenous administration, BONEFOS, AREDIA and ZOMETA.

A reduction in bone pain and/or bone complications according to the present invention may result in a reduction in the amount of the anti-pain medication to be administered to a patient and/or in the amount of any medications that are administered to counteract those complications. This reduction may be (i) relative to a previously administered amount, when said patient underwent (a) a treatment of said disease that causes bone pain and/or bone complications that differs from the treatments according to the present invention or (b) no treatment, or (ii) relative to an amount administered to another patient that suffers from the same disease and is at about the same stage of the disease. Such a reduction is preferably an about 10%, about 20%, about 30%, about 40%, about 50%, about 60%, about 70%, about 80%, about 90% reduction and preferably a complete cessation of the administration of the medication. When the latter is accomplished, that is, when the patient does subjectively not require any medication against bone pains and/or bone complications as a result of being administered the immunoconjugate according to the present invention either alone or as part of an anticancer combination according to the invention, the administration of said immunoconjugate is said to have reduced the bone pain and/or bone complications to an acceptable level. As a result adverse side effects resulting from medication administered to alleviate bone pain and/or bone complication should be reduced or abolished.

Following the homing of multiple myeloma cells to the bone marrow stromal compartment, adhesion between multiple myeloma cells and BMSCs upregulates many cytokines like interleukin-6 (IL-6) and insulin like growth factor 1 (IGF-1) which have angiogenic and tumor growth promoting activities (Hideshima et al. 2007). The signalling cascades initiated by these cytokines eventually result in MM cell resistance to conventional therapeutics (Anderson et al. 2000; Hideshima et al. 2006).

In the normal human hematopoietic compartment, CD138 expression is restricted to plasma cells (Wijdenes, 1996; Chilosi, 1999) and CD138 is not expressed on peripheral blood lymphocytes, monocytes, granulocytes, and red blood cells. In particular, $CD34^+$ stem and progenitor cells do not express CD138 and anti-CD138 mAbs do not affect the number of colony forming units in hematopoietic stem cell cultures (Wijdenes, 1996). In non-hematopoietic compartments, CD138 is mainly expressed on simple and stratified epithelia within the lung, liver, skin, kidney and gut. Only a weak staining was seen on endothelial cells (Bernfield, 1992; Vooijs, 1996). It has been reported that CD138 exists in polymorphic forms in human lymphoma cells (Gattei, 1999).

Monoclonal antibodies B-B4, BC/B-B4, B-B2, DL-101, 1 D4, MI15, 1.BB.210, 2Q1484, 5F7, 104-9, 281-2 in particular B-B4 have been reported to be specific to CD138. Of those B-B4, 1 D4 and MI15 recognized both the intact molecule and the core protein of CD138 and were shown to recognize either the same or closely related epitopes (Gattei, 1999). Previous studies reported that B-B4 did not recognize soluble CD138, but only CD138 in membrane bound form (Wijdenes, 2002).

The initial anti-CD138 antibody was developed by Diaclone SAS (Besancon, France) as the murine parental Mab B-B4 generated by immunization with the human multiple myeloma cell line U266, using standard hybridoma technology (Clement, 1995; Wijdenes, 1996). B-B4 binds to a linear epitope between residues 90-93 of the core protein on human syndecan-1 (CD138) (Wijdenes, 1996; Dore, 1998). Consistent with the expression pattern of CD138, B-B4 was shown to strongly react with plasma cell line RPM18226, but not to react with endothelial cells. Also consistent with the expression pattern of CD138, B-B4 also reacted with epithelial cells lines A431 (keratinocyte derived) and HepG2 (hepatocyte derived). An immunotoxin B-B4-saporin was also highly toxic towards the plasma cell line RPMI8226, in fact considerably more toxic than free saporin. However, from the two epithelial cell lines tested, B-B4-saporin showed only toxicity towards cell line A431, although in a clonogenic assay B-B4-saporin showed no inhibitory effect on the outgrowth of A431 cells (Vooijs, 1996). Other researchers reported lack of specificity of MM-associated antigens against tumors (Couturier, 1999).

B-B4 covalently linked to the maytansinoid DM1 showed selective cytotoxicity on multiple myeloma cell lines and cells, as well as anticancer activity in human multiple myeloma xenograft models in SCID mice (Tassone, 2004).

The present invention uses the term tumor cell to include cancer cells as well as pre-cancerous cells which may or may not form part of a solid tumor.

A targeting agent according to the present invention is able to associate with a molecule expressed by a target cell and includes peptides and non-peptides. In particular, targeting agents according to the present invention include targeting antibodies and non-immunoglobulin targeting molecules, which may be based on non-immunoglobulin proteins, including, but not limited to, AFFILIN® molecules, ANTICALINS® and AFFIBODIES®. Non-immunoglobulin targeting molecules also include non-peptidic targeting molecules such as targeting DNA and RNA oligonucleotides (aptamers), but also physiological ligands, in particular ligands of the antigen in question, such as CD138.

A targeting antibody according to the present invention is or is based on a natural antibody or is produced synthetically or by genetic engineering and binds to an antigen on a cell or cells (target cell(s)) of interest. A targeting antibody according to the present invention includes a monoclonal antibody, a polyclonal antibody, a multispecific antibody (for example, a bispecific antibody), or an antibody fragment. The targeting antibody may be engineered to, for example, improve its affinity to the target cells (Ross, 2003) or diminish its immunogenicity. The targeting antibody may be attached to a liposomal formulation including effector molecules (Carter, 2001). An antibody fragment comprises a portion of an intact antibody, preferably the antigen binding or variable region of the intact antibody. Examples of antibody fragments according to the present invention include Fab, Fab', $F(ab')_2$, and Fv fragments, but also diabodies; domain antibodies (dAb) (Ward, 1989; U.S. Pat. No. 6,005,079); linear antibodies; single-chain antibody molecules; and multispecific antibodies formed from antibody fragments. In a single chain variable fragment antibody (scFv) the heavy and light chains (VH and VL) can be linked by a short amino acid linker having, for example, the sequence $(glycine_4 serine)_n$, which has sufficient flexibility to allow the two domains to assemble a functional antigen binding pocket. Addition of various signal sequences may allow for more precise targeting of the targeting antibody. Addition of the light chain constant region (CL) may allow dimerization via disulphide bonds, giving increased stability and avidity. Variable regions for constructing the scFv can, if a mAb against a target of interest is available, be obtained by RT-PCR which clones out the variable regions from mRNA extracted from the parent hybridoma. Alternatively, the scFv can be generated de novo by phage display technology (Smith, 2001). As used herein, the term "functional fragment", when used in reference to a targeting antibody, is intended to refer to a portion of the targeting antibody which is capable of specifically binding an antigen that is specifically bound by the antibody reference is made to. A bispecific antibody according to the present invention may, for example, have at least one arm that is reactive against a target tissue and one arm that is reactive against a linker moiety (United States Patent Publication 20020006379). A bispecific antibody according to the present invention may also bind to more than one antigen on a target cell (Carter, 2001). An antibody according to the present invention may be modified by, for example, introducing cystein residues to introduce thiol groups (Olafsen, 2004).

In accordance with the present invention, the targeting antibody may be derived from any source and may be, but is not limited to, a camel antibody, a murine antibody, a chimeric human/mouse antibody or a chimeric human/monkey antibody, in particular, a chimeric human/mouse antibody such as nBT062.

Humanized antibodies are antibodies that contain sequences derived from a human-antibody and from a non-human antibody and are also within the scope of the present invention. Suitable methods for humanizing antibodies include CDR-grafting (complementarity determining region grafting) (EP 0 239 400; WO 91/09967; U.S. Pat. Nos. 5,530, 101; and 5,585,089), veneering or resurfacing (EP 0 592 106; EP 0 519 596; Padlan, 1991; Studnicka et al., 1994; Roguska et al., 1994), chain shuffling (U.S. Pat. No. 5,565,332) and Delmmunosation™ (Biovation, LTD). In CDR-grafting, the mouse complementarity-determining regions (CDRs) from, for example, mAb B-B4 are grafted into human variable frameworks, which are then joined to human constant regions, to create a human B-B4 antibody (hB-B4). Several antibodies humanized by CDR-grafting are now in clinical use, including MYLOTARG (Sievers et al., 2001) and HECEPTIN (Pegram et al, 1998).

The resurfacing technology uses a combination of molecular modeling, statistical analysis and mutagenesis to alter the non-CDR surfaces of antibody variable regions to resemble the surfaces of known antibodies of the target host. Strategies and methods for the resurfacing of antibodies, and other methods for reducing immunogenicity of antibodies within a different host, are disclosed, for example, in U.S. Pat. No. 5,639,641. Human antibodies can be made by a variety of methods known in the art including phage display methods. See also U.S. Pat. Nos. 4,444,887, 4,716,111, 5,545,806, and 5,814,318; and international patent application publications WO 98/46645, WO 98/50433, WO 98/24893, WO 98/16654, WO 96/34096, WO 96/33735, and WO 91/10741.

Targeting antibodies that have undergone any non-natural modification such as chimeric human/mouse antibodies or a chimeric human/monkey antibodies, humanized antibodies or antibodies that were engineered to, for example, improve their affinity to the target cells or diminish their immunogenicity but also antibody fragments, in particular functional fragments of such targeting antibodies that have undergone any non-natural modification, diabodies; domain antibodies; linear antibodies; single-chain antibody molecules; and multispecific antibodies are referred to herein as engineered targeting antibodies.

Chimerized antibodies, maintain the antibody binding region (ABR or Fab region) of the non-human antibody, e.g., the murine antibody they are based on, while any constant regions may be provided for by, e.g., a human antibody. Generally, chimerization and/or the exchange of constant regions of an antibody will not affect the affinity of an antibody because the regions of the antibody which contribute to antigen binding are not affected by this exchange. In a preferred embodiment of the present invention, the engineered, in particular chimerized, antibody of the present invention, may have a higher binding affinity (as expressed by $K_D$ values) than the respective non-human antibody it is based on. In particular, the nBT062 antibody and antibodies based thereon may have higher antibody affinity than the murine B-B4.

In another preferred embodiment of the present invention, immunoconjugates comprising those engineered/chimerized antibodies also display this higher antibody affinity. These immunconjugates may also display in certain embodiments other advantageous properties, such as a higher reduction of tumor load than their B-B4 containing counterparts. In a preferred embodiment, the engineered, in particular chimerized targeting antibodies display binding affinities that are characterized by dissociation constants $K_D$ (nM) of less than 1.6, less than 1.5 or about or less than 1.4, while their murine counterparts are characterized by dissociation constants $K_D$ (nM) of about or more than 1.6. Immunoconjugates comprising targeting agents such as targeting antibodies may be characterized by dissociation constants of $K_D$ (nM) of less than 2.6, less than 2.5, less than 2.4, less than 2.3, less than 2.2, less than 2.1, less than 2.0, less than or about 1.9 are preferred, while immunoconjugates comprising the murine counterpart antibodies may be characterized by dissociation constants $K_D$ (nM) of about or more than 2.6 (compare Table 9, Materials and Methods).

The basic antibody molecule is a bifunctional structure wherein the variable regions bind antigen while the remaining constant regions may elicit antigen independent responses. The major classes of antibodies, IgA, IgD, IgE, IgG and IgM, are determined by the constant regions. These classes may be further divided into subclasses (isotypes). For example, the IgG class has four isotypes, namely, IgG1, IgG2, IgG3, and IgG4 which are determined by the constant regions. Of the various human antibody classes, only human IgG1, IgG2, IgG3 and IgM are known to effectively activate the complement system. While the constant regions do not form the antigen binding sites, the arrangement of the constant regions and hinge region may confer segmental flexibility on the molecule which allows it to bind with the antigen.

Different IgG isotypes can bind to Fc receptors on cells such as monocytes, B cells and NK cells, thereby activating the cells to release cytokines. Different isotypes may also activate complement, resulting in local or systemic inflammation. In particular, the different IgG isotypes may bind FcγR to different degrees. FcγR5 are a group of surface glycoproteins belonging to the Ig superfamily and expressed mostly on leucocytes. The FcγR glycoproteins are divided into three classes designated FcγRI (CD64), FcγRII (CD32) and FcγRIII (CD16). While IgG1, IgG2 and IgG3 bind strongly to a variety of these classes of FcγR glycoproteins, IgG4 display much weaker binding. In particular, IgG4 is an intermediate binder of FcγRI, which results in relatively low or even no ADCC (antibody dependent cellular cytotoxicity), and does not bind to FcγRIIIA or FcγRIIA. IgG4 is also a weak binder of FcγRIIB, which is an inhibitory receptor. Furthermore, IgG4 mediates only weak or no complement fixation and weak or no complement dependent cytotoxicity (CDC). In the context of the present invention, IgG4 may be specifically employed to prevent Fc-mediated targeting of hepatic FcR as it displays no interaction with FcRγII on LSECs (liver sinusoidal endothelial cells), no or weak interaction with FcRγI-III on Kupffer cells (macrophages) and no interaction with FcRγIII on hepatic NK cells. Certain mutations that further reduce any CDC are also part of the present invention. For example IgG4 residues at positions 327, 330 and 331 were shown to reduce ADCC (antibody dependent cellular cytotoxicity) and CDC (Amour, 1999; Shields, 2001). One of more mutations that stabilize the antibody are also part of the present invention (also referred to herein as "stabilizing mutations"). Those mutations include in particular, leucine-to-glutamic acid mutations in the CH2 region of IgG4 and serine-to-proline exchanges in the IgG4 hinge core. These mutations decrease, in certain embodiments of the invention, the amount of half-molecules to less than 10%, less than 5% and preferably less than 2% or 1%. Moreover, the in vivo half life of so stabilized antibodies might be increased several days, including 1, 2, 3, 4 or more than 5 days (Schuurman, 1999).

When the present invention refers to an immunoconjugate comprising an engineered targeting antibody conferring IgG4 isotype properties, this means that the engineered targeting antibody shows significantly reduced affinity to Fc receptor expressing cells as compared to the affinity of antibodies of IgG1 isotype. These properties are preferably conferred by a further antibody region, which is distinct from the ABR, wherein said further antibody region is in whole or part of a human antibody. The result is a significantly reduced (more than 90% relative to its IgG1 isotype counterpart) or the total lack of a potential to induce CDC or ADCC as compared to the potential to induce CDC or ADCC usually observed with IgG1 isotype antibodies. This property can be measured in cell based assays by using the engineered targeting antibody in its unconjugated form. CDC and ADCC can be measured via different methods such as the one disclosed in Cancer Immunol. Immunother., 36, 373 (1993) or the GUAVA Cell Toxicity Assay. The overall benefit of immunoconjugates comprising at least part of an engineered targeting antibody conferring IgG4 isotype properties is an improvement of binding specificity and a reduced toxicity. Also the resulting reduced affinity to Fc receptors improves antigen-specific targeting of tumor cells leading to reduced toxicity against CD138 negative cells.

Targeting agents, including targeting antibodies disclosed herein may also be described or specified in terms of their binding affinity to antigen, in particular to CD138.

Preferred binding affinities of targeting agents such as targeting antibodies are characterized by dissociation constants $K_D$ (nM) of less than 1.6, less than 1.5 or about or less than 1.4. For immunoconjugates comprising said targeting agents such as targeting antibodies dissociation constants $K_D$ (nM) of less than 1.6, less than 1.5 or less than 2.5, less than 2.4, less than 2.3, less than 2.2, less than 2.1, less than 2.0, less than or about 1.9 are preferred.

An antigen binding region (ABR) according to the present invention will vary based on the type of targeting antibody or engineered targeting antibody employed. In a naturally occurring antibody and in most chimeric and humanized antibodies, the antigen binding region is made up of a light chain and the first two domains of a heavy chain. However, in a heavy chain antibody devoid of light chains, the antigen binding region will be made up of, e.g., the first two domains of the heavy chain only, while in single chain antibodies (ScFv), which combine in a single polypeptide chain the light and heavy chain variable domains of an antibody molecule, the ABR is provided by only one polypeptide molecule. FAB fragments are usually obtained by papain digestion and have one light chain and part of a heavy chain and thus comprise an ABR with only one antigen combining site. On the other hand, diabodies are small antibody fragments with two antigen-binding regions. In the context of the present invention, however, an antigen binding region of a targeting antibody or engineered targeting antibody is any region that primarily determines the binding specificity of the targeting antibody or engineered targeting antibody.

If an ABR or another targeting antibody region is said to be "of a certain antibody", e.g., a human or non-human antibody, this means in the context of the present invention that the ABR is either identical to a corresponding naturally occurring ABR or is based thereon. An ABR is based on a naturally occurring ABR if it has the binding specificity of the naturally occurring ABR. However, such an ABR may comprise, e.g., point mutations, additions, deletions or posttranslational modification such as glycosylation. Such an ABR may in particular have more than 70%, more than 80%, more than 90%, preferably more than 95%, more than 98% or more than 99% sequence identity with the sequence of the naturally occurring ABR.

nBT062 (see also FIG. 1) is a murine human chimeric IgG4 mAb, namely a chimerized version of B-B4. This chimerized version of B-B4 was created to reduce the HAMA (Human Anti-Mouse Antibody) response, while maintaining the functionality of the antibody binding region of the B-B4 for CD138. Surprisingly, the results obtained using an immunoconjugate comprising this engineered targeting antibody were much more homogenous (the variance in the results was reduced). The protocol for producing nBT062 is specified below. Chinese hamster ovary cells expressing nBT062 have been deposited with the DSMZ-Deutsche Sammlung von Mikroorganismen and Zellkulturen GmbH, Mascheroder Weg 1, D-38124 Braunschweig on Dec. 11, 2007. The identification number is DSM ACC2875. A CD138 specific chimeric antibody based on B-B4 is generically referred to herein as c-B-B4.

The amino acid sequence for both, the heavy and the light chains has been predicted from the translation of the nucleotide sequence for nBT062. The amino acid sequences predicted for the heavy chain and light chain are presented in Table 3. Predicted variable regions are bolded, predicted CDRs are underlined.

TABLE 3

Predicted Amino Acid Sequence for nBT062 nBT062 heavy chain predicted sequence (SEQ ID NO: 1):

```
  1 QVQLQQSGSE LMMPGASVKI SCKATGYTFS NYWIEWVKQR PGHGLEWIGE

51 ILPGTGRTIY NEKFKGKATF TADISSNTVQ MQLSSLTSED SAVYYCARRD

101 YYGNFYYAMD YWGQGTSVTV SSASTKGPSV FPLAPCSRST SESTAALGCL

151 VKDYFPEPVT VSWNSGALTS GVHTFPAVLQ SSGLYSLSSV VTVPSSSLGT

201 KTYTCNVDHK PSNTKVDKRV ESKYGPPCPS CPAPEFLGGP SVFLFPPKPK

251 DTLMISRTPE VTCVVVDVSQ EDPEVQFNWY VDGVEVHNAK TKPREEQFNS

301 TYRVVSVLTV LHQDWLNGKE YKCKVSNKGL PSSIEKTISK AKGQPREPQV

351 YTLPPSQEEM TKNQVSLTCL VKGFYPSDIA VEWESNGQPE NNYKTTPPVL
```

TABLE 3-continued

Predicted Amino Acid Sequence for nBT062

401 DSDGSFFLYS RLTVDKSRWQ EGNVFSCSVM HEALHNHYTQKSLSLSLG (K)

nBT062 light chain predicted sequence (SEQ ID NO: 2):

1 DIQMTQSTSS LSASLGDRVT ISC<u>SASQGIN</u> <u>NYLNWYQQKP DGTVELLIYY</u>

51 <u>TSTLQSGVPS RFSGSGSGTD YSLTISNLEP EDIGTYYCQQ</u> <u>YSKLPRTFGG</u>

101 <u>GTKLEIK</u>RTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201 LSSPVTKSFN RGEC

The C-terminal lysine is prone to clipping and might be present due to incomplete clipping to a certain extent. The (K) in parentesis is not part of SEQ ID NO: 1.

Table 4. shows a comparision of the general CDR definitions of Krabat and Chothia and the predicted CDRs for nBT062

|  | Kabat CDR definition | nBT062 |
|---|---|---|
| Light chain | CDR1: residues 24-34 | CDR1: residues 24-34 |
|  | CDR2: residues 50-56 | CDR2: residues 50-56 |
|  | CDR3: residues 89-97 | CDR3: residues 89-97 |
| Heavy chain | CDR1: residues 31-35 | CDR1: residues 31-35 |
|  | CDR2: residues 50-56 | CDR2: residues 51-68 |
|  | CDR3: residues 95-102 | CDR3: residues 99-111 |
|  | Chothia CDR definition | nBT062 |
| Light chain | CDR1: residues 26-32 | CDR1: residues 24-34 |
|  | CDR2: residues 50-52 | CDR2: residues 50-56 |
|  | CDR3: residues 91-96 | CDR3: residues 89-97 |
| Heavy chain | CDR1: residues 26-32 | CDR1: residues 31-35 |
|  | CDR2: residues 52-56 | CDR2: residues 51-68 |
|  | CDR3: residues 96-101 | CDR3: residues 99-111 |

Fully human antibodies may also be used. Those antibodies can be selected by the phage display approach, where CD138 or an antigenic determinant thereof is used to selectively bind phage expressing, for example, B-B4 variable regions (see, Krebs, 2001). This approach is advantageously coupled with an affinity maturation technique to improve the affinity of the antibody. All antibodies referred to herein are isolated antibodies (See US Patent Publication 20090175863).

In one embodiment, the targeting antibody is, in its unconjugated form, moderately or poorly internalized. Moderate internalization constitutes about 30% to about 75% internalization of total antibody, poor internalization constitutes about 0.01% to up to about 30% internalization after 3 hours incubation at 37° C. In another preferred embodiment the targeting antibody binds to CD138, for example, antibodies B-B4, BC/B-B4, B-B2, DL-101, 1 D4, MI15, 1.BB.210, 2Q1484, 5F7, 104-9, 281-2 in particular B-B4. Hybridoma cells, which were generated by hybridizing SP02/0 myeloma cells with spleen cells of Balb/c mice have been deposited with the DSMZ-Deutsche Sammlung von Mikroorganismen and Zellkulturen GmbH, Mascheroder Weg 1, D-38124 Braunschweig on Dec. 11, 2007. The identification number of these B-B4 expressing hybridoma cells is DSM ACC2874. In another embodiment, the targeting antibody does not substantially bind non-cell-surface expressed CD138. When, in the context of the present invention, the name of a specific antibody is combined with the term "targeting antibody" such as "nBT062 targeting antibody," this means that this targeting antibody has the binding specificity of the antibody nBT062. If a targeting antibody is said to be "based on" a specified antibody, this means that this targeting antibody has the binding specificity of this antibody, but might take any form consistent with the above description of a targeting antibody. When, in the context of the present invention, the name of a specific antigen is combined with the term "targeting antibody" such as "CD138 targeting antibody," this means that this targeting antibody has binding specificity for CD138. If, in the context of the present invention, for example, a targeting antibody is said to do something "selectively" such as "selectively targeting cell-surface expressed CD138" or, to be "selective" for something, this means that there is a significant selectivity (i.e. a higher affinity towards CD138-positive cells compared with CD138-negative cells) for, in the case of the example provided, cell-surface expressed CD138, compared to any other cell-surface expressed antigen. Adverse side effects in a given environment may be substantially reduced or even avoided due to this selectivity.

"Non-immunoglobulin targeting molecules" according to the present invention include targeting molecules derived from non-immunoglobulin proteins as well as non-peptidic targeting molecules. Small non-immunoglobulin proteins which are included in this definition are designed to have specific affinities towards, in particular surface expressed CD138. These small non-immunoglobulin proteins include scaffold based engineered molecules such as Affilin® molecules that have a relatively low molecular weight such as between 10 kDa and 20 kDa. Appropriate scaffolds include, for example, gamma crystalline. Those molecules have, in their natural state, no specific binding activity towards the target molecules. By engineering the protein surfaces through locally defined randomization of solvent exposed amino acids, completely new binding sites are created. Former non-binding proteins are thereby transformed into specific binding proteins. Such molecules can be specifically designed to bind a target, such as CD138, and allow for specific delivery of one or more effector molecules (see, scil Proteins GmbH at www.scilproteins.com, 2004). Another kind of non-immunoglobulin targeting molecules are derived from lipocalins, and include, for example ANTICALINS®, which resemble in structure somewhat immunoglobulins. However, lipocalins are composed of a single polypeptide chain with 160 to 180 amino acid residues. The binding pocket of lipocalins can be reshaped to recognize a molecule of interest with high affinity and specificity (see, for example, Beste et al., 1999). Artificial bacterial receptors such as those marketed under the trademark Affibody® (Affibody AB) are also within the scope of the present invention. These artificial bacterial receptor molecules are small, simple proteins and may be composed of a three-helix bundle based on the scaffold of one of the IgG-binding domains of Protein A (*Staphylococcus aureus*). These molecules have binding properties similar to many immunoglobulins, but are substantially smaller, having a molecular weight often not exceeding 10 kDa and are also comparatively stable. Suitable artificial bacterial receptor molecules are, for example, described in U.S. Pat. Nos. 5,831, 012; 6,534,628 and 6,740,734.

Other "non-immunoglobulin targeting molecules" are physiological ligands of the antigen in question. Physiological ligands of CD138 include for example, but not limited to, ADAMTS4 (aggrecanase-1), antithrombin-3, bFGF, cathepsin G, CCL5 (RANTES), CCL7, CCL11, CCL17, CD44, collagens (collagen type 1, collagen type 2, collagen type 3, collagen type 4, collagen type 5, collagen type 6), CXCL1, elastase, gp120, HGF [hepatocyte growth factor], laminin-1, laminin-2, laminin-5, midkine, MMP-7, neutrophil elastase, and pleiotrophin (HBNF, HBGF-8). Non-peptidic targeting molecules include, but are not limited to, to DNA and RNA oligonucleotides that bind to CD138 (aptamers).

An "effector molecule" according to the present invention is a molecule or a derivative, or an analogue thereof that is attached to a targeting agent, in particular a targeting antibody and/or an engineered targeting antibody, and that exerts a desired effect, for example, apoptosis, or another type of cell death, or a continuous cell cycle arrest on the target cell or cells. Effector molecules according to the present invention include molecules that can exert desired effects in a target cell and include, but are not limited to, cytotoxic drugs, including low molecular weight cytotoxic drugs (Molecular mass of less than 1500 Da, preferably less than 1400, less than 1200, less than 1000, less then 800, less then 700, less then 600, less than 500, less than 300 but generally more than 120 Da). These cytotoxic drugs are, according to the present invention, generally non-proteinaceous biological cytotoxic drugs and contain or induce, upon administration, the production of another cytotoxic drug of at least 5 C atoms, 10 C atoms, preferably more than 12 C atoms, often more than 20 C atoms and sometimes more than 30, 40 or 50 C atoms and generally at least one ring structure, such as a benzene ring, which is often substituted. However, often interconnecting ring structures are part of these molecules. These non-proteinaceous biological cytotoxic drugs may intercalate into DNA (DNA intercalators) or alkylate DNA, inhibit microtubule formation, are inhibitors of mitosis, inhibitors of enzymes involved in the DNA structural integrity, such as histone deacetylate or inhibitors of enzymes that are otherwise vital to a cell and cause disruption of cell metabolism. Effectors can also be categorized as radionuclides, biological response modifiers, pore-forming agents, ribonucleases, proteins of apoptotic signaling cascades with apoptosis-inducing activities, antisense oligonucleotides, anti-metastatic agents, anti-oxidative substances, antibodies or cytokines as well as functional derivatives or analogues/fragments thereof.

Toxins may include bacterial toxins, such as, but not limited to, Diphtheria toxin or Exotoxin A, plant toxins, such as but not limited to, Ricin other alkaloids and polyphenols, mycotoxins, such as alpha amanitin or more specially Ama-toxins and phallotoxins. Toxins might not only be of bacterial origin, but also fungal, plant, vertebrate and invertebrate origin, all of which can be genetically or chemically modified. Moreover toxins might also be environmental toxins such as, but not limited to, methylmercury. Effector molecules might be proteins, such as those of apoptotic signaling cascades with apoptosis-inducing activities, including, but are not limited to, Granzyme B, Granzyme A, Caspase-3, Caspase-7, Caspase-8, Caspase-9, truncated Bid (tBid), Bax and Bak. Toxins may also be dolastatins 10 and 15 are small peptides isolated from the marine sea hare Dolabella auricularia that have been shown to interact with tubulin.

| Effector | Molecular mass (g/mol [Da] |
|---|---|
| Doxorubicin | 564 |
| Danurubicin | 528 |
| Vinblastin | 811 |
| Docetaxel | 808 |
| Paclitaxel | 854 |
| Epothilone B | 508 |
| Vorinostat | 264 |
| Neocarzinostatin | 660 |
| Calicheamicin γ1 | 1368 |
| Esperamicin | 1342 |
| Methotrexate | 454 |
| Sylimarin compoments | 482 |
| Masoprocol | 302 |
| Aminolevulinic acid | 132 |
| Miltefosine | 407 |
| Epigallocatechin gallate (EGCG) | 459 |
| Psoralene | 186 |
| Melphalan | 304 |

Table 5 provides examples of low molecular weight cytotoxic drugs that may serve as effector molecules.

In a preferred embodiment, the effector molecule increases internal effector delivery of the immunoconjugate, in particular when the natural form of the antibody on which the targeting antibody of the immunoconjugate is based is poorly internalizable. In another preferred embodiment the effector is, in its native form, non-selective. In certain embodiments the effector has high non-selective toxicity, including systemic toxicity, when in its native form. The "native form" of an effector molecule of the present invention is an effector molecule before being attached to the targeting agent to form an immunoconjugate. In another preferred embodiment, the non-selective toxicity of the effector molecule is substantially eliminated upon conjugation to the targeting agent. In another preferred embodiment, the effector molecule causes, upon reaching the target cell, death or cell cycle arrest, inclusing continous cell cycle arrest, in the target cell.

An effector molecule according to the present invention includes, but is not limited to, antineoplastic agents, in particular intracellular chemotherapeutic agents, which are defined below.

Low molecular weight cytotoxic drugs (see above for molecular weights) may preferably be antimitotics, more particular, tubulin affecting agents, which include inhibitors of tubulin polymerization such as maytansinoids, dolastatins (and derivatives such as auristatin) and crytophycin and potent taxoid (taxane) drugs (Payne, 2003). Further included in the definition of small highly cytotoxic drug are other tubulin interfering agents such as epothilones (e.g. ixabepilone) and colchicine derivatives (tubulin interfering agents are further discussed below).

An effector molecule that is a maytansinoid includes maytansinoids of any origin, including, but not limited to synthetic maytansinol and maytansinol analogue and derivative.

Maytansine is a natural product originally derived from the Ethiopian shrub Maytenus serrata (Remillard, 1975; U.S. Pat. No. 3,896,111). This drug inhibits tubulin polymerization, resulting in mitotic block and cell death (Remillard, 1975; Bhattacharyya, 1977; Kupchan, 1978). The cytotoxicity of maytansine is 200-1000-fold higher than that of anti-cancer drugs in clinical use that affect tubulin polymerization, such as Vinca alkaloids or taxol. However, clinical trials of maytansine indicated that it lacked a therapeutic window due to its high systemic toxicity. Maytansine and maytansinoids are highly cytotoxic but their clinical use in cancer therapy has been greatly limited by their severe systemic side-effects primarily attributed to their poor selectivity for tumors. Clinical trials with maytansine showed serious adverse effects on the central nervous system and gastrointestinal system.

Maytansinoids have also been isolated from other plants including seed tissue of Trewia nudiflora (U.S. Pat. No. 4,418, 064)

Certain microbes also produce maytansinoids, such as maytansinol and C-3 maytansinol esters (U.S. Pat. No. 4,151, 042).

The present invention is directed to maytansinoids of any origin, including synthetic maytansinol and maytansinol analogues which are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,371,533; 4,424,219 and 4,151,042.

In a preferred embodiment, the maytansinoid is a thiol-containing maytansinoid and is more preferably produced according to the processes disclosed in U.S. Pat. No. 6,333, 410 to Chari et al or in Chari et al. (Chari, 1992).

DM-1 ($N^2$-deacetyl-$N^2$-(3-mercapto-1-oxopropyl)-maytansine) is a preferred effector molecule in the context of the present invention. DM1 is 3- to 10-fold more cytotoxic than maytansine, and has been converted into a pro-drug by linking it via disulfide bond(s) to a monoclonal antibody directed towards a tumor-associated antigen. Certain of these conjugates (sometimes called "tumor activated prodrugs" (TAPs)) are not cytotoxic in the blood compartment, since they are activated upon associating with a target cells and internalized, thereby releasing the drug (Blather, 2001). Several antibody-DM1 conjugates have been developed (Payne, 2003), and been evaluated in clinical trials. For example, huC242-DM1 treatment in colorectal cancer patients was well tolerated, did not induce any detectable immune response, and had a long circulation time (Tolcher, 2003).

Figure 3:
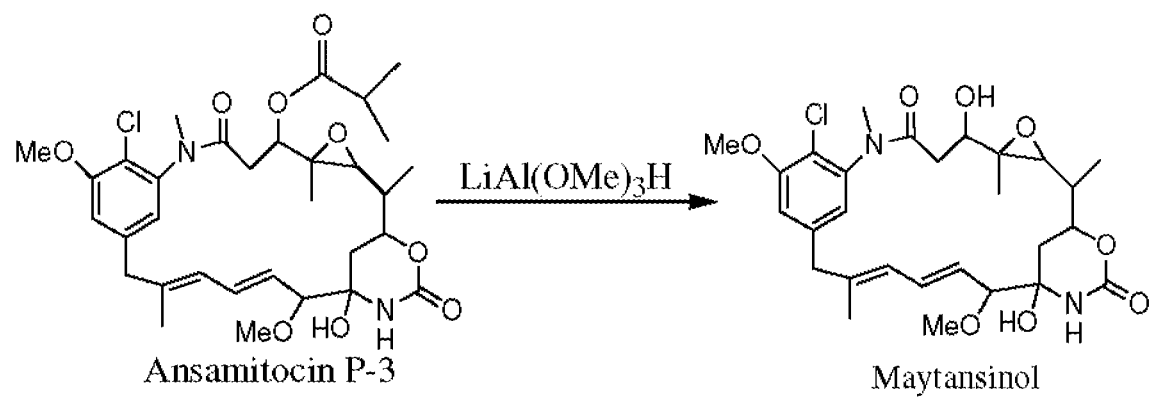
FIG. 3 shows the conversion of ansamitocin P-3 to maytansinol (stereochemistry is omitted for simplicity).
Figure 4:
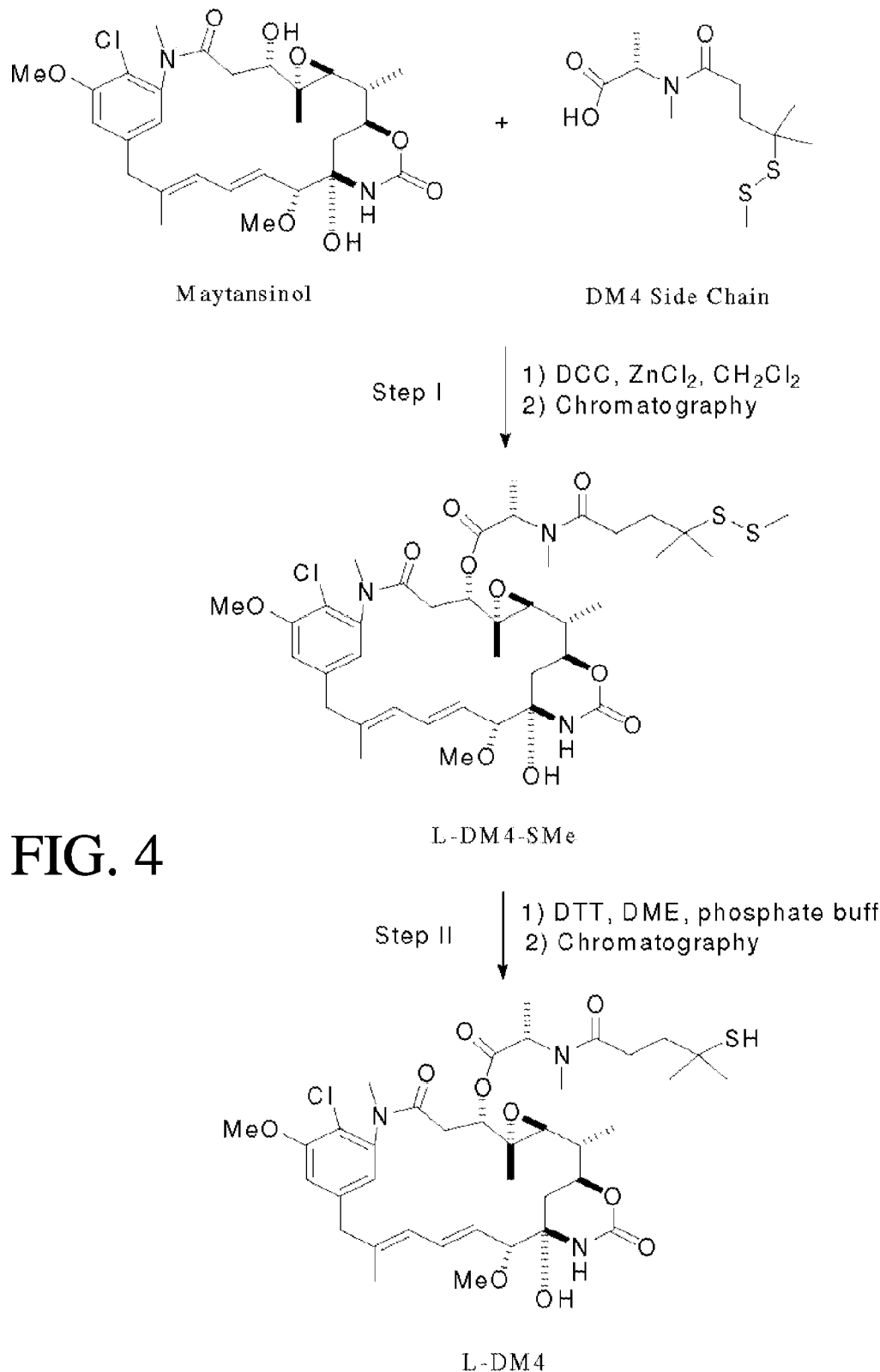
FIG. 4 shows a representative synthesis scheme of DM4.

Other particularly preferred maytansinoids comprise a side chain that contains a sterically hindered thiol bond such as, but not limited to, maytansinoids $N^{2'}$-deacetyl-$N^{2'}$-(4-mercapto-1-oxopentyl)-maytansine, also referred to as "DM3," and $N^{2'}$-deacetyl-$N^{2'}$-(4-methyl-4-mercapto-1-oxopentyl)-maytansine, also referred to as "DM4." The synthesis of DM4 is shown in FIGS. 3 and 4 and is described elsewhere herein. DM4 differs from DM1 and DM3 in that it bears methyl groups at its aC. This results in a sterical hindrance when DM4 is attached via a linker in particular, but not limited to, a linker comprising a disulfide bond, to a targeting agent such as nBT062. A wide variety of maytansinoids bearing a sterically hindered thiol group (possessing one or two substituents, in particular alkyls substituents, such as the methyl substituents of DM4) are disclosed U.S. Patent Publication 2004/0235840, published Nov. 25, 2004, which is incorporated herein in its entirety by reference. The steric hindrance conferred by alkyl groups such as the methyl groups on the carbon adjacent to the sulfur atom of DM3 and DM4 may affect the rate of intracellular cleavage of the immunoconjugate. The variable alkyl unit may therefore affect potency, efficacy, and safety/toxicity in vitro and in vivo.

As reported by Goldmahker et al. in U.S. Patent Publication 2006/0233814, such a hindrance induces alkylation (e.g., methylation) of the free drug, once the drug is released at its target. The alkylation may increase the stability of the drug allowing for the so-called bystander effect. However, as the person skilled in the art will appreciate, other effector molecules comprising substitutents such as alkyl groups at positions that result in a sterical hindrance when the effector is attached to a targeting agent via a linker are part of the present invention (U.S. Patent Publication 2004/0235840). Preferably this hindrance induces a chemical modification such as alkylation of the free drug to increase its overall stability, which allows the drug to not only induce cell death or continuous cell cycle arrest in CD138 expressing tumor cells but, optionally, also to affect auxiliary cells that, e.g., support or protect the tumor from drugs, in particular cells of the tumor stroma and the tumor vasculature and which generally do not express CD138 to diminish or lose their supporting or protecting function.

Maytansine was evaluated in Phase I and Phase II clinical trials sponsored by the National Cancer Institute (NCI) under IND #11,857 (submitted to FDA on Sep. 19, 1975). Both complete and partial responses were seen in patients with hematological malignancies and partial responses in patients with a broad spectrum of solid tumors (Blum and Kahlert., 1978, Issell and Crooke, 1978, Chabner et al., 1978, Eagan et al., 1978, Cabanillas et al., 1978). However, significant toxicities, including nausea, vomiting, diarrhea, elevations of liver function tests, lethargy, and peripheral neuropathy were noted (see Maytansine IND #11,857, Annual Report, February, 1984; Blum and Kahlert., 1978, Issell and Crooke, 1978, Chabner et al., 1978). Toxic effects precluded further development.

A class of tubulin interfering agents comprise taxanes (Payne 2003), especially highly potent ones and those that contain thiol or disulfide groups. Taxanes are mitotic spindle poisons that inhibit the depolymerization of tubulin, resulting in an increase in the rate of microtubule assembly and cell death. Taxanes that are within the scope of the present invention are, for example, disclosed in U.S. Pat. Nos. 6,436,931; 6,340,701; 6,706,708 and United States Patent Publications 20040087649; 20040024049 and 20030004210. Other taxanes are disclosed, for example, in U.S. Pat. No. 6,002,023, U.S. Pat. No. 5,998,656, U.S. Pat. No. 5,892,063, U.S. Pat. No. 5,763,477, U.S. Pat. No. 5,705,508, U.S. Pat. No. 5,703, 247 and U.S. Pat. No. 5,367,086. As the person skilled in the art will appreciate, PEGylated taxanes such as the ones described in U.S. Pat. No. 6,596,757 are also within the scope of the present invention.

The present invention includes further DNA affecting effector molecules, in more particular, intercalating agents such as anthracyclines and derivatives (daunorubicin, valrubicin, doxorubicin, aclarubicin, epirubicin, idarubicin, amrubicin, pirarubicin, zorubicin) and anthracenediones, such as Streptomyces derived substances (actinomycin, mitomycin, bleomycin, aactinomycin) or amsacrine.

A effector molecule might represent more particular DNA alkylating agents like, and more particular, Nitrogen mustard and analogues (e.g. Cyclophosphamide, Melphalan, Estramustin), Alkylsulfonates, Nitrosoureas, Aziridines, Hydrazines, Ethylene (mines, and other substances such as Trenimon and Mitobronitol (a mannitol analogue). In particular, preferred DNA alkylating agents are CC-1065 analogues or derivatives (U.S. Pat. Nos. 5,475,092; 5,585,499; 6,716,821) and duocarmycin.

CC-1065 represents a potent antitumor-antibiotic isolated from cultures of Streptomyces zelensis and has been shown to be exceptionally cytotoxic in vitro (U.S. Pat. No. 4,169,888). Within the scope of the present invention are, for example the CC-1065 analogues or derivatives described in U.S. Pat. Nos. 5,475,092, 5,585,499 and 5,739,350. As the person skilled in the art will readily appreciate, modified CC-1065 analogues or derivatives as described in U.S. Pat. No. 5,846,545 and prodrugs of CC-1065 analogues or derivatives as described, for example, in U.S. Pat. No. 6,756,397 are also within the scope of the present invention. In certain embodiments of the invention, CC-1065 analogues or derivatives may, for example, be synthesized as described in U.S. Pat. No. 6,534,660.

Other DNA alkylating effector molecules such as platinum based substances are further included (e.g. e.g. carboplatin, nedaplatin, oxaliplatin, triplatin, satraplatin).

Among the DNA affecting effector molecules, also Topoisomerase I and II inhibitors are included, such as Camptotheca derived substances (belotecan, topotecan) and Podophyllotoxin and derivatives (etoposide, teniposide).

Further subclass of DNA affecting effector molecules include antimetabolites such as folic acid analguoes (methotrexate, known as a dihydrofolate reductase inhibitors) or Aminopterin. Also included are metabolites interfering with purine or pyrimidine metabolism, in particular adenosine deaminase inhibitor (pentostatin), or halogenated/ribonukleotide reductase inhibitor (cladribine, clofarabine), thiopurine and tiazof urine. Further antimetabolites include DNA polymerase inhibitor (cytarabine), ribonucleotide reductase inhibitor (gemcitabine), and hypomethylating agents (azacitidine, decitabine) and ribonucleotide reductase inhibitors. More general included are also DNA crosslinking substances such as cisplatin.

An effector molecule according to the present invention may be antitumor antibiotics, defined as DNA modifiying or damaging effector molecules including enediyne antibiotics such as calicheamicin which include, e.g., gamma 1I, N-acetyl calicheamicin and other derivatives of calicheamicin. Calicheamicin binds in a sequence-specific manner to the minor groove of DNA, undergoes rearrangement and exposes free radicals, leading to breakage of double-stranded DNA, resulting in cell apoptosis and death. One example of a calicheamicin effector molecule that can be used in the context of the present invention is described in U.S. Pat. No. 5,053,394. This compound is used in immunoconjugates with the monoclonal antibodies published as gemtuzumab ozogamicin and inotuzumab ozogamicin.

A subgroup of enediyne comprises the chromoproteins esperamycin and neocarzinostatin. In particular, Trabectedin, which is also categorized as a DNA damaging agent, termed anti-tumor antibiotics. Trabectedin causes DNA backbone cleavage and can be isolated from a sea squirt (also known as ecteinascidin 743 or ET-743) is sold by ZELITA and JOHNSON & JOHNSON under the brand name YONDELIS.

Another group of preferred effector molecules are substances such as, but not limited to, toxins affecting cell metabolism. In particular enzyme inhibitors such as but not only, olaprib, or more preferred proteasome (e.g. bortezomib) and protein kinase inhibtors, or lipoxygenase inhibitors such as masoprocol are part of the present invention. Also included are receptor antagonists such as, but not limited to, endothelin A receptor antagonist (e.g. atrasentan), or sex steroids such as testolactone, interfering with estrone metabolism. Further included are estrogen receptor interacting substances such as plant derived polyphenols, for example but not only isoflavonoids, stilbenes, silymarin, phenylpropanoid glycosides as referred to hytoestrogens.

Also suitable as effector molecules are substances affecting cell metabolism, such as substances used for photodynamic or radiation therapy, including, but not limited to, porphyrin derivatives e.g. 5-Aminolevulinic acid. Efaproxiral represents a radiosensitizer, which increases oxygen levels by decreasing hemoglobin-oxygen affinity. Further included are retinoids (first, second and third generation), in particular Tretinoine (ATRA), all trans retinoic acid, which is used to treat acute promyelocytic leukemia (APML) sold for this indication by ROCHE under the brand name VESANOID. Retinoids are a class of chemical compounds that are related chemically to vitamin A, exerting diverse functions as for example activation of tumor suppressor genes. At present they are used to treat skin cancer and inflammatory skin disorders.

In another preferred embodiment, effector molecules might affect signalling pathways, such as but not limited to, calcium signaling. Examples are arsenic trioxide or trimethyltin chloride, the latter of which is a highly toxic organotin compound.

The present invention also includes effector molecules that are affecting drug resistance mechanisms which might include, for example, anti-multidrug resistance activity (via P-glycoprotein inhibition). Bicyclic heteroaromatic compounds and derivatives might severe as non-limiting examples.

Another effector molecule class might include substances, or more particular proteins interfering with apoptotic signaling pathways, including, but not limited to, antisense oligonucleotides, more particular, oligodeoxynucleotides such as Oblimersen (INN, trade name Genasense; also known as Augmerosen and bcl-2 antisense oligodeoxynucleotide G3139) which is an antisense oligodeoxyribonucleotide actually studied as a possible treatment for several types of cancer, including chronic lymphocytic leukemia, B-cell lymphoma, and breast cancer. It has been proposed that this compound may kill cancer cells by blocking the production of Bcl-2 and by rendering them more sensitive to chemotherapy. A further apoptosis inducing class of substances that may serve as effector molecules comprise plant polyphenols such as, but not limited to, siliymarins, which are able to interfere with cell cycle regulators and proteins involved in apoptosis Other effector molecules might include enzymes such as but not limited to, asparaginase or other enzymes with antineoplastic activities.

A drug-effector molecule according to the present invention may also be an antiprotozoal drug such as Miltefosine.

In another embodiment effector molecules might represent plant polyphenoles, such as, but not limited to, psoralens and their hydroxy metabolites.

Plant polyphenoles such as flavonoids, tannins (proanthocyanidins), stilbenoids, curcuminoids and lignans having one of the above mentionend antitumor activities (e.g. apoptosis inducing, cell cycle arrest) or additional activity such as free radical scavenging, metal chelating activity, estrogen receptor interfering activity, antioxidant, interfering with drug metabolizing enzymes) are also possible effector molecules. More specifically, psoralens and their hydroxy metabolites which are able to intercalate into DNA acting as metal chelators having antioxidant and cytoprotective properties are preferred effector molecules. Particually preferred are reservatol and polyhydroxylated derivativesand flavonoids, such as catechins and epicatechins, more specifically epigallocatechin 3-O gallate, which may act as antioxidants.

A broad classification of effector molecules according to their mechanism is also possible:
  Antineoplastic agents and immunomodulating agents (According to ATC code L01) in particular "Intracellular chemotherapeutic agents"

ATC: Anatomical Therapeutical Chemical classification system (WHO)
1) Antimitotics, or molecules affecting microtubules (tubulin binding agents) such as vinca alkaloids and analogues (Vinca alkaloids (Vinblastine, Vincristine, Vinflunine, Vindesine, Vinorelbine) and Taxanes (Paclitaxel, Larotaxel, Docetaxel) dolastatins (and derivatives e.g. auristatin) and crytophycin, maytansines and colchicine derivatives, epothilones (e.g. ixabepilone)
2) affecting DNA replication
   a) Intercalating agents such as Anthracyclines (Daunorubicin, valrubicin, Doxorubicin, Aclarubicin, Epirubicin, Idarubicin, Amrubicin, pirarubicin, Zorubicin) and Anthracenediones, such as *Streptomyces* derived substances (Actinomycin, Mitomycin, Bleomycin, Dactinomycin) or Amsacrine
   b) Alkylating agents such as Nitrogen mustards, Nitrosoureas, Alkylsulfonates, Aziridines, Hydrazines (Procarbazine), Triazenes, Epoxides, Ethylene Imines, Altretamine, Mitobronitol, duocarmycin and analogues/stereoisomers, Trenimon, Estramustine, CC-1065
   c) Alkylating-like agents such as Platinum (e.g. Carboplatin Nedaplatin, Oxaliplatin, Triplatin Tetranitrate, Satraplatin)
   d) Topoisomerase I specific inhibitors such as camptotheca (Belotecan, Topotecan)
   e) Topoisomerase II specific inhibitors such as Podophyllotoxin and derivatives (Etoposide, Teniposide)
   f) Antimetabolites affecting DNA/RNA synthesis by interfering with
      folic acid such as Dihydrofolate reductase inhibitors (e.g. Aminopterin, Methotrexate), thymidilate synthase inhibitor
      purine such as adenosine deaminase inhibitor (Pentostatin), halogenated/ribonukleotide reductase inhibitor (Cladribine, Clofarabine), Thiopurine, Tiazofurine
      Pyrimidine such as DNA Polymerase inhibitor (Cytarabine), ribonucleotide reductase inhibitor (Gemcitabine), hypomethylating agent (Azacitidine, Decitabine)
      deoxyribonukleotide such as ribonukleotide reductase inhibitor Hydroxycarbamid
   g) other DNA crosslinking agents such as platinum based compounds (e.g. Cisplatin)
3) Other DNA interfering substances e.g. "antitumor/cytotoxic antibiotics" such as Elsamicin A, further antibiotics such as CC-1065, and subclasses of antibiotics such as bacteria derived enediyne chalicheamin or chromoprotein enediyne Esperamicin (extremely toxic DNA splicing agent) or Neocarzinostatin (Other members of the neocarzinostatin group of antibiotics are macromomycin, actinoxanthin, kedarcidin and maduropeptin.) or Trabectedin (DNA backbone cleavage)
4) toxins affecting cell metabolism e.g. HSP90 inihibitors, Lonidamide (inhibits both respiration and glycolysis leading to a decrease in cellular ATP)
   a) Enzyme inhibitors e.g. Olaprib (PARP inhibitor), CDK inhibitors (Alvocidib), Proteasome (Bortezomib), Protein kinase inhibitors, Masoprocol (Lipoxyenase Inhibitor)
   b) Receptor antagonists such as tutin (Glycin receptor antagonist (plant toxin), Atrasentan, retinoid X receptor (Bexarotene), sex steroids such as testolactone, estrogen receptor interfering substances
   c) Photosensitizers or other compounds used for photodynamic therapy (Porfirmer Sodium), Porphyrin derivatives e.g. δ-Aminolevulinic acid)
   d) Radiosensitizer such as Efaproxiral which increases oxygen levels by decreasing hemoglobin-oxygen affinity
   e) Substances afffecting signaling pathways e.g. $Ca^{2+}$ signaling such as arsenic trioxide and trimethyltin chloride
   f) Other substances interfering with metabolism such as retinoids and derivatives Tretinoine (ATRA)
5) Affecting epigenetic processes such as HDAC inhibtors (e.g. Panobinostat, Vorinostat, Valporic acid, MGCD0103 (Mocetinostat), which are at present in clinical development for cutaneous T-cell lymphoma, acute myeloid leukemia, Hodgkin lymphoma or follicular lymphoma)
6) Affecting drug resistance mechansims such as bicyclic heteroaraomatic compounds, which inhibit P-glycoprotein
7) Substances inducing apoptotic signaling/mechanisms include proteins but also antisense oligodeoxyncleotides such as Oblimersen (tradename Genasense)
8) Enzymes such as Asparaginase
9) Antiprotozoal drugs such as Miltefosine
10) Plant polyphenoles such as Flavonoids, Tannins (Proanthocyanidins), Stilbenoids, curcuminoids and lignans having one of the above mentionend antitumor activities (e.g. apoptosis inducing, cell cycle arrest) or additional activity such as free radical scavenging, metal chelating activity, estrogen receptor interfering activity, antioxidant, interfering with drug metabolizing enzymes). More specifically psoralens and their hydroxy metabolites, reservatol and polyhydroxylated derivatives, Flavonoids, such as Catechins and Epicatechins, more specifically epigallocatechin 3-O gallate
11) Further natural substances and deribvatives such as Eotoxin A, Diphteria toxin, and derivatives thereof, wherein the derivatives can be chemically or genetically modified.

Effector molecules can also be categorized according to substance class they belong to such as anorganic compounds, aromatic compounds, metal based compounds, proteins related to cell metabolism, enzymes, peptides, oligonucleotides, such as antisense nucleotides, bacterial toxins, plant derived toxins and polyphenols such as tannins, flavonoids and coumarins as well as terpenoids, alkaloids, anti-tumor antibiotics (e.g. enediyne antibiotics), mycotoxins, toxins from invertebrates as well as vertebrates, environmental toxins.

An immunoconjugate according to the present invention comprises at least one targeting agent, in particular targeting antibody and one effector molecule. The immunoconjugate might comprise further molecules for example for stabilization. For immunoconjugates, the term "conjugate" is generally used to define the operative association of the targeting agent with one or more effector molecules and is not intended to refer solely to any type of operative association, and is particularly not limited to chemical "conjugation". So long as the targeting agent is able to bind to the target site and the attached effector functions sufficiently as intended, particularly when delivered to the target site, any mode of attachment will be suitable. The conjugation methods according to the present invention include, but are not limited to, direct attachment of the effector molecule to the targeting antibody, with or without prior modification of the effector molecule and/or the targeting antibody or attachment via linkers. Linkers can be categorized functionally into, for example, acid labile, photolabile linkers, enzyme cleavable linkers, such as linkers that can be cleaved by peptidases. Cleavable linkers are, in many embodiments of the invention preferred. Such cleavable linkers can be cleaved under conditions present in the cellular environment, in particular, an intracellular environment and that have no detrimental effect on the drug released upon cleavage. Low pHs such as pH of 4 to 5, as they exist in certain intracellular departments, will cleave acid labile linkers, while photolabile linkers can be cleaved by, e.g., infrared light. However, linkers that are cleaved by/under physiological conditions present in the majority of cells are preferred and are referred to herein as physiologically cleavable linkers. Accordingly, disulfide linkers are being preferred in many embodiments of the invention. These linkers are cleavable through disulfide exchange, which can occur under physiological conditions. Preferred heterobifunctional disulfide linkers include, but are not limited to, N-succinimidyl 3-(2-pyridyldithio)propionate (SPDP) (see, e.g., Carlsson et al. (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohexane-1-carboxylate (SMCC) (see, e.g., Yoshitake et al., (1979)), and N-succinimidyl 4-methyl-4-[2-(5-nitro-pyridyl)-dithio]pentanoate (SMNP) (see, e.g., U.S. Pat. No. 4,563,304). The most preferred linker molecules for use in the inventive composition are SPP, SMCC, and SPDB.

Other suitable linkers may include "non-cleavable" bonds, such as, but not limited to Sulfosuccinimidyl maleimidomethyl cyclohexane carboxylate (SMCC), which is a heterobifunctional linker capable of linking compounds with SH-containing compounds. Bifunctional and heterobifunctional linker molecules, such as carbohydrate-directed heterobifunctional linker molecules, such as S-(2-thiopyridyl)-L-cysteine hydrazide (TPCH), are also within the scope of the present invention (Vogel, 2004). The effector molecule, such as a maytansinoid, may be conjugated to the targeting antibody via a two reaction step process, including as a first step modification of the targeting antibody with a cross-linking reagent such as N-succinimidyl pyridyldithiopropionate (SPDP) to introduce dithiopyridyl groups into the targeting antibody. In a second step, a reactive maytansinoid having a thiol group, such as DM1, may be added to the modified antibody, resulting in the displacement of the thiopyridyl groups in the modified antibody, and the production of disulfide-linked cytotoxic maytansinoid/antibody conjugate (U.S. Pat. No. 5,208,020). However, one-step conjugation processes such as the one disclosed in United States Patent Publication 20030055226 to Chari et al are also within the scope of the present invention. In one embodiment of the present invention multiple effector molecules of the same or different kind are attached to a targeting antibody. As discussed elsewhere herein, the nature of the linkers employed may influence bystander killing (Kovtun et al., 2006). See also discussion of FIG. 13. See also U.S. Pat. Nos. 5,208,030; 5,416,064; 6,333,410; 6,441,163; 6,716,821; 6,913,748; 7,276,497 and US Application No. 2005/0169933 for method for preparing immunconjugates.

CC-1065 analogues or derivatives may be conjugated to the targeting agent via for example PEG linking groups as described in U.S. Pat. No. 6,716,821.

Calicheamicins may be conjugated to the targeting antibodies via linkers (U.S. Pat. No. 5,877,296 and U.S. Pat. No. 5,773,001) or according to the conjugation methods disclosed in U.S. Pat. No. 5,712,374 and U.S. Pat. No. 5,714,586. Another preferred method for preparing calicheamicin conjugates is disclosed in Unites States Patent Publication 20040082764. The immunoconjugates of the present invention may take the form of recombinant fusion proteins.

Operational association in form of an attachment with or without a linker is referred to herein as "functional attachment."

An immunoconjugate consisting essentially of certain components means in the context of the present invention that the antibody/immunoconjugate consists of the specified components and any additional materials or components that do not materially affect the basic characteristics of the antibody.

Figures 9A, 9B:
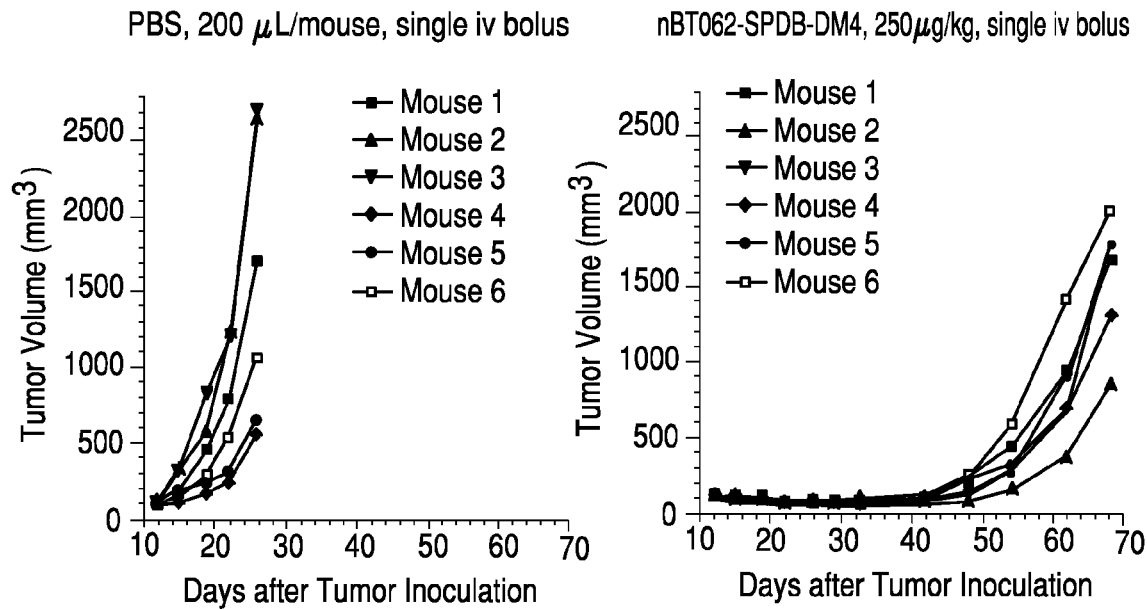
FIG. 9 shows tumor volumes for individual mice treated with (A) PBS, (B) nBT062-SPDB-DM4, (C) B-B4-SPP-DM1 or (D) nBT062-SPP-DM1 over time (days) post-inoculation with MOLP-8 tumor cells.
Figures 9C, 9D:
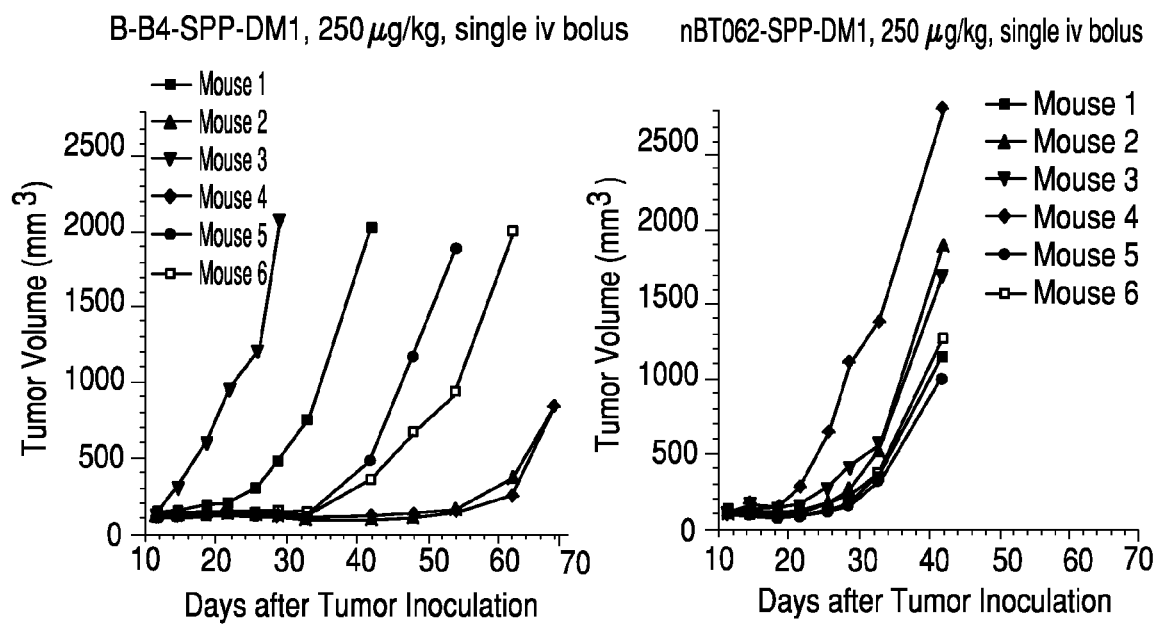

FIG. 9 shows in (C) and (D) the differences in homogenity of targeting/binding between immunoconjugates comprising murine antibody BB4 (BB4-SPP-DM1; FIG. 9C) and the engineered targeting antibody nBT062 (nBT062-SPP-DM1; FIG. 9D) based thereon. As can be seen from these graphs, results obtained with the immunoconjugate comprising the engineered targeting antibody are substantially more homogenous than the ones obtained with the immunoconjugates comprising the murine antibody. This is particulary notable since the antibody binding region of BB4 was not modified in nBT062. Thus, the immunoconjugate comprising the antibody binding region of the murine antibody, but no other parts of the murine antibody, showed properties that far exceeded results the person skilled in the art would have expected.

Some of the immunoconjugates of the present invention have an effector molecule that is sterically hindered, and contains a cleavable linker (HICL—hindered immunconjugate, cleavable linker). An unhindered counterpart (UI: unhindered immunoconjugate) of an immunoconjugate comprising an engineered targeting antibody against CD138 attached to an effector molecule via a cleavable linker (CL) and is described herein as UICL. The UICL is an immunoconjugate equivalent to the HICL comprising an engineered targeting antibody in which the effector molecule is, however, not sterically hindered. Examples of a pair of HICL/UICL are BT062 and nBT062-SPP-DM1. An unhindered counterpart of such an immunoconjugate comprising a non-cleavable linker (UINCL) refers to the equivalent immunoconjugate comprising an engineered targeting antibody in which the effector molecule is not sterically hindered and comprises a noncleavable linker. For BT062 (nBT062-SPDB-DM4), nBT062-SMCC-DM1 would constitute an example of such an unhindered counterpart comprising a non-cleavable linker (UNICL).

A growth of a tumor inhibiting activity (=tumor growth inhibiting activity) of an immunoconjugate is a relative measure. It describes the tumor growth inhibiting activity of a conjugate relative to the activity of the highest performing immunoconjugate whose activity is set as 100%. For example if the activity of the highest performing immunoconjugate, say, BT062, which causes a tumor growth delay (TGD) of 32 days, is set as 100%, the activity of, e.g., nBT062-DM1, which displays a tumor growth delay (TGD) of 18 days is calculated as follows:

Tumor Growth Inhibiting Activity=100×
($TGD_{nBT062-DM1}/TGD_{BT062}$), more generically:

Tumor Growth Inhibiting Activity=100×($TGD_{Sample}/TGD_{Reference}$).

Figure 11A:
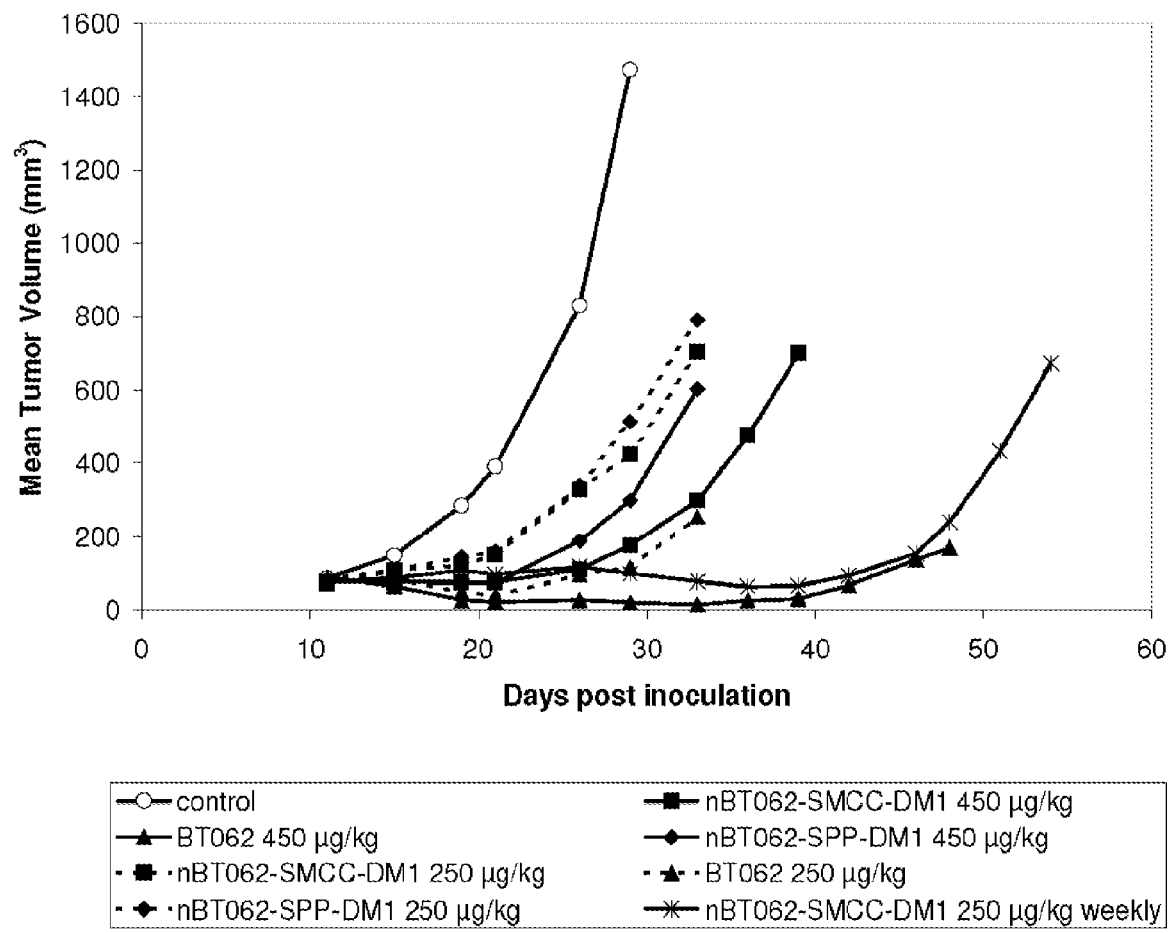
FIGS. 11A and B show the anti-tumor activity of nBT062-DMx against CD138+ MOLP-8 tumor cells in a bulky MOLP-8 tumor model in SCID mice. Tumor volume is given as mean (+/−SD) for each group.
Figure 11B:
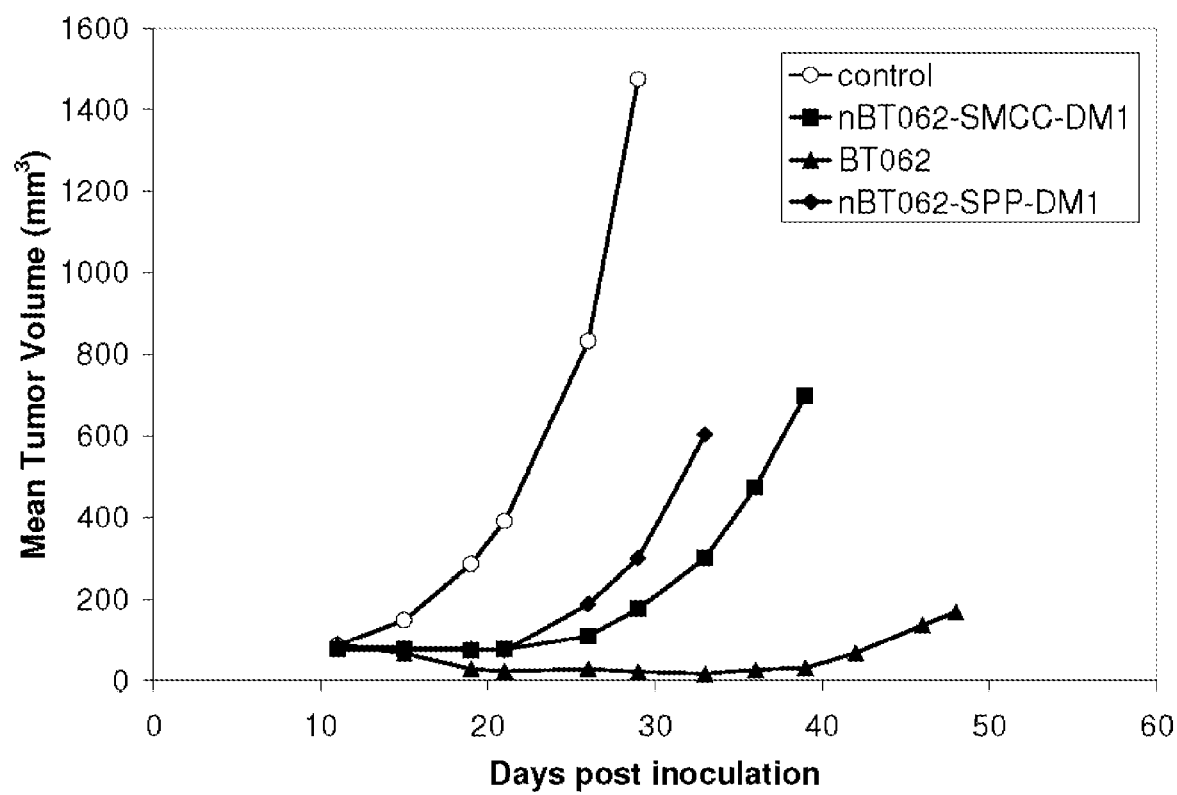

Table 6 provides suitable examples from the results depicted in FIG. 11B:

TABLE 6

Tumor growth delay (TGD) and % Activity of nBT062-DMx against MOLP-8 tumor xenografts in SCID mice based on treatment groups receiving a 450 µg/kg dose.

|  | TGD* (days) | % Activity** |
|---|---|---|
| PBS | 0 | 0 |
| nBT062-SMCC-DM1 | 18 | 56 |
| BT062 | 32 | 100 |
| nBT062-SPP-DM1 | 13 | 40 |

*Tumor growth delay in days (TGD) as mean time in days for treatment group to reach a predetermined size (160 mm$^3$) minus the mean time for the control group to reach this predetermined size.
**Tumor Growth Inhibiting Activity = 100 × (TGD$_{Sample}$/TGD$_{BT062}$). The activity of BT062 is defined to be 100%.

In the example provided in Table 6, BT062 provides a growth of a tumor inhibiting activity that exceeds that of its unhindered counterpart (nBT062-SPP-DM1) by 60%, and a growth of a tumor inhibiting activity that exceeds that of its unhindered counterpart immunoconjugate comprising a non-cleavable linker (nBT062-SMCC-DM1) by 44%.

As discussed above, certain drugs such as maytansinoids, while effective, are highly toxic, destroying in their native, i.e., unconjugated form, cells non-selectively. Linking the cytotoxic maytansinoid to an antibody can keep the drug inactive until it reaches the target cell (Lambert 2005). Several antibody-maytansinoid conjugates have undergone clinical development.

Phase I and II studies with IMGN901 (huN901-DM1, BB-10901) for treating CD56-positive solid tumors (small cell lung cancer and neuroendocrine cancers) were performed. In these studies IMGN901 was administered on 4 consecutive weeks every 6 weeks and was generally well tolerated (Fossella et al., 2005, Lorigan et al., 2006, McCann et al., 2007, Carter and Senter, 2008, Johnson et al. 2008). The antibody portion of the immunoconjugate, huN901, shows significant CDC or ADCC activity. The same immunoconjugate is investigated for treatment of CD56-positive multiple myeloma. In a phase I study administration of IMGN901 on 2 consecutive weeks every 3 weeks to patients with CD56-positive multiple myeloma who have failed established multiple myeloma treatments has shown preliminary evidence of safety as well as clinical activity. Eighteen patients were reported to have received IMGN901 (3 patients each at 40, 60, 75, 90, 112, and 140 mg/m$^2$/week). Preliminary PK results were reported to indicate an approximately linear relationship between dosing and observed maximal serum concentration. Interesting clinical activity has been observed with a tolerable safety profile. A confirmed minor response (MR) was documented in 3 heavily pretreated patients (1 patient each at 60, 90, and 112 mg/m$^2$/week) using the European Bone Marrow Transplant criteria. Durable stable disease was reported at doses of 60, 90, 112, and 140 mg/m$^2$/week (Chanan-Khan et al., 2007, Chanan-Khan et al., 2008). IMGN901 is also being investigated in a phase I study in solid tumors. The immunoconjugate is administered daily for 3 days every 3 weeks. Preliminary clinical activity has been noted in patients with small cell lung cancer, merkel cell carcinoma and other solid tumors. Dose escalation is ongoing.

MLN2704 (huJ591-DM1) is investigated for treating castration-resistant prostate cancer (Milowsky et al., 2006, Brand and Tolcher 2006). A Phase I trial of MLN2704 in patients with progressive metastatic castration-resistant prostate cancer investigated the safety profile, pharmacokinetics, immunogenicity, and antitumor activity of MLN2704 when administered once every four weeks. Results demonstrated that therapeutic doses of MLN2704 can be administered safely on a repetitive basis (Galsky et al., 2008). Parallel trials were performed with another DM1-immunoconjugate, namely bivatuzumab mertansine which targets CD44v6, which is expressed on head and neck carcinomas and other solid tumors. In the clinical trial with the most condensed administration schedule (weekly administration) binding to CD44v6 on skin keratinocytes mediated serious skin toxicity with a fatal outcome in one patient, which led to the termination of the development program of bivatuzumab mertansine (Tijink et al., 2006, Sauter et al., 2007, Rupp et al., 2007, Riechelmann et al., 2008).

CD44v6 is not only expressed on various cancer cells, but also in normal skin tissue and resembles in this respect CD138 which is also expressed not only on cancer cells but in normal skin tissue. Surprisingly, it was found that BT062 shows clinical efficacy without intolerable side effects like skin toxicity as found in bivatuzumab mertansine. See FIG. 23, which shows that repeated single doses BT062 of up to 160 mg/m$^2$ led to at least stable disease with manageable side effects. The results depicted in FIG. 23 also show that 10 repeated single doses of 20 mg/m$^2$ (treatment over more than 6 months), 5 repeated single doses of 40 mg/m$^2$, 5 repeated single doses of 80 mg/m$^2$, 6 repeated single doses of 160 mg/m$^2$, and 1 single doses of 200 mg/m$^2$ followed by 6 repeated single doses of 160 mg/m$^2$ (ergo, a total dose of 1160 mg/m$^2$) were well tolerated (patients associated with 003-005 and 002-012, and 002-011 are still in ongoing treatment).

CD138 is also expressed on normal blood cells and other cells, such as cells of the epithelium, whose destruction would lead to intolerable side effects. Irrespective of this, no dose limiting toxicity towards non-cancer/non-tumor cells expressing CD138 of any sort were found in the treatment regimes depicted in FIG. 23 up to 120 mg/m$^2$, while the maximum tolerable dose (MTD) was in this study determined to be 160 mg/m$^2$ and the maximum administered dose (MAD) was determined to be 200 mg/m$^2$. Dosages between 160 mg/m$^2$ and 200 mg/m$^2$ were not tested. Higher doses were generally not given in view of dose limiting toxicities (DLT) at 200 mg/m$^2$. However, it was observed that the DLT dose was still acceptable when administered with subsequent lower dosages such as dosages of 160 mg/m$^2$. A clinically non-significant toxicity against non cancer/non-tumor cells expressing CD138 (non-target cells expressing CD138) is referred to herein as "clinically acceptable toxicity" or "tolerable toxicity" against such cells and the respective organ(s). The respective amount of immunoconjugate administered is referred to herein as "tolerable amount". Thus, in one embodiment of the present invention, the immunoconjugate displays clinically acceptable toxicity towards such non-target cells expressing CD138, in particular cells of the epithelium expressing CD138, which are not detected by BT062 in the xenograft mouse model due to human specificity.

Clinically acceptable toxicity includes that an adverse reaction, up to a manageable or tolerable level, takes place. An adverse reaction is defined as an undesirable effect, reasonably associated with the use of a drug, here the immunoconjugate, which may occur as part of the pharmacological action of the drug or may be unpredictable in its occurrence. This definition does not include all adverse events observed during use of a drug, only those for which there is some basis to believe there is a causal relationship between the drug and the occurrence of the adverse event. Adverse reactions may include signs and symptoms, changes in laboratory parameters, and changes in other measures of critical body function, such as vital signs and ECG.

If a cell, such as a non-target cell especially a non-target cell (non-tumor cell) expressing CD138, is said to be "substantially unaffected" by the administration, in particular the administration of a certain dosage, of a compound, such as an immunoconjugate, means that any interaction that such a compound had with said non-target cell, resulted in no or a manageable/tolerable adverse reaction.

Phase I studies with the immunoconjugated form of trastuzumab (T-DM1) for treatment of HER2 over-expressing metastatic breast cancer are performed to investigate safety and pharmacokinetics of T-DM1 administered weekly or once every 3 weeks. In both studies AEs of grade 2 related to T-DM1 have been infrequent and manageable. Objective tumor responses have been observed at doses at or below the MTD (Burris et. al., 2006, Krop et al., 2007, Beeram et al., 2008, Holden et al., 2008). A phase II study investigating T-DM1 in HER2-positive metastatic breast cancer when administered once every 3 weeks has been initiated (Beeram et al., 2008, Carter and Senter, 2008, Holden et al., 2008). A Phase III clinical trial evaluating T-DM1 for second-line HER2-positive metastatic breast cancer and Phase II clinical trials evaluating T-DM1 for first-, second- and third-line HER2-positive metastatic breast cancer are ongoing. A Phase Ib clinical trial in combination with pertuzumab for HER2-positive metastatic breast cancer patients who have been progressed on Herceptin-based treatment is planned. Three phase I clinical trials have been completed with cantuzumab mertansine, a DM1-conjugate of the huC242 antibody that targets an antigen found on colorectal cancers and other C242-expressing cancers. Treatment with huC242-DM1 administered on a weekly basis as well as once every 3 weeks was found to be safe and tolerated (Rowinsky et al., 2002, Tolcher et al., 2003, Helft et al., 2004).

Four studies are investigating immunoconjugates using the thiol-containing DM4 maytansinoid, which is also a component of BT062:

An analog of cantuzumab mertansine, IMGN242 (huC242-DM4), was investigated in a phase I study in subjects with CanAg-expressing cancer (Tolcher et al., 2006). Subjects received a single IV infusion of IMGN242 once every 3 weeks with a dose ranging from 18 to 297 mg/m$^2$. Dose-limiting toxicity was experienced by 2 of 6 subjects treated at the 223 mg/m$^2$ dose level during their second cycle of treatment. The drug was well tolerated at the 168 mg/m$^2$ level and did not induce any detectable antibody response (Mita et al., 2007). Based on first safety results from the Phase I study, a Phase II study was initiated to evaluate IMGN242 for treating CanAg-expressing gastric cancer at the dose of 168 mg/m$^2$ (Sankhala et al., 2007). Forty-five patients have been treated with IMGN242 in two clinical trials. Based on the safety and thorough clinical pharmacokinetc (PK)/pharmacodynamic (PD) analyses, the Phase II study was amended to treat patients with low plasma CanAg levels at the dose of 126 mg/m$^2$ and patients with high plasma CanAg levels at 168 mg/m$^2$ (Qin et al. 2008). A phase I study with huMy9-6 antibody conjugated to DM4 (AVE9633) was also performed for the treatment of subjects with CD33-positive Acute Myeloid Leukemia (AML). The treatment regimen consisted of IV infusions once every 3 week using a dose range of 15 to 260 mg/m$^2$. Neither associated myelosuppression nor responses have been noted in a single-dose study (Giles et al., 2006). A second phase I study investigating AVE9633 with a treatment regimen consisting of IV infusions on day 1 and day 8 of a 28-day cycle also shows that AVE9633 was well tolerated, and shows evidence of antileukemia activity including 1 subject with complete response (inadequate platelet response, transfusion dependent) lasting for at least 4 months (Legrand et al., 2007). Two further DM4-immunoconjugates (SAR3419 and BIIB015) have entered into Phase I clinical trials.

Also, it is known from other immunoconjugates, such as Mylotarg which is targeting CD33, that the activity of the immunoconjugate may not be sufficient to treat patients at low doses. This problem has been alleviated by, e.g., administration of recombinant human granulocyte colony-stimulating factor (rhG-CSF) to sensitize CD33 expressing target cells (Fianchi et al., Annals of Oncology 2008 19(1):128-134).

The above studies demonstate that the responses to different immunoconjugates, in particular maytansinoid (such as DM1 or DM4) containing immunoconjugates, vary widely. The BT062 trials in human subjects showed tolerable toxicity against non-cancer cells expressing CD138 at different stable disease doses, especially at doses up to 160 mg/m$^2$.

The immunoconjugate described herein can be administered in combination with cytotoxic agents. These combination are referred to herein as anticancer combinations.

Currently, many combinations of in particular anti-myeloma drugs are investigated in clinical trials. The purpose of the use of a combination is generally either to enhance effectiveness, to overcome a refractory phenotype, e.g., of myeloma cells, to reduce side effects due to the use of lower concentrations of one of the combination partners or a combination thereof. Using a low dose, for example, of lenalidomide plus a low dose of dexamethasone was shown to reduce toxicity (Rajkumar et al., 2010).

Especially in patients with relapsed or refractory multiple myeloma several drug combination are and have been investigated.

A standard example for combined chemotherapeutics represents the triple combination of vincristine, dexamethasone, doxorubicin (VAD Regimen).

Proteasomal inhibitors such as bortezomib have been combined with myeloma drugs such as melphalan and prednisone (VMP). This combination resulted in a complete response rate of 16% and an overall response rate of 89% (Mateos et al., 2006).

Bortezomib has been also approved for use in combination with liposomal doxorubicin for relapsed or refractory patients (Ning et al., 2007).

Bortezomib is investigated in several clinical studies for use in combination with dexamethasone, melphalan, prednisone and/or thalidomide.

Bortezomib is also under investigation combined with liposomal doxorubicin, cyclophosphamide and dexamethasone in multiple myeloma patients. Combinations with Vorinostat are currently under investigation aiming at resensitizing patients to bortezomib which are refractory to this drug.

Thalidomide, which is administered orally, has been combined with melphalan/prednisone (MPT) (Facon et al., 2006) or dexamethasone or bendamustine (Ponisch et al., 2008).

Moreover, lenalidomide, an immunomodulatory drug, used in combination with dexamethasone, resulted in a prolonged time to tumor progression and increased survival compared to dexamethasone alone (Weber et al., 2006). Lenalidomide combined with dexamethasone has been also studied in newly diagnosed patients (Rajkumar et al., 2005) as well as the combination with melphalan/prednisone (RMP) (Palumbo et al., 2006).

US Patent Publication 2010/0028346 to Lutz et al., describes synergistic effects of certain immunoconjugates with chemotherapeutic agents.

In the present context, one goal of employing combinations are a reduction in the effective doses of the immunconjugate of the present invention, lowering their side effects and opening new therapeutic windows with acceptable side effects. Another goal is to reduce the effective dose of previously employed cytotoxic agents such as VELCADE or lenalidomide and preferably reducing the side effects of these agents. Similarly, the dosages Positive consequences include, but are not limited to, prolongation of treatment, higher dosages, other application schedules, better and more sustained response to treatment.

Patients displaying a refractory phenotype towards drugs such as lenalidomide, melphalan (study ongoing) might be rendered sensitive again by the use of immunoconjugates according to the present invention.

The term "cytotoxic agents" comprises "cytotoxic/cancer drugs" including chemotherapeutic agents, in particular chemotherapeutic agents that are generally used in rapidly dividing cells, namely:

Alkylating agents such as nitrogen mustards (e.g. melphalan, cyclophosphamide, mechlorethamine, uramustine, chlorambucil, ifosfamide) or nitrosureas (e.g. carmustine, lomustine, streptozocin) or alkylsulfonates;

Alkylating like agents such as cisplatin, carboplatin, nedaplatin, oxaliplatin; or non classical alkylating agents such as tetrazines, dacarbizine, procarbazine, altretamine Anthracyclines such as doxorubicin and liposomal doxorubicin (DOXIL)

Alkaloids such as vincristine

The term "cytotoxic agents" also comprises immunomodulatory drugs (ImiDs) such as thalidomide (or analoges), lenalidomide (CC-5013), pomalidomide, actimid, which are used for myeloma therapy in view of their pleitropic immunomodulatory properties. They commonly display anti-inflammatatory activity by inhibition of TNF alpha production, but display also anti-angiogenic activity and immunomodulatory properties such as T-cell costimulation and influence on regulatory T-cells (Quach et al., 2010).

The term "cytotoxic agent" also comprises steroids, such as, but not limited to, dexamethasone and prednisone as well as proteasomal inhibitors such as bortezomib (VELCADE) or carfilzomib which induces the activation of programmed cell death in neoplastic cells dependent upon suppression of pro-apoptotic pathways. Further potent cytotoxic agents, include etoposide, which inhibits the enzyme topoisomerse II, cytarabine, which, upon conversion damages DNA when a cell cycle holds in the S phase (synthesis of DNA) and thus in particular affects rapidly dividing cells such as cancer cells. In addition, microtubule inhibitory agents such as vinca alkaloids, taxanes (as described above in the context of effector molecules) can also serve as cytotoxic agents according to the present invention.

Also included in the definition are kinase inhibitor such as sorafenib or HDAC (histone deacetylase) inhibitors such as romidepsin as well as growth inhibitory agents, anti-hormonal agents, anti-angiogenic agents, cardioprotectants, immunostimulatory agents, immunosuppressive agents, angiogenesis inhibitors, protein tyrosine kinase (PTK) inhibitors.

Further included in this definition are antibody based cytotoxic agents including immunoconjugates and antibodies that have an art recognized cytotoxic effect. Anti-CD40 is a preferred antibody. Other antibodies include, but are not limited to, e.g., AVASTIN (bevacizumab) or MYELOMACIDE (milatuzumab).

Thalomide (α-(N-phthalimido) glutarimide; thalidomide), is an immunomodulatory agent. The empirical formula for thalidomide is $C_{13}H_{10}N_2O_4$ and the gram molecular weight is 258.2. The CAS number of thalidomide is 50-35-1. It appears to have multiple actions, including the ability to inhibit the growth and survival of myeloma cells in various ways and to inhibit the growth of new blood vessels.

Lenalidomide (REVLIMID) is a derivative of thalidomide representing the second generation of immunomodulatory compounds (ImiDs) which were initially developed as inhibitors of TNF alpha. Effects of lenalidomide include growth arrest or apoptosis, abrogation of myeloma cell adhesion to bone marrow stromal cells and modulation of cytokines promoting cell growth, survival and drug resistance of myeloma cells (Morgan et al., 2006). Lenalidomide is effective in patients refractory to thalidomide. In addition to effects on immune cells, ImiDs such as lenalidomide were suggested to cause cell cycle arrest in G0/G1 phase. In addition it is assumed that ImiDs downregulate cell adhesion receptors (VLA-4, VLA-5, CD138) (Quach et al., 2010).

A downregulation of CD138 would be expected to cause a reduced binding of any CD138 targeting agent, such as BT062, to target cells.

Proteasomal inhibitors can be divided into further subgroups:

a) naturally occurring peptide derivatives which have a C-terminal epoxy ketone structure, beta-lactone derivatives, aclacinomycin A, lactacystin, clastolactacystin; and b) synthetic inhibitors (comprising modified peptide aldehyds, alpha, beta epoxyketon structures, vinyl sulfones, boric acid residues, pinacolesters. A preferred proteasomal inhibitor of the present invention is bortezomib (PS 341; VELCADE, see discussion below). One of the proposed mechanisms suggests that proteasomal inhibition may prevent degradation of pro-apoptotic factors, permitting activation of programmed cell death in neoplastic cells dependent upon suppression of pro-apoptotic pathways. In addition, bortezomib causes G2/M cell cycle arrest (Wang et al., 2009). Thus, bortezomib might interfere with anti-mitotic agents which are part of the immunconjugate of the present invention, e.g., with the effect of maytansinoid DM4, which acts also at this cell cycle phase. Furthermore, PARP (Poly(ADP-ribose) Polymerase) cleavage, which takes part in apoptosis, is also affected by both DM4 and bortezomib. Accordingly, the combination of an immunoconjugate comprising an anti-mitotic agent and a proteasomal inhibitor displaying the features of bortezomib do not conform with the general guidelines set forth previously to obtain synergistic effects (Takimoto et al, 2009).

VELCADE (bortezombid) is a proteasome inhibitor used to treat mutiple myeloma. It is believed that VELCADE acts on myeloma cells to cause cell death, and/or acts indirectly to inhibit myeloma cell growth and survival by acting on the bone microenvironment. Without being limited to a specific theory or mode of action, VELCADE thus disrupts normal cellular processes, resulting in proteasome inhibition that promotes apoptosis.

Dexamethasone is a synthetic glucocorticoid steroid hormone that acts as an anti-inflammatory and immunosuppressant. When administered to cancer patients, dexamethasone can counteract side effects of cancer therapy. Dexamethasone can also be given alone or together with other anticancer agents, including thalidomide, lelinalidomide, bortezomib, adriamycin or vincristine.

Substances for treatment, which may be used in combination with BT062 also include immunomodulatroy agents (e.g. thalidomide, and lenalidomide, and pomalidomide), proteasome inhibitors (e.g. bortezomib and carfilzomib), steroids (e.g. dexamethasone), alkylating agents and high-dose chemotherapy, combinations (e.g. Melphalan and Prednisone (MP), Vincristine, doxorubicin (Adriamycin), and dexamethasone (VAD)), and bisphosphonates.

The term "in combination with" is not limited to the administration at exactly the same time. Instead, the term encompassed administration of the immunoconjugate of the present invention and the other regime (e.g. radiotherapy) or agent, in particular the cytotoxic agents referred to above in a sequence and within a time interval such that they may act together to provide a benefit (e.g., increased activity, decreased side effects) that is increased compared to treatment with only either the immunoconjugate of the present invention or, e.g., the other agent or agents. It is preferred that the immunoconjugate and the other agent or agents act additively, and especially preferred that they act synergistically. Such molecules are suitably provided in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration. As used in the context of the present invention "co-administration" refers to administration at the same time as the immunoconjugate, often in a combined dosage form.

Synergistic effects, that are effects of two components such as an immunoconjugate and a cytotoxic agent, that exceed a strictly additive effect. These synergistic effects might be counteracted by a number of factors further discussed below.

Synergism has been calculated as follows (Yu et al., 2001; Gunaratnam et al., 2009):

$$\text{RATIO}(r) = \text{expected FTV(combination)/observed FTV(combination)}$$

FTV: Fractional tumor volume=mean tumor volume (test)/mean tumor volume (control)

A ratio>1 is regarded as synergistic, whereas r<1 is less than additive.

The ratio (r) is, when above 1, also referred to herein as "SYNERGY RATIO."

The ACTIVITY RATING is another measurement for the effects of a combination. This rating is based on the $\text{Log}_{10}$ cell kill $$\text{Log}_{10} \text{ cell kill} = (T-C)/T_d \times 3.32$$

where (T–C) or tumor growth delay, is the median time in days required for the treatment group (T) and the control group (C) tumors, to reach a predetermined size (600 mm³). $T_d$ is the tumor doubling time, based on the median tumor volume in the control mice, and 3.32 is the number of cell doublings per log of cell growth. (Bissery et al., 1991). A $\text{Log}_{10}$ cell kill of higher than 2.8 indicates that the combination is highly active, a $\log_{10}$ cell kill of 2.0-2.8 indicates that the combination is very active, a $\log_{10}$ cell kill of 1.3-1.9 indicates that the combination is active, a $\log_{10}$ cell kill of 0.7-1.2 indicates that the combination is moderately active and a $\log_{10}$ cell kill of less than 0.7 indicates that the combination is inactive.

Selection of Drug Combination Partners

A set of guidelines for designing combination chemotherapy regimens has been developed (Takimoto, 2006). Abiding to these guidelines will generally increase the chances that a particular combination realizies at least one of the three most important theoretical advantages of combination chemotherapy over single-agent therapy:
1.) Maximize cell kill while minimizing host toxicities by using agents with noninterfering dose-limiting toxicities;
2.) Increasing the range of drug activity against tumor cells with endogenous resistance to specific types of therapy; and
3.) Preventing or slowing the development of newly resistant tumor cells.

Recommended principles to consider for selecting agents for use in combination chemotherapy regimens comprise:
a) selecting drugs known to induce complete remission as single agents,
b) selecting drugs with different mode of actions and with additive or synergistic cytotoxic effects should be combined,
c) selecting drugs with different dose limiting toxicities,
d) selecting drugs with different patterns of resistance to minimize cross resistance.

Also, drugs should be administered at their optimal dose and schedule (e), and the administration should be performed at consistent intervals, whereas the treatment free period should be as short as possible to allow for recovery of the normal tissue (f) (Takimoto et al, 2009).

Synergistic effects or just addititve effects can be counteracted by a variety of factors: For example, the components of an anticancer combination might inactivate each other, e.g., by binding each other. In addition, one component of an anticancer combination might interfere with the mode of action of another component. For example: Lenalidomide downregulates cell adhesion receptors such as CD138, which is the target of the immunoconjugate of present invention (Quach et al., 2010). The proteasome inhibitor bortezomib causes G2/M cell cycle arrest (Wang et al., 2009) which is also affected by anti-mitotic agents. Thus, if the effector molecule of the immunoconjugate is a maytansinoid, it will share a target for action with bortezombid, which is considered disadvanageous.

Dosages, routes of administration and recommended usage of the cytotoxic agents according of the present invention which have been widely used in cancer therapy are known in the art and have been described in such literature as the Physician's Desk Reference (PDR). The PDR discloses dosages of the agents that have been used in treatment of various cancers. The dosing regimen and dosages of these cytotoxic agents that are effective will depend on the particular cancer being treated, the extent of the disease and other factors familiar to the physician of skill in the art and can be determined by the physician. The 2006 edition of the Physician's Desk Reference (PDR) discloses the mechanism of action and preferred doses of treatment and dosing schedules for thalidomide (p 979-983), VELCADE (p 2102-2106) and melphalan (p 976-979). One of skill in the art can review the PDR, using one or more of the following parameters, to determine dosing regimen and dosages of the chemotherapeutic agents and conjugates that can be used in accordance with the teachings of this invention. These parameters include:
1. Comprehensive index according to a) Manufacturer b) Products (by company's or trademarked drug name) c) Category index (for example, "proteasome inhibitors", "DNA alkylating agents," "melphalan" etc.) d) Generic/chemical index (non-trademark common drug names).
2. Color images of medications 3. Product information, consistent with FDA labeling including a) Chemical information b) Function/action c) Indications & Contraindications d) Trial research, side effects, warnings.

As the person skilled in the art will appreciate, the amino acid sequence of the preferred engineered targeting antibody portion of an immunoconjugate, nBT062, can be varied without loss of the functionality of the antibody portion in targeting CD138. This is in particular true when the heavy chain variable region CDR3 comprising amino acid residues 99 to 111 of SEQ ID NO: 1, and light chain variable region CDR3 comprising amino acid residues 89 to 97 of SEQ ID NO: 2, respectively of the antigen binding region (ABR). Advantageously, the heavy chain variable region CDR1 and CDR2 comprising amino acid residues 31 to 35 and 51 to 68 of SEQ ID NO: 1, and/or (b) light chain variable region CDR1 and CDR 2 comprising amino acid residues 24 to 34 and 50 to 56 of SEQ ID NO: 2, respectively of the antigen binding region (ABR) are also maintained.

The term "sequence identity" refers to a measure of the identity of nucleotide sequences or amino acid sequences. In general, the sequences are aligned so that the highest order match is obtained. "Identity", per se, has recognized meaning in the art and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., SIAM J Applied Math 48:1073 (1988)).

Whether any particular nucleic acid molecule is at least 50%, 60%, 70%, 75%, 80%, 85%, 90%, 95%, 96%, 97%, 98% or 99% identical to, for instance, the nBT062 nucleic acid sequence, or a part thereof, can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments.

Whether the amino acid sequence is at least 50%, 60%, 70%, 75%, 80%, 85%, 90%, 95%, 96%, 97%, 98% or 99% identical to, for instance SEQ ID NO:1 or SEQ ID NO:2, or a part thereof, can be determined conventionally using known computer programs such the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences.

When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleic acid or amino acid sequence and that gaps in homology of up to 5% of the total number of nucleotides in the reference sequence are allowed.

If, in the context of the present invention, reference is made to a certain sequence identity with a combination of residues of a particular sequence, this sequence identity relates to the sum of all the residues specified.

As discussed above, BT062 is an immunoconjugate comprising the CD138 targeting chimeric antibody nBT062 that is attached via a linker, here SPDB, to the cytostatic maytansinoid derivative DM4. A chemical representation of BT062 is provided in FIGS. 1 and 2. Immunoconjugates comprising nBT062 and a maytansinoid effector molecule are often characterized in terms of their linker and maytansinoid effector, e.g., nBT062-SMCC-DM1, is an immunoconjugate comprising nBT062, SMCC (a "noncleavable" linker containing a thioester bond) and DM1 as an effector. More generically, an immunoconjugate containing nBT062 and an effector molecule may also be described as nBT062-linker-effector or just as nBT062-effector (nBT062N, wherein N is any effector described herein (see also US Patent Publication 20090232810).

In one embodiment, BT062 binds to CD138-positive multiple myeloma cells. Once the target cell internalizes and/or releases the immunoconjugate, DM4 is released from the targeting molecule, thereby restoring its original cytotoxic potency of DM4. Thus, BT062 provides a targeted antibody payload (TAP), wherein the functional attachment of DM4 to nBT062 keeps the cytotoxic drug inactive until it reaches/is internalized into the CD138 expressing target cell.

Data from nonclinical studies investigating cytotoxicity of BT062 in multiple myeloma cells and animal models discussed herein demonstrate that BT062 has highly significant antimyeloma activity at doses that are well tolerated in a murine model.

A phase I open-label, dose escalation, repeated single dose study in patients with relapsed or relapsed/refractory multiple myeloma is being conducted.

The immunoconjugates disclosed herein can be administered by any route, including intravenously, parenterally, orally, intramuscularly, intrathecally or as an aerosol. The mode of delivery will depend on the desired effect. A skilled artisan will readily know the best route of administration for a particular treatment in accordance with the present invention. The appropriate dosage will depend on the route of administration and the treatment indicated, and can readily be determined by a skilled artisan in view of current treatment protocols.

Pharmaceutical compositions containing the immunoconjugate of the present invention and/or any further cytotoxic agent as active ingredients can be prepared according to conventional pharmaceutical compounding techniques. See, for example, Remington's Pharmaceutical Sciences, 17th Ed. (1985, Mack Publishing Co., Easton, Pa.). Typically, effective amounts of active ingredients will be admixed with a pharmaceutically acceptable carrier. The carrier may take a wide variety of forms depending on the form of preparation desired for administration, for example, intravenous, oral, parenteral, intrathecal, transdermal, or by aerosol.

The anticancer combinations of the present invention can preferably be either in the form of pharmaceutical compositions or in the form of kits comprising the components of the anticancer combination in different containers. The components of the kit are usually administered in combination with each other, often they are co-administered either in a combined dosage form or in separate dosage forms. Such kits can also include, for example, other components, a device for administering the components or combination, a device for combining the components and/or instructions how to use and administer the components.

For oral administration, the immunoconjugate and/or cytotoxic agent can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent must be stable to passage through the gastrointestinal tract. If necessary, suitable agents for stable passage can be used, and may include phospholipids or lecithin derivatives described in the literature, as well as liposomes, microparticles (including microspheres and macrospheres).

For parenteral administration, the immunoconjugate and/or cytotoxic agent may be dissolved in a pharmaceutical carrier and administered as either a solution or a suspension. Illustrative of suitable carriers are water, saline, phosphate buffer solution (PBS), dextrose solutions, fructose solutions, ethanol, or oils of animal, vegetative or synthetic origin. The carrier may also contain other ingredients, for example, preservatives, suspending agents, solubilizing agents, buffers and the like. When the unconjugated targeting agent and/or immunoconjugate and/or cytotoxic agent are being administered intracerebroventricularly or intrathecally, they may also be dissolved in cerebrospinal fluid.

Dosages administered to a subject may be specified as amount, per surface area of the subject (which include humans as well as non-human animals). The dose may be administered to such a subject in amounts, preferably, but not exclusively from about 5 mg/m$^2$ to about 300 mg/m$^2$, including about 10 mg/m$^2$, about 20 mg/m$^2$, about 40 mg/m$^2$, about 50 mg/m$^2$, about 60 mg/m$^2$, about 80 mg/m$^2$, about 100 mg/m$^2$, about 120 mg/m$^2$, about 140 mg/m$^2$, about 150 mg/m$^2$, about 160 mg/m$^2$ and about 200 mg/m$^2$. The immunoconjugates are suitably administered at one time or over a series of treatments. In a multiple dose regime these amounts may be administered once a day, once a week or once every two weeks. Loading doses with a single high dose or, alternatively, lower doses that are administered shortly after one another followed by dosages timed at longer intervals constitute a preferred embodiment of the present invention. In a preferred embodiment, the timing of the dosages are adjusted for a subject so that enough time has passed prior to a second and/or any subsequent treatment so that the previous dose has been metabolized substantially, but the amount of immunoconjugate present in the subject's system still inhibits, delays and/or prevents the growth of a tumor. An exemplary "repeated single dose" regime comprises administering doses of immunoconjugate of about 10, 20, 40, 60, 80, 100, 120, 140, 160, 180 or 200 mg/m$^2$ once every three weeks. Alternatively, a high initial dose of, e.g., 160 mg/m$^2$ may be followed by a one, two, or tri-weekly maintenance dose of, e.g., about 20 mg/m$^2$. Other combinations can be readily ascertained by the person skilled in the art. However, other dosage regimens may be useful. The progress of this therapy is easily monitored by known techniques and assays. Dosage may vary, amongst others, depending on whether they are administered for preventive or therapeutic purposes, the course of any previous therapy, the patient's clinical history, the patient's disease status, the patient's tumor load, the patient's genetic predisposition, the patient's concomitant diseases, the disease stage upon first treatment and response to the targeting agent/immunoconjugate, the side effects experienced by the patient and the discretion of the attending physician.

The present invention is, in one embodiment, directed to a low dose administration regime with rapid plasma clearance and, in another embodiment, to a low dose administration regime without rapid plasma clearance for administering immunoconjugates as set forth herein. The first regime provides generally less than 160 mg/m$^2$, preferably not more than about 120 mg/m$^2$, not more than about 100 mg/m$^2$, not more than about 80 mg/m$^2$, including no more than about 40 mg/m$^2$, more preferably no more than about 20 mg/m$^2$, even more preferably no more than about 10 mg/m$^2$ in a given three week interval (cycle). The 10 mg/m$^2$ to 120 mg/m$^2$ range translates to an average daily dose of about 475 µg/m$^2$ to about 5.71 mg/m$^2$, or an average weekly dose of about 3.33 mg/m$^2$ to about 40 mg/m$^2$. Thus, average daily doses of about 400 µg/m$^2$ to about 5.71 mg/m$^2$, including about 500 µg/m$^2$, about 1 mg/m$^2$, about 2 mg/m$^2$ and about 3 mg/m$^2$, 4 mg/m$^2$, 5 mg/m$^2$ are part of the present invention and so are average weekly dose of about 3 mg/m$^2$ to about 40 mg/m$^2$, including about 5 mg/m$^2$, about 10 mg/m$^2$, about 15 mg/m$^2$, about 20 mg/m$^2$, about 25 mg/m$^2$, 30 mg/m$^2$ or 35 mg/m$^2$. This low dose administration schemes is associated with rapid plasma clearance at the in early elimination phase, that is, any time during administration up to two hours after administration is completed. What distinguishes the low dose administration regime from other low dose regimes is the rapid plasma clearance, which is defined by a measured cmax during that period that is preferably less than 55%, less than 50%, less than 40%, or less than 30% of the theoretical cmax.

Low dose administration regimes are, at higher levels, accompanied by less rapid plasma clearance, that is by plasma clearances that exceed 55%, often 60%, 70% 80% or 90% of the theoretical cmax value, which are referred to herein as moderate (equal or >55%, but <80% of the theoretical cmax value) or slow plasma clearance (equal or >80% of the theoretical cmax value). At these clearances it was surprisingly found that, despite the relative high concentration of immunoconjugate in the plasma, these administration regimes were still associated with tolerable toxicities. This is despite the fact that expression levels of CD138 on non target cells that express CD138, e.g., cells of vital organs, such as the epithelium which are not target of any treatment, are also relative high in CD138 (immunohistochemistry analyses with the CD138 antibody BB4 showed that the reactivity to this antibody to the epithelium matched that of MM patient plasma cells (US Patent Publication 20070183971)). Expression levels of CD138 on target and non target cells that produce equal scores (e.g. plus three as in the above example) in immunhistochemistry analyses are referred to herein comparable expression levels and are part of the present invention. In an alternative embodiment, the expression levels on target cells were actually consistently below that of the epithelium (e.g., plus one or plus two vs. plus three for the epithelium). Some tumor target cells show mixed expression levels, such as, some cells have an expression level of plus two and some an expression level of plus three. The mean of a representative number of cells (such as 100 randomly sampled cells) will determine whether these tumor target cells in question fall uder the definition of having expression levels comparable or below that of epithelium. These treatment regimes are generally above 120 mg/m$^2$, but below 200 mg/m$^2$ in a given three week interval (cycle), which translates to a daily doses of about 5.71 mg/m² to about 9.52 mg/m² or an average weekly dose of about 40 mg/m² to about 66.67 mg/m².

Figure 25:
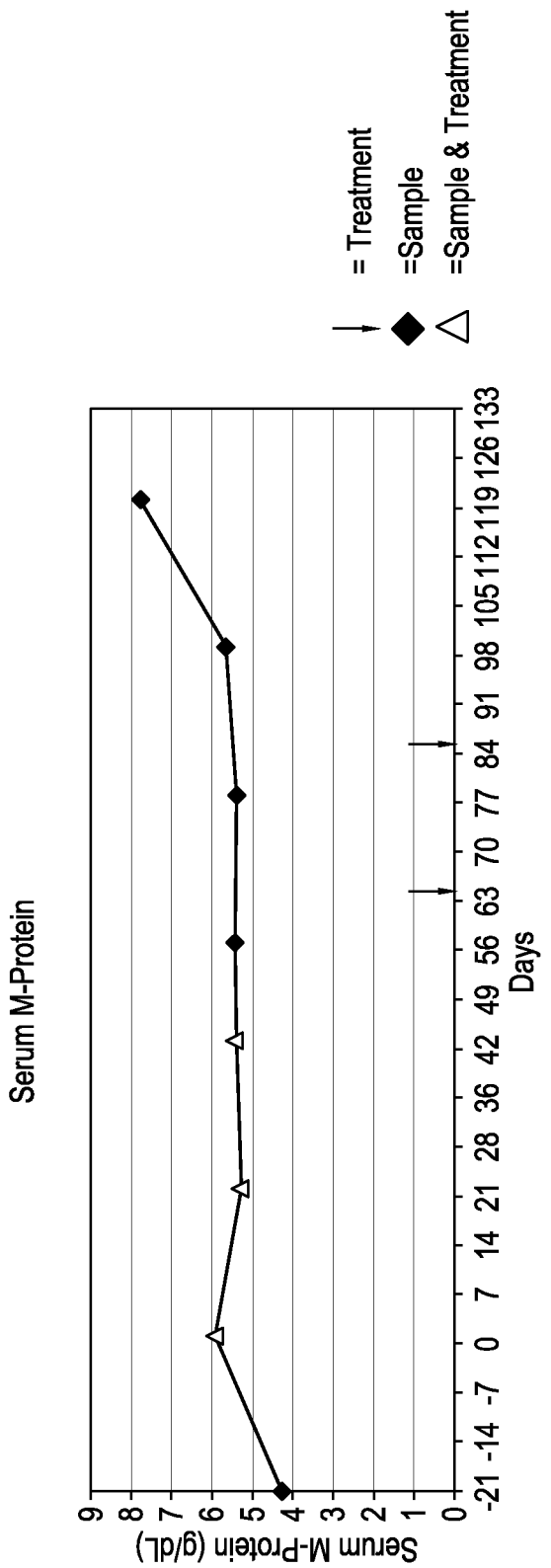
FIG. 25 shows the level of serum M-protein measured for a patient receiving 40 $mg/m^2$ at three weeks intervals. Days −21 to 119 are shown.

With respect to Patient 001-006 it was noticeable, that this patient had disease progression only after the termination of the treatment, reflecting the efficacy of BT062 administration (FIG. 25).

A repeated single dose refers to a sequence of administrations, wherein the administration following an administration is regarded to be independent of this preceding administration. Thus, in the present context, the level of immunoconjugate in a subject's blood can be regarded as equal after each administration. Each time the immunoconjugate is administered, it is expected that equal levels of immunconjugate are initially present in the blood.

Administration intervals between the "single doses" of the repeated single doses are defined according to the theoretically calculated half life of an isotype of an immunoconjugate, in the case of BT062, IgG4.

In general, the half life of therapeutic antibodies depends mainly on the antibody characteristics/its structural features (e.g. binding to Fc receptors) and the target. For example, the binding affinity of the Fc part to the neonatal receptor FcRn is affecting the half life. By binding to FcRn in endosomes, the antibody is salvaged from lysosomal degradation and recycled to the circulation, which prolongs the half life. For an IgG4 a half life of 15.6 (+/−4.5) days (Alyanakian et al., 2003; Salfeld et al., 2007) has been reported. In the study referenced herein, a "repeated single dose" has been chosen that has administration intervals of three weeks. However, about three weeks, about four weeks, but also about five or about six weeks are alternative intervals for repeated single doses. A reference to "about" refers in the context of three weeks to +/−96 hours and in the context of four to six weeks to +/−120 hours.

The progress of the therapy is easily monitored by known techniques and assays. Dosage may vary, amongst others, depending on whether they are administered for preventive or therapeutic purposes, the course of any previous therapy, the patient's clinical history, the patient's disease status, the patient's tumor load, the patient's genetic predisposition, the patient's concomitant diseases, the disease stage upon first treatment and response to the targeting agent/immunoconjugate, the side effects experienced by the patient and the discretion of the attending physician.

The advantages of a low dose regime are wide-ranging. However, the probably most significant advantage is minimizing the risk of adverse side effects. While immunoconjugates generally permit sensitive discrimination between target and normal cells, resulting in fewer toxic side effects than most conventional chemotherapeutic drugs, many immunoconjugates are still not completely free of side effects. Despite superior targeting, the antigen of interest is generally also expressed on non-cancer cells whose destruction during therapy can lead to adverse side effects. In the case of CD138, the antigen is in particular expressed on epithelial cells. Also, the immunoconjugate might undergo processing within the body that is unrelated to the procession in or at a target cell and a certain percentage of effector molecule might be released at locations remote from the target cells leading to toxic side effects.

Surprisingly, it was shown that the immunoconjugate of the present invention, was effective at low doses, while displaying clinically acceptable toxicities. Low doses in the present invention refer to dosages up to 200 mg/m². At doses up to at least 120 mg/m² but in any event at doses of less than 160 mg/m², the tested immunoconjugate of the present invention also showed rapid plasma clearance in human subjects. Tables 7 and 8 show the clearance observed.

TABLE 7

Plasma concentrations after end of infusion and effective cmax mean values of BT062 from plasma obtained in patients having received a single dose/repeated single dose BT062 (first and fourth cycle). Repeated dose administration in cycles of 21 days. Cmax values were obtained between 0 and 2 hours post infusion. Administration cycles: cycle 1: day 1, cycle 2: day 22; cycle 3: day 43; cycle 4: day 64 etc. n.a. data not available

| | plasma level of BT062 (µg/ml) human | | |
|---|---|---|---|
| dosage BT062 (mg/m²) | theoretical cmax | effective cmax (cycle 1) mean (lowest; highest) | effective cmax (cycle 4) mean (lowest; highest) |
| 10 | 7 | 1.11 | n.a. |
| 20 | 14 | 2.9 (1.66; 4.44) | 7.06 (6.79; 7.34) |
| 40 | 27 | 4.31 (0.97; 9.86) | 2.51 (1.02; 3.68) |
| 80 | 54 | 18.8 (13.4; 23.6) | 14.2 (7.4; 21) |
| 120 | 81 | 21.4 (15.1; 28.7) | n.a. |
| 160 | 109 | 81.2 (73.7; 85.5) | 77.4 |
| 200 | 136 | 82.0 (68.0; 102.4) | n.a. |

TABLE 8

| | | plasma level of BT062 (µg/ml) human | | | |
|---|---|---|---|---|---|
| Dosage BT062 (mg/m²) | theoretical cmax | effective cmax (cycle 1) | percentage of theoretical cmax (n) | effective cmax (cycle 4) | percentage of theoretical cmax (n) |
| 10 | 7 | 1.1 | 15% (3) | n.a. | n.a. |
| 20 | 14 | 2.9 | 20% (4) | 7.06 | 49% (2) |
| 40 | 27 | 4.31 | 16% (3) | 2.51 | 9% (3) |
| 80 | 54 | 18.8 | 34% (3) | 14.2 | 26% (2) |
| 120 | 81 | 21.4 | 26.5% (3) | n.a. | n.a. |
| 160 | 109 | 81.2 | 74.5% (4) | 77.4 | 71% (1) |
| 200 | 136 | 82.0 | 60% (3) | n.a. | n.a | n.a. data not available
n: number of patients
Effective cmax mean values of BT062 from plasma obtained in patients having received a single dose/repeated single dose BT062 (first and fourth cycle). Repeated dose administration in cycles of 21 days. Maximum values were obtained within the first 2 hours post injection. Cmax values were obtained between 0 and 2 hours post infusion. Effective cmax is indicated in percentage of theoretically calculated cmax. Administration cycles: cycle 1: day 1, cycle 2: day 22; cycle 3: day 43; cycle 4: day 64 etc.
Theoretical cmax was calculated according to the following assumed parameters:
Patients Body Surface Area 1.9 m²
Patients Weight 70 Kg
Patients 40 ml/kg $$\frac{\text{(Administered dose} \times \text{surface area)} / \text{body weight}}{\text{Plasma Volume}}$$

Although the half life of BT062 in plasma of human subjects treated proved to be significantly lower than the plasma half life observed in cynomolgus monkeys (days) and in human plasma ex vivo (14 days), the immunoconjugate still showed efficacy in human subjects, even at administrations as low as 20 mg/m². This fact suggests an accelerated tumor targeting and tumor cell binding which results in an increased efficacy. This property of the immunoconjugates of the present invention is likely to result from the IgG4 isotype of the antibody/targeting molecule.

Figure 24:
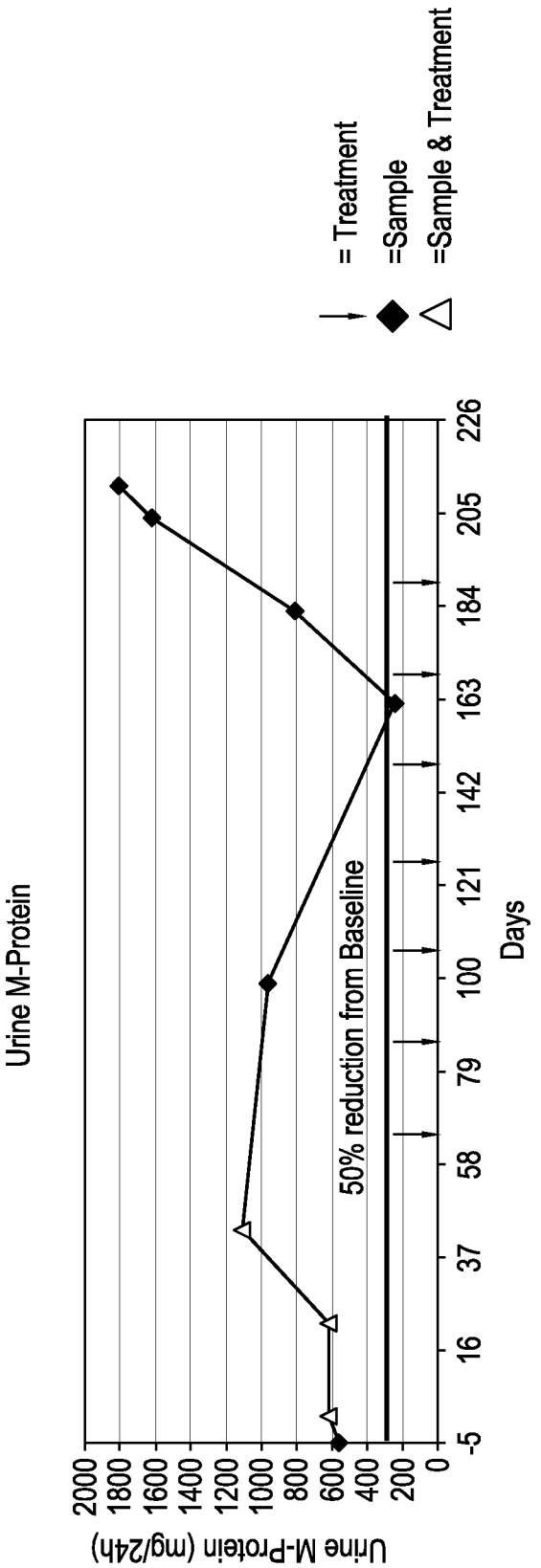
FIG. 24 shows the level of urine M-protein measured for a patient receiving 20 $mg/m^2$ at three weeks intervals. Days −5 to 205 are shown.

As noted above, unusual rapid clearance from plasma of treated MM patients was observed in the early elimination phase (during infusion and about 0 to 2 hours post infusion)

followed by generally normal terminal elimination phase at dose levels up to 120 mg/m², whereas a more typical clearance profile was observed for all 4 patients at the 160 mg/m² and 200 mg/m² dose (3 patients), even though the clearance was still below the theorectical cmax value. In addition, in the administration regimes that showed rapid plasma clearance at the early elimination phase, e.g. 20, 40, 80 and 120 mg/m²) not only rapid plasma clearance at the early elimination phase was observed, but a response (decrease of urine M-protein) was observed, including responses that manifested themselves in a decrease of urine M-protein by more than 50% after repeated single dosages (FIG. 24).

Figure 17:
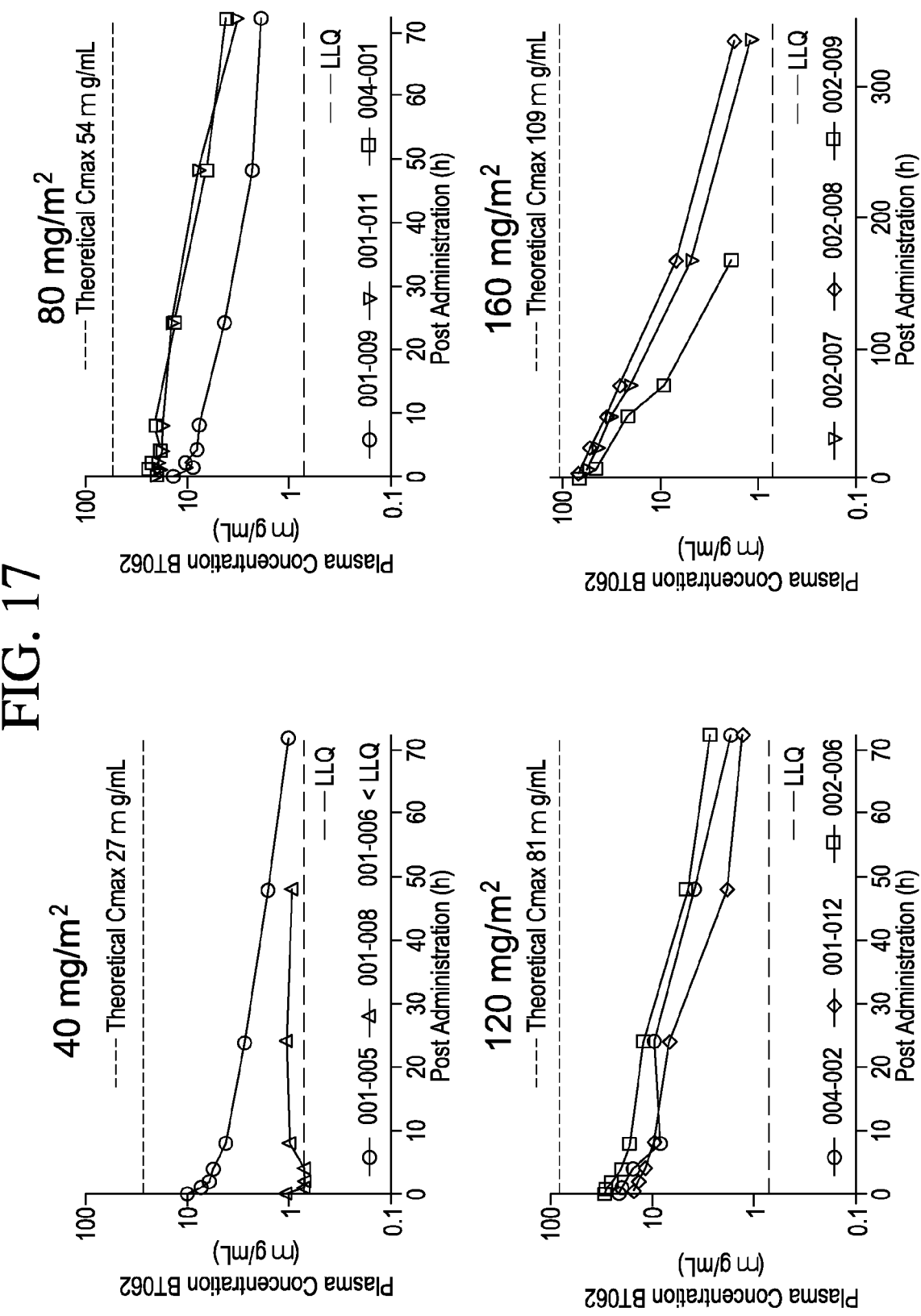
FIG. 17 illustrates the rapid plasma clearance for dosages ranging from 40 $mg/m^2$ to 120 $mg/m^2$, while higher doses as illustrated here by a dose of 160 $mg/m^2$, showed plasma clearance closer to the expected value.
Figure 18:
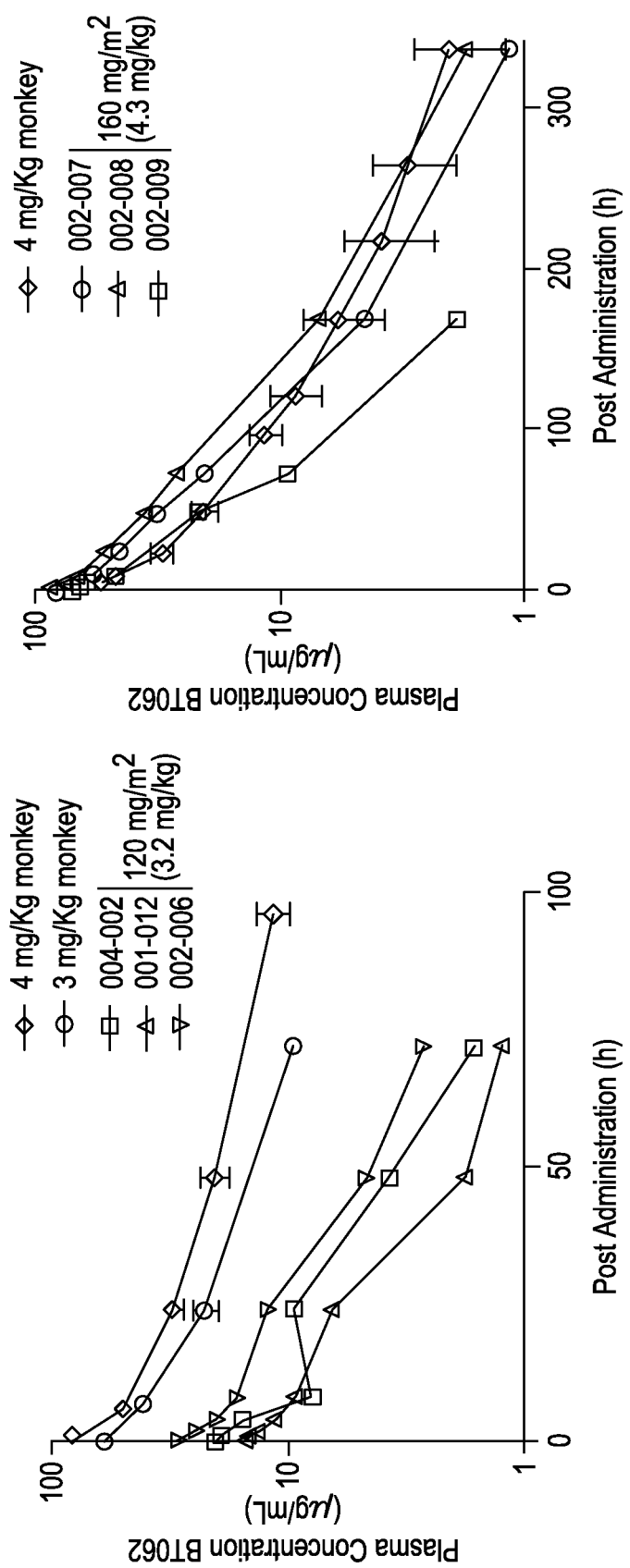
FIG. 18 compares the BT062 plasma profile to that of monkeys treated at the same doses. The comparison clarifies that the rapid plasma clearance at low doses cannot be extrapolated from available animal models and appears to be specific to humans.
Figure 19:
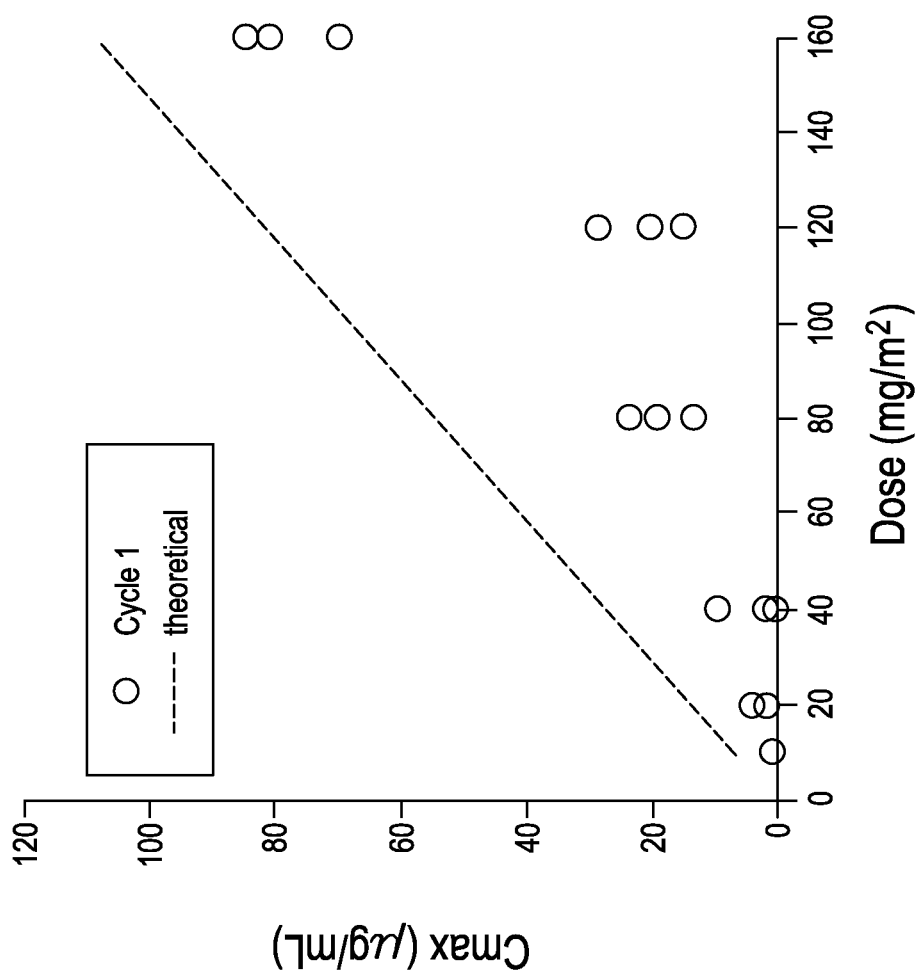
FIG. 19 shows the measured cmax values of BT062 compared to the theoretical cmax vales.
Figure 22:
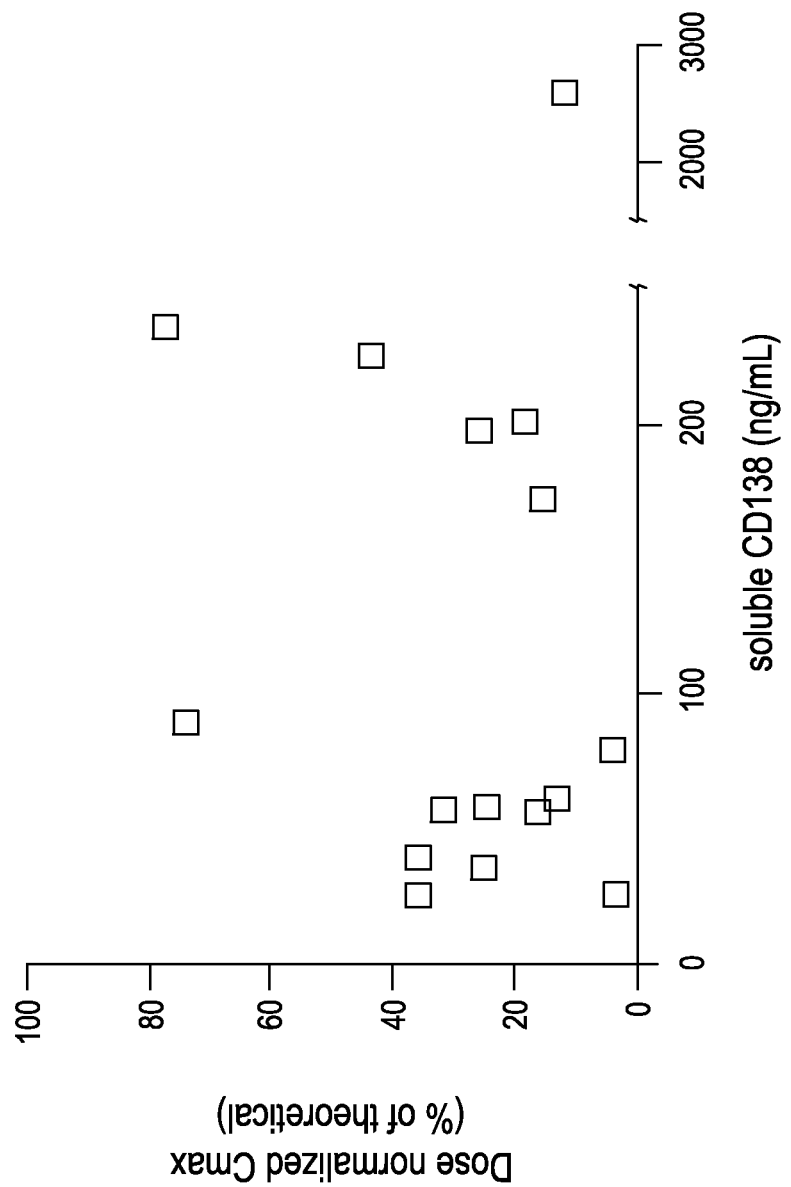
FIG. 22 clarifies that the rapid plasma clearance cannot be attributed to a buffering effect caused by soluble CD138.
Figure 27:
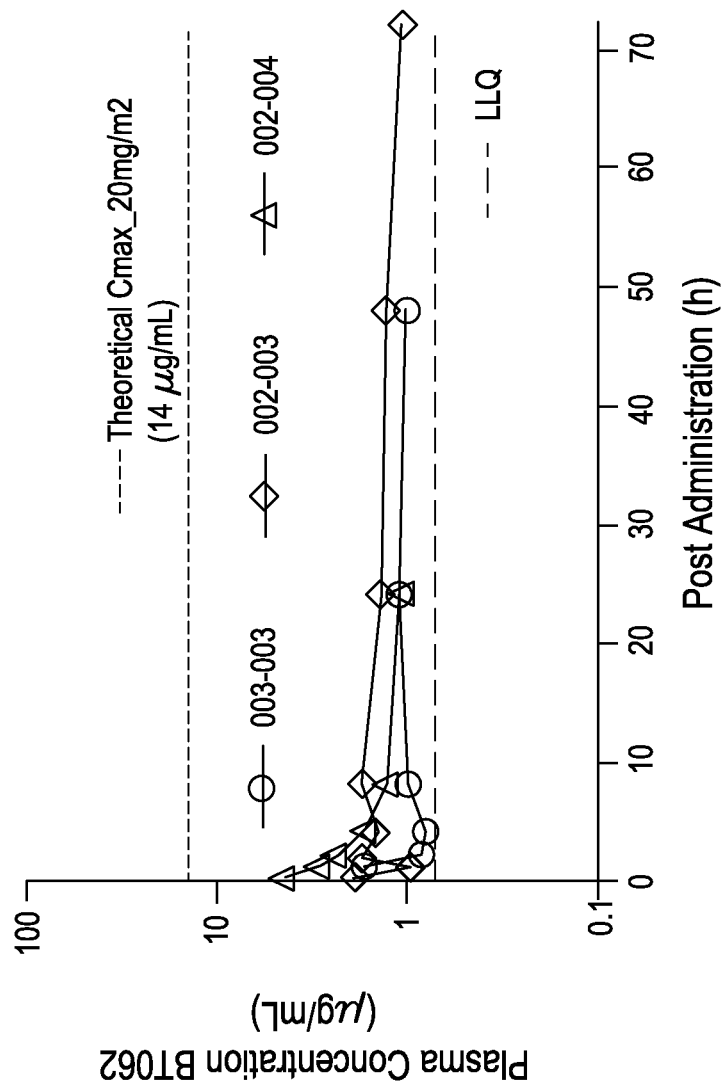
FIG. 27 shows the plasma concentration fo BT062 in the 20 $mg/m^2$ cohort of patients.

FIG. 17 illustrates the rapid plasma clearance for dosages ranging from 40 mg/m² to 120 mg/m², while higher doses as illustrated here by a dose of 160 mg/m², showed plasma clearance closer to the theoretical value. See FIG. 27 for plasma clearance observed at a 20 mg/m² dose. FIG. 18 compares the BT062 plasma profile to that of monkeys treated at comparable doses. The comparison clarifies that the rapid plasma clearance at low doses cannot be deduced from available animal models and appears to be specific to humans. FIG. 22 clarifies that the rapid plasma clearance cannot be attributed to a buffering effect caused by soluble CD138. FIG. 19 shows the measured cmax values of BT062 compared to the theoretical cmax values.

Figure 26:
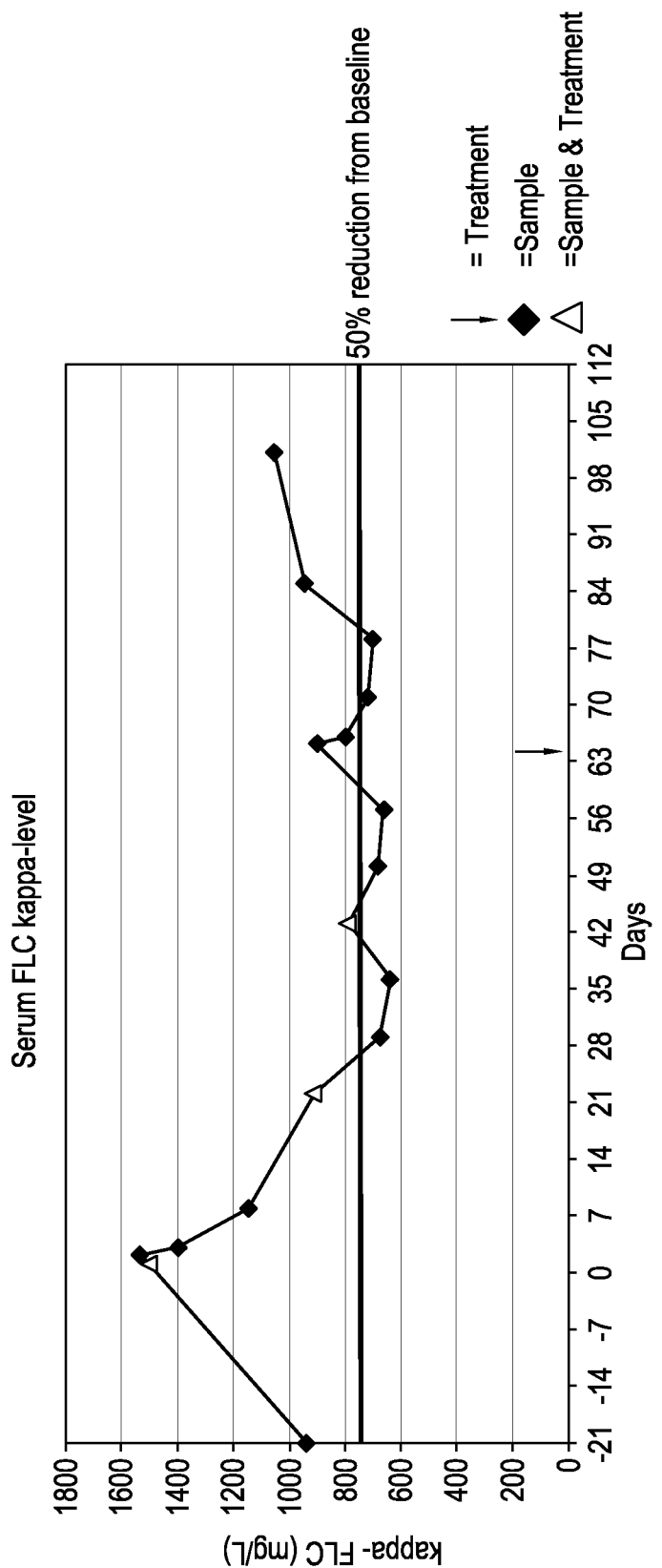
FIG. 26 shows the level of kappa FLC measured for a patient receiving 160 $mg/m^2$ at three weeks intervals. Days −21 to 101 are shown.

At higher doses, e.g. 160 mg/m², which are, however, relative low doses compared to administration schemes of other immunconjugates, terminal clearance profiles were closer to normal, that is closer to the theoretical cmax values. However, a rapid reduction of FLC in the serum could be observed after just a single administration, which manifested itself in a partial response after the $2^{nd}$, $3^{rd}$ and $4^{th}$ administration (FIG. 26).

Thus, in one embodiment, the invention is directed at a low dose administration regime, such as a repeated single dosage regime, wherein a response is observed, preferably at least a MR, preferably a VGPR, a CR, a sCR or a PR.

The invention is also directed at a low dose treatment regime, such as a repeated single dosage administration regime, wherein stable disease is achieved over multiple treatment cycles, lasting more than 3, 4, 5, 6, 7, 8, 9, 10, 11, 12, 13, 14, 15, 16, 17, 18, 19 or 20, 30, 40, 50, 60, 70, 80, 90, 100 or more weeks.

Analogues and Derivatives

One skilled in the art of therapeutic agents, such as cytotoxic agents, will readily understand that each of the such agents described herein can be modified in such a manner that the resulting compound still retains the specificity and/or activity of the starting compound. The skilled artisan will also understand that many of these compounds can be used in place of the therapeutic agents described herein. Thus, the therapeutic agents of the present invention include analogues and derivatives of the compounds described herein.

For illustrative purposes of the uses of the immunconjugates some non-limiting applications will now be given and illustrated.

Materials and Methods
Chimeric Antibody Construction (cB-B4: nBT062)
B-B4

Murine antibody B-B4 as previously characterized (Wijdenes et al., Br J Haematol., 94 (1996), 318) was used in these experiments.

Cloning and Expression of B-B4 and cB-B4/nBT062

Standard recombinant DNA techniques were performed as described in detail in text books, for example in J. Sambrook; Molecular Cloning, A Laboratory Manual; 2nd Ed. (1989), Cold Spring Harbor Laboratory Press, USA, or as recommended by the manufacturer's instruction in the cases when kits were used. PCR-cloning and modification of the mouse variable regions have been conducted using standard PCR methodology. Primers indicated in the respective results section have been used.

Expression of cB-B4/nBT062

Exponentially growing COS cells, cultured in DMEM supplemented with 10% FCS, 580 µg/mL-glutamine, 50 Units/ml penicillin and 50 µg/ml streptomycin were harvested by trypsinisation and centrifugation and washed in PBS. Cells were resuspended in PBS to a final concentration of 1×10⁷ cells/ml. 700 µl of COS cell suspension was transferred to a Gene Pulser cuvette and mixed with heavy and kappa light chain expression vector DNA (10 µg each or 13 µg of Supervector). Cells were electroporated at 1900 V, 25 µF using a Bio-Rad Gene Pulser. Transformed cells were cultured in DMEM supplemented with 10% gamma-globulin free FBS, 580 µg/ml L-glutamine, 50 Units/ml penicillin and 50 µg/ml streptomycin for 72 h before antibody-containing cell culture supernatants were harvested.

Capture ELISA to Measure Expression Levels of cB-B4/nBT062

96 well plates were coated with 100 µA aliquots of 0.4 µg/ml goat anti-human IgG antibody diluted in PBS (4° C., overnight). Plates were washed three times with 200 µl/well washing buffer (PBS+0.1% Tween-20). Wells were blocked with 0.2% BSA, 0.02% Tween-20 in PBS, before addition of 200 µA cell culture supernatants containing the secreted antibody (incubation at 37° C. for one hour). The wells were washed six times with washing buffer, before detection of bound antibody with goat anti-human kappa light chain peroxidase conjugate.

Purification of cB-B4/nBT062 from Cell Culture Supernatants

The cB-B4 antibody was purified from supernatants of transformed COS 7 cells using the Protein A ImmunoPure Plus kit (Pierce, Rockford, Ill.), according to the manufacturer's recommendation.

cB-B4 Binding and Competition Assay

Analysis of binding activity of B-B4 and cB-B4 to CD138 was performed using the Diaclone (Besançon, France) sCD138 kit according to the manufacturer's recommendation, considering the changes described in the results section.

RNA Preparation and cDNA Synthesis

Hybridoma B-B4 cells were grown and processed using the Qiagen Midi kit (Hilden, Germany) to isolate RNA following the manufacturer's protocol. About 5 µg of B-B4 RNA was subjected to reverse transcription to produce B-B4 cDNA using the Amersham Biosciences (Piscataway, N.J.) 1st strand synthesis kit following the manufacturer's protocol.

Cloning of B-B4 Immunoglobulin cDNA

Immunoglobulin heavy chain (IgH) cDNA was amplified by PCR using the IgH primer MHV7 (5'-ATGGGCATCAA-GATGGAGTCACAGACCCAGG-3') [SEQ ID NO:3] and the IgG1 constant region primer MHCG1 (5'-CAGTGGATA-GACAGATGGGGG-3') [SEQ ID NO:4]. Similarly, immunoglobulin light chain (IgL) was amplified using the three different Igκ primers MKV2 (5'-ATGGAGACAGACA-CACTCCTGCTATGGGTG-3') [SEQ ID NO:5], MKV4 (5'-ATGAGGGCCCCTGCTCAGTTTTTTGGCTTCTTG-3') [SEQ ID NO:6] and MKV9 (5'-ATGGTATCCACACCT-CAGTTCCTTG-3') [SEQ ID NO:7], each in combination with primer MKC (5'-ACTGGATGGTGGGAAGATGG-3') [SEQ ID NO:8]. All amplification products were directly ligated with the pCR2.1-TOPO vector using the TOPO-TA cloning kit (Invitrogen, Carlsbad, Calif.) according to the manufacturer's instruction.

E. coli TOP10 bacteria (Invitrogen) transformed with the ligated pCR2.1 vector constructs were selected on LB-ampicillin-Xgal agar plates. Small scale cultures were inoculated with single white colonies, grown overnight and plasmids were isolated using the QIAprep Spin Miniprep kit according to the manufacturer's instruction.

cDNA Sequence Determination

Plasmids were sequenced using the BigDye Termination v3.0 Cycle Sequencing Ready Reaction Kit (ABI, Foster City, Calif.). Each selected plasmid was sequenced in both directions using the 1210 and 1233 primers cycled on a GeneAmp9600 PCR machine. The electrophoretic sequence analysis was done on an ABI capillary sequencer.

The complete cycle of RT-PCR, cloning and DNA sequence analysis was repeated to obtain three completely independent sets of sequence information for each immunoglobulin chain.

B-B4 VK DNA Sequence

1st strand synthesis was performed in three independent reactions. The PCR products generated by using primers MKC and MKV2 (sequences given above) were ligated into pCR2.1-TOPO vectors according to the manufacturer's instruction. Clones from each independent set of RT-PCR reactions were sequenced in both directions. MKV2-primed product sequence was highly similar to sterile kappa transcripts originating from the myeloma fusion partner such as MOPC-21, SP2 and Ag8 (Carroll et al., Mol. Immunol., 25 (1988), 991; Cabilly et al., Gene, 40 (1985); 157) and was therefore disregarded.

The PCR products using MKC with MKV4 and MKV9 primers were similar to each other and differed only at the wobble positions within the leader sequence primer.

B-B4 VH DNA Sequence

1st strand synthesis was performed in three independent reactions and PCR products were cloned and sequenced from each 1st strand product. Five clones were sequenced from each 1st strand.

Construction of Chimeric cB-B4 Expression Vectors

The construction of the chimeric expression vectors entails adding a suitable leader sequence to VH and Vκ, preceded by a BamHI restriction site and a Kozak sequence. The Kozak consensus sequence is crucial for the efficient translation of a variable region sequence. It defines the correct AUG codon from which a ribosome can commence translation, and the single most critical base is the adenine (or less preferably, a guanine) at position −3, upstream of the AUG start. The leader sequence is selected as the most similar sequence in the Kabat database (Kabat et al., NIH National Technical Information Service, 1991). These additions are encoded within the forward (For) primers (both having the sequence 5'-AGAG AAGCTTGCCGCCACCAT-GATTGCCTCTGCTCAGTT-CCTTGGTCTCC-3' [SEQ ID NO:9]; restriction site is underlined; Kozak sequence is in bold type). Furthermore, the construction of the chimeric expression vectors entails introducing a 5' fragment of the human gammal constant region, up to a natural ApaI restriction site, contiguous with the 3' end of the J region of B-B4 and, for the light chain, adding a splice donor site and HindIII site. The splice donor sequence is important for the correct in-frame attachment of the variable region to its appropriate constant region, thus splicing out the V:C intron. The kappa intron+CK are encoded in the expression construct downstream of the B-B4 Vκ sequence. Similarly, the gamma-4 CH is encoded in the expression construct downstream of the B-B4 VH sequence.

The B-B4 VH and VK genes were first carefully analyzed to identify any unwanted splice donor sites, splice acceptor sites, Kozak sequences and for the presence of any extra sub-cloning restriction sites which would later interfere with the subcloning and/or expression of functional whole antibody. An unwanted HindIII site was found in the VK sequence which necessarily was removed by site-directed mutagenesis via PCR without changing the amino acid sequence. For this reactions, oligonucleotide primers BTO3 (5'-CAACAGTATAGTAAGCTCCCTCGGACGT-TCGGTGG-3') [SEQ ID NO:10] and BTO4 (5'-CCAC-CGAACGTCCGAGGGAGCTTACTATACTGTTG-3') [SEQ ID NO:11] were used and mutagenesis was performed according to the Stratagene (La Jolla, Calif.) Quickchange Mutagenesis Kit protocol.

Kappa Chain Chimerization Primers

The non-ambiguous B-B4 Vκ leader sequence, independent of the PCR primer sequence, was aligned with murine leader sequences in the Kabat database. The nearest match for the B-B4 VH leader was VK-10 ARS-A (Sanz et al., PNAS, 84 (1987), 1085). This leader sequence is predicted to be cut correctly by the SignalP algorithm (Nielsen et al., Protein Eng, 10 (1997); 1). Primers CBB4K for (see above) and g2258 (5'-CGCGGGATCCACTCACGTTTGATTT-CCAGCTTGGTGCCTCC-3' [SEQ ID NO:12]; Restriction site is underlined) were designed to generate a PCR product containing this complete leader, the B-B4 Vκ region, and HindIII and BamHI terminal restriction sites, for cloning into the pKN100 expression vector. The forward primer, CBB4K introduces a HindIII restriction site, a Kozak translation initiation site and the VK-10 ARS-A leader sequence. The reverse primer g2258 introduces a splice donor site and a BamHI restriction site. The resulting fragment was cloned into the HindIII/BamHI restriction sites of pKN100.

Heavy Chain Chimerization Primers

The non-ambiguous B-B4 VH leader sequence, independent of the PCR primer sequence, was aligned with murine leader sequences in the Kabat database. The nearest match for the B-B4 VK leader was VH17-1A (Sun et al., PNAS, 84 (1987), 214). This leader sequence is predicted to be cut correctly by the SignalP algorithm. Primers cBB4H for (see above) and g22949 (5'-CGAT GGGCCCTTGGTGGAGGCTGAGGA-GACGGTGACT-GAGGTTCC-3' [SEQ ID NO:13]; Restriction site is underlined) were designed to generate a PCR product containing VH17-1A leader, the B-B4 VH region, and terminal HindIII and ApaI restriction sites, for cloning into the pG4D200 expression vector. The forward primer cBBHFor introduces a HindIII restriction site, a Kozak translation initiation site and the VH17-1A leader sequence. The reverse primer g22949 introduces the 5' end of the gamma4 C region and a natural ApaI restriction site. The resulting fragment was cloned into the HindIII/ApaI restriction sites of pG4D200, resulting in vector pG4D200cBB4.

Production of cBB4 Antibody

One vial of COS 7 cells was thawed and grown in DMEM supplemented with 10% Fetal clone I serum with antibiotics. One week later, cells (0.7 ml at $10^7$ cells/ml) were electroporated with pG4D200cBB4 plus pKN100cBB4 (10 μg DNA each) or no DNA. The cells were plated in 8 ml growth medium for 4 days. Electroporation was repeated seven times.

Detection of Chimeric Antibody

A sandwich ELISA was used to measure antibody concentrations in COS 7 supernatants. Transiently transformed COS 7 cells secreted about 6956 ng/ml antibody (data not shown).

Binding Activity of cB-B4

To assay the binding activity of cB-B4 in COS 7 culture supernatants, the Diaclone sCD138 kit has been used, a solid phase sandwich ELISA. A monoclonal antibody specific for sCD138 has been coated onto the wells of the microtiter strips provided. During the first incubation, sCD138 and biotinylated B-B4 (bio-B-B4) antibody are simultaneously incubated together with a dilution series of unlabeled test antibody (B-B4 or cB-B4).

The concentrations of bio-B-B4 in this assay have been reduced in order to obtain competition with low concentrations of unlabeled antibody (concentration of cB-B4 in COS 7 cell culture supernatants were otherwise too low to obtain sufficient competition). Results from this assay reveal that both antibodies have the same specificity for CD138 (data not shown).

Purification of cB-B4

Chimeric B-B4 was purified from COS 7 cell supernatants using the Protein A ImmunoPure Plus kit (Pierce), according to the manufacturer's recommendation (data not shown).

$K_D$-Determination: Comparison nBT062/BB4

Purification of Soluble CD 138

Soluble CD138 antigen from U-266 cell culture supernatant was purified by FPLC using a 1 mL "HiTrap NHS-activated HP" column coupled with B-B4. Cell culture supernatant was loaded in PBS-Buffer pH 7.4 onto the column and later on CD138 antigen was eluted with 50 mM tri-ethylamine pH 11 in 2 mL fractions. Eluted CD138 was immediately neutralised with 375 µL 1 M Tris-HCl, pH 3 to prevent structural and/or functional damages.

Biotinylation of CD 138

Sulfo-NHS-LC (Pierce) was used to label CD138. NHS-activated biotins react efficiently with primary amino groups like lysine residues in pH 7-9 buffers to form stable amide bonds.

For biotinylation of CD138, 50 µl of CD138 were desalted using protein desalting spin columns (Pierce). The biotinylation reagent (EZ-Link Sulfo NHS-LC-Biotin, Pierce) was dissolved in ice-cooled deionised $H_2O$ to a final concentration of 0.5 mg/mL. Biotinylation reagent and capture reagent solution were mixed having a 12 times molar excess of biotinylation reagent compared to capture reagent (50 pmol CD138 to 600 pmol biotinylation reagent) and incubated 1 h at room temperature while shaking the vial gently. The unbound biotinylation reagent was removed using protein desalting columns.

Immobilization of bCD 138

The sensorchip (SENSOR CHIP SA, BIACORE AB) used in the BIACORE assay is designed to bind biotinylated molecules for interaction analysis in BIACORE systems. The surface consists of a carboxymethylated dextran matrix pre-immobilized with streptavidin and ready for high-affinity capture of biotinylated ligands. Immobilization of bCD138 was performed on SENSOR CHIP SA using a flow rate of 10 µL/min by manual injection. The chip surface was conditioned with three consecutive 1-minute injections of 1 M NaCl in 50 mM NaOH. Then biotinylated CD138 was injected for 1 minute.

$K_D$-Determination of Different Antibodies Using BIACORE

The software of BIACORE C uses pre-defined masks, so called "Wizards" for different experiments where only certain settings can be changed. As the BIACORE C was originally developed to measure concentrations, there is no wizard designed to carry out affinity measurements. However, with the adequate settings, the wizard for "non-specific binding" could be used to measure affinity rate constants and was therefore used for $K_D$-determination. With this wizard, two flow cells were measured and the dissociation phase was set to 90 s by performing the "Regeneration 1" with BIACORE running buffer. "Regeneration 2" which is equivalent to the real regeneration was performed with 10 mM Glycine-HCl pH 2.5. After this step, the ligand CD138 was in its binding competent state again. During the whole procedure HBS-EP was used as running and dilution buffer. To determine binding of the different antibodies (~150 kDa) to CD138, association and dissociation was analysed at different concentrations (100, 50, 25 12.5, 6.25 and 3.13 nM). The dissociation equilibrium constants were determined by calculating the rate constants ka and kd. Afterwards, the $K_D$-values of the analytes were calculated by the quotient of kd and ka with the BIAevaluation software. The results are shown in Table 9.

TABLE 9

Comparative analysis of $K_D$ values of nBT062 and B-B4.

| Antibody | Affinity | |
|---|---|---|
| | $K_D$ (nM) | mean $K_D$ (nM) |
| nBT062 | 1.4 | 1.4 +/− 0.06 |
| | 1.4 | |
| | 1.5 | |
| B-B4 | 1.7 | 1.6 +/− 0.06 |
| | 1.7 | |
| | 1.6 | |
| nBT062-SPDB-DM4 | 1.9 | 1.9 +/− 0.00 |
| | 1.9 | |
| | 1.9 | |
| B-B4-SPP-DM1 | 2.6 | 2.6 +/− 0.06 |
| | 2.7 | |
| | 2.6 | |

Standard deviations are given for mean $K_D$ values.

Discussion

Mean $K_D$ values for each antibody were calculated from three independent experiments. The results show that in all measurements nBT062 exhibits slightly decreased $K_D$ values compared to B-B4 (mean $K_D$ values were 1.4 and 1.6 nM, respectively).

Preparation of Immunoconjugates nBT062-DM1 and huC242-DM1

The thiol-containing maytansinoid DM1 was synthesized from the microbial fermentation product ansamitocin P-3, as previously described by Chari (Chari et al., Cancer Res. 1 (1992), 127). Preparation of humanized C242 (huC242) (Roguska et al., PNAS, 91 (1994), 969) has been previously described. Antibody-drug conjugates were prepared as previously described (Liu et al., PNAS, 93 (1996), 8618). An average of 3.5 DM1 molecules was linked per antibody molecule.

nBT062-DM4

BT062 is an antibody-drug conjugate composed of the cytotoxic maytansinoid drug, DM4, linked via disulfide bonds through a linker to the nBT062 chimerized monoclonal antibody. Maytansinoids are anti-mitotics that inhibit tubulin polymerization and microtubule assembly (Remillard et al., Science 189 (1977), 1002). Chemical and schematic representations of BT062 (nBT062-DM4) are shown in FIGS. 1 and 2.

Synthesis of DM4

DM4 is prepared from the well known derivative maytansinol (Kupchan et al., J. Med. Chem., 21 (1978), 31). Maytansinol is prepared by reductive cleavage of the ester moiety of the microbial fermentation product, ansamitocin P3, with lithium trimethoxyaluminum hydride (see FIG. 3).

DM4 is synthesized by acylation of maytansinol with N-methyl-N-(4-methydithiopentanoyl)-L-alanine (DM4 side chain) in the presence of dicyclohexylcarbodiimide (DCC) and zinc chloride to give the disulfide-containing maytansinoid DM4-SMe. The DM4-SMe is reduced with dithiothreitol (DTT) to give the desired thiol-containing maytansinoid DM4 (see FIG. 4 for the DM4 process flow diagram).

Immunoconjugate BT062

Figure 5:
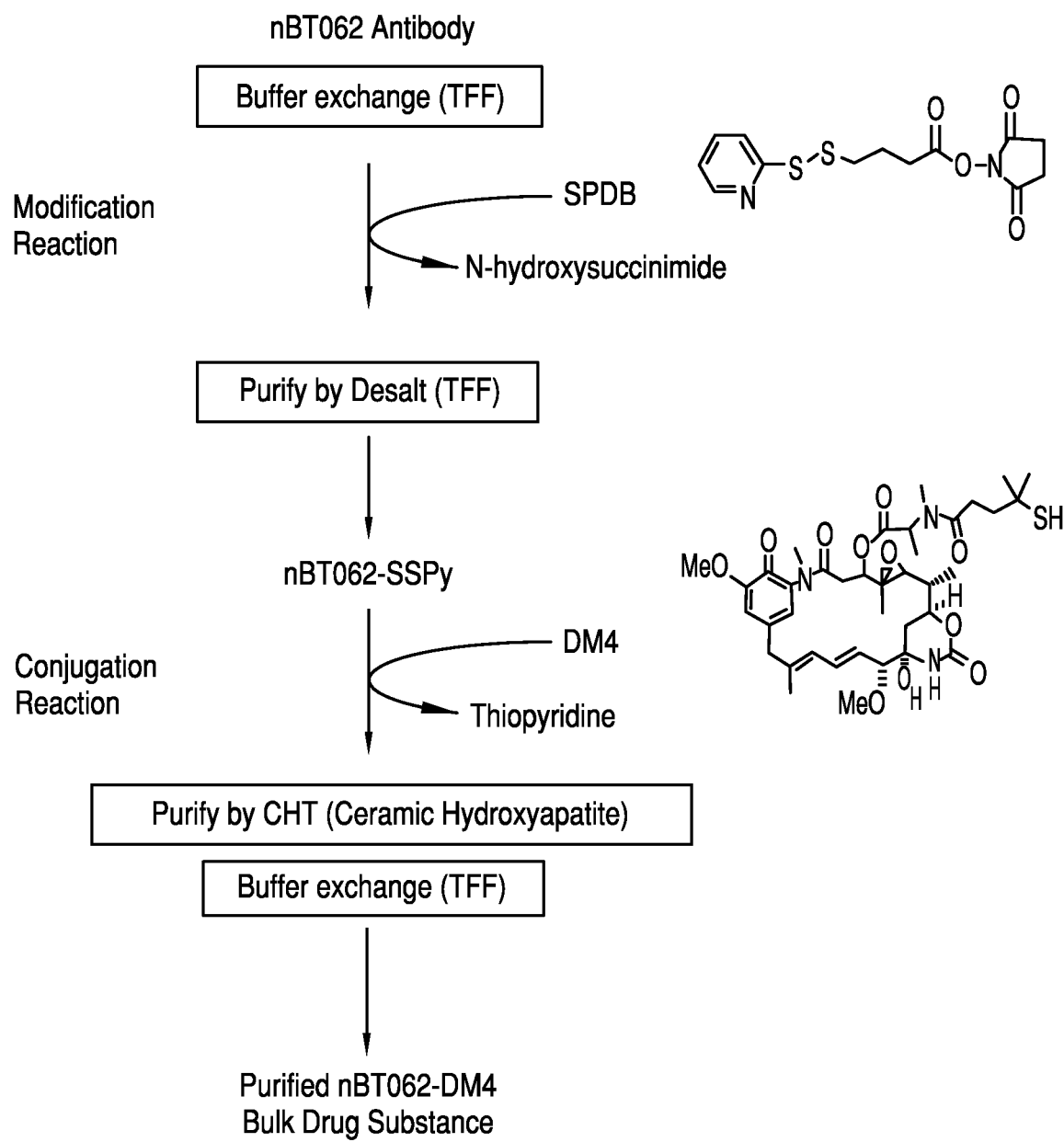
FIG. 5 is a schematic representation of an antibody conjugation (nBT062 to DM4).

The procedure for the preparation of nBT062-DM4 is outlined in FIG. 5. The nBT062 antibody is modified with N-succinimidyl-4-(2-pyridyldithio) butyrate (SPDB linker) to introduce dithiopyridyl groups. DM4 is mixed with the modified antibody at a concentration in excess of the equivalents of dithiopyridyl groups. The BT062 conjugate forms by a disulfide exchange reaction between the thiol group of DM4 and the dithiopyridyl groups introduced into the antibody via the linker. Purification by chromatography and diafiltration removes the low molecular weight reactants (DM4) and reaction products (thiopyridine), as well as aggregates of conjugated antibody, to produce the bulk drug substance.

FACS Analysis and WST Cytotoxicity Assays

FACS Analysis

OPM-2 cells are plasma cell leukemia cell lines showing highly expressing CD138. OPM-2 cells were incubated with nBT062, nBT062-SPDB-DM4, nBT062-SPP-DM1 or nBT062-SMCC-DM1 at different concentrations (indicated in FIG. 6). The cells were washed and CD138-bound antibody or conjugates were detected using a fluorescence-labeled secondary antibody in FACS analysis. The mean fluorescence measured in these experiments was plotted against the antibody concentration.

Cell Viability Assay $CD138^+$ MOLP-8 cells were seeded in flat bottom plates at 3000 cells/well. $CD138^-$ BJAB control cells were seeded at 1000 cells/well. The cells were treated with nBT062-SPDB-DM4, nBT062-SPP-DM1 or nBT062-SMCC-DM1 at different concentrations (indicated in FIG. 7) for five days. WST reagent (water-soluble tetrazolium salt, ROCHE) was added in order to measure cell viability according to the manufacturer's instruction (ROCHE). The reagent was incubated for 7.5 h on MOLP-8 cells and for 2 h on BJAB cells. The fraction of surviving cells was calculated based on the optical densities measured in a microplate reader using standard procedures.

Discussion

Figure 6:
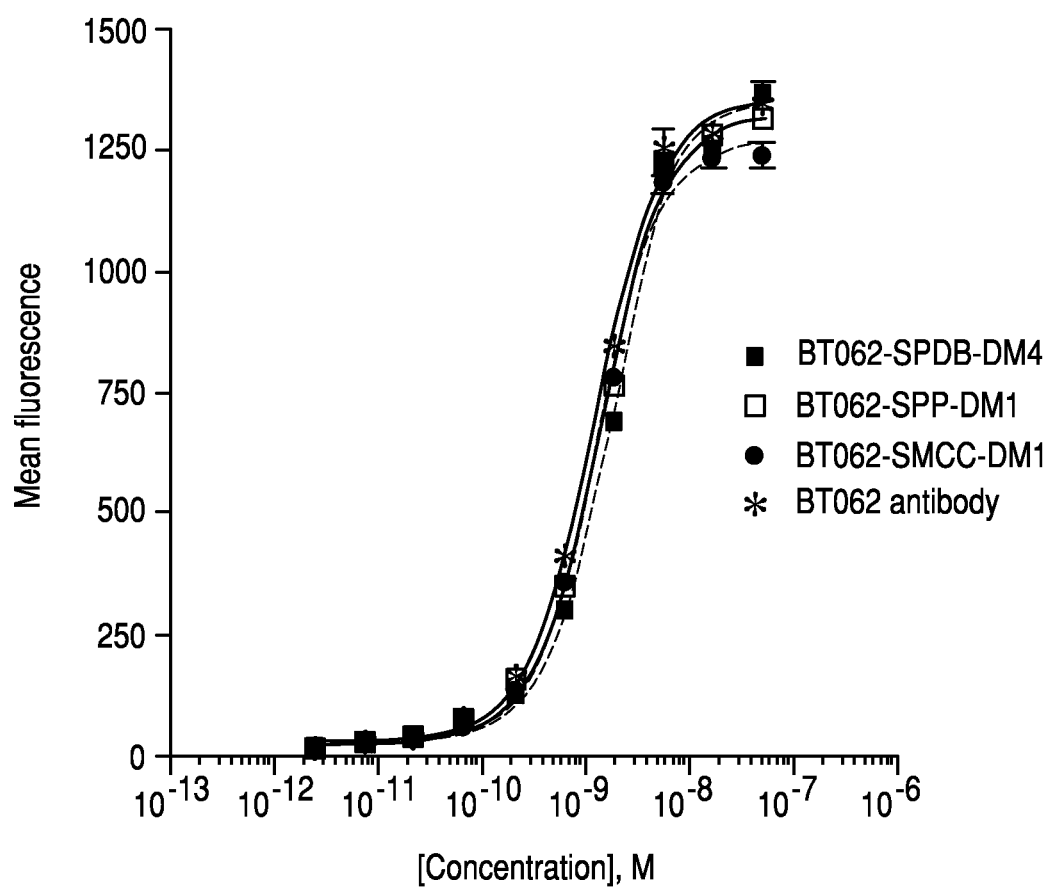
FIG. 6 shows an analysis of the binding of nBT062-SPDB-DM4, nBT062-SPP-DM1, nBT062-SMCC-DM1 and nBT062 antibody to OPM-2 cells. Different concentrations of nBT062 and conjugates were given to the cells and mean fluorescence was measured by FACS analysis.
Figure 7A:
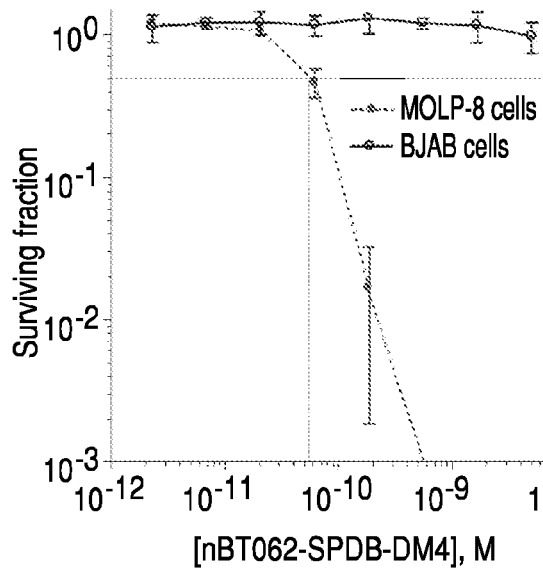
FIG. 7(A)-(D) depict in vitro cytotoxicity of nBT062-DMx conjugates towards MOLP-8 (CD138+) and BJAB (CD138−) cells. The cells were cultured in flat bottom plates and incubated with the indicated concentrations of immunoconjugates for 5 days. WST reagent was added for further 3 hours to asses cell viability. In (D) cytotoxic activity of nBT062-SPDB-DM4 was analyzed in the presence or absence of blocking antibody (1 μM nBT062).
Figure 7B:
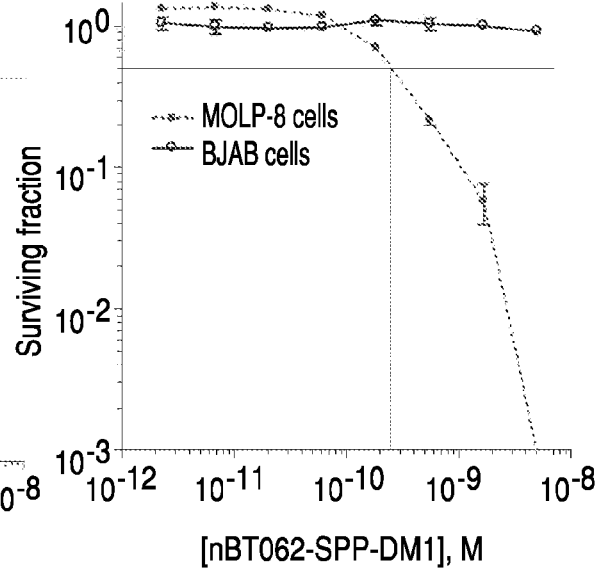
Figure 7C:
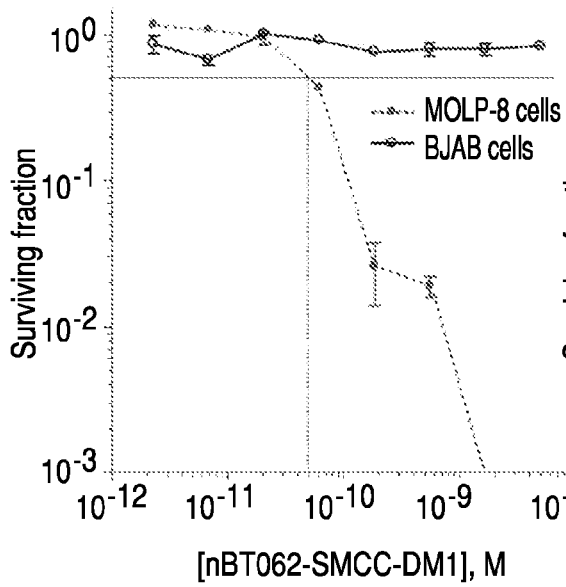
Figure 7D:
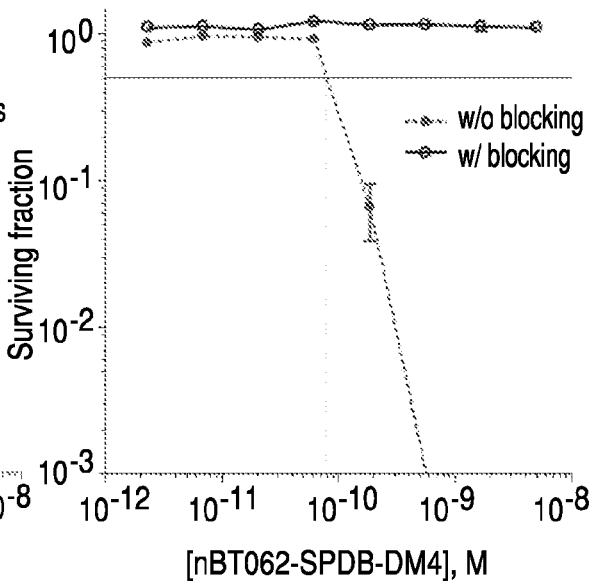
Figure 8A:
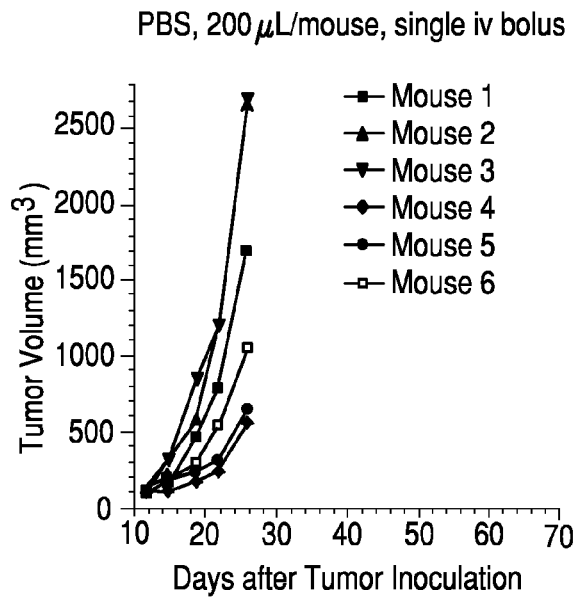
FIG. 8 shows tumor volumes for individual mice treated with (A) PBS, (B) nBT062 antibody, (C) free DM4 or (D) non-targeting conjugate huC242-DM4 over time (days) post-inoculation with MOLP-8 tumor cells.
Figure 8B:
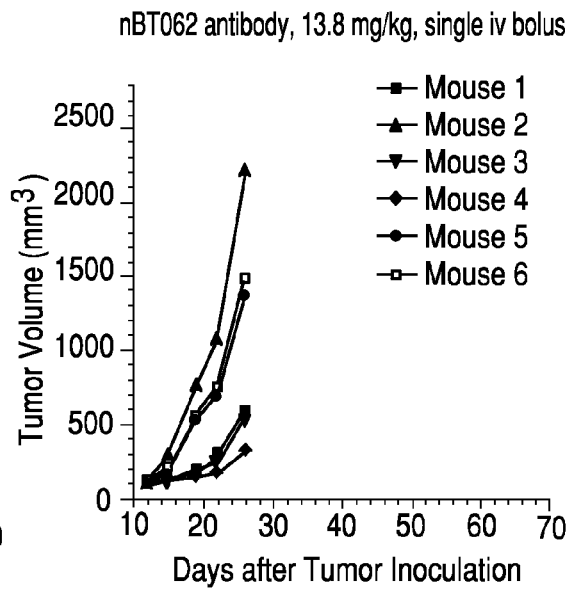
Figure 8C:
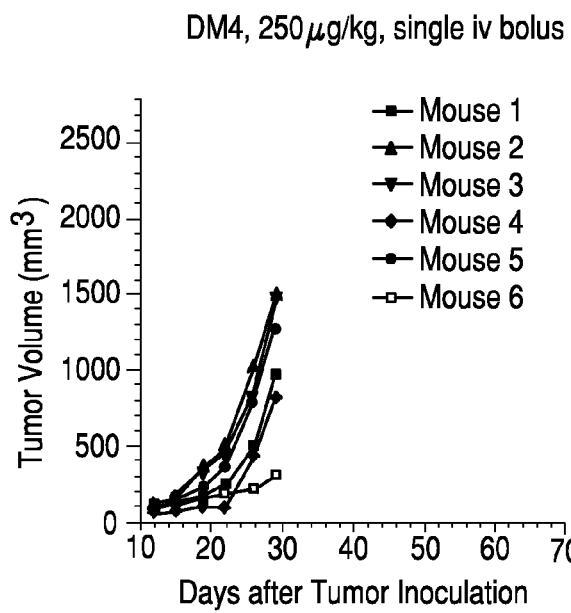
Figure 8D:
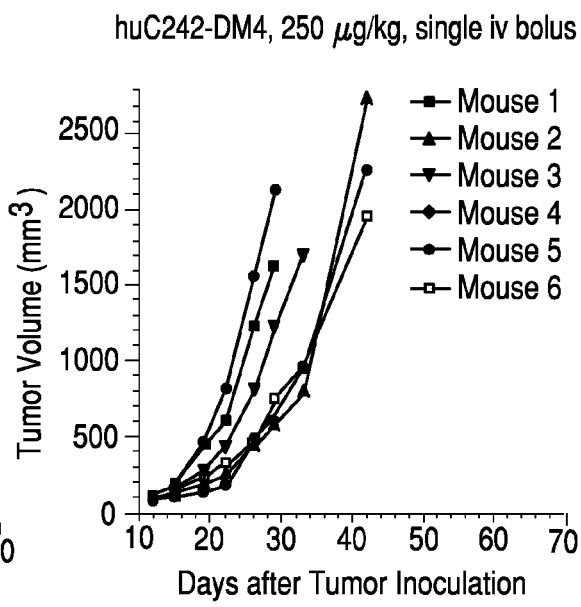

Binding of nBT062-SPDB-DM4, nBT062-SPP-DM1, nBT062-SMCC-DM1 or nBT062 was analyzed by FACS. $CD138^+$ OPM-2 as target cells were incubated with nBT062 or immunoconjugates and cell-bound molecules were detected using a fluorescence-labeled secondary antibody. In FIG. 6, the mean fluorescences as measure for the amount of cell bound antibody is plotted against different antibody or conjugate concentrations. The results show, that nBT062-SPDB-DM4, nBT062-SPP-DM1 and nBT062-SMCC-DM1 show very similar binding characteristics. In addition, the results strongly suggest that the binding characteristics of the unconjugated antibody is not affected by the conjugated toxins.

In cell viability assays, the cytotoxic activity of the antibody against $CD138^+$ MOLP-8 target cells and against $CD138^-$ BJAB B-lymphoblastoma control cells were analyzed. Both cell lines were seeded in flat-bottom plates and incubated with increasing concentrations of the immunoconjugates. Unconjugated antibody was used as a control. The cytotoxic activity was analyzed five days after addition of the immunoconjugates by using WST reagent in order to measure cell viability. In FIG. 7 (A)-(C), the fraction of surviving cells relative to control cells treated with vehicle control is plotted against increasing immunoconjugate concentrations. The results show that cytotoxic activity of nBT062-SPDB-DM4, nBT062-SPP-DM1 and nBT062-SMCC-DM1 against MOLP-8 cells is very similar. As expected, $CD138^-$ BJAB control cells were not killed by the immunoconjugates, indicating that all immunoconjugates act via cell specific binding to CD138. In competition experiments, in which MOLP-8 cells were preincubated with a molar excess of unconjugated nBT062. Preincubation substantially blocked the cytotoxicity of nBT062-SPDB-DM4, providing further evidence that the immunoconjugates kill the cells via specific binding to CD138 onto the cell surface (FIG. 7 (D)).

Xenograft Mouse Experiments

To evaluate the importance of CD138 targeting on the anti-tumor activity of antibody-maytansinoid conjugates of a human chimeric version of the B-B4 antibody, nBT062, xenograft mouse experiments were performed. Two versions of nBT062-maytansinoid conjugates were prepared that may differ in the chemical stability of their disulfide linkages (nBT062-SPP-DM1 and nBT062-SPDB-DM4). The anti-tumor activity of these antibody-drug conjugates was compared to the activity of the B-B4-SPP-DM1 conjugate (comprising the murine parental antibody), as well as unconjugated free maytansinoid (DM4), native unmodified nBT062 antibody, and a non-targeting (irrelevant) IgG1-maytansinoid conjugate. The conjugates were evaluated in a CD138-positive xenograft model (MOLP-8) of human multiple myeloma in severe combined immunodeficient (SCID) mice.

In these mice, subcutaneous tumors were established (female CB.17 SCID mice) by inoculation with MOLP-8 cell suspensions. Treatment with a single bolus intravenous injection was conducted when tumor volumes reached an average 113 $mm^3$. Changes in tumor volume and body weight were monitored twice per week. Experiments were carried out over 68 days after tumor cell inoculation.

Xenograft Mouse Experiments A

Mice

Female CB.17 SCID mice, five weeks old, were obtained from Charles River Laboratories.

Human Tumor Cell Lines

MOLP-8, a human multiple myeloma cell line, was supplied from ATCC. MOLP-8 cells, which express the CD138 antigen on their cell surface and develop xenograft tumors in SCID mice, were maintained in RPMI-1640 medium supplemented with 4 mM L-glutamine (Biowhittaker, Walkersville, Md.), 10% fetal bovine serum (Hyclone, Logan, Utah) and 1% streptomycin/penicillin, at 37° C. in a humidified atmosphere that contained 5% $CO_2$.

Part I

Tumor Growth in Mice

Each mouse was inoculated with $1\times10^7$ MOLP-8 cells subcutaneously into the area under the right shoulder. The total volume was 0.2 ml per mouse, in which the ratio of serum-free medium to matrigel (BD Bioscience, Bedford, Mass.) was 1/1 (v/v). Prior to treatment, the xenograft tumors were monitored daily and were allowed to become established. The tumor volume reached approximately 113 $mm^3$ about 11 days after tumor cell inoculation. Tumor take rate of CB.17 SCID mice was 100%.

Eleven days after tumor cell inoculation, 42 mice were selected based on tumor volumes and body weights. The tumor volume was in a range of 68.2 to 135.9 $mm^3$. The forty-two mice were randomly divided into seven groups (A-G) of six animals each based on tumor volume.

Each of six mice in Group A received 200 μl of PBS as vehicle control. Each mouse in group B received 13.8 mg/kg of nBT062 naked antibody. This dose is equivalent to the amount of nBT062 antibody component in 250 μg/kg of linked maytansinoid. The ratio of molecular weights of maytansinoids to nBT062 antibody in a conjugate molecule is approximate 1/55. Each mouse in Group C received 250 μg/kg of DM4. Each mouse in Group D received 250 μg/kg of huC242-DM4. Mice in groups E, F and G received 250 μg/kg of nBT062-SPDB-DM4, B-B4-SPP-DM1 and nBT062-SPP-DM1 each, respectively.

All agents were intravenously administered as a single bolus injection through a lateral tail vein with a 1 ml syringe fitted with a 27 gauge, ½ inch needle. Prior to administration, the stock solutions of nBT062 antibody, nBT062-SPDB-DM4 and nBT062-SPP-DM1 were diluted with sterile PBS to concentrations of 2 mg/ml, 28.1 μg/ml and 28.1 μg/ml, respectively, so that the injected volume for each mouse was between 120-220 μl.

Part II

In a second set of experiments, MOLP-8 cells ($1.5 \times 10^7$ cells per mouse), suspended in a 50:50 mixture of serum free media and matrigel were injected subcutaneously in the area under the right shoulder in 100 μl. Tumor volumes reached about 80 mm$^3$ at day 11 and the mean of the controls was about 750 mm$^3$ at day 25, post cell inoculation. The tumor doubling time was estimated to be 4.58 days. Each mouse in the control group (n=6) received 0.2 ml of sterile PBS administered into the lateral tail vein (i.v.) in a bolus injection. All treatment doses were based on conjugated maytansinoid. Nine groups (n=6) were treated with a single intravenous injection of nBT062-SMCC-DM1, nBT062-SPDB-DM4, or nBT062-SPP-DM1, each at doses of 450, 250 and 100 μg/kg. An additional group (n=6) received 250 μg/kg nBT062-SMCC-DM1 in a repeated dosing (weekly for five weeks). Mice were randomized into eleven groups (n=6) by tumor volume using the LabCat Program. The tumor volumes ranged from 40.0 to 152.5 mm$^3$. The mice were dosed based on the individual body weight.

Tumor size was measured twice per week in three dimensions using the LabCat System (Tumor Measurement and Tracking, Innovative Programming Associated, Inc., Princeton, N.J.). The tumor volume in mm$^3$ was calculated using the methodology described in Tomayko et al. (Tomayko et al., 1989):

$$\text{Volume} = \text{Length} \times \text{Width} \times \text{Height} \times \frac{1}{2}$$

Log$_{10}$ cell kill was calculated with the formula described in Bissery et al. (Bissery et al., 1991)

$$\text{Log}_{10} \text{ cell kill} = (T-C)/T_d \times 3.32$$

where (T−C) or tumor growth delay, is the median time in days required for the treatment group (T) and the control group (C) tumors, to reach a predetermined size (600 mm$^3$). $T_d$ is the tumor doubling time, based on the median tumor volume in the control mice, and 3.32 is the number of cell doublings per log of cell growth.

Results

Figure 10:
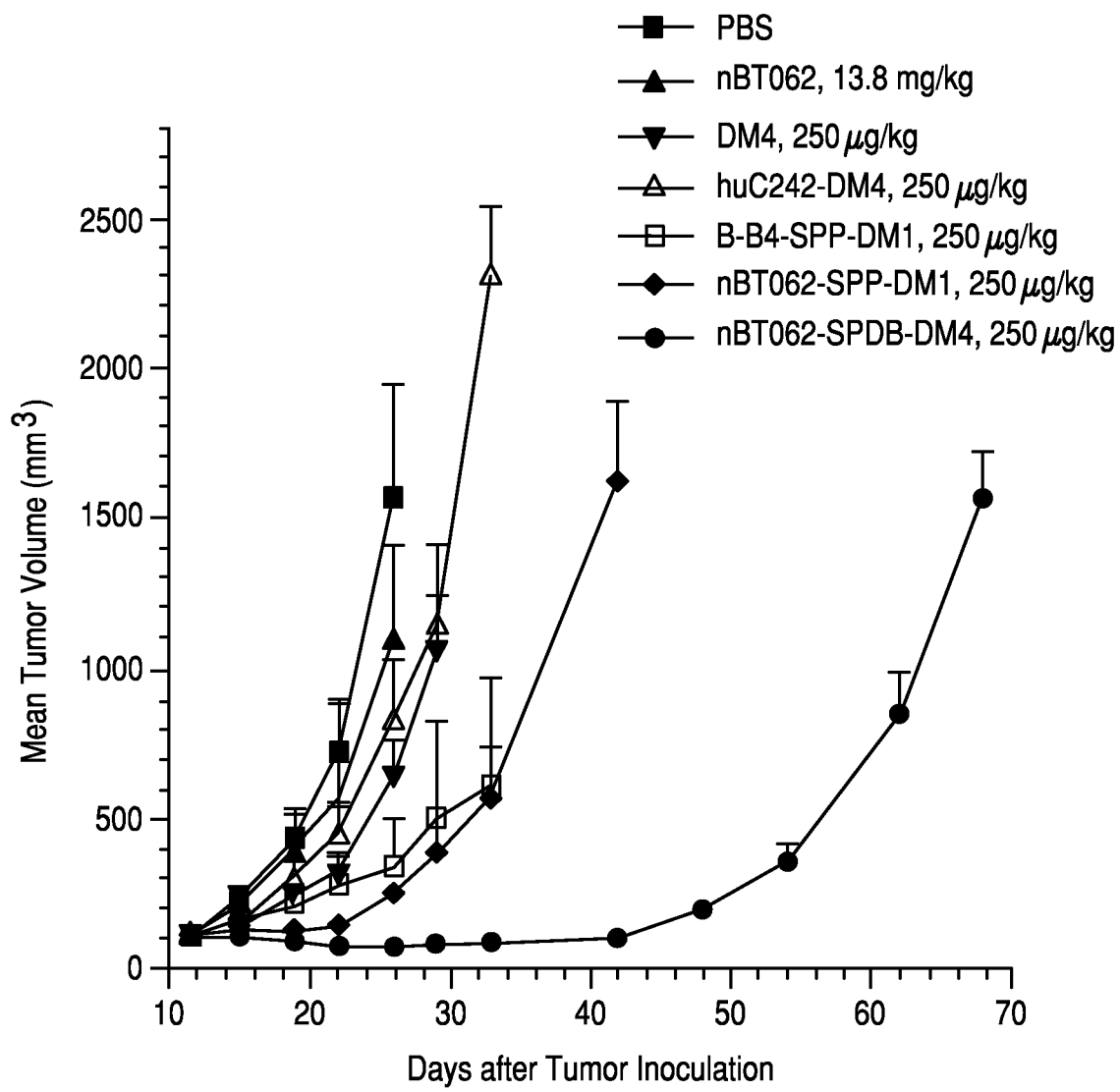
FIG. 10 depicts mean tumor volume (+/−SD) of MOLP-8 human multiple myeloma xenografts in CB.17 SCID mice over time (days) post-inoculation.

The tumor growth in individual mice is shown in FIGS. 8 and 9. The mean (+/−SD) tumor growth for each group is shown in FIG. 10.

As compared with tumor growth in the PBS-treated animals, treatment with nBT062 antibody, unconjugated free DM4 or the irrelevant non-targeting conjugate huC242-DM4 did not cause any significant inhibition of tumor growth.

All three CD138-targeting conjugates, nBT062-SPDB-DM4, B-B4-SPP-DM1 and nBT062-SPP-DM1, at a dose of 250 μg/kg caused marked delay in tumor growth. Based on the mean tumor volumes measured in the treatment groups, the DM4 conjugate nBT062-SPDB-DM4 was the most active one, while the nBT062-SPP-DM1 conjugate showed slightly increased activity as compared to its murine counterpart B-B4-SPP-DM1 (FIG. 10). The results obtained in individual mice show in addition that the anti-tumor activity obtained with B-B4-SPP-DM1 is more heterogeneously and therefore less predicable than that measure in mice treated with nBT062-SPP-DM1. In terms of homogeneity of anti tumor activity, the other conjugate that uses nBT062 as targeting antibody nBT062-SPDB-DM4 behaved similar to nBT062-SPP-DM1.

No body weight reduction was observed in any treatment group suggesting that the treatments were well tolerated.

Discussion

The results of the analysis of three CD138-targeting conjugates in experimental animals demonstrate the importance of targeted delivery for the anti-tumor activity. While the maytansinoid conjugates of the human chimeric nBT062 and the murine B-B4 antibodies show significant activity as measured by log cell kill, there was no significant impact on tumor growth from treatment with unconjugated DM4, unmodified native huBT062 antibody, or a non-targeting control conjugate (huC242-DM4).

The immunoconjugate prepared from the human chimeric antibody, nBT062-SPP-DM1, gave slightly higher anti-tumor activity then the conjugate prepared from its murine counterpart, B-B4-SPP-DM1. In addition, treatment with nBT062-SPP-DM1 and nBT062-SPDB-DM4 resulted in more homogenous responses in individual mice as compared to treatment with B-B4-SPP-DM1. The high binding variation of B-B4-SPP-DM1 explained that the measurement of the median tumor volume (+/−SD) of MOLP-8 human multiple myeloma xenografts in CB.17 SCID mice over time (days) post-inoculation actually provided for relatively better results for B-B4-SPP-DM1 than for nBT062-SPP-DM1 (data not shown). This feature of immunoconjugates using nBT062 as a targeting antibody seems to be beneficial especially for therapeutic use of the conjugates.

Lastly, the most potent of the maytansinoid conjugates, following single iv administration in the MOLP-8 xenograft models in SCID mice, was nBT062-SPDB-DM4.

Bystander Killing (Cell Viability Assay)

CD138$^+$ OPM2 cells and CD138$^-$ Namalwa cells were seeded in round bottom plates either in separate wells or in coculture. The cells were treated with nBT062-SPDB-DM4 at concentrations ranging from $1 \times 10^{-8}$ to $1 \times 10^{-9}$ M. The fraction of viable cells was detected using WST reagent (water-soluble tetrazolium salt, ROCHE) according to the manufacturer's instruction (ROCHE). The fraction of surviving cells was calculated based on the optical densities measured in a microplate reader using standard procedures.

Discussion

Figure 13:
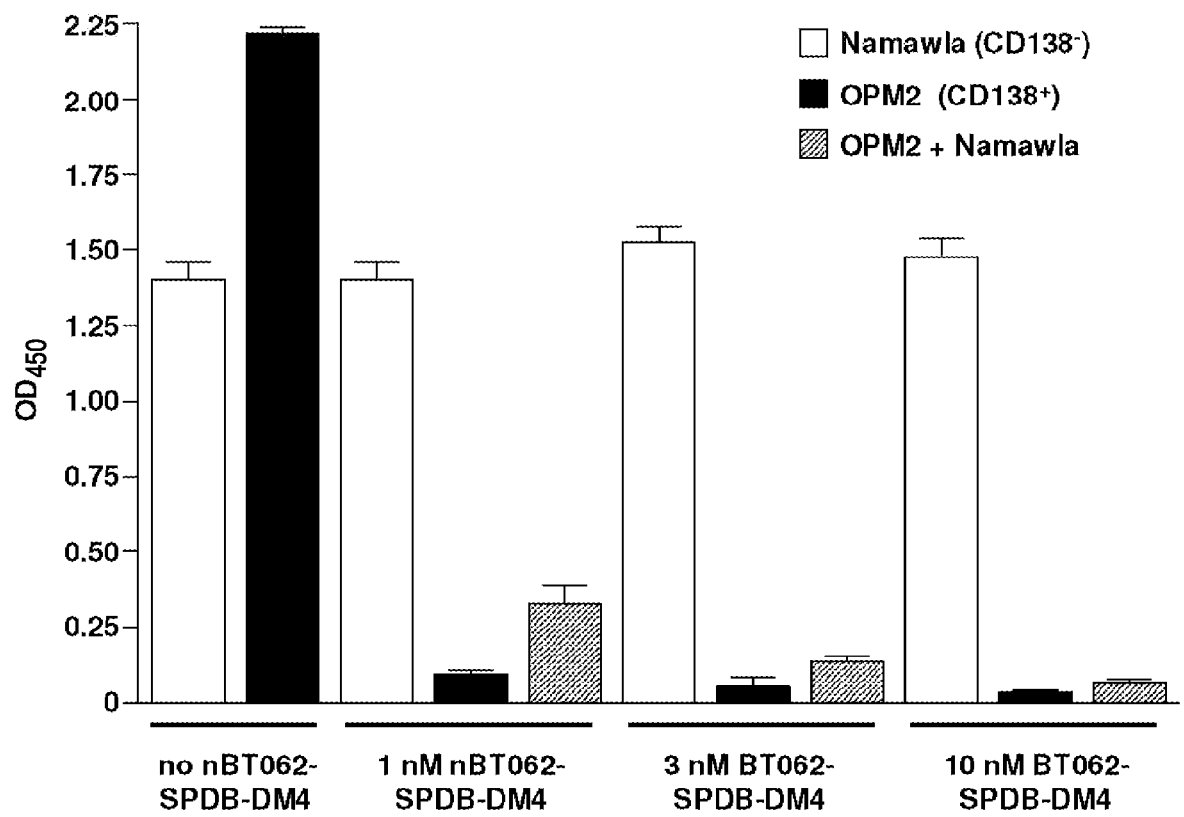
FIG. 13 shows nBT062-SPDB-DM4 mediated bystander killing in vitro. CD138 positive OPM2 cells and CD138 negative Namawla cells were cultured with nBT062-SPDB-DM4 at different concentrations and cell viablility was measured. $OD_{450}$ values represent a measure for cell viability.

Bystander killing of non-target cells in close proximity (as present in round bottom wells) to multiple myeloma cells upon nBT062-SPDB-DM4 treatment was analysed in an in vitro study in which CD138-positive OPM2 cells were cultured in coculture with CD138-negative Namawla cells (FIG. 13). Generally, while CD138-positive cells are efficiently killed by nBT062-SPDB-DM4, CD138-negative cells were not affected by the conjugate. In the coculture in round bottom wells, however, nBT062-SPDB-DM4 also killed the antigen-negative cells in close proximity to the antigen-positive cells (an effect that is often referred to as bystander killing). Kovtun et al. (2006) discussed that bystander killing mediated by maytansinoid conjugates occurs only in close proximity to antigen-positive cells. Kovtun et al. (2006), which is incorporated herein by reference in its entirety, also discusses the importance of the linker of the immunoconjugate. In vivo, bystander killing may contribute to 1) the eradication of tumour cells that heterogeneously express CD138, 2) the destruction of the tumour microenvironment by the killing of tumour stroma cells, and 3) the prevention of the selection of CD138-negative nBT062-SPDB-DM4-resistant cells.

The bystander effect is of particular importance if the activity of an immunoconjugate is impaired by a target antigen that is expressed in tumors in a heterogeneous fashion. If this is the case, a particular cell of a tumor expresses, if at all, the antigen not in amount that would allow effective direct targeting and killing of said cell by the respective immunoconjugate. The anti-tumor efficacy of nBT062-SPDB-DM4 on CD138-negative cells in coculture with CD138-positive cells clarified that the presence of target cells influences, under the appropriate circumstances, the cytotoxic activity of nBT062-SPDB-DM4 towards non-target cells.

Xenograft Mouse Experiments B

In this set of experiments, eighty-five mice were inoculated with MOLP-8 cells ($1.5 \times 10^7$ cells/mouse) subcutaneously in the right shoulder. Tumor take rate was 100%. Sixty-six SCID mice bearing bulky MOLP-8 tumors with a mean tumor volume of about 80 mm$^3$ were randomized into eleven treatment groups (n=6). Mice were treated with a single dose of one of three conjugates (nBT062-SMCC-DM1, nBT062-SPDB-DM4 or nBT062-SPP-DM1). An additional group received five weekly doses of nBT062-SMCC-DM1 and a control group received a single dose of PBS. Mean tumor volumes are shown in FIG. 11A. A dose response was established for each conjugate. A median tumor volume of 750 mm$^3$ in the PBS-treated animals was reached on day 25. Tumor doubling time determined by the best-fit linear regression curve fit on a log-linear plot of control tumor growth was 4.58 days. Animals treated with nBT062-SPDB-DM4 at 450 µg/kg had the highest log cell kill (LCK=2.89), followed by animals treated with nBT062-SMCC-DM1 at 250 µg/kg weekly dosing (LCK=2.1; see Table 10). Comparison of the mean tumor growth curves for the treatment groups by repeated measures ANOVA performing Dunnett's Multiple Comparisopn Test showed a significant difference between the PBS control group and 450 µg/kg nBT062-SPDB-DM4 ($p<0.01$), 250 µg/kg nBT062-SPDB-DM4 ($p<0.05$) and five weekly doses of 250 µg/kg nBT062-SMCC-DM1 ($p<0.05$). No partial or complete tumor regression in any of the treatment groups occurred with the exception of one animal receiving 450 µg/kg nBT062-SPDB-DM4, which had partial regression of the tumor until day 85 post-inoculation.

TABLE 10

Log cell kill (LCK) values as measure for anti-tumor activity of different nBT062-DMx conjugates in different dosing schemes. Refer to the Materials and methods section for information on calculation of LCK values.

| Test Material | Dose (µg/kg) | LCK | Dosing |
|---|---|---|---|
| PBS | | | single dose |
| nBT062-SMCC-DM1 | 450 | 0.85 | single dose |
| nBT062-SMCC-DM1 | 250 | 0.53 | single dose |
| nBT062-SMCC-DM1 | 100 | 0 | single dose |
| nBT062-SPDB-DM4 | 450 | 2.89 | single dose |
| nBT062-SPDB-DM4 | 250 | 1.05 | single dose |
| nBT062-SPDB-DM4 | 100 | 0.39 | single dose |
| nBT062-SPP-DM1 | 450 | 0.8 | single dose |
| nBT062-SPP-DM1 | 250 | 0.39 | single dose |
| nBT062-SPP-DM1 | 100 | 0.2 | single dose |
| nBT062-SMCC-DM1 | 250 | 2.1 | weekly for 5 weeks |

In Vivo Efficacy of nBT062-SPDB-DM4 and nBT062-SPP-DM1 in the Bone Marrow Environment
Preparation of SCID Mice Having Human Fetal Bone Implants Human fetal long bones (human fetal bone chips) were implanted into the upper body of CB17 SCID-mice (SCID-hu) as previously described (Urashima et al., 1997) and thus provided for a model in mouse for the homing of human MM cells to human BM cells.

Treatment Regime (SCID-hu/INA-6 Mice)

4 weeks following bone implantation, $2.5 \times 10^6$ INA-6 cells in a final volume of 100 µL RPMI-1640 cell culture medium were injected directly into the human bone marrow cavity in the SCID-hu mice described above. An increase in the levels of soluble human IL-6 receptor (shuIL-6R), which is released by INA-6 cells, was used as a parameter of MM cell growth and disease burden.

Figure 12:
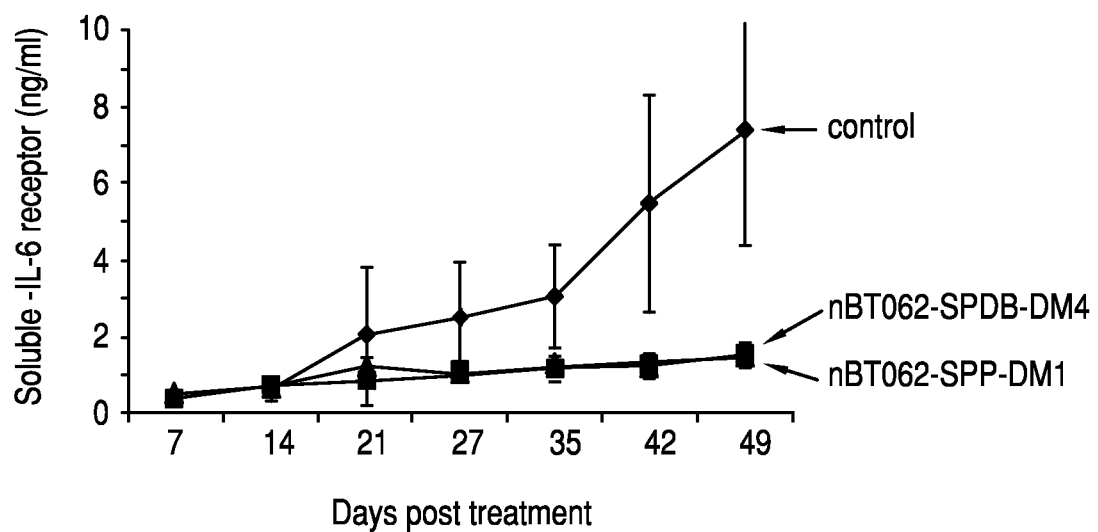
FIG. 12 is a graph reflecting the anti-tumour efficacy of nBT062 containing DMx conjugates in the SCIDhu/INA-6 model towards multiple myeloma cells in the environment of human bone marrow. Soluble human IL-6 Receptor produced by multiple myeloma cells (shuIL-6R) was used as an indicator for tumor burden. Triangle: nBT062-SPP-DM1, Square: nBT062-SPDB-DM4; Diamond: vehicle control.

Mice developed measurable serum shuIL-6R approximately 4 weeks following INA-6 cell injection and then received 0.176 mg conjugate or vehicle control via tail vein injection weekly for 7 weeks. After each treatment, blood samples were collected and measured for shuIL-6R levels by an enzyme-linked immunosorbent assay (ELISA, R&D Systems, Minneapolis, Minn.). The results are depicted in FIG. 12.

Discussion

Interleukin 6 (IL-6) is a growth and survival factor for multiple myeloma cells. INA-6 is an IL-6-dependent human myeloma cell line, which also requires bone marrow stromal cells (BMSC) to proliferate. INA-6 cell lines produce soluble IL-6 receptor (shuIL-6R). An increase in the levels of shuIL-6R can be used as a parameter of MM cell growth and disease burden.

Thus, the sCID-hu/INA-6 mice provide a model for multiple myeloma cells growing in their normal bone marrow environment. The tumor cells of this model, which directly interact with the human bone marrow, closely resemble the situation in patients, in which tumor cell growth is also promoted by the presence of stromal cells. As INA-6 cells release soluble human interleukin-6 receptor (shuIL-6R), serum concentrations of this protein can be used as a measure for tumor cell load in these mice. The in vivo potency of nBT062-SPDB-DM4 and nBT062-SPP-DM1 were tested in this environment.

Treatment of SCIDhu/INA-6 mice with weekly i.v. administrations of nBT062-SPDB-DM4 or nBT062-SPP-DM1 for seven weeks induced efficient tumour regression, as detected by a decrease in serum shuIL-6R levels relative to the control, indicating good efficacy of the conjugates even in the environment of human bone marrow, which reflect the relevant situation in patients (FIG. 12).

Dosages in Mice

Figure 14:
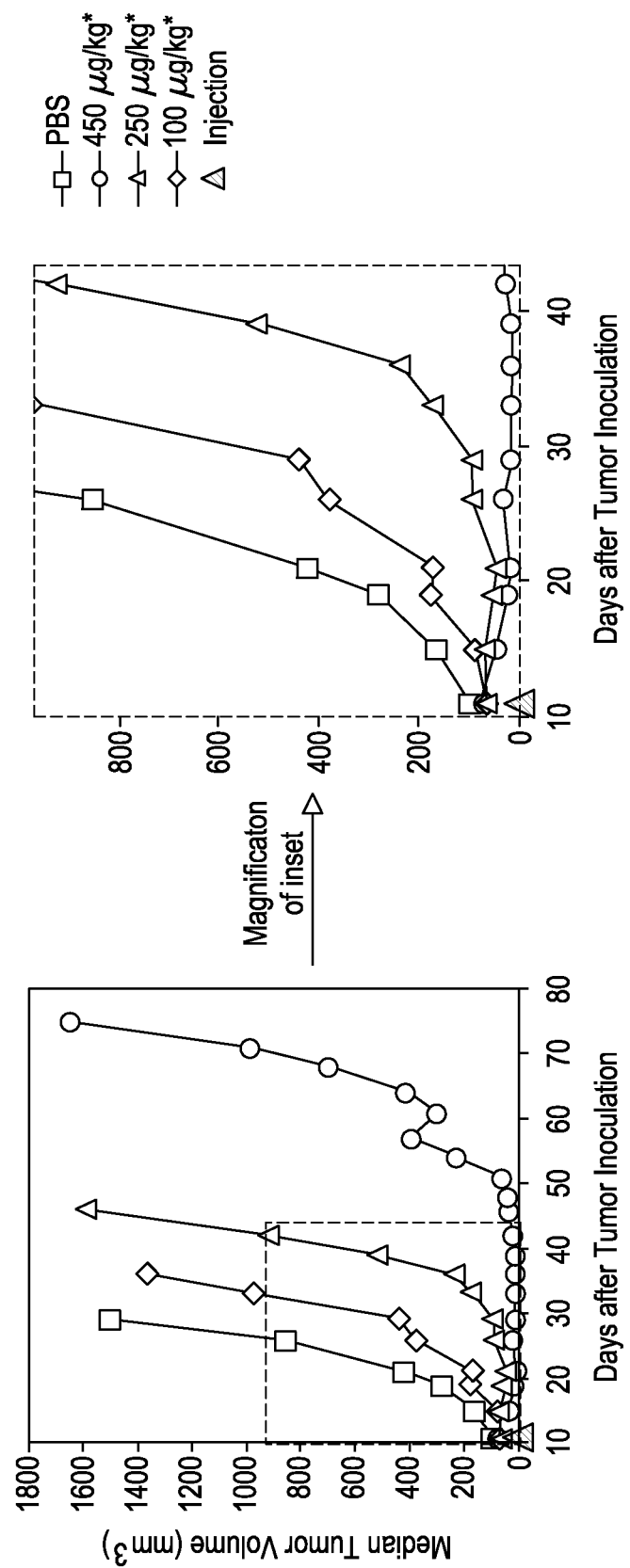
FIG. 14 shows a tumor growth curves in a xenograft mouse model a single injection of BT062. The doses marked with an asterix (*) are based on the molecular weight of linked DM4.
Figure 15:
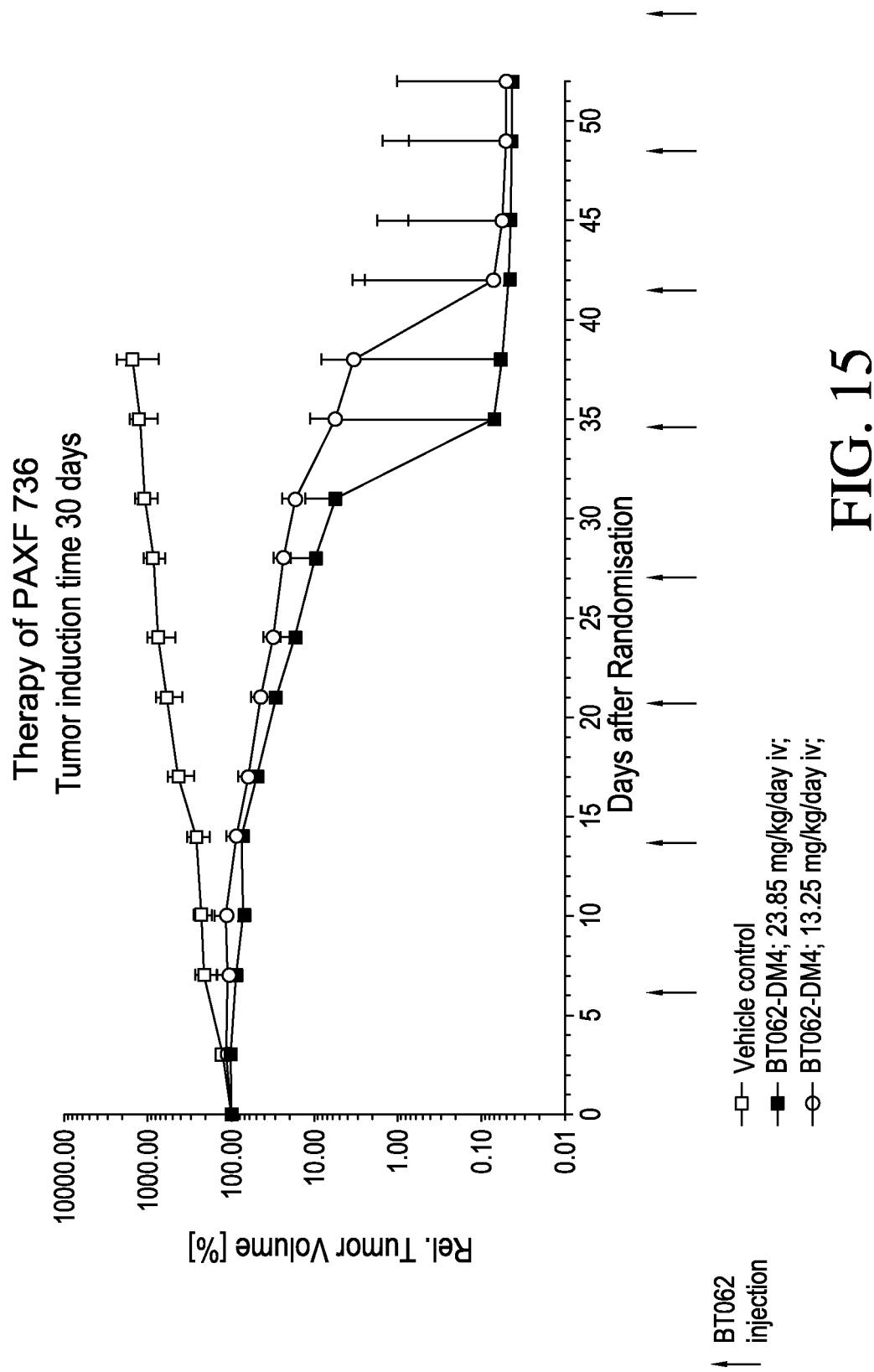
FIG. 15 shows the complete remission of a xenograft pancreas carcinoma in mice treated with BT062 vs. a control.
Figure 16:
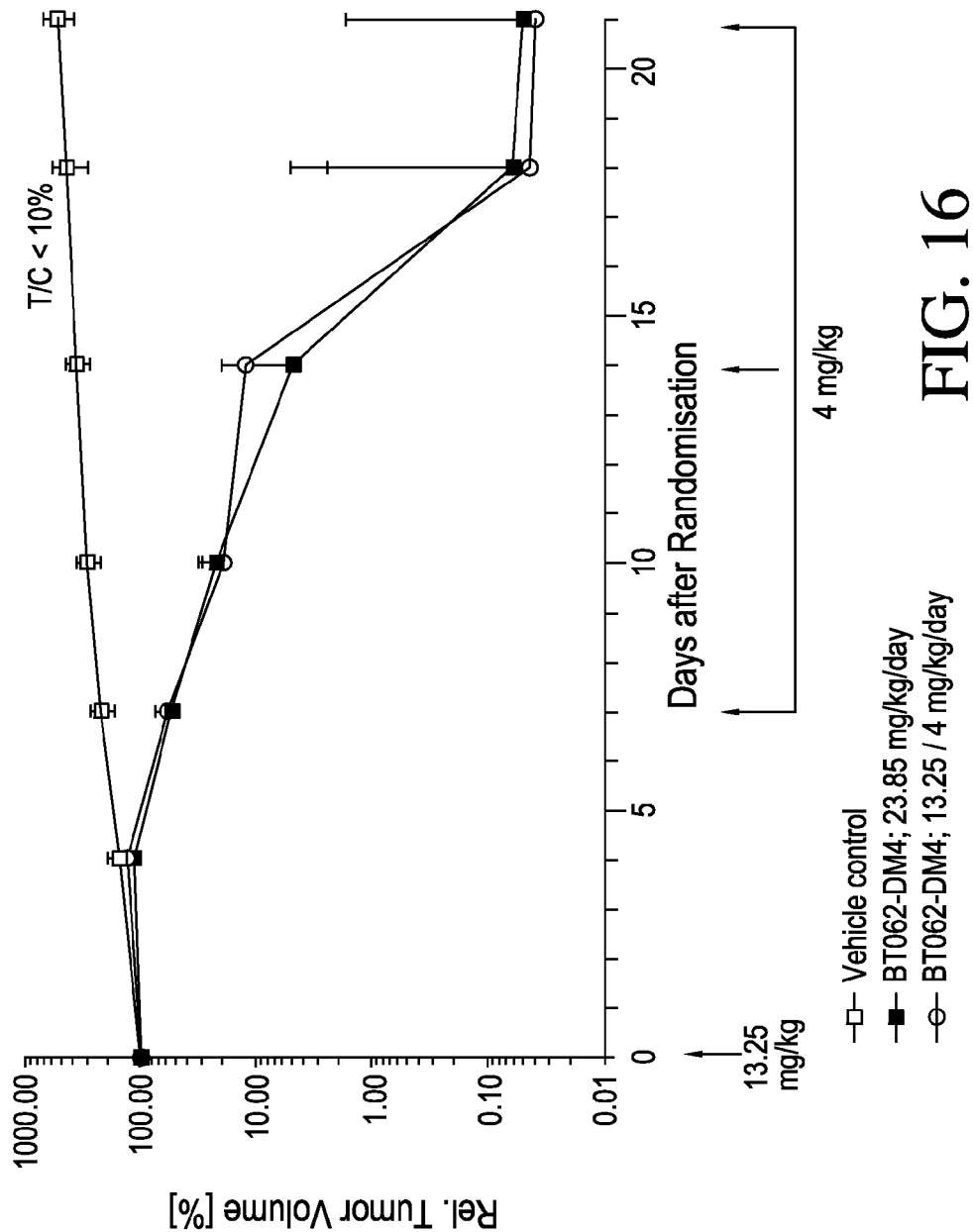
FIG. 16 shows the complete remission of a xenograft mammary carcinoma in mice treated with BT062 vs. a control.

In order to determine relevant doses, a single administration of BT062 at doses of 100, 250 and 450 µg/kg (based on the DM4 concentration) was given to mice when tumors reached a mean tumor volume of 80 mm$^3$ (FIG. 14). Doses are reported as the concentration of conjugated DM4 (1 µg DM4 equals approximately 55 µg antibody protein). Anti-tumor efficacy was dose-dependent with the highest dose tested (450 µg/kg) resulting in a log cell kill (LCK) of 2.9 (Compare also Table 10). Animals gained weight throughout the course of the study indicating that the treatment was not toxic to the mice.

FIG. 14 indicates 250 µg/kg as a first effective dose in mice, which translates to a comparable human dose of 166 mg/m$^2$.

Indicator: Pancreas/Mammary and other Carcinoma—Xenograft Models

General Experimental Set-Up

In accordance with the CD138 expression analysis (Immunohistochemistry analysis on tumor tissue microarrays) tumor candidates were selected from a primary tumor collection, that is, from patient derived tumors. Following subcutaneous transplantation and establishment of tumors (induction time 30 days), the immunoconjugate BT062 was injected intravenously at 2 different concentrations of the maytansinoid DM4, 450 µg/kg and 250 µg/kg (each based on the molecular weight of the linked DM4 (1 mg of DM4 is conjugated to 52 mg of antibody, equalling a total mass of 53 mg; 450 µg/kg DM4=23.850 µg) The immunoconjugate was administered once weekly for 10 weeks (in case of treatment of pancreatic tumor implanted mice) and 5 weeks (in case of mammary tumor implanted mice).

Example 1

Pancreas Carcinoma

Pancreatic tumor tissue (PAXF 736 (Kuesters et al., 2006) was implanted (bilateral) into NMRI mice. The implanted tumor originated from a patient's primary pancreatic carcinoma (poorly differentiated, infiltrating adenocarcinoma (an exocrine carcinoma)). No side effects were observed. The tumor of this patient was identified as a high CD138 expressing tissue by Immunohistochemistry studies. However, CD138 is not expressed to an degree comparable to myelomatous plasma cells in multiple myeloma patients, as detected on tumorigenic cell lines by flow cytometric surface staining.

Treatment with BT062 was initiated after tumors have reached a size of approx. 6-8 mm diameter (minimum 5 mm). Tumor diameters have been measured two times a week. Tumor volumes were calculated according to the formula a*b*b/2 where "a" is the longest axis and "b" the perpendicular axis thereto. Inhibition of tumor volume in the test groups relative to the vehicle control group was calculated as the ratio of the median relative tumor volumes (T/C).

Tumor inhibition for a particular day (T/C in %) was calculated from the ratio of the median RTV (relative tumor volume) values of test versus control groups multiplied by 100%.

$$T/C(Day_x) = \frac{\text{Median relative tumor volume of the test group } Day_x}{\text{Median relative tumor volume of the control group } Day_x} \times 100\%$$

Figure 28:
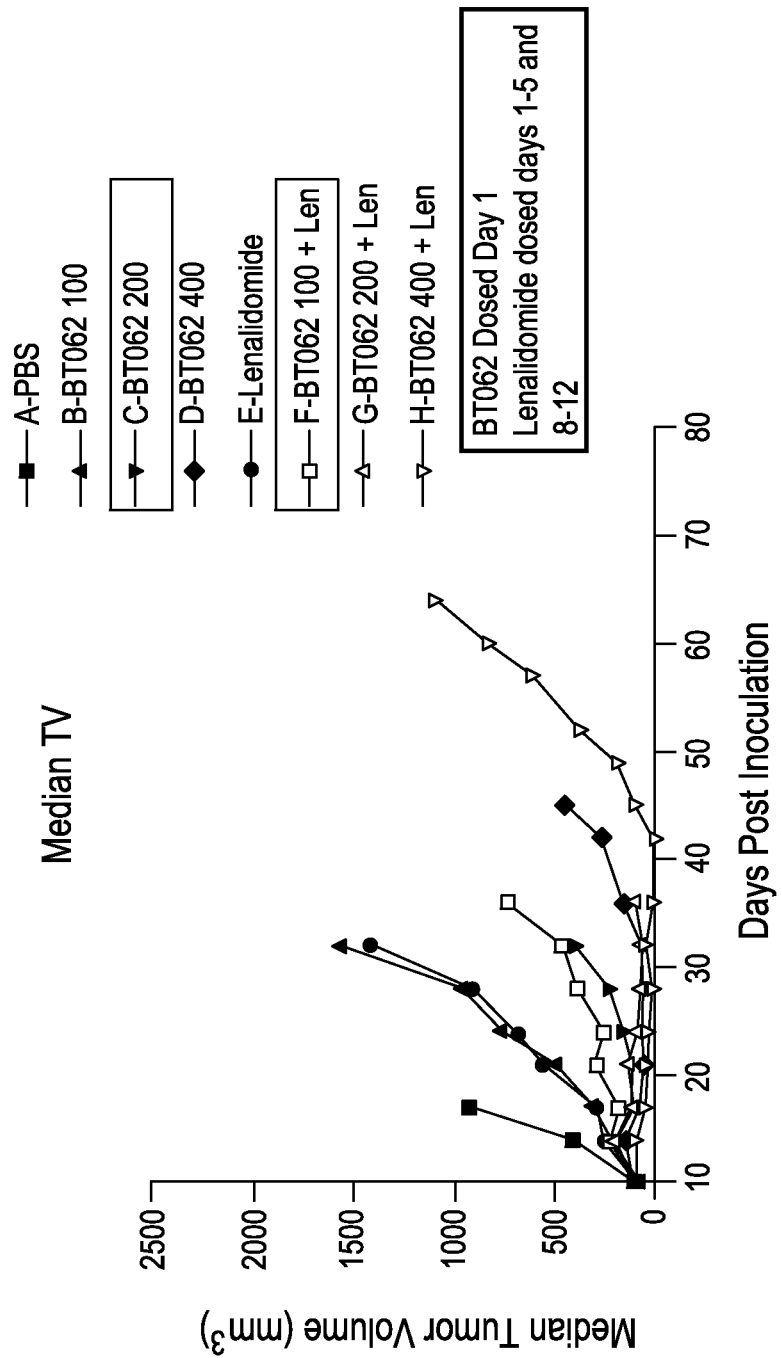
FIG. 28 shows the effect of the combination therapy on median tumor volume (TV) in a xenograft mouse model. The result show the effects of the combination of BT062 and lenalidomide.

Tumor volume could be significantly reduced by this weekly administration of BT062. As can be seen in FIG. 28, dose dependent partial and complete remission was observed. The Figure shows that at a dose of 23.85 mg/kg, complete remission could be obtained 28 days after tumor implantation, while at a dose of 13.25 mg/kg, complete remission could be obtained 35 days after tumor implantation. Notably, after 52 days all mice in both administration regimes were still alive (⅜), which the eight mice of the control group hd been reduced to 1. A T/C value below 10% indicates complete remission (CR) (Bissery et al., 1991). According to this criteria, CR was achieved in both treatment groups, reflecting the complete remission that was achieved by BT062. Remarkably in a treatment free observation phase, no tumor regrowth was detected, comfirming the complete curance of in this model.

TABLE 11

Tumor volume is pancreatic cancer xenograft mouse model

| Relative Tumor Volume (%) | Day 52: Mean (±) | Range | T/C (%) |
|---|---|---|---|
| Control | 2055 | 2055 | |
| BT062-DM4; 13.25 mg/kg | 0 (±1.0) | 0-3.5 | 0.0 |
| BT062-DM4; 23.85 mg/kg | 0 (±0.01) | 0-0.1 | 0.0 |

Example 2

Mammary Carcinoma

NMRI (nude) mice were implanted (bilateral) with primary mammary tumor of a patient (determined via IHC analysis as CD138 strong positive). A breast carcinoma skin metastasis was taken stage M1. It was a tumor which did not respond to Herceptin, (low $Her_2$ with an intermediate expression). The tumor was estrogen receptor negative and progesterone receptor negative. Tumors to be implanted were selected according to IHC staining results (strong, homogenous expression of CD138 detected by BT062, triple negativity (negative expression of hormone receptors estrogen and progesterone); Her2 expression scored 2 or less (regarded as Herceptin non responsive).

Treatment with BT062 was initiated after tumors had reached a size of approx. 6-8 mm diameter (minimum 5 mm). Tumor diameters were measured two times a week. Tumor volumes were calculated according to the formula a*b*b/2, with "a" being the longest axis and "b" the perpendicular axis thereto. Inhibition of tumor volume in the test groups relative to the vehicle control group was calculated as the ratio of the median relative tumor volumes (T/C).

Tumor volume could be significantly reduced by weekly administration of BT062. A dose dependent partial and complete remission was observed. The immunoconjugate was well tolerated, having no influence on body weight after each injection. A T/C value below 10% was obtained in both treatment groups, reflecting a complete remission achieved by the administration of BT062. As can be seen in Figure YYY, the anti-tumor effect (i.e., complete remission) was achieved after 21 days, which can be considered a rapid response to BT062. Compared to the pancreatic model, duration of treatment could be cut short by half (5 weeks instead of 10 weeks) and the low dose of 13.25 mg/kg was reduced to 4 mg/kg to achieve a similar effect, namely complete remission and no tumor regrowth. The shorter treatment period for mammary carcinoma was not expected, since on IHC analysis the level of CD138 expression was similar. Thus, no conclusions can be drawn from the level of CD138 expression to a general recommendation for the treatment duration. After 21 days all mice of both the treated groups as well as the control group were still alive. In a treatment free observation period (39 days after the last administration of the immunoconjugate) no tumor regrowth was detected, confirming the complete curance.

TABLE 12a

Tumor volume is mammary carcinoma xenograft mouse model.

| Relative Tumor Volume (%) | Mean (Day 21) | Range | T/C |
|---|---|---|---|
| Control (PBS) | 533 (±149.5) | 339-878 | |
| BT062-DM4; 13.25 mg/kg/4 mg/kg | 0 (±0.02) | 0-0.1 | 0.0 |
| BT062-DM4; 23.85 mg/kg | 0 (±1.75) | 0-6.6 | 0.0 |

TABLE 12b

Expression of CD138 on mammary carcinoma cells vs. epithelium cells

| | Staining score (membrane) | |
|---|---|---|
| FFPE tissue samples | 0.25 µg/mL | 0.05 µg/mL |
| Breast, tumor Mets, -061909-13 | 3 Homo | 2-3 Homo |
| Breast, tumor Unknown, -061909-12 | 2-3 Homo | 1-2 Hetero |
| Breast, tumor Mets, -061909-09 | 3 Hetero | 2 Focal |
| Breast, tumor Primary, -111904-4 | 3 Hetero | 1-3 Hetero |
| Breast, tumor Primary, -111904-1 | 3 Hetero | 1 Hetero |
| Normal Skin sample 1 | 3 Homo | 3 Homo |
| Normal Skin sample 1 | 3 Homo | 3 Homo |

Example 3

Bladder Carcinoma

NMRI (nude) mice are implanted with a bladder tumor (determined via IHC analysis as CD138 strong positive), namely a transitional cell carcinoma.

Treatment with BT062 is initiated after tumors had reached a size of more than 5 mm. Tumor diameters are measured two times a week. Tumor volumes are calculated according to the formula a*b*b/2, with "a" being the longest axis and "b" the perpendicular axis thereto. Inhibition of tumor volume in a test groups relative to the vehicle control group is calculated as the ratio of the median relative tumor volumes (T/C).

Tumor volume is sought to be significantly reduced by weekly administration of BT062. Any dose dependent partial and complete remission is tracked.

Example 4

Lung Carcinoma

NMRI (nude) mice are implanted with a Lung carcinoma (determined via IHC analysis as CD138 strong positive).

Treatment with BT062 is initiated after tumors had reached a size of more than 5 mm. Tumor diameters are measured two times a week. Tumor volumes are calculated according to the formula a*b*b/2, with "a" being the longest axis and "b" the perpendicular axis thereto. Inhibition of tumor volume in a test groups relative to the vehicle control group is calculated as the ratio of the median relative tumor volumes (T/C).

Tumor volume is sought to be significantly reduced by weekly administration of BT062. Any dose dependent partial and complete remission is tracked.

Preclinical Toxicity Studies

Xenograft mouse models are excellent for determining whether or not the immunconjugates of the present invention are effective in context of the cancer modelled by the mouse. However, since these models lack the appropriate inherent expression of CD138, they cannot serve as a reliable model for toxicity studies and thus cannot be used to fully determine tolerable amounts of the immunconjuages of the present invention.

Cynomolgus and rhesus monkeys have also not shown that BT062 binds to any CD138-related antigens but are currently the best suitable animal species for toxicology studies of BT062 known. It is expected, therefore, that the toxicity profile of BT062 in mice and monkeys will be due to the non-targeted effects of the cytotoxic component of the conjugate (DM4).

Single-dose toxicity studies were conducted fulfilling GLP requirements in cynomolgus monkeys and in CD-1 mice. These studies were designed to identify doses that cause severe toxicity and those which have no (or minimal) adverse effects in animals, to identify potential toxicities in humans and to identify a safe starting dose for a Phase I clinical trial using a single bolus infusion of BT062.

Acute Mouse Toxicity Study

A single dose toxicity study was performed in mice with BT062 administered by a single bolus IV injection at doses ranging from 60-255 mg/m$^2$ (20-85 mg/kg). The highest non-severely toxic dose (HNSTD) of BT062 in mice was 45 mg/kg (135 mg/m$^2$), with an estimated STD$_{10}$ of 57 mg/kg (171 mg/m$^2$).

Acute Monkey Toxicity Study

A single dose toxicity study was performed in cynomolgus monkeys with BT062 IV-administered at doses ranging from 48-336 mg/m$^2$ (4-28 mg/kg). The HNSTD of BT062 in cynomolgus monkey was 12 mg/kg (144 mg/m$^2$).

Human Trials with BT062

In the context of the present invention, human subjects responded well to a low dose regime. This was even the case in absence of any additional treatments that would compensate for potential variations in qualitative or quantitative expression of the CD138 on the target cells (compare MYLO-TARG). While mouse models demonstrated that BT062 has highly significant antimyeloma activity at doses that are well tolerated in mice, effectiveness was considerably better at relatively high doses (see FIG. 14), posing the question how higher doses would be tolerated by human subjects that express CD138 on a wide variety of non-tumor cells.

Phase I Research Study

This study is being performed to test the effects (good and bad) and to determine the MTD (maximum tolerated dose) of BT062 in treating patients with relapsed or relapsed refractory multiple myeloma.

Up to now, 26 patients were recruited. At least 11 out of 26 patients experienced diminished disease progression as represented by receiving at least a forth treatment cycle, while 4 patients are still undergoing treatment. The trial is being performed at different sites, with groups of 3 and 4 patients being treated with different dose levels (10 mg/m$^2$, 20 mg/m$^2$, 40 mg/m$^2$, 80 mg/m$^2$, 120 mg/m$^2$, 160 mg/m$^2$, 200 mg/m$^2$) for anywhere between 1 to 10 treatment cycles (see FIG. 23). As the person skilled in the art will appreciate a higher number of treatment cycles is possible and within the scope of the present inventions, such as 10 to 50, 10 to 100, 10 to 200 and more. Disease progression diminished with relatively low dosage levels, namely 20 mg/m$^2$, 40 mg/m$^2$, 80 mg/m$^2$ and 120 mg/m$^2$, with one patient at the $2^{nd}$ dosage level of 20 mg/m$^2$ displaying no disease progression for 10 treatment cycles of 21 days. See FIG. 23, where in patient samples 001-001, 003-001, 002-002, 002-003, 002-004, 003-003, 001-005, 001-006, 001-008, 001-009, 004-001, 001-011, 004-002 and 001-012 it was observed that the disease eventually progressed, even though stable disease and responses, including minor and partial responses could be observed. In patient sample 001-006, the dose was held.

At these dose levels, as described above (see Tables 7 and 8), rapid clearance of BT062 from plasma was also observed. Some pharamcokinetic profiles of these low dose administration schemes are shown in FIG. 17. A comparision of BT062 plasma profiles in humans with that of monkeys is shown in FIG. 18. The graph on the left shows the differences at 120 mg/m$^2$, while those on the right (160 mg/m$^2$) show considerably less differences.

Doses of 160 mg/m$^2$ and 200 mg/m$^2$ were also administered. A dose of 160 mg/m$^2$ was identified as MTD and studies in this group was expanded. A dose of 200 mg/m$^2$ was identified as MAD. Dose limiting toxicities (DLT) were determined using a grading according to NCI CTCAE v3.0 (Aug. 9, 2006, http://ctep.cancer.gov). Study specific DLT criteria are listed below:

Nonhematological
    Alopecia, of any grade, is not considered a DLT
    Grade 3-4 nausea and vomiting lasting longer than 3 days despite optimal antiemetic medication.$^a$
    Grade 3-4 diarrhea lasting longer than 3 days despite optimal antidiarrheal medication.$^a$
        a. Optimal antidiarrheal and antiemetic treatment were determined by each investigator.

Hematologic
    Grade 4 neutropenia lasting longer than 5 days.
    Grade 3 or higher neutropenia with temperature greater than or equal 101° F., for 2 consecutive determinations spaced 4 hours apart.
    Grade 4 thrombocytopenia
    Grade 3 or higher thrombocytopenia with bleeding and requiring the use of platelet transfusion.
    Grade 3 neutropenia, grade 3 thrombocytopenia were NOT considered DLTs.

All adverse events (AEs) were be evaluated according to the NCI-CTCAE v3.0 For AEs not listed in the NCI-CTCAE v3.0, severity were assessed by the investigator according to these criteria. Only grade 1 and grade 2 were acceptable, whereby grade 1 (Mild) requires minimal or no treatment and do not interfere with the patient's daily activities and grade 2 (Moderate) results in a low level of inconvenience or concern with the therapeutic measures. Moderate events may cause some interference with the subject's functioning.

AEs of Grade 3 (Severe) and Grade 4 (Life threatening) considered related to BT062 were considered not acceptable and defined as DLT, if not otherwise defined by study specific DLT criteria.

Patient samples 003-005, 002-012, and 002-011 were at the time still participating in the study.

Patients of samples 002-003, 001-002 and 002-008 had withdrawn.

Figure 23:
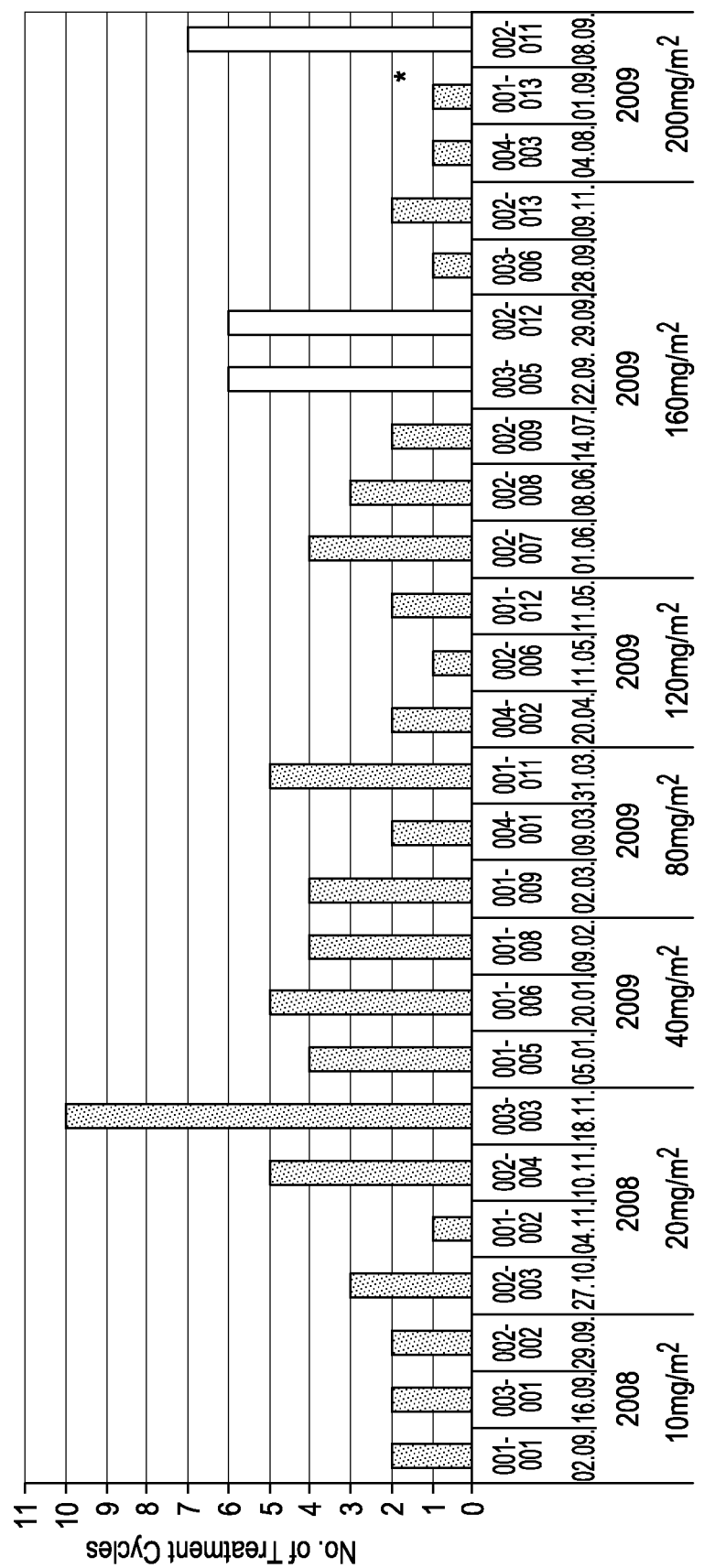
FIG. 23 depicts a treatment chart in human subjects with different dosages of BT062 administed in the course of the indicated treatment cycles, wherein each treatment cycle lasted 21 days and the respective dosage was administered on day 1 of each cycle.

As indicated in FIG. 23, repeated single doses of regime 10 mg/m$^2$, 20 mg/m$^2$, 40 mg/m$^2$, 80 mg/m$^2$, 120 mg/m$^2$, 160 mg/m$^2$, 200 mg/m$^2$ were performed every 21 day, meaning on day 1, day 22, day 43, day 64, day 85, day 106, and so forth. The disease has been and will be monitored by physician's assessment of hematology, clinical symptoms and clinical chemistry as well as by measuring M-Protein levels in the serum and urine of patients in (g/dL) and free light-chain (FLC) levels in the serum of patients over time.

Immunoglobulin Assessment

The amount of Ig antibodies including determination of IgG subgroups was analyzed at screening.

M-protein Quantification and Serum Free Light Chain Assay

Initially, the response to treatment was evaluated at day 1 of treatment cycles 1-3 by M-protein quantification using immunoelectrophoresis (IEP) and immunofixation electrophoresis (IFE) from serum and 24-hour urine collection. For treatment cycles 3 and beyond, M-protein quantification was performed at the Day 15 visit in order for the results to be available to assess response prior to initiating the next treatment cycle. A general quantitative immunoglobulin assessment was done together with M-protein quantification.

Serum samples were used to perform FLC assays to examine multiple myeloma subjects with no detectable M-protein (nonsecretory/oligosecretory myeloma) and to allow for detection of early response to treatment. Therefore serum FLC assays were performed on day 1, 2, 3, and 8 of treatment cycle 1, on day 2, 3, 8 and 15 of cycle 4, as well as on day 1, 8 and 15 of all other treatment cycles. M-protein and FLC were be analyzed at the screening and at the close-out visit. Evaluations at day 1 of cycle 1 served as baseline values.

| Dose mg/m$^2$ | FIG. | Urine/Serum M-protein measurements and FLC measurements |
|---|---|---|
| 20 | FIG. 24 | Urine M-Protein decreased after 3$^{rd}$ treatment for about 17 weeks and increased after 9$^{th}$ treatment |
| | | M-Protein criteria for Minor Response reached after 8$^{th}$ treatment |
| | | Decrease in Urine M-Protein level from baseline by more than 50% and from Day 42 (3$^{rd}$ treatment) by more than 75% |
| | | Diseases progression after Cycle 10 |
| | | Serum M-Protein between 0.06 and 0.1 g/dL (defined as not measurable) |
| 40 | FIG. 25 | Stable disease for 14 weeks |
| | | Serum M-Protein decreased after 1$^{st}$ treatment and stabilized for 14 weeks |
| | | Diseases progression observed after treatment was held at the start of cycle 6 (day 105) |
| | | Urine M-Protein increased from 0 at screening to a maximum of about 16 mg/24 h (defined as not measurable) |
| 160 | FIG. 26 | Serum FLC level increased during the screening period starting −21 days before day 1 of the treatment |
| | | Serum FLC level decreased very soon after 1$^{st}$ treatment and was already close to 25% decrease at day 8 |
| | | In comparision to baseline, FLC levels are reduced by about |

| Dose mg/m² | FIG. | Urine/Serum M-protein measurements and FLC measurements |
|---|---|---|
| | | 40% during 1$^{st}$ cycle and by more than 50% after 2$^{nd}$, 3$^{rd}$ and 4$^{th}$ treatment<br>FLC criteria for Partial Response were reached very early<br>Disease progession after the end of the 4$^{th}$ treatment cycle<br>Serum M-Protein not measurable = 0; Urine M-Protein decreased from 140 mg/24 h at baseline to 120 mg/24 h before 2$^{nd}$ treatment (defined as not measurable) => non-secretory Myeloma |

Table 13 provides observations made regarding Urine/Serum M-protein and serum FLC measurements in selected patients.

Determination of BT062 and DM4 from Plasma

To assess single dose PK properties of BT062, after IV administration of BT062, extensive plasma sampling was performed during the first treatment cycle. The same evaluation was performed during treatment cycle 4. To a lesser extent plasma samples were also be obtained at day 1 and 8 of all other treatment cycles, as well as on close-out and follow-up visit.

Determination of Shed CD138 and NAPA

All pre-dose plasma samples were evaluated for levels of shed/soluble CD138 (sCD138) to investigate a potential correlation between levels of sCD138 and antitumor activity. These measurements also allowed to determine that the lower than expected cmax values are not dependent on the amount of sCD138 present prior to administration of BT062 (see FIG. 22). Predose plasma samples from day 1 of each treatment cycle and from close out and follow-up visit were evaluated for the presence of humoral responses against BT062 (drug product) by assessment of human antiproduct antibodies (HAPA).

Shed CD138 Measurements Observed

In Myeloma patients high levels of sCD138 can be observed and might be an indicator of prognosis of myeloma patients (Maisnar et al., 2005).

Patients with MGUS and MM might display high levels of soluble CD138 concomitant with higher levels of β2-microglobulin and elevated plasma cell content in the bone marrow (Aref et al., 2003).

A kit was used for determining soluble CD138. Surprising, it was found that at 20 mg/m² of BT062 in patient 003-003, this patient displayed a minor response with regard to urine M-protein levels, although this patient displayed high levels of sCD138 before treatment.

Soluble (s) CD138 values were determined in different subjects.

TABLE 14

| Subject | sCD138 (ng/mL) |
|---|---|
| 002-003 | 61.3 |
| 001-002 | 196 |
| 002-004 | 56.7 |
| 003-003 | 2583 |
| Mean | 724.1 |

Patient 003-003 (dose 20 mg/m²) displayed very high values of sCD138. Nonetheless, this patient achieved a minor response in M-Protein level.

Combination Studies

Possible anti-myeloma drug candidates have been evaluated as combination partners for BT062 in cell lines.

Cell Line Studies

Combination studies in xenograph mouse models were preceded by studies in cell lines. The synergy determination in different cell lines was performed according to Chou and Tallay (1984), using the median effect analysis. Here, $IC_{50}$ values for the cytotoxic effects for each drug and each cell line are calculated, and then $IC_{50}$ ratios for each drug pair. The cells were then exposed to dilution series of either these drug mixtures, or the drugs alone. Experimental data were analyzed using the CompuSyn software (ComboSyn, Inc., Paramus, N.J.). Combination Indexes (CI) for each independent experiment were calculated and reported separately. In the analysis, CI less than 1, equal to 1 and more than 1 indicates synergy, additivity and antagonism, respectively. According to the classification of T. C. Chou (CompuSyn. User's guide, 2004), the author of the method, the scale of synergism and antagonism is as follows:

| Combination Index | Description |
|---|---|
| <0.1 | Very strong synergism |
| 0.1-0.3 | Strong synergism |
| 0.3-0.7 | Synergism |
| 0.7-0.85 | Moderate synergism |
| 0.85-0.9 | Slight synergism |
| 0.9-1.1 | Nearly additive |
| 1.1-1.2 | Slight antagonism |
| 1.2-1.45 | Moderate antagonism |
| 1.45-3.3 | Antagonism |
| 3.3-10 | Strong antagonism |
| >10 | Very strong antagonism |

TABLE 15

Estimates of synergitic results obtained in cell lines according to the method of Chou and Talalay (1984).

| | Cells | | |
|---|---|---|---|
| Drug | RPMI 8226 | MOLP8 | U266 |
| Bortezomib | Additive | Slightly antagonistic | Antagonistic |
| Thalidomide | Additive to synergistic | Additive to slightly antagonistic | Antagonistic |
| Lenalidomide | Synergistic | Additive to synergistic | Slightly to moderately antagonistic |
| Melphalan | Additive to synergistic | Slightly to moderately antagonistic | Additive to slightly synergistic |
| Dexamethasone | Not determined | additive | additive |

In this example MOLP 8 cell lines were used for combination of BT062 with bortezomib, thalidomide, lenalidomide, melphalan and dexamethasone.

Combination with thalidomide or bortezomib, did neither result in a syngeristic nor an additive effect, but rather an antagonistic effect. In contrast to these cell culture studies combination with bortezomib was synergistic in the xenograft model described below.

Possible anti-myeloma drug candidates have been evaluated as combination partners for BT062 in Xenograft studies using MOLP8 human multiple myeloma cells.

Example 1

Anti-Myeloma Effect of Combination Therapy with BT062 and Lenalidomide

Female SCID mice were subcutaneously inoculated with MOLP 8 human myeloma cells. Treatment with BT062 alone or in combination with Lenalidomide was initiated day 11 post tumor inocculation. BT062 was used in concentrations of 100 µg, 200 µg and 400 µg alone and in combination with Lenalidomide which was dosed intraperitoneally at 100 mg/kg on days 1 to 5 and days 8 to 12. A control group of animals received Phosphate buffered saline (PBS) using the same schedule and route of administration. Tumor growth was monitored by measuring tumor size and calculated with the formula length×width×height×½, determined on days 10, 14, 18 and 21.

Synergism was calculated as follows (Yu et al., 2001; Gunaratnam et al., 2009):

RATIO($r$)=expected FTV(combination)/observed FTV(combination)

FTV: Fractional tumor volume=mean tumor volume (test)/mean tumor volume (control)

A ratio>1 is regarded as synergistic, whereas r<1 is less than additive.

The ratio (r) is, when above 1, referred to herein as "SYNERGY RATIO."

As can be seen from Table 15 synergism was observed after 28 days in concentrations

TABLE 16

Fractional tumor volume in MOLP 8 xenografts.

| Days | BT062 100 | Lenalidomide | BT062 100 + Len (observed) | BT062 100 + Len expected | ratio (exp/obs) |
|---|---|---|---|---|---|
| 10 | 0.93 | 1.00 | 0.97 | 0.93 | 0.96 |
| 14 | 0.75 | 0.82 | 0.59 | 0.61 | 1.04 |
| 17 | 0.52 | 0.45 | 0.23 | 0.23 | 1.02 |
| 21 | 0.53 | 0.42 | 0.19 | 0.22 | 1.19 |
| 24 | 0.44 | 0.55 | 0.18 | 0.24 | 1.30 |
| 28 | 0.33 | 0.46 | 0.17 | 0.15 | 0.90 |

| | BT062 200 | Lenalidomide | BT062 200 + Len (observed) | BT062 100 + Len expected | ratio (exp/obs) |
|---|---|---|---|---|---|
| 10 | 1.02 | 1.00 | 1.00 | 1.02 | 1.02 |
| 14 | 0.45 | 0.82 | 0.51 | 0.37 | 0.73 |
| 17 | 0.13 | 0.45 | 0.14 | 0.06 | 0.41 |
| 21 | 0.08 | 0.42 | 0.07 | 0.03 | 0.45 |
| 24 | 0.11 | 0.55 | 0.06 | 0.06 | 1.08 |
| 28 | 0.13 | 0.46 | 0.03 | 0.06 | 1.86 |

| | BT062 400 | Lenalidomide | BT062 400 + Len (observed) | BT062 100 + Len expected | ratio (exp/obs) |
|---|---|---|---|---|---|
| 10 | 0.94 | 1.00 | 0.91 | 0.95 | 1.04 |
| 14 | 0.44 | 0.82 | 0.24 | 0.36 | 1.49 |
| 17 | 0.09 | 0.45 | 0.06 | 0.04 | 0.63 |
| 21 | 0.04 | 0.42 | 0.04 | 0.02 | 0.44 |
| 24 | 0.04 | 0.55 | 0.03 | 0.02 | 0.80 |
| 28 | 0.04 | 0.46 | 0.01 | 0.02 | 1.43 |

Different concentrations of BT062 either alone or in combination with Lenalidomide have been administered into tumor bearing xenograft. FTV represents the relative tumor volume. Synergistic effects are determined using Ratio values expected FTV versus observed FTV. A ratio >1 indicates synergy.

TABLE 17

Lenalidomide BT062 combination: effects at different dosages.

| Agent | Dosage per injection | Total dose | T/C (%) (DAY 17) | Regressions Partial | Regressions Complete | Tumor free survivors day 77 | Result |
|---|---|---|---|---|---|---|---|
| PBS | (0.2 ml) | — | — | 0/6 | 0/6 | 0/6 | |
| BT062 | 100 ug/kg | 100 ug/kg | 35 | 0/6 | 0/6 | 0/6 | Active |
| BT062 | 200 ug/kg | 200 ug/kg | 14 | 0/6 | 0/6 | 0/6 | Active |
| BT062 | 400 ug/kg | 400 ug/kg | 9 | 4/6 | 1/6 | 0/6 | highly active |
| lenalidomide | 100 mg/kg | 1 g/kg | 31 | 0/6 | 0/6 | 0/6 | Active |
| BT062 lenalidomide | 100 ug/kg 100 mg/kg | 100 ug/kg 1 g/kg | 19 | 0/6 | 0/6 | 0/6 | Active |
| BT062 | 200 ug/kg | 200 ug/kg | 12 | 2/6 | 0/6 | 0/6 | Active |

TABLE 17-continued

Lenalidomide BT062 combination: effects at different dosages.

| Agent | Dosage per injection | Total dose | T/C (%) (DAY 17) | Regressions Partial | Complete | Tumor free survivors day 77 | Result |
|---|---|---|---|---|---|---|---|
| lenalidomide BT062 Lenalidomide | 100 mg/kg 400 ug/kg 100 mg/kg | 1 g/kg 400 ug/kg 1 g/kg | 6 | 5/6 | 4/6 | 0/6 | highly active |

FIG. 28 shows the effect of the combination therapy on median tumor volume (TV) in a xenograft mouse model. The result show addtitive effects of the combination. Notably the combination resulted in a dose of 100 µg/kg of the immunoconjugate, when combined with a dose of 100 mg/kg lenamidomide. Please refer to the table above for the synergy ratio.

Example 2

Anti-Myeloma Effect of Combination Therapy with BT062 and VELCADE

VELCADE has been evaluated as potential multiple myeloma drug combination partner for BT062 in Xenograft studies using MOLP8 multiple myeloma cells (IMGN Inc.). Treatment with BT062 alone or in combination with VELCADE was initiated 11 days past tumor implantation. BT062 was used in concentrations of 100 µg, 200 µg and 400 µg alone and in combination with VELCADE which was dosed at 100 mg/kg on days 1, 4, 8 and 11. A control group of animals received Phosphate buffered saline (PBS) using the same schedule and route of administration. Tumor growth was monitored by measuring tumor size and calculated with the formula length×width×height×½, determined on days 10, 14, 17, 21, 24 and 28, respectively.

Synergism was calculated as in Example 1 of the combination studies.

As can be seen from Table 18, synergism is observed in the combination BT062 with VELCADE at day 25 in all BT062 dose regimens. R values reported in the literature are even higher (Yu et al., 2001).

TABLE 18

Combination treatment with VELCADE.

| Day | BT062 100 | Velcade | BT062 100 + Velcade (observed) | expected | ratio (exp/obs) |
|---|---|---|---|---|---|
| 10 | 1.06 | 1.05 | 1.04 | 1.12 | 1.07 |
| 14 | 0.74 | 0.84 | 0.56 | 0.62 | 1.11 |
| 18 | 0.44 | 0.96 | 0.28 | 0.42 | 1.54 |
| 21 | 0.39 | 0.80 | 0.23 | 0.31 | 1.38 |
| 25 | 0.48 | 0.95 | 0.26 | 0.46 | 1.75 |

| Days | BT062 200 | Velcade | BT062 200 + Vel (observed) | expected | ratio (exp/obs) |
|---|---|---|---|---|---|
| 10 | 1.02 | 1.05 | 1.07 | 1.12 | 1.07 |
| 14 | 0.52 | 0.84 | 0.45 | 0.44 | 0.98 |
| 18 | 0.13 | 0.96 | 0.10 | 0.12 | 1.19 |
| 21 | 0.10 | 0.80 | 0.05 | 0.08 | 1.47 |
| 25 | 0.10 | 0.95 | 0.04 | 0.09 | 2.09 |

| Days | BT062 400 | Velcade | BT062 400 + Vel (observed) | expected | synergy ratio (exp/obs) |
|---|---|---|---|---|---|
| 10 | 1.09 | 1.05 | 1.04 | 1.15 | 1.10 |
| 14 | 0.45 | 0.84 | 0.43 | 0.38 | 0.88 |
| 18 | 0.08 | 0.96 | 0.09 | 0.08 | 0.89 |
| 21 | 0.05 | 0.80 | 0.04 | 0.04 | 0.98 |
| 25 | 0.04 | 0.95 | 0.02 | 0.03 | 1.36 |

Fractional tumor volume (FTV) represents the mean tumor volume (test)/mean relative tumour volume (control). Ratio of expected FTV (combination) vs. observed FTV (observed). Ratio value >1 indicate synergy, values less than 1 indicate an additive effect.

TABLE 19

VELCADE BT062 combination: effects at different dosages.

| Agent | Dosage per injection | Treatment days (TX start date = day 10 post inoc.) | T/C (%) | (T-C) in days | log cell kill | Regressions Partial | Complete | Tumor free survivors day 67 | Result |
|---|---|---|---|---|---|---|---|---|---|
| PBS | (0.2 ml) | Day 1 | — | — | — | 0/6 | 0/6 | 0/6 | |
| BT062 | 100 ug/kg | Day 1 | 43 | 5.5 | 0.5 | 0/6 | 0/6 | 0/6 | Inactive |

TABLE 19-continued

VELCADE BT062 combination; effects at different dosages.

| Agent | Dosage per injection | Treatment days (TX start date = day 10 post inoc.) | T/C (%) | (T-C) in days | log cell kill | Regressions | | Tumor free survivors day 67 | Result |
|---|---|---|---|---|---|---|---|---|---|
| | | | | | | Partial | Complete | | |
| BT062 | 200 ug/kg | Day 1 | 11 | 14.5 | 1.3 | 1/6 | 0/6 | 0/6 | Active |
| BT062 | 400 ug/kg | Day 1 | 7 | 31.5 | 2.8 | 4/6 | 2/6 | 0/6 | highly active |
| Velcade | 1 mg/kg | days 1, 4, 8, 11 | 100 | 0.5 | 0.0 | 0/6 | 0/6 | 0/6 | Inactive |
| BT062 | 100 ug/kg | Day 1 | 20 | 10.5 | 0.9 | 1/6 | 0/6 | 0/6 | Active |
| Velcade BT062 | 100 mg/kg 200 ug/kg | days 1, 4, 8, 11 Day 1 | 7 | 23.5 | 2.1 | 4/6 | 1/6 | 0/6 | highly active |
| Velcade BT062 | 100 mg/kg 400 ug/kg | days 1, 4, 8, 11 Day 1 | 7 | 36.5 | 3.2 | 6/6 | 0/6 | 0/6 | highly active |

Figure 29:
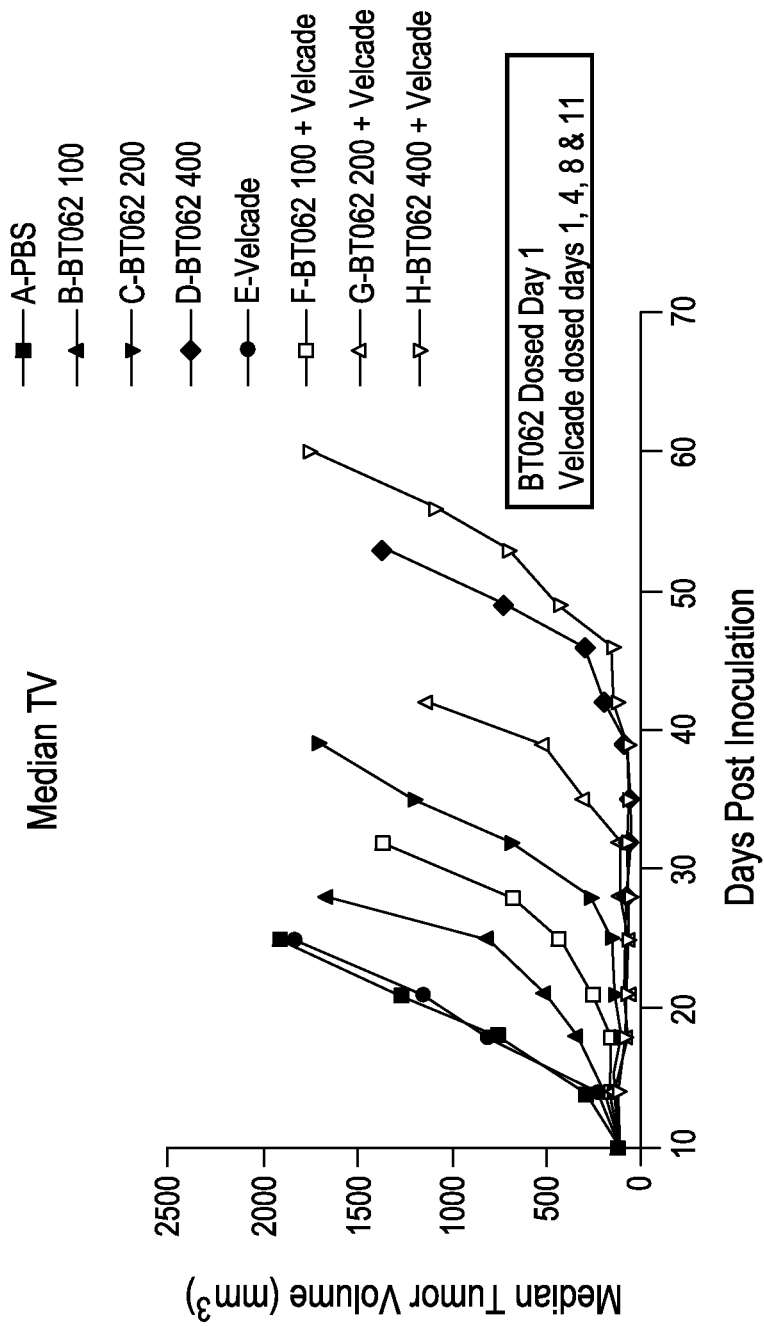
FIG. 29 shows the effect of the combination therapy on median tumor volume (TV) in a xenograft mouse model. The result show the effects of the combination of BT062 and VELCADE.

FIG. 29 shows the effect of the combination therapy on median tumor volume (TV) in a xenograft mouse model. The result show that in the model used, VELCADE treatment alone had no effect on the tumor volume. The combination with BT062 provided synergistic effects. Notably the synergism resulted in a dose of 100 µg/kg of the immunoconjugate, when combined with a dose of 100 mg/kg VELCADE. Please refer to the table above for the synergy ratio.

Example 3

BT062/Melphalan

Figure 30:
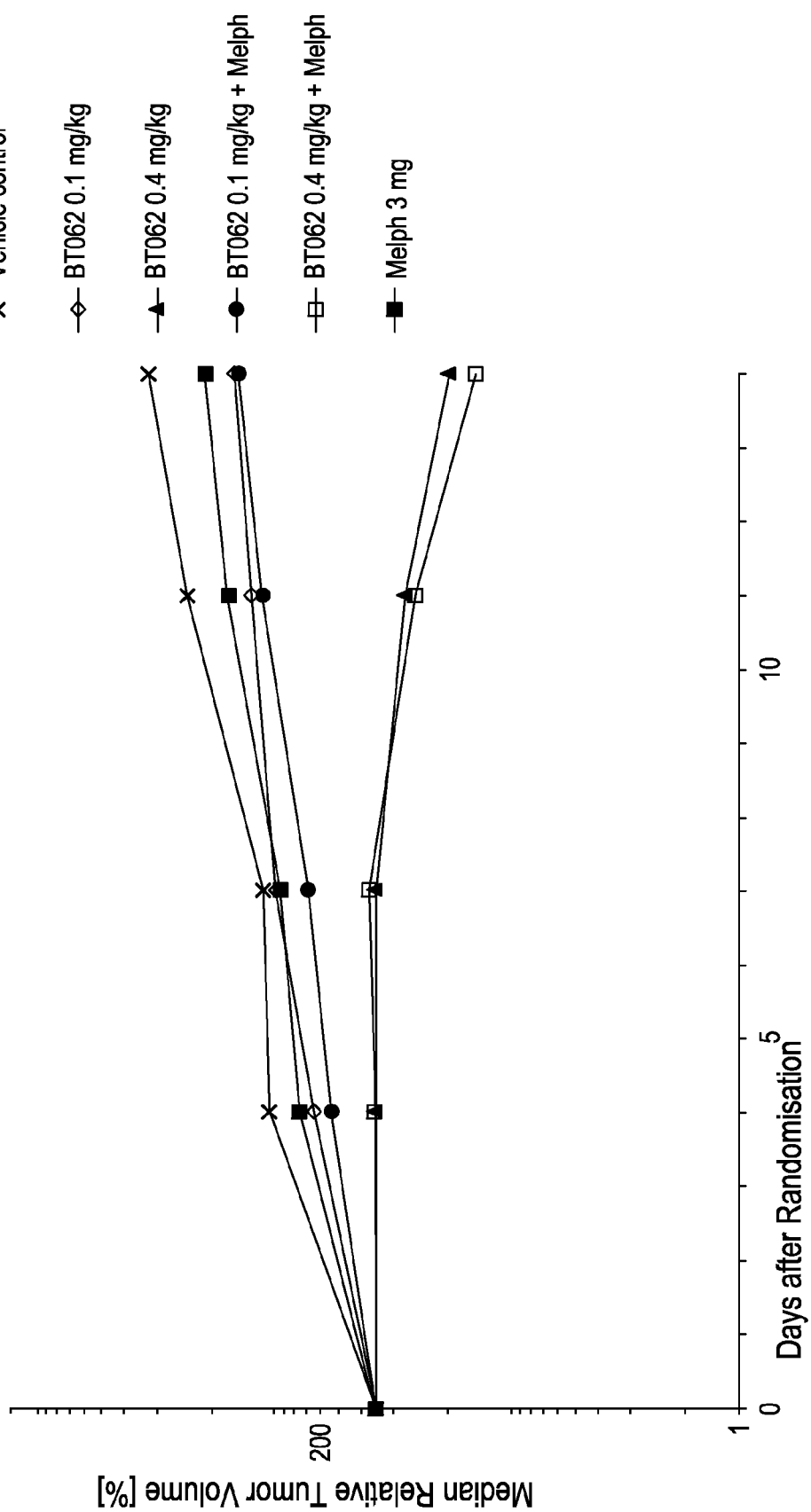
FIG. 30 shows the effect of the combination therapy on median tumor volume (TV) in a xenograft mouse model. The result show the effects of the combination of BT062 and melphalan.

RPMI cells have been implanted subcutaneously into nude mice. Mice were randomized when tumor reached a total volume of approx 100 mm$^3$. BT062 was injected intravenously at 2 different concentrations: 400 µg/kg and 100 µg/kg; each based on the molecular weight of the linked DM4. PBS served as negative control. Per group, 8 mice with one tumor each (unilateral implantation) were used. BT062 was dosed weekly followed by Melphalane once weekly (3 mg/kg) one day after BT062 injection intraperitoneally. The results are shown in FIG. 30.

Once given the above disclosure, many other features, modifications, and improvements will become apparent to the skilled artisan. Such other features, modifications, and improvements are therefore considered to be part of this invention, the scope of which is to be determined by summary of the invention and the following claims.

Bibliography

Abdelkefi et al.; "Single autologous stem-cell transplantation followed by maintenance therapy with thalidomide is superior to double autologous transplantaion in multiple myeloma: results of a multicenter randomized clinical trial;" Blood; 111; 2008; pp. 1805-1810.

Akkina et al.; "Modeling human lymphoid precursor cell gene therapy in the SCID-hu mouse;" Blood; 84; 1994; pp. 1393-1398.

Armour et al.; "Recombinant human IgG molecules lacking Fcgamma receptor I binding and monocyte triggering activities;" Eur J Immunol; 29(8); 1999; pp. 2613-24.

Anderson et al.; "Multiple Myeloma: New Insights and Therapeutic Approaches; Hematology; 2000; pp. 147-165.

Anderson et al.; "Multiple Myeloma; Hematology Am Soc Hematol Educ Program; 2002; pp. 214-40.

Anttonen et al.: "Syndecan-1 expression has prognostic significance in head and neck carcinoma;" Br J of Cancer 79 (3/4), 1999, pp. 558-564.

Anttonen et al.; "High syndecan-1 expression is associated with favourable outcome in squamous cell lung carcinoma treated with radical surgery;" Lung Cancer; 32(3); June 2001; pp. 297-305.

Aref et al.: "Syndecan-1 in multiple myeloma: relationship to conventional prognostic factors;" Hematology; 8; 2003; pp. 221-228.

Barbareschi et al.; "High syndecan-1 expression in breast carcinoma is related to an aggressive phenotype and to poorer prognosis;" Cancer; 98(3); Aug. 1, 2003; pp. 474-83.

Bataille et al.; "The phenotype of normal, reactive and malignant plasma cells. Identification of "many and multiple myelomas" and of new targets for myeloma therapy;" Haematologica; 91(9); September 2006; pp. 1234-40.

Bayer-Garner et al.; "Syndecan-1 (CD138) immunoreactivity in bone marrow biopsies of multiple myeloma: shed syndecan-1 accumulates in fibrotic regions;" Mod Pathol.; 14(10); October 2001; pp. 1052-8.

Beeram et al.; "A phase I study of trastuzumab-DM1 (T-DM1), a first-in-class HER2 antibody-drug conjugate (ADC), in patients (pts) with advanced HER2+ breast cancer (BC);" ASCO Meeting; Abstracts; May 20, 2008; pp. 1028.

Berenson et al.; "New drugs in multiple myeloma;" Curr Opin Support Palliat Care; 2(3); September 2008; pp. 204-10.

Bernfield et al.; "Biology of the syndecans: a family of transmembrane heparan sulfate proteoglycans;" Annu Rev Cell Biol; 8; 1992; pp. 365-393.

Beste et al.; "Small antibody-like proteins with prescribed ligand specificities derived from the lipocalin fold;" Proc. Natl. Acad. Sci. USA; 96; 1999; pp. 1898-1903.

Bhattacharyya et al.; "Maytansine binding to the vinblastine sites of tubulin;" FEBS Lett.; 75; 1977; pp. 159-162.

Bisping et al., "Targeting receptor kinases by a novel indolinone derivative in multiple myeloma: abrogation of stroma-derived interleukin-6 secretion and induction of apoptosis in cytogenetically defined subgroups;" Blood; 107(5); Mar. 1, 2006; pp. 2079-89.

Bissery et al., "Experimental Antitumor Activity of Taxotere (RP 56976, NSC 628503), a Taxol Analogue", Cancer Research 51, 1991, PP. 4845-4852.

Bladé et al.; "Advances in therapy of multiple myeloma;" Curr Opin Oncol; 20(6); November 2008; pp. 697-704.

Blum et al.; "Maytansine: A Phase I study of an ansa macrolide with antitumor activity;" Cancer Treat Rep; 62; 1978; pp. 435-438.

Brand et al.; "Management of high risk metastatic prostate cancer: the case for novel therapies;" J Urol Dec; 176 (6Pt 2); 2006; pp. S76-80.

Bläther et al.; "Drugs to Enhance the Therapeutic Potency of Anticancer Antibodies: Antibody-Drug Conjugates as Tumor-Activated Prodrugs;" Ojima, I., Vite, G. D. and Altmann, K.-H., Editors; Anticancer Agents-Frontiers in Cancer Chemotherapy, American Chemical Society, Washington, D.C., 2001; 2001; pp. 317-338.

Bross et al.; "Approval summary: gemtuzumab ozogamicin in relapsed acute myeloid leukemia;" Clin Cancer Res; 7; 2001; pp. 1490-1496.

Burris et al.; "A Phase I study of a first-in-class HER2 antibody-drug conjugate in subjects with HER2-overexpressing metastatic breast cancer;" 29$^{th}$ Annual San Antonio Breast Cancer Symposium (SABCS); Poster Abstract #2070; 2006.

Cabanillas et al., "Phase I study of maytansine using a 3 day schedule;" Cancer Treat Rep; 62; 1978; pp. 425-428.

Carbone et al.; "AIDS-related plasma-blastic lymphomas of the oral cavity and jaws: a diagnostic dilemma. Ann;" Otol. Rhinol. Laryngol; 108; 1999; pp. 95-99.

Carlsson et al., "Protein thiolation and reversible protein-protein conjugation. N-succinimidyl-3-(2-pyridyldithio) propionate, a new heterobifunctional reagent;" Biochem J; 173; 1978; pp. 723-737.

Carter P; "Improving the efficacy of antibody-based cancer therapies;" Nat Rev Cancer; 1; 2001; pp. 118-129.

Carter and Senter, "Antibody-Drug Conjugates", The Cancer Journal, Vol. 14(3), 2008, pp. 154-169

Chabner et al.; "Initial clinical trials of maytansine, an antitumor plant alkaloid;" Cancer Treat Rep; 62; 1978; pp. 429-433.

Chanan-Khan et al.; "Phase I Study of huN901-DM1 (BB-10901) in Patients with Relapsed and Relapsed/Refractory CD56-Positive Multiple Myeloma;" Blood; 108(11); Abstract #1174 (ASH Meeting); Nov. 16, 2007.

Chanan-Khan et al.; "Phase I Study of IMGN901 in Patients with Relapsed and Relapsed/Refractory CD56-Positive Multiple Myeloma;" Blood (ASH Annual Meeting Abstracts); 112; November 2008; pp. 3689.

Chari et al.; "Immunoconjugates containing novel maytansinoids: promising anticancer drugs;" Cancer Res; 52; 1992; pp. 127-131.

Chari et al.; "Enhancement of the selectivity and antitumor efficacy of a CC-1065 analogue through immunoconjugate formation;" Cancer Res.; 55; 1995; pp. 4079-4084.

Charnaux et al.; "RANTES (CCL5) induces a CCR5-dependent accelerated shedding of syndecan-1 (CD138) and syndecan-4 from HeLa cells and forms complexes with the shed ectodomains of these proteoglycans as well as with those of CD44;" Glycobiology; 15(2); 2005; pp. 119-130.

Chen et al.; "Engraftment of human hematopoietic precursor cells with secondary transfer potential in SCID-hu mice;" Blood; 84; 1994; pp. 2497-2505.

Chilosi et al.; "CD138/syndecan-1: a useful immunohistochemical marker of normal and neoplastic plasma cells on routine trephine bone marrow biopsies;" Mod Pathol.; 12; 1999; pp. 1101-1106.

Choi et al.; "Syndecan-1, a key regulator of cell viability in endometrial cancer;" Int J Cancer 121(4); 2007; pp. 741-50.

Chou and Talalay; "Quantitative analysis of dose-effect relationships: the combined effects of multiple drugs on enzyme inhibitors;" Adv. Enzyme Regul. 22; 1984; pp. 27-55.

Clément et al.; "B-B2 and B-B4, two new mAb against secreting plasma cells;" Leucocyte Typing V; Oxford Press.; 1; 1995; pp. 714-715.

Conejo et al.; "Syndecan-1 expression is up-regulated in pancreatic but not in other gastrointestinal cancers;" Int J Cancer; 88(1); 2000 Oct. 1; pp. 12-20.

Couturier et al.; "Validation of 213Bi-alpha radioimmunotherapy for multiple myeloma;" Clinical Cancer Research 5(10 Suppl.); October 1999; pp. 3165s-3170s.

Davies E J et al.; "Distribution and Clinical Significance of Heparan Sulfate Proteoglycans;" Ovarian Cancer Clin Cancer Res; 10(15); 2004; pp. 5178-86.

DeGeorge et al.; "Regulatory considerations for preclinical development of anticancer drugs;" Cancer Chemother Pharmacol; 41(3); 1998; p. 173-85.

Dmoszyńska A.; "Diagnosis and the current trends in multiple myeloma therapy;" Pol Arch Med Wewn; 118(10); October 2008; pp. 563-6.

Dhodapkar et al.; "Syndecan-1 is a multifunctional regulator of myeloma pathobiology: control of tumor cell survival, growth, and bone cell differentiation;" Blood; 91; 1998; pp. 2679-2688.

Dimopoulos et al.; "The role of novel drugs in multiple myeloma;" Annals of Oncology 19 (Supplement 7); 2008; pp. vii121-127.

Dore et al.; "Identification and location on syndecan-1 core protein of the epitopes of B-B2 and B-B4 monoclonal antibodies;" FEBS Lett; 26; 1998; pp. 67-70.

Dowell et al.; "Pharmacokinetics of gemtuzumab ozogamicin, an antibody-targeted chemotherapy agent for the treatment of patients with acute myeloid leukemia in first relapse;" J Clin Pharmacol; 41; 2001; pp. 1206-1214.

Durie et al.; "Myeloma management guidelines: a consensus report from the Scientific Advisors of the International Myeloma Foundation;" Hematol J, 4(6); 2003; pp. 379-98.

Durie et al.; "International uniform response criteria for multiple myeloma;" Leukemia; 20(12); December 2006; pp. 2220.

Eagan et al.; "Early clinical study of an intermittent schedule for maytansine (NSC-153858): brief communication;" J Natl Cancer Insti (Bethesda); 60; 1978; pp. 93-96.

Edinger et al.; "Noninvasive assessment of tumor cell proliferation in animal models;" Neoplasia; 1; 1999; pp. 303-310.

Facon et al.; "Superiority of melphalan-prednisone (MP)+ thalidomide (THAL) over MP and autologous stem cell transplantation in the treatment of newly diagnosed elderly patients with multiple myeloma;" J. Clin. Oncol.; 24(Suppl. 18); Abstract 1; 2006.

Fossella et al.; "Phase II Trial of BB-10901 (huN901-DM1) given weekly for four consecutive weeks every 6 weeks in patients with relapsed SCLC and CD56-positive small cell carcinoma;" J Clin Onco, ASCO Annual Meeting Proceedings; 23(16S), Part I of II; Jun. 1, 2005; 7159; Supplement.

Galsky et al.; "Phase I Trial of the Prostate-Specific Membrane Antigen-Directed Immunoconjugate MLN2704 in Patients With Progressive Metastatic Castration-Resistant Prostate Cancer;" Journal of Clinical Oncology; May 1, 2008; pp. 2147-2154.

Gattei et al.; "Characterization of Anti-CD138 monoclonal antibodies as tools for investigating the molecular polymorphism of syndecan-1 in human lymphoma cells;" Br Haematol.; 104; 1999; pp. 152-162.

Ghobrial et al.; "Emerging drugs in multiple myeloma;" Expert Opin Emerg Drugs; 12(1); March 2007; pp. 155-63.

Giles et al.; "Phase I study of AVE9633, an AntiCD33-Maytansinoid Immunoconjugate, Administered as an Intravenous Infusion in Patients with Refractory/Relapsed CD33-Positive Acute Myeloid Leukemia (AML);" Blood; 108 (11); Nov. 16, 2006.

Greipp et al.; "International staging system for multiple myeloma," J Clin Oncol; 23(15); Mary 20, 2005; pp. 3412-20.

Greipp and Lust; "Pathogenetic relation between monoclonal gammopathies of undetermined significance and multiple myeloma;" Stem Cells. Aug. 13 Suppl 2; 1995; pp. 10-21.

Gunaratnum et al.; "G-quadruplex compounds and cis-platin act synergistically to inhibit cancer cell growth in vitro and in vivo;" Biochemical Pharmacology; 78; 2009; pp. 115-122.

Hamann et al.; "An anti-CD33 antibody-calicheamicin conjugate for treatment of acute myeloid leukemia;" Choice of linker; Bioconjug Chem; 13; 2002; pp. 40-46.

Han et al.; "New insights into syndecan-2 expression and tumourigenic activity in colon carcinoma cells;" J Mol Histol; 35(3); 2004; pp. 319-26.

Hashimoto et al.; "Colorectal Association of loss of epithelial syndecan-1 with stage and local metastasis of colorectal adenocarcinomas: an immunohistochemical study of clinically annotated tumors;" BMC Cancer 8; 2008; p. 185.

Helft et al.; "A phase I study of cantuzumab mertansine administered as a single intravenous infusion once weekly in patients with advanced solid tumors;" Clin Cancer Res; 10(13); 2004 Jul 1; pp. 4363-8.

Hideshima et al.; "Perifosine, an oral bioactive novel alkylphospholipid, inhibits Akt and induces in vitro and in vivo cytotoxicity in human multiple myeloma cells;" Blood; 107(10); 2006; pp. 4053-62.

Hideshima et al.; "Understanding multiple myeloma pathogenesis in the bone marrow to identify new therapeutic targets;" Nat Rev Cancer; 7(8); 2007; pp. 585-98.

Hiroshi et al.; "The Monoclonal Antibody nBT062 Conjugated to Cytotoxic Maytansinoids Has Potent and Selective Cytotoxicity against CD138 Positive Multiple Myeloma Cells in Vitro and in Vivo;" Blood; (ASH Annual Meeting Abstracts); 112; November 2008; p. 1716.

Holden et al.; "A phase I study of weekly dosing of trastuzumab-DM1 (T-DM1) in patients (pts) with advanced HER2+ breast cancer (BC);" ASCO Meeting Abstracts; May 20, 2008; p. 1029.

Horvathova et al.; In: al. SFSe, ed. Leucocyte Typing V.; Oxford: Oxford University Press; 1995; pp. 713-714.

Huang et al.; "Validation and reduction of FACT/GOG-Ntx subscale for platinum/paclitaxel-induced neurologic symptoms: a gynecologic oncology group study;" Int J Gynecol Cancer; 17; 2007; pp. 387-93.

Hwang et al.; "New Frontiers in the Treatment of Multiple Myeloma;" Scientific World Journal; 6; Dec. 6, 2006; pp. 1475-503.

Ikeda et al.; "The monoclonal antibody nBT062 conjugated to maytansinoids has potent and selective cytotoxicity against CD138 positive multiple myeloma cells in vitro and in vivo;" Clin. Cancer Research; 15(12); 2009.

Ishitsuka et al.; "Targeting CD56 by the maytansinoid immunoconjugate IMGN901 (huN901-DM1): a potential therapeutic modality implication against natural killer/T cell malignancy;" Br. J. Haematol; 141(1); April 2008; pp. 129-31.

Issell et al.; "Maytansine;" Cancer Treat Rev; 5; 1978; pp. 199-207.

Jemal et al.; "Cancer statistics;" CA Cancer J Clin; 58; 2008; pp. 71-96.

Johnson et al.; "Novel and Targeted Agents for Small Cell Lung Cancer;" ASCO Educational Book; Jan. 1, 2008; pp. 363-367.

Kovtun et al.; "Antibody-drug conjugates designed to eradicate tumors with homogeneous and heterogeneous expression of the target antigen;" Cancer Res; 66(6); 2006; pp. 3214-21.

Kuesters et al.; "Correlation of ErbB2 Gene Status, mRNA and Protein Expression in a Panel of >100 Human Tumor Xenografts of Different Origin; Onkologie; 29; 2006; pp: 249-256

Krebs et al.; "High-throughput generation and engineering of recombinant human antibodies;" J. Immunol. Methods; 254; 2001; pp. 67-84.

Krop et al.; "A Phase I Study of Trastuzumab-DM1, a First-in-Class HER2 Antibody-Drug Conjugate (ADC), in patients with HER2+ Metastatic Breast Cancer;" 14th European Cancer Conference (ECCO 14); Poster #2118; 2007.

Kupchan et al.; "Structural requirements for antileukemic activity among the naturally occurring and semisynthetic maytansinoids;" J Med Chem; 21; 1978; pp. 31-37.

Kyle; "Benign monoclonal gammopathy-after 20 to 35 years of follow-up;" Mayo Clin Proceedings 68(1); 1993; pp. 26-36.

Kyle et al.; "Multiple myeloma;" N Engl J Med; 351(18); Oct. 28, 2004; pp. 1860-73.

Kyle et al.; "Criteria for diagnosis, staging, risk stratification do response assessment of multiple myeloma;" Leukemia; 23; 2009; pp. 3-9.

Kyoizumi et al.; "Implantation and maintenance of functional human bone marrow in SCID-hu mice;" Blood; 79; 1992; pp. 1704-1711.

Kyoizumi et al.; "Preclinical analysis of cytokine therapy in the SCID-hu mouse;" Blood; 81; 1993; pp. 1479-1488.

Lambert J M; "Drug-conjugated monoclonal antibodies for the treatment of cancer;" Current Opinion in Pharmacology; 5; 2005; pp. 543-549.

Langford et al.; "Multiple heparan sulfate chains are required for optimal syndecan-1 function;" J Biol Chem; 273(45); Nov. 6, 1998; pp. 29965-71.

Legrand et al.; "An open label, dose escalation study of AVE9633 administered as a single agent by intravenous (IV) infusion weekly for 2 weeks in a 4-week cycle to patients with relapsed or refractory CD33-positive Acute Myeloid Leukemia (AML);" Blood; 118(11); Nov. 16, 2007.

Li et al.; "Clinicopathological significance of expression of paxillin, syndecan-1 and EMMPRIN in hepatocellular carcinoma;" World J Gastroenterol. 11(10); 2005; pp. 1445-51.

Liu et al.; "Eradication of large colon tumor xenografts by targeted delivery of maytansinoids;" Proc Natl Acad Sci USA; 93; 1996; pp. 8618-8623.

Loussouarn et al.; "Prognostic impact of syndecan-1 expression in invasive ductal breast carcinomas;" Br J Cancer; 28; 2008; pp. 1993-1998

Lorigan et al.; "Phase I trial of BB-10901 (huN901-DM1) given daily by IV infusion for three consecutive days every three weeks in patients with SCLC and other CD56-positive solid tumors;" European Journal of Cancer Supplements; 4(12); 2006; pp. 195.

Ludwig et al.; "Supportive care in multiple myelom Best Practice & Research Clinical Haematology;" 20; Issue 4; 2007; pp. 817-835.

McCann et al.; "Phase II trial of huN901-DM1 in patients with relapsed small cell lung cancer (SCLC) and CD56- positive small cell carcinoma;" J Clin Onco; ASCO Annual Meeting Proceedings Part 1; 25(18S); 2007 Jun. 20; Supplement; p. 18084.

Mateos et al.; "Bortezomib plus melphalan and prednisone in elderly untreated patients with multiple myeloma: results of a multicenter phase ½ study;" Blood; 108; 2006; pp. 2165-2172.

McCune et al.; "The SCID-hu mouse: murine model for the analysis of human hematolymphoid differentiation and function;" Science; 241; 1998; pp. 1632-1639.

Mennerich et al.; "Shift of syndecan-1 expression from epithelial to stromal cells during progression of solid tumours;" Eur J Cancer; 40(9); June 2004; pp. 1373-82.

Milowsky et al.; "Phase I/II trial of the prostate-specific membrane antigen (PSMA)-targeted immunoconjugate MLN2704 in patients (pts) with progressive metastatic castration resistant prostate cancer (CRPC);" J Clin Onco; ASCO Annual Meeting Proceedings Part I; 24(18S); 2006 p. 4500.

Mita et al.; "A phase I study of a CanAg-targeted immunoconjugate, huC242-DM4, in subjects with CanAg-expressing solid tumors;" J Clin Onco; ASCO Annual Meeting Proceedings Part 1; 25(18S); 2007 Jun. 20; Supplement; p. 3062.

Mitsogiannis et al; "Plasmacytoid transitional cell carcinoma of the urinary bladder;" Urology 66(1); 2005; p. 194.

Morgan et al.; "Advances in oral therapy for multiple myeloma;" Lancet Oncol; 7(4); April 2006; pp. 316-25.

Mosmann T.; "Rapid colorimetric assay for cellular growth and survival: application to proliferation and cytotoxicity assays;" J Immunol Methods; 65; 1983 pp. 55-63.

Munshi et al.; "Plasma cell disorders;" In: Braunwald E, Fauci A S, Kasper D L, Hauser S L, Longo D L, Jameson J L, editors; Harrison's Principles of Internal Medicine; 16th ed; New York: McGraw-Hill Medical Publishing Division; 2008. pp. 700-707.

Namikawa et al.; "Growth of human myeloid leukemias in the human marrow environment of SCID-hu mice;" Blood; 82; 1993; pp. 2526-2536.

NCCN Guidelines; "NCCN Clinical Practice Guidelines in Oncology;" Multiple Myeloma V.2. 2009; National Comprehensive Cancer Network; Nov. 9, 2008; available at www.nccn.org.

Ning et al.; "Liposomal doxorubicin in combination with bortezomib for relapsed or refractory multiple myeloma;" Oncology (Williston Park); 21(12); November 277; pp. 1503-8.

Numa et al.; "Syndecan-1 expression in cancer of the uterine cervix: association with lymph node metastasis; Int J Oncol. 20(1); pp. 2002 39-43.

Ocio et al., "New drugs in multiple myeloma: mechanisms of action and phase I/II clinical findings;" Lancelt Oncol: 9(12); December 2008; pp. 1157-65.

O'Connell et al.; "CD138 (Syndecan-1), a Plasma Cell Marker Immunohistochemical Profile in Hematopoietic and Nonhematopoietic Neoplasms;" Am J Clin Pathol; 121; 2004; pp. 254-263.

Ojima et al.; "Tumor-specific novel taxoid-monoclonal antibody conjugates;" J. Med. Chem.; 45; 2002; pp. 5620-5623.

Oken et al.; "Toxicity And Response Criteria Of The Eastern Cooperative Oncology Group;" Am J Clin Oncol; 5; 1982; pp. 649-655.

Olafsen et al.; "Covalent disulfide-linked anti-CEA diabody allows site-specific conjugation and radiolabeling for tumor targeting applications;" Prot. Eng. Design & Selection 17; 1; 2004; pp. 21-27.

Orosz et al.; "Syndecan-1 expression in different soft tissue tumours;" Anticancer Res; 21(1 B); 2001; pp. 733-7.

Padlan, E A; "A possible procedure for reducing the immunogenicity of antibody variable domains while preserving their ligand-binding properties;" Mol. Immunol.; 28; 1991; pp. 489-498.

Palacios et al.; "B-B4 monoclonal antibody and identification of human bone marrow plasma cells;" Br J Haematol; 96(3); March 1997; pp. 655-657.

Palumbo et al.; "Oral revlimid plus melphalan and prednisone (R-MP) for newly diagnosed multiple myeloma: results of a multicenter Phase I/II study;" Blood; 108; (ASH Annual Meeting Abstracts); Abstract 800; 2006.

Palumbo et al.; "Treatment of newly diagnosed myeloma;" Leukemia; 23; Nov. 13, 2008; pp. 449-456.

Patriarca et al.; "Considerations in the treatment of multiple myeloma: a consensus statement from Italian experts;" Eur J Haematol; 82(2); February 2009; pp. 93-105.

Payne G.; "Progress in immunoconjugate cancer therapeutics;" Cancer Cell; 3; 2003; pp. 207-212.

Pegram et al.; "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment;" J. Clin. Oncol.; 16; 1998; pp. 2659-2671.

Podar et al.; "Bone marrow microenvironment and the identification of new targets for myeloma therapy;" Leukemia; 23(1); January 2009; pp. 10-24.

Qin et al.; "The pharmacokinetics and pharmacodynamics of IMGN242 (huC242-DM4) in patients with CanAg-expressing solid tumors;" Journal of Clinical Oncology, 2008 ASCO Annual Meeting Proceedings (Post-Meeting Edition); 26(15S); May 20, 2008; Supplement; p. 3066.

Quach et al.: "Mechanism of action of immunomodulatory drugs (ImiDS) in multiple myeloma," Leukemia; 24; 2010; pp. 22-32.

Raje et al.; "Therapeutic use of immunomodulatory drugs in the treatment of multiple myeloma;" Expert Rev Anticancer Ther; 6(9); September 2006; pp. 1239-47.

Rajkumar et al.; "Combination therapy with lenalidomide plus dexamethasone (Rev/Dex) for newly diagnosed myeloma;" Blood; Dec. 15, 2005; 106(13); pp. 4050-4053.

Rajkumar et al.; "Phase III clinical trial of thalidomide plus dexamethasone compared with dexamethasone alone in newly diagnosed multiple myeloma: A clinical trial coordinated by the Eastern cooperative Oncology Group;" J Clin Oncol 2006; 24; pp. 431-436.

Rajkumar et al.; "A Randomized Trial of Lenalidomide Plus High-Dose Dexamethasone (RD) Versus Lenalidomide Plus Low-Dose Dexamethasone (Rd) in Newly Diagnosed Multiple Myeloma (E4A03): A Trial Coordinated by the Eastern Cooperative Oncology Group;" Blood; 110; 2007; p. 74.

Rawstron et al.; "Circulating plasma cells in multiple myeloma: characterization and correlation with disease stage;" Br J Haematol; 97; 1997; pp. 46-55.

Remillard et al.; "Antimitotic activity of the potent tumor inhibitor maytansine;" Science; 198; 1975; pp. 1002-1005.

Richardson et al.; "New treatments for multiple myeloma;" Oncology (Williston Park); 19(14); December 2005; pp. 1781-92.

Richardson et al.; "Lenalidomide in multiple myeloma;" Expert Rev Anticancer Ther, 6(8); August 2006; pp. 1165-73.

Richardson et al.; "New Drugs for Myeloma;" Oncologist Jun; 12(6); 2007; pp. 664-89.

Richardson et al.; "Lenalodomide, bortezomib, and dexamethasone as front-line-therapy for patients with multiple myeloma (MM): preliminary results of a phase I/II study;" Blood; 110; 2007; p. 63a.

Riechelmann et al.; "Phase I trial with the CD44v6-targeting immunoconjugate bivatuzumab mertansine in head and neck squamous cell carcinoma;" Oral Oncol; 44(9); September 2008; pp. 823-9.

Roh et al.; "Syndecan-1 expression in gallbladder cancer and its prognostic significance;" Eur Surg Res. 41(2); 2008; pp. 245-50.

Roguska et al.; "Humanization of murine monoclonal antibodies through variable domain resurfacing;" Proc Natl Acad Sci USA; 91; 1994; pp. 969-973.

Ross et al.; "Prostate stem cell antigen as therapy target: tissue expression and in vivo efficacy of an immunoconjugate;" Cancer Res.; May 1, 2002; 62(9) pp. 2546-53.

Ross et al.; "Anticancer Antibodies;" Am J Clin Path; 119; Apr. 17, 2003; pp. 472-485.

Rowinsky et al.; "SB-408075, a tumor-activated immunoconjugate targeting the C242 CanAg antigen with a potent maytansinoid payload: phase I, pharmacokinetic (PK), and biological studies;" Proc Am Soc Clin Oncol 21: Abstract #118; 2002.

Rupp et al.; "Safety and pharmacokinetics of bivatuzumab mertansine in patients with CD44v6-positive metastatic breast cancer: final results of a phase I study;" Anticancer Drugs; 18(4); April 2007; pp. 477-485.

Salfeld, "Isotype selection in antibody engineering", Nat. Biotechnol. 25 (12), 2007, pp. 1369-1372.

Sanderson et al.; "B lymphocytes express and lose syndecan at specific stages of differentiation;" Cell Regul.; 1989; 1; pp. 27-35.

Sandhu et al.; "Human hematopoiesis in SCID mice implanted with human adult cancellous bone;" Blood; 88; 1996; pp. 1973-1982.

Sankhala et al.; "A phase I and pharmacokinetic study of a CanAg-targeted immunoconjugate, HuC242-DM4, in patients with CanAg-expressing solid tumors;" AACR-NCI-EORTC "Molecular Targets and Cancer Therapeutics" International Conference; Abstract #B70; 2007.

Sasaki et al.; "Bisphosphonate risedronate reduces metastatic human breast cancer burden in bone in nude mice;" Cancer Res.; 55; 1995; pp. 3551-3557.

Sauter et al.; "Pharmacokinetics, immunogenicity and safety of bivatuzumab mertansine, a novel CD44v6-targeting immunoconjugate, in patients with squamous cell carcinoma of the head and neck;" Int J Oncol.; 30(4); April 2007; pp. 927-35.

Schneider et al.; "Two subsets of peripheral blood plasma cells defined by differential expression of CD45 antigen;" Br J Haematol; 97; 1997; pp. 56-64.

Schuurman, et al.; "Normal human immunoglobulin G4 is bispecific: it has two different antigen-combining sites;" Immunology; 97; 1999; pp. 693-698.

Sebestyen et al.; "Syndecan-1 (CD138) expression in human non-Hodgkin lymphomas. Br J Haematol;" 104(2); 1999; pp. 412-9.

Seftalioglu et al.; "Syndecan-1/CD138 expression in normal myeloid, acute lymphoblastic and myeloblastic leukemia cells;" Acta Histochem; 105; 2003; pp. 213-221.

Seftalioglu et al.; "Syndecan-1 (CD138) expression in acute myeloblastic leukemia cells—an immuno electron microscopic study;" Acta Oncol; 42; 2003; pp. 71-74.

Senter et al.; "Cures and regressions of established tumors with monoclonal antibody auristatin conjugates;" Abstract #2062, American Assoication for Cancer Res. (San Francisco, Calif.: American Association for Cancer Res.); 2007; p. 414.

Shah et al.; "Expression of syndecan-1 and expression of epidermal growth factor receptor are associated with survival in patients with nonsmall cell lung carcinoma;" Cancer 101(7); 2004; pp. 1632-8.

Shields et al.; "High resolution mapping of the binding site on human IgG1 for Fc gamma RI, Fc gamma RII, Fc gamma RIII, and FcRn and design of IgG1 variants with improved binding to the Fc gamma R.;" J Biol Chem; 276(9); 2001; pp. 6591-604.

Sievers et al.; "Efficacy and safety of gemtuzumab ozogamicin in patients with CD33-positive acute myeloid leukemia in first relapse;" J. Clin. Oncol.; 19; 2001; pp. 3244-3254.

Sievers et al.; "Mylotarg: antibody-targeted chemotherapy comes of age;" Curr. Opin. Oncol.; 13; 2001; pp. 522-527.

Smith R.; "Single chain antibody variable region fragments;" available at www.stanford.edu/~smithr/science/scfv.html (last updated on May, 2001).

Strobeck M; "Multiple Myeloma therapies;" Nature Reviews Drug Discovery; 6(3); March 2007; pp. 181-82.

Studnicka et al.; "Human-engineered monoclonal antibodies retain full specific binding activity by preserving non-CDR complementarity-modulating residues;" Protein Eng.; 7(6); 1994 pp. 805-814.

Tai et al; "Immunomodulatory drug lenalidomide (CC-5013, IMiD3) augments anti-CD40 SGN-40-induced cytotoxicity in human multiple myeloma: clinical implications;" Cancer Res. 2005 Dec. 15; 65(24):11712-20.

Takimoto et al.; "Principles of oncologic pharmacotherapy;" Cancer Management: A multidisciplinary Approach; 11$^{th}$ Edition; Chapter 3; 2008; Apr. 15, 2009; available at http://www.cancernetwork.com/display/article/10165/1402628.

Tassone et al.; "Cytotoxic activity of the maytansinoid immunoconjugate B-B4-DM1 against CD138$^+$ multiple myeloma cells;" Blood; 104(12); 2004; pp. 3688-3696.

Terpos et al.; "European Myeloma NetworkThe use of bisphosphonates in multiple myeloma: recommendations of an expert panel on behalf of the European Myeloma Network;" Ann Oncol. 20(8); 2009; pp. 1303-17.

Tijink et al.; "A phase I dose escalation study with anti-CD44v6 bivatuzumab mertansine in patients with incurable squamous cell carcinoma of the head and neck or esophagus;" Clin Cancer Res; 12(20 Pt 1); Oct. 15, 2006; pp. 6064-72.

Tolcher et al.; "A Phase I study of huC242-DM4 to assess the safety and pharmacokinetics of huC242-DM4 administered as a single intravenous infusion once every three weeks to subjects with solid tumors;" European Journal of Cancer Supplements; 12(4); 2006 p. 66.

Tolcher et al.; "Cantuzumab mertansine, a maytansinoid immunoconjugate directed to the CanAg antigen: a phase I, pharmacokinetic, and biologic correlative study;" J Clin Oncol; 21; 2003; pp. 211-222.

Tomayko et al., "Determination of subcutaneous tumor size in athymic (nude) mice;" Cancer Chemother. Pharmacol, 24; 1989; pp. 148.

Toyoshima et al.; "Expression of syndecan-1 is common in human lung cancers independent of expression of epidermal growth factor receptor;" Lung Cancer 31(2-3); 2001; pp. 193-202.

Urashima et al; "The development of a model for the homing of multiple myeloma cells to human bone marrow;" Blood; 90; 1997; pp. 754-765.

Vogel, C W; "Preparation of immunoconjugates using antibody oligosaccharide moieties;" Methods in Molecular Biology: Bioconjugation protocols strategies and methods; 283; 2007 pp. 87-108.

Vooijs et al; "Efficacy and toxicity of plasma-cell-reactive monoclonal antibodies B-B2 and B-B4 and their immunotoxins;" Cancer Immunol Immunother; 42; 1996; pp. 319-328.

Wang et al.; "Targeted proteasome inhibition by Velcade induces apoptosis in human mesothelioma and breast cancer cell lines;" Cancer Chemother Pharmacol; Dec. 4, 2009.

Ward et al.; "Binding activities of a repertoire of single immunoglobin variable domains secreted from *Escherichia coli*;" Nature; 341; 1989; pp. 544-546.

Wargalla et al.; "Rate of internalization of an immunotoxin correlates with cytotoxic activity against human tumor cells;" Proc. Natl. Acad. Sci. USA; 86; 1989; pp. 5146-5150.

Weber et al.; "Lenalidomide plus high-dose dexamethasone provides improved overall survival compared to high-dose dexamethasone alone for relapsed or refractory multiple myeloma (MM): results of 2 Phase III studies (MM-009, MM-010) and subgroup analysis of patients with impaired renal function;" Blood; 108; (ASH Annual Meeting Abstracts); Abstract 3547; 2006.

Wiksten et al.; "Comparison of the prognostic value of a panel of tissue tumor markers and established clinicopathological factors in patients with gastric cancer;" Gastric: Anticancer Res. 28(4C); 2008; pp. 2279-87.

Wijdenes et al.; "A plasmocyte selective mAb (B-B4) recognizes syndecan-1;" Br J Haematol; 94(2) August 1996; pp. 318-23.

Wijdenes et al.; "CD138;" J Biol Regul Homeost Agents; 16(2) April-June 2002; pp. 152-155.

Witzig et al; "Detection of myeloma cells in the peripheral blood by flow cytometry;" Cytometry; 26; 1996; pp. 113-120.

Xie et al.; "Pharmacokinetics and biodistribution of the anti-tumor immunoconjugate, cantuzumab mertansine (huC242-DM1), and its two components in mice;" J Pharmacol Exp Ther.; 308(3); March 2004; pp. 1073-82.

Yang et al.; "Genetically fluorescent melanoma bone and organ metastasis models;" Clin Cancer Res; 5; 1999; pp. 3549-3559.

Yang et al.; "Whole-body optical imaging of green fluorescent protein-expressing tumors and metastases;" Proc Natl Acad Sci USA; 97; 200; pp. 1206-1211.

Yang et al.; "The syndecan-1 heparan sulfate proteoglycan is a viable target for myeloma therapy;" Blood; 110(6); Sep. 15, 2007 pp. 2041-8.

Yasui et al.; "Recent advances in the treatment of Multiple Myeloma;" Curr Pharm Biotechnol; 7(5); October 2006; pp. 381-93.

Yoshitake et al.; "Conjugation of glucose oxidase from *Aspergillus niger* and rabbit antibodies using N-hydroxysuccinimide ester of N-(4-carboxycyclohexylmethyl)-maleimide;" Eur J Biochem; 101; 1979; pp. 395-399.

Yu et al.; "Antitumor synergy of CV787, a prostate cancer-specific adenovirus, and paclitaxel and docetaxel;" Cancer Research; 61; Jan. 15, 2001; pp. 517-525.

Zellweger et al.; "Tissue microarray analysis reveals prognostic significance of syndecan-1 expression in prostate cancer;" Prostate 55(1); 2003; pp. 20-9.

---

What is claimed is:

1. A method for treating a subject with cancer having target cells expressing CD138, wherein said subject has a refractory disease phenotype, comprising:
   (i) identifying said subject as not responding, or responding poorly, to treatment with one or more cytotoxic agents, and
   (ii) administering to said subject that does not respond, or responds poorly, to treatment with one or more cytotoxic agents an effective amount of an immunoconjugate comprising at least one targeting antibody targeting CD138 expressing cells, and at least one maytansinoid effector molecule, wherein said targeting antibody is functionally attached to said effector molecule to form said immunoconjugate, wherein said immunoconjugate is BT062 or has a light chain having at least about 70% sequence identity with SEQ ID No: 2 and a heavy chain having at least about 70% sequence identity with SEQ ID No: 1, wherein said immunoconjugate comprises residues 24-34 (CDR1), residues 50-56 (CDR2) and residues 89-97 (CDR3) of SEQ ID NO: 2 as well as residues 31-35 (CDR1), residues 51-68 (CDR2) and residues 99-111(CDR3) of SEQ ID No:1.

2. The method of claims 1, wherein the immunoconjugate is administered to the subject in an amount from 20 mg/m$^2$ to 200 mg/m$^2$ or a pharmacokinetic equivalent of 20 mg/m$^2$ to 200 mg/m$^2$ when administered in combination with an agent for treating adverse side effects.

3. The method of claim 1, wherein a maximum concentration of the immunoconjugate in the subject's plasma between 0 to 2 hours after an end of said first intravenous administration is less than 40% of the theoretical maximum concentration for said immunoconjugate.

4. The method of claim 1, wherein the immunoconjugate is intravenously administered at least four times and a maximum concentration of the immunoconjugate in the subject's plasma between 0 to 2 hours after an end of each of said administrations is less than 55% of the theoretical maximum concentration for said immunoconjugate.

5. The method of claim 1, wherein said immunoconjugate is administered in a repeated single dose, of not more than about 120 mg/m$^2$, an average daily dose of about 400 µg/m$^2$ to about 6 mg/m$^2$, and/or an average weekly dose of about 3 mg/m$^2$ to about 40 mg/m$^2$.

6. The method according to claim 1, wherein for about 20, 30, 40, 50, 60, 70, 80, 90 100, 120, 140, 160, 180, 190, 200, 210 or more days stable disease is maintained.

7. The method according to claim 1, wherein for about 1, 2, 3, 4, 5, 6, 7, 8, 9, 10, 11, 12 treatment cycles each of about three weeks stable disease is maintained.

8. The method of claim 7, wherein at least stable disease is maintained for 5, 6, 7, 8, 9 or 10 treatment cycles at 20 mg/m$^2$.

9. The method of claim 8, wherein a minor response is observed after up to 8 treatment cycles.

10. The method of claim 1, wherein said method results in a minor response, a partial response, a very good partial response, a stringent complete response or a complete response durable for 1, 2, 3, 4, 5, 6, 7, 8, 9, 10, 11, 12 treatment cycles or more wherein said treatment cycles each comprise about 3 weeks with an administration of said immunoconjugate on day 1 of each said treatment cycle or for 7, 14, 21, 28, 35, 42, 49, 56, 63, 70, 77 or 82 days, respectively.

11. The method of claim 1, wherein the immunoconjugate is administered to the subject in an amount from 5 mg/m$^2$ or 10 m g/m$^2$ to less than 160 mg/m$^2$.

12. The method of claim 3, wherein said maximum concentration is less than 3 µg/ml for 10 mg/m$^2$, less than 8 µg/ml for 20 mg/m$^2$, less than 15 µg/ml for 40 mg/m$^2$, less than 25 µg/ml for 80 mg/m$^2$, less than 30 µg/ml for 120 mg/m$^2$.

13. The method of claim 4, wherein said maximum concentration is less than 14 µg/ml for 20 mg/m$^2$, less than 15 µg/ml for 40 mg/m$^2$ or less than 25 µg/ml for 80 mg/m$^2$.

14. The method of claim 1, wherein said CD138 is, in said subject, expressed on said target cells and on non-target cells, wherein said non-target cells expressing CD138 including epithelial cells, are substantially unaffected.

15. The method of claim 14, wherein expression level of CD138 on said target and non-target cells expressing CD138 is comparable.

16. The method of claim 14 or 15, wherein said immunoconjugate is administered to the subject as a single dose, a repeated single dose or in multiple doses in an amount from 5 mg/m$^2$ to 200 mg/m$^2$ or a pharmacokinetic equivalent of 5 mg/m$^2$ to 200 mg/m$^2$ when administered in combination with an agent for treating adverse side effects and wherein said administering results in a response in said subject, after less than 40, 30, 20, 15, 10, 9, 8, 7, 6, 5 hours.

17. The method of claim 16, wherein said effective amount is more than 120 mg/m².

18. The method of claim 14, wherein said effective amount is administered as a single dose, a repeated single dose or in multiple doses.

19. The method of claim 18, wherein a cmax value after each administration is more than 55% of a theoretical cmax value.

20. The method of claim 14, wherein said administration results in at least stable disease, a minor response or a partial response in said subject after a first administration.

21. The method of claim 1, wherein said immunoconjugate comprises nBT062 or a targeting antibody having at least 80%, 85%, 90%, 95%, 98%, 99% or 100% sequence identity with nBT062.

22. The method of claim 1, wherein the method consists essentially of administering a pharmaceutical composition comprising said immunoconjugate and a pharmaceutically acceptable carrier, wherein an active ingredient of said composition consists essentially of said immunoconjugate.

23. The method of claim 1, wherein the immunoconjugate is administered intravenously.

24. The method of claim 23, wherein the immunoconjugate is administered intravenously in a repeated single dose.

25. The method of claim 1 or 2, wherein said cancer is selected from the group consisting of renal cell carcinoma, endometrial cancer, cervical cancer, prostate adenocarcinoma, pancreatic carcinoma, gastric cancer, bladder cancer, mammary carcinoma, hepato-carcinoma, colorectal carcinoma, colon carcinoma, squamous cell carcinoma, lung cancer including squamous cell lung carcinoma, non Hodgkin lymphoma, thymus, uterus, urinary or ovarian carcinoma.

26. The method according to claim 1, wherein the cancer is associated with bone pains and/or bone complications and wherein administration of said immunoconjugate reduces said bone pains and/or bone complications to an acceptable level.

27. The method of claim 1, wherein the immunoconjugate overcomes the refractory phenotype.

28. A method of treating a patient with cancer having target cells expressing CD138, comprising
  (i) identifying said cancer of said patient as being associated with target cells expressing CD138, including multiple myeloma and as not responding, or responding poorly, to treatment with one or more cytotoxic agents including immunomodulators and/or proteasome inhibitors, and
  (ii) administering to said patient that does not respond, or responds poorly, to treatment with one or more cytotoxic agents including immunomodulators and/or proteasome inhibitors, intravenously an effective amount of an immunoconjugate comprising nBT062 or a targeting antibody having at least 70%, 80%, 85%, 90%, 95%, 98%, 99% or 100% sequence identity with nBT062, wherein said immunoconjugate comprises residues 24-34 (CDR1), residues 50-56 (CDR2) and residues 89-97 (CDR3) of SEQ ID NO: 2 as well as residues 31-35 (CDR1), residues 51-68 (CDR2) and residues 99-111 (CDR3) of SEQ ID No: 1 and wherein said cancer is treated.

29. The method of claim 28, wherein said cancer is relapsed or refractory multiple myeloma.

30. The method of claim 28, wherein the patient displays levels of sCD138 of more than 50 ng/ml, more than 60 ng/ml, more than 70 ng/ml more than 80 ng/ml, more than 100 ng/ml, more than 150 ng/ml, more than 200 ng/ml, more than 200, 400, 500, 600, 700, 800, 900, 1000, 1100, 1200, 1300, 1400, 1500 ng/ml, and wherein an amount of the immunoconjugate as low as 20 mg/m² or as low as 40 mg/m² is effective to provide a minor response.

31. The method of claim 30, wherein said patient is displaying levels of sCD138 of more than 1000ng/ml.

32. The method of claim 30, wherein the cytotoxic agents to which the patient did not respond or responded poorly were lenalidomide and/or bortezomib.

33. The method of claim 1, comprising:
  administering to the subject an effective amount of an anticancer combination comprising at least one cytotoxic agent and the at least one immunoconjugate.

34. A method for treating a non-plasmaproliferative cancer expressing CD138 in a subject, said subject having a refractory disease phenotype, comprising:
  (i) identifying said subject as not responding, or responding poorly, to treatment with one or more cytotoxic agents, and
  (ii) administering to said subject that does not respond, or responds poorly, to treatment with one or more cytotoxic agent an effective amount of an immunoconjugate comprising
at least one antibody targeting CD138 expressing cells, and at least one maytansinoid effector molecule, wherein said antibody is functionally attached to said effector molecule to form said immunoconjugate,
wherein said CD138 is, in said subject, expressed on said target cells and on non-target cells at comparable levels or wherein said CD138 is, in said subject, expressed on said target cells at levels below that of said non-target cells expressing CD138,
wherein said immunoconjugate is administered to the subject in an amount from 5 mg/m² to 200 mg/m² or a pharmacokinetic equivalent of 5 mg/m² to 200 mg/m² when administered in combination with an agent for treating adverse side effects, wherein a maximum concentration of the immunoconjugate in the subject's plasma, based on a measurement between 0 to 2 hours after an end of a first intravenous administration, of less than 50% of a theoretical maximum concentration and wherein the theoretical maximum concentration (in (µg/ml)) is calculated as follows:

$$\frac{(\text{immunoconjugate administered ((in mg/m}^2) \times \text{estimated surface area of patient (in m}^2))/\text{body weight of patient (in Kg)}}{\text{estimated plasma volume of patient (in ml/kg)}},$$

wherein the immunoconjugate is administered in a single dose, a repeated single dose or in multiple doses and wherein the immunoconjugate overcomes the refractory phenotype, wherein said immunoconjugate comprises residues 24-34 (CDR1), residues 50-56 (CDR2) and residues 89-97 (CDR3) of SEQ ID NO: 2 as well as residues 31-35 (CDR1), residues 51-68 (CDR2) and residues 99-111 (CDR3) of SEQ ID No: 1.

35. The method of claim 33, wherein said non-target cells expressing CD138 are epithelium cells.

36. The method of claim 33, wherein said target cells of said cancer shed CD138 over a period of 24 hours, 2, 3, 4, 5, 6 days.

37. The method of claim 36, wherein said cancer is mammary carcinoma.

38. The method of claim 33 or 34, wherein immunoconjugate induces remission of a solid tumor.

39. The method of claim 38, wherein solid tumor is a pancreatic carcinoma or a mammary carcinoma.

40. The method of claim 38, wherein said remission is followed by time interval which is free of re-growth of said tumor.

41. The method of claim 33 or 34, wherein said cancer is renal cell carcinoma, endometrial cancer, cervical cancer, prostate adenocarcinoma, pancreatic carcinoma, gastric cancer, bladder cancer, mammary carcinoma, hepato-carcinoma, colorectal carcinoma, colon carcinoma, squamous cell carcinoma, lung cancer in particular squamous cell lung carcinoma, non Hodgkin lymphoma, thymus, uterus, urinary or ovarian carcinoma.

42. The method of claim 38, wherein the tumor is a mammary carcinoma, which is estrogen receptor negative and/or progesterone receptor negative and/or trastuzumab resistant.

43. The method according to claim 1, wherein the targeting antibody is an engineered antibody.

44. A method of claim 33, wherein the cytotoxic agent is bortezomib, thalidomide, pomalidomide, lenalidomide, melphalan or a mixture of two or more thereof.

45. The method of claim 1, further comprising measuring a maximum concentration of the immunoconjugate in the subject's plasma, based on a measurement between 0 to 2 hours after an end of a first intravenous administration, is less than 50% of a theoretical maximum concentration and wherein the theoretical maximum concentration (in (μg/ml)) is calculated as follows:

$$\frac{(\text{immunoconjugate administered } ((\text{in mg/m}^2) \times \text{estimated surface area of patient (in m}^2))/\text{body weight of patient (in Kg)}}{\text{estimated plasma volume of patient (in ml/kg)}}, \text{ and}$$

and wherein the theoretical maximum concentration is calculated as follows:

$$\frac{(\text{amount of said immunoconjugate administered} (\text{in mg/m}^2) \times 1.9 \text{ m}^2/70 \text{ Kg}}{40 \text{ ml/kg}}.$$

46. The method of claim 1, wherein said immunoconjugate comprises a chimeric antibody comprising amino acids 1 to 107 of SEQ ID NO. 2 and amino acids 1 to 120 of SEQ ID NO: 1.

47. The method of claim 29, wherein said cancer is relapsed myeloma.

48. The method of claim 29, wherein said cancer is relapsed/refractory or refractory multiple myeloma.

49. The method of claim 44, wherein the cytotoxic agents are lenalidomide and/or pomalidomide.

* * * * *

SEQUENCE LISTING

```
<160> NUMBER OF SEQ ID NOS: 13

<210> SEQ ID NO 1
<211> LENGTH: 448
<212> TYPE: PRT
<213> ORGANISM: Artificial Sequence
<220> FEATURE:
<223> OTHER INFORMATION: Amino Acid sequence (predicted) of heavy chain
      of chimeric human/mouse antibody
<220> FEATURE:
<221> NAME/KEY: CDR1
<222> LOCATION: (31)..(35)
<220> FEATURE:
<221> NAME/KEY: CDR2
<222> LOCATION: (51)..(68)
<220> FEATURE:
<221> NAME/KEY: CDR3
<222> LOCATION: (99)..(111)

<400> SEQUENCE: 1

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
```

```
                        85                  90                  95
Ala Arg Arg Asp Tyr Tyr Gly Asn Phe Tyr Tyr Ala Met Asp Tyr Trp
                100                 105                 110

Gly Gln Gly Thr Ser Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Amino Acid sequence (predicted) of light chain
      of chimeric human/mouse antibody
<220> FEATURE:
<221> NAME/KEY: CDR1
<222> LOCATION: (24)..(34)
```

-continued

```
<220> FEATURE:
<221> NAME/KEY: CDR2
<222> LOCATION: (50)..(56)
<220> FEATURE:
<221> NAME/KEY: CDR3
<222> LOCATION: (89)..(97)

<400> SEQUENCE: 2

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 31
<212> TYPE: DNA
<213> ORGANISM: Artificial Sequence
<220> FEATURE:
<223> OTHER INFORMATION: IgH primer MHV7

<400> SEQUENCE: 3
atgggcatca agatggagtc acagacccag g                              31

<210> SEQ ID NO 4
<211> LENGTH: 21
<212> TYPE: DNA
<213> ORGANISM: Artificial Sequence
<220> FEATURE:
<223> OTHER INFORMATION: IgG1 constant region primer MHCG1

<400> SEQUENCE: 4
cagtggatag acagatgggg g                                         21

<210> SEQ ID NO 5
<211> LENGTH: 30
<212> TYPE: DNA
```

```
<213> ORGANISM: Artificial Sequence
<220> FEATURE:
<223> OTHER INFORMATION: Ig kappa primer MKV2

<400> SEQUENCE: 5
atggagacag acacactcct gctatgggtg                                    30

<210> SEQ ID NO 6
<211> LENGTH: 33
<212> TYPE: DNA
<213> ORGANISM: Artificial Sequence
<220> FEATURE:
<223> OTHER INFORMATION: Ig kappa primer MKV4

<400> SEQUENCE: 6
atgagggccc ctgctcagtt ttttggcttc ttg                                33

<210> SEQ ID NO 7
<211> LENGTH: 25
<212> TYPE: DNA
<213> ORGANISM: Artificial Sequence
<220> FEATURE:
<223> OTHER INFORMATION: Ig kappa primer MKV9

<400> SEQUENCE: 7
atggtatcca cacctcagtt ccttg                                         25

<210> SEQ ID NO 8
<211> LENGTH: 20
<212> TYPE: DNA
<213> ORGANISM: Artificial Sequence
<220> FEATURE:
<223> OTHER INFORMATION: primer MKC

<400> SEQUENCE: 8
actggatggt gggaagatgg                                               20

<210> SEQ ID NO 9
<211> LENGTH: 50
<212> TYPE: DNA
<213> ORGANISM: Artificial Sequence
<220> FEATURE:
<223> OTHER INFORMATION: forward (For) primer

<400> SEQUENCE: 9
agagaagctt gccgccacca tgattgcctc tgctcagttc cttggtctcc              50

<210> SEQ ID NO 10
<211> LENGTH: 35
<212> TYPE: DNA
<213> ORGANISM: Artificial Sequence
<220> FEATURE:
<223> OTHER INFORMATION: oligonucleotide primer BT03

<400> SEQUENCE: 10
caacagtata gtaagctccc tcggacgttc ggtgg                              35

<210> SEQ ID NO 11
<211> LENGTH: 35
<212> TYPE: DNA
<213> ORGANISM: Artificial Sequence
<220> FEATURE:
<223> OTHER INFORMATION: oligonucleotide primer BT04

<400> SEQUENCE: 11
ccaccgaacg tccgagggag cttactatac tgttg                              35
```

```
<210> SEQ ID NO 12
<211> LENGTH: 41
<212> TYPE: DNA
<213> ORGANISM: Artificial Sequence
<220> FEATURE:
<223> OTHER INFORMATION: primer g2258

<400> SEQUENCE: 12
cgcgggatcc actcacgttt gatttccagc ttggtgcctc c          41

<210> SEQ ID NO 13
<211> LENGTH: 45
<212> TYPE: DNA
<213> ORGANISM: Artificial Sequence
<220> FEATURE:
<223> OTHER INFORMATION: Primer g22949

<400> SEQUENCE: 13
cgatgggccc ttggtggagg ctgaggagac ggtgactgag gttcc      45
```